US005691373A

United States Patent [19]

Berryman et al.

[11] Patent Number: 5,691,373
[45] Date of Patent: Nov. 25, 1997

[54] NONPEPTIDE ENDOTHELIN ANTAGONISTS I

[75] Inventors: Kent Alan Berryman; Annette Marian Doherty, both of Ann Arbor; Jeremy John Edmunds, Ypsilanti; William Chester Patt, Chelsea; Mark Stephen Plummer, Dexter; Joseph Thomas Repine, Ann Arbor, all of Mich.

[73] Assignee: Warner-Lambert Company, Morris Plains, N.J.

[21] Appl. No.: 384,083

[22] Filed: Feb. 6, 1995

Related U.S. Application Data

[63] Continuation-in-part of Ser. No. 278,882, Jul. 26, 1994, abandoned, which is a continuation-in-part of Ser. No. 217,578, Mar. 24, 1994, abandoned, which is a continuation-in-part of Ser. No. 109,751, Aug. 19, 1993, abandoned.

[51] Int. Cl.$^6$ ............... A61K 31/36; A61K 31/38; A61K 31/44; A61K 31/535

[52] U.S. Cl. ............... 514/464; 514/233.8; 514/314; 514/336; 514/338; 514/414; 514/397; 514/444; 514/452; 514/464; 514/465; 514/466; 514/469; 514/473; 549/60; 549/318; 549/313; 549/321; 549/438; 548/311.7; 548/454; 548/466; 546/152; 546/283.7; 546/284.4; 544/153

[58] Field of Search ............... 514/464, 473, 514/466, 465, 452, 444, 414, 336, 338, 314, 469, 397, 233.8; 549/447, 60, 318, 313, 321, 438; 546/152, 283.7, 284.4; 548/454, 466, 311.7

[56] References Cited

U.S. PATENT DOCUMENTS

| | | |
|---|---|---|
| 4,594,443 | 6/1986 | Bianchi et al. ............... 560/53 |
| 4,968,817 | 11/1990 | Brima ............... 549/295 |

FOREIGN PATENT DOCUMENTS

| | | |
|---|---|---|
| 0010347 | 4/1980 | European Pat. Off. . |
| 0099692 | 2/1984 | European Pat. Off. . |
| 0134179 | 3/1985 | European Pat. Off. . |
| 0403891 | 12/1990 | European Pat. Off. . |
| 0436189A1 | 12/1990 | European Pat. Off. . |
| 5178706 | 7/1993 | Japan . |
| 91/16055 | 10/1991 | WIPO . |
| 92/19610 | 11/1992 | WIPO . |
| 9623773 | 8/1996 | WIPO . |

OTHER PUBLICATIONS

Watanabe, T., et al., "Endothelin in Myocardial Infarction," *Nature*, (Lond.) 1990, 344:114.
Margulies, K.B., et al., "Increased Endothelin in Experiment Heart Failure," *Circulation* 1990, 82:2226.
Kon, V., et al., "Glomerular Actions of Endothelin In Vivo, *J. Clin. Invest*," 1989, 83:1762.
Perico, N., et al., "Endothelin Mediates the Renal Vasoconstriction Induced by Cyclosporine in the Rat," *J Am Soc Nep* 1990, 1:76.
Koshi, T., et al., *Chem Pharm Bull.*, 1991, 39:1295.
Miyamori, I., et al., *Clin. Exp. Pharmacol. Physiol.*, (1990) 17:691.
Ohno, A., *J Tokyo Women's Med. Coll.*, (1991) 61:951.
Lerman, A., et al., *Circulation* (1991) 83:1808.
Rodeheffer, R.J., et al., *Am J Hypertension*, (1991) 4:9A.
Arai, H., et al., *Nature*, (1990) 348:730.
Sakurai, T., et al., *Nature*, (1990) 348:732.
Lin, H.Y., et al., *Proc Natl Acad Sci*, (1991) 88:3185.
Sakamoto, A., et al, *Biochem Biophys Res Chem* (1991) 178:.
Hosoda, K., et al., *FEBS Lett*, (1991) 287:23.
Takayanagi, R., et al., *FEBS Lett* (1991) 282:103.
Panek, R.L., et al., *Biochem Biophys Res Commun*, (1992) 183(2):566.
Saeki, T., et al., *Biochem Biophys Res Commun*, (1991) 179.
Nakagawa, K., et al., *Nippon Hifuka Gakkai Zasshi*, (1990) 100, 1453–1456.
Noguchi, et al., *Am Rev. Respir Dis*, (1992) 145 (4 Part 2).
Clark, B.A., et al., *Am J Obstet Gynecol* (1992) 166, 962–968.
Pittet, J., et al., *Ann Surg*, (1991) 213 (3), 262.
Gandhi, C.B., et al., *Journal of Biological Chemistry*, (1990) 265(929) 17432.
Collier, A., et al., *Diabetes Care*, (1992) 15(8) 1038.
Basil, M.K., et al., *J Hypertension*, (1992) 10 (Suppl 4) 549.
Han, S.-P, et al., *Life Sci*, (1990) 46, 767.
Nikolov, R.K., et al., *Drugs of Today*, (1992) 28(5) 303–310.
Lerman, A., et al., *New England J. Med*, (1991) 325, 997–1001.
Kanno, K., et al., *J. Amer MEd Assoc*, (1990) 264, 2868.
Zamora, M.R., et al., *Lancet*, (1990) 336, 1144–1147.
Tahara, A., et al., *Metab Clin Exp*, (1991) 40, 1235–1237.
Stewart, D. J., et al., *Ann Internal Medicine*, (1991) 114 464–469.
Stewart, J. T., et al., *Br Heart J*, (1991) 66, 7–9.
Lopez-Farre, A., et al., *J Physiology*, (1991) 444, 513–522.
Stockenhuber, F., et al., *Clin Sci (Lond)*, (1992) 82, 255–258.
Mirua, S., et al., *Digestion*, (1991) 48, 163–172.
Masuda, E., et al., *Am J Physiol* (1992) 262, G785–G790.
Murch, S.H., et al., *Lancet* (1992) 339, 381–384.

(List continued on next page.)

*Primary Examiner*—Amelia Owens
*Attorney, Agent, or Firm*—Elizabeth M. Anderson

[57] ABSTRACT

Novel nonpeptide antagonists of endothelin I are described, as well as methods for the preparation and pharmaceutical compositions of the same, which are useful in treating elevated levels of endothelin, acute and chronic renal failure, hypertension, myocardial infarction, myocardial ischemia, cerebral vasospasm, cerebral ischemia, cerebral infarction, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, pulmonary hypertension, ischemic disease, gastric mucosal damage, hemorrhagic shock, ischemic bowel disease, stroke, benign prosthatic hyperplasia (BPH), and diabetes.

10 Claims, No Drawings

OTHER PUBLICATIONS

Clozel, M., et al., Third Intl Conf on Endothelin, Abstract Book, Feb. 5–17, 1993.

Clozel, M., et al., *Life Sci*, 52, (1993) 825–834.

Rovero, P., et al., *British J of Pharmacology* 101(1990) 232–236.

Allen, C.F.H., et al., *Can J Chem* 34 (1956) 926.

Allen, C.F.H., et al., *Can J Research* 6 (1932) 605.

Allen, C.F.H., et al., *Can J Research* 8 (1993) 137.

Allen, C.F.H., et al., *Can J Research* 11 (1934) 382.

Doherty, A.M., et al., *Bioorg & Med Chem Lett* vol. 3, No. 4, (1993) 497–502.

Yasuda, M., et al., *Amer Heart J*, (1990) 119, 801–806.

Clozel, M., et al., *Life Sci*, 1993, 52:825.

Lee, K.S., et al., *Cerebral Vasospasm*, 1993, 217.

Nirei, H., et al., *Life Sci*, 1993, 52:1869.

Yano, M., et al., *Biochem Biophys Res Commun*, 1993, 195:969.

Clozel, M., et al., *Circulation*, 1993, 88(4) part 2:0907.

Clozel, M., et al., *Nature*, 1993, 365, 759.

P. Foley, et al., *Neurosurgery*, 1994, 34:1, 108–114.

G. Rio, et al., *Bull de la Soc Chim de France*, 1970, 10, 3572–3578.

K. Channabasavalah, et al., *Indian J of Chem*, 1973, 11:9, 1333–1334.

F. McEvoy, et al., *J Med Chem*, 1974, 17:3, 281–286.

D.K. Dikshit, et al., *Indian J of Chemistry*, 1990, 29B, 954–960.

H. Krapf, et al., *Chem. Ber*, 1976, 109, 576–596.

H.L.K. Schmand, *Liebigs Ann Chem*, 1976, 1560–1576.

C. von Rohrscheidt, et al., *Liebigs Ann Chem*, 1978, 680–693.

A. Padwa, et al., *J Am Chem Soc*, 1978, 100:26, 8247–8259.

E. Chelain, et al., *J Am Chem Soc*, 1992, 114, 8088–8098.

J.S. Weinberg, et al., *J Org Chem*, 1979, 44:25, 4722–4725.

J.C. Canevet, et al., *Tetrahedron*, 1978, 34, 1935–1942.

T. Mise, et al., *J Org Chem*, 1983, 48, 238–242.

C. Anselmi, *J Heterocyclic Chem*, 1983, 20, 687–689.

H. Yoshida, et al., *Bull Chem Soc Jpn Notes*, 1983, 56, 3849–3850.

A. Daroca, et al., *Monatsheft fur Chemie*,1984, 115, 357–373.

G. Falsone, *Arch Pharm*, 1984, 317, 802–807.

P. Verma, et al., *J Syn Org Chem*, 1988, 1, 68–70.

S. Pratapan, et al., *J Org Chem*, 1988, 53, 5826–5831.

M. E. Kraft, et al., *Tetrahedron Letters*, 1990, 31;36, 5139–5142.

B. Alcaide, et al., *J Chem Soc Berkin Trans*, 1990, 1, 2451–2457.

I.G. Dinulescu, et al., *J. Organometallic Chem*, 1977, 140, 91–96.

K.S. Chan, et al., *J. Organometallic Chem*, 1987, 334, 9–56.

S. I. Pennanen, *Heterocycles*, 1977, 6, 701–706.

Y. Endo, et al., *Heterocycles*, 1992, 33:1, 91–95.

K.H. Dotz, et al., *J of Organometallic Chem*, 1993, 459, 169–176.

J.W. Herndon, et al., *Synlett*, 1993, 363–364.

V.I. Tyvorskii, et al. *Russian J Org Chem*, 1993, 29:5:2, 841–843.

NONPEPTIDE ENDOTHELIN ANTAGONISTS I

CROSS-REFERENCE TO RELATED APPLICATIONS

This is a Continuation-in-Part application of U.S. Ser. No. 08/278,882, filed Jul. 26, 1994, now pending; which is a Continuation-in-Part application of U.S. Ser. No. 08/217,578, filed Mar. 24, 1994, now pending; which is a Continuation-in-Part application of U.S. Ser. No. 08/109,751, filed Aug. 19, 1993, now abandoned.

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, acute and chronic renal failure, hypertension, myocardial infarction and myocardial ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, pulmonary hypertension, ischemic disease, gastric mucosal damage, hemorrhagic shock, ischemic bowel disease, and diabetes.

Also, the compounds will be useful in cerebral ischemia or cerebral infarction resulting from a range of conditions such as thromboembolic or hemorrhagic stroke, cerebral vasospasm, head injury, hypoglycemia, cardiac arrest, status epilepticus, perinatal asphyxia, anoxia such as from drowning, pulmonary surgery, and cerebral trauma.

Several studies have been reported with both peptide and non-peptide ET antagonists showing efficacy in various models of subarachnoid hemorrhage (SAH). For example, BQ-123-prevents early cerebral vasospasm following SAH in various rat (Clozel M., et al., *Life Sci*, 1993;52:825) and rabbit (Lee K. S., et al., *Cerebral Vasospasm* 1993:217; and *Neurosurgery* 1994; 34:108) models. FR 139317 significantly inhibited the vascoconstriction of the basilar artery after 7 days in a canine two-hemorrhage model of SAH (Nirei H., et al., *Life Sci.* 1993;52:1869). BQ-485 also significantly inhibited the vascoconstriction of the basilar artery after 7 days in a canine two-hemorrhage model of SAH (Yano, et al., *Biochem Biophys. Res Commun.* 1993; 195:969). Ro 46-2005 (Clozel M., et al., *Nature* 1993;365:759) has been shown to prevent early cerebral vasospasm following SAH in the rat with no significant effect on systemic arterial blood pressure. Treatment with Ro 47-0203=Bosentan (Clozel et al., *Circulation* 1993;88(4) part 2:0907) to rabbits with SAH had a 36±7% reduction of basilar artery cross-sectional area compared to sham rabbits. All of these studies show in vivo efficacy of endothelin antagonists in cerebral vasospasm resulting from SAH.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs).

Endothelin is involved in many human disease states.

Several in vivo studies with ET antibodies have been reported in disease models. Left coronary artery ligation and reperfusion to induce myocardial infarction in the rat heart, caused a 4- to 7-fold increase in endogenous endothelin levels. Administration of ET antibody was reported to reduce the size of the infarction in a dose-dependent manner (Watanabe T., et al., "Endothelin in Myocardial Infarction," *Nature* (Lond.) 1990;344:114). Thus, ET may be involved in the pathogenesis of congestive heart failure and myocardial ischemia (Margulies K. B., et al., "Increased Endothelin in Experimental Heart Failure," *Circulation* 1990;82:2226).

Studies by Kon and colleagues using anti-ET antibodies in an ischemic kidney model, to deactivate endogenous ET, indicated the peptide's involvement in acute renal ischemic injury (Kon V., et al., "Glomerular Actions of Endothelin In Vivo," *J. Clin. Invest*, 1989;83:1762). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico N., et al., "Endothelin Mediates the Renal Vasoconstriction Induced by Cyclosporine in the Rat," *J. Am. Soc. Nephrol.* 1990;1:76).

Others have reported inhibition of ET-1 or ET-2-induced vasoconstriction in rat isolated thoracic aorta using a monoclonal antibody to ET-1 (Koshi T., et al., "Inhibition of Endothelin (ET)-1 and ET-2-Induced Vasoconstriction by Anti-ET-1 Monoclonal Antibody," *Chem. Pharm. Bull,* 1991;39:1295).

Combined administration of ET-1 and ET-1 antibody to rabbits showed significant inhibition of the blood pressure (BP) and renal blood flow responses (Miyamori I., et al., Systemic and Regional Effects of Endothelin in Rabbits: Effects of Endothelin Antibody," *Clin. Exp. Pharmacol, Physiol.* 1990;17:691).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno A. Effects of Endothelin-Specific Antibodies and Endothelin in Spontaneously Hypertensive Rats," *J. Tokyo Women's Med. Coll.* 1991;61:951).

In addition, elevated levels of endothelin have been reported in several disease states (see Table I below).

Burnett and co-workers recently demonstrated that exogenous infusion of ET (2.5 ng/kg/mL) to anesthetized dogs, producing a doubling of the circulating concentration, did have biological actions (Lerman A., et al., "Endothelin has Biological Actions at Pathophysiological Concentrations," *Circulation* 1991; 83:1808). Thus heart rate and cardiac output decreased in association with increased renal and systemic vascular resistances and antinatriuresis. These studies support a role for endothelin in the regulation of cardiovascular, renal, and endocrine function.

In congestive heart failure in dogs and humans, a significant 2- to 3-fold elevation of circulating ET levels has been reported (Rodeheffer R. J., et al., "Circulating Plasma Endothelin Correlates With the Severity of Congestive Heart Failure in Humans," *Am. J. Hypertension* 1991;4:9A).

The distribution of the two cloned receptor subtypes, termed $ET_A$ and $ET_B$, have been studied extensively (Arai H., et al., *Nature* 1990;348:730, Sakurai T., et al., *Nature* 1990;348:732). The $ET_A$, or vascular smooth muscle receptor, is widely distributed in cardiovascular tissues and in certain regions of the brain (Lin H. Y., et al., *Proc. Natl. Acad. Sci.* 1991;88:3185). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto A., et al., *Biochem. Biophys. Res. Chem.* 1991;178:656, Hosoda K., et al., *FEBS Lett.* 1991;287:23). The $ET_A$ receptor clearly mediates vasoconstriction and there have been a few reports implicating the $ET_B$ receptor in the initial vasodilatory response to ET (Takayanagi R., et al., *FEBS Lett.* 1991;282:103). However, recent data has shown that the $ET_B$ receptor can also mediate vasoconstriction in some tissue beds (Panek R. L., et al., *Biochem. Biophys. Res. Commun.* 1992;183(2):566).

A recent study showed that selective $ET_B$ agonists caused only vasodilation in the rat aortic ring, possibly through the release of EDRF from the endothelium (ibid). Thus, reported selective $ET_B$ agonists, for example, the linear analog ET[1, 3,11,15-Ala] and truncated analogs ET[6-21, 1,3,11,15-Ala], ET[8-21,11,15-Ala], and N-Acetyl-ET[10-21,11,15-Ala] caused vasorelaxation in isolated, endothelium-intact porcine pulmonary arteries (Saeki T., et al., *Biochem. Biophys. Res. Commun.* 1991;179:286). However, some ET analogs are potent vasoconstrictors in the rabbit pulmonary artery, a tissue that appears to possess an $ET_B$, nonselective type of receptor (ibid).

Plasma endothelin-1 levels were dramatically increased in a patient with malignant hemangioendothelioma (Nakagawa K. et al., *Nippon Hifuka Gakkai Zasshi* 1990;100:1453-1456).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al., *Am. Rev. Repair. Dis.* 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark B. A., et al., *Am. J. Obstet. Gynecol.* 1992;166:962-968).

Plasma immunoreactive endothelin-1 concentrations are elevated in patients with sepsis and correlate with the degree of illness and depression of cardiac output (Pittett J., et al., *Ann Surg.* 1991;213(3):262).

In addition the ET-1 antagonist BQ-123 has been evaluated in a mouse model of endotoxic shock. This $ET_A$ antagonist significantly increased the survival rate in this model (Toshiaki M., et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Journal of Biological Chemistry* 1990;265(29):17432). In addition increased levels of plasma ET-1 have been observed in microalbuminuric insulin-dependent diabetes mellitus patients indicating a role for ET in endocrine disorders such as diabetes (Collier A., et al., *Diabetes Care* 1992;15(8):1038).

$ET_A$ antagonist receptor blockade has been found to produce an antihypertensive effect in normal to low renin models of hypertension with a time course similar to the inhibition of ET-1 pressor responses (Basil M. K., et al., *J. Hypertension* 1992; 10(Suppl 4): S49). The endothelins have been shown to be arrhythmogenic, and to have positive chronotropic and inotropic effects, thus ET receptor blockade would be expected to be useful in arrhythmia and other cardiovascular disorders (Hah S. -P., et al., *Life Sci.* 1990;46:767).

The widespread localization of the endothelins and their receptors in the central nervous system and cerebrovascular circulation has been described (Nikolov R. K., et al., *Drugs of Today* 1992;28(5):303-310). Intracerebroventricular administration of ET-1 in rats has been shown to evoke several behavioral effects. These factors strongly suggest a role for the ETs in neurological disorders. The potent vasoconstrictor action of ETs on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1 induced lesion development in a new model of local ischemia in the brain has been described.

Circulating and tissue endothelin immunoreactivity is increased more than twofold in patients with advanced atherosclerosis (Lerman A., et al., *New England J. Med.* 1991;325:997-1001). Increased endothelin immunoreactivity has also been associated with Buerger's disease (Kanno K., et al., *J. Amer. Med. Assoc.* 1990;264:2868) and Raynaud's phenomenon (Zamora M. R., et al., *Lancet* 1990;336:1144-1147).

An increase of circulating endothelin levels was observed in patients that underwent percutaneous transluminal coronary angioplasty (PTCA) (Tahara A., et al., *Metab. Clin. Exp.* 1991;40:1235-1237.

Increased plasma levels of endothelin have been measured in rats and humans (Stewart D. J., et al., *Ann. Internal Medicine* 1991;114:464-469) with pulmonary hypertension.

Elevated levels of endothelin have also been measured in patients suffering from ischemic heart disease (Yasuda M., et al., *Amer. Heart J.* 1990;119:801-806) and either stable or unstable angina (Stewart J. T., et al., *Br. Heart J.* 1991;66:7-9).

Infusion of an endothelin antibody 1 hour prior to and 1 hour after a 60 minute period of renal ischaemia resulted in changes in renal function versus control. In addition, an increase in glomerular platelet-activating factor was attributed to endothelin (Lopez-Farre A., et al., *J. Physiology* 1991;444:513-522). In patients with chronic renal failure as well as in patients on regular hemodialysis treatment mean plasma endothelin levels were significantly increased (Stockenhuber F., et al., *Clin. Sci. (Lond.)* 1992;82:255-258).

Local intra-arterial administration of endothelin has been shown to induce small intestinal mucosal damage in rats in a dose-dependent manner (Mirua S., et al., *Digestion* 1991;48:163-172). Furthermore, it has been shown that an anti-ET-1 antibody reduced ethanol-induced vasoconstriction in a concentration-dependent manner (Masuda E., et al., *Am. J. Physiol.* 1992;262:G785-G790). Elevated endothelin levels have been observed in patients suffering from Crohn's disease and ulcerative colitis (Murch S. H., et al., *Lancet* 1992;339:381-384).

Recently at the 3rd International Conference on Endothelin, Houston, Tex., February 1993, the nonpeptide endothelin antagonist RO 46-2005 has been reported to be effective in models of acute renal ischemia and subarachnoid hemorrhage in rats (Clozel M., et al., "Pathophysiological role of endothelin revealed by the first orally active endothelin receptor antagonist," *Nature*, 1993;365:759). In addition, the $ET_A$ antagonist BQ-123 has been shown to prevent early cerebral vasospasm following subarachnoid hemorrhage (Clozel M. and Watanabe H., *Life Sci.* 1993;52:825-834.

Most recently an $ET_A$ selective antagonist demonstrated an oral antihypertensive effect (Stein P. D., et al., "The Discovery of Sulfonamide Endothelin Antagonists and the Development of the Orally Active $ET_A$ Antagonist 5-(Dimethylemino)-N-(3,4-dimethyl-5-isoxazolyl)-1-naphthalenesulfonamide," *J. Med. Chem.*, 1994;37:329-331.

TABLE I

Plasma Concentrations of ET-1 in Humans

| Condition | Normal Control | ET Plasma Levels Reported (pg/mL) |
|---|---|---|
| Atherosclerosis | 1.4 | 3.2 pmol/L |
| Surgical operation | 1.5 | 7.3 |
| Buerger's disease | 1.6 | 4.8 |
| Takayasu's arteritis | 1.6 | 5.3 |
| Cardiogenic shock | 0.3 | 3.7 |
| Congestive heart failure (CHF) | 9.7 | 20.4 |
| Mild CHF | 7.1 | 11.1 |
| Severe CHF | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
|  | 0.76 | 4.95 |
|  | 0.50 | 3.8 |
| Subarachnoid hemorrhage | 0.4 | 2.2 |
| Crohn's Disease | 0-24 fmol/mg | 4-64 fmol/mg |
| Ulcerative colitis | 0-24 fmol/mg | 20-50 fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperative cardiac | 6.1 | 11.9 |
| Inflammatory arthritides | 1.5 | 4.2 |
| Malignant hemangioendothelioma | 4.3 (after removal) | 16.2 |

Allen C. F. H., Frame G. F., *Can. J. Research* 1932; 6:605 teaches the condensation of methyl and ethyl α-phenyl-β-(para-substituted)benzoylpropionates with benzaldehyde and piperonal in the presence of sodium methylate, followed by acidification, produces cyclic compounds.

Allen C. F. H., Frame G. F., Normington J. B., Wilson C. V., *Can. J. Research* 1933;8:137 teaches the condensation of benzaldehyde with methyl and ethyl α-aryl-β-benzoylpropionates in the presence of sodium methylate, followed by acidification, to give unsaturated ketonic acids.

Allen, C. F., Normington, J. B., Wilson, C. V., *Can. J. Research* 1934;11:382 recites a number of highly substituted acrylic acids or their lactols.

Allen, C. F. H., Davis, T. J., Stewart, D. W., VanAllan, J. A., *Can. J. Chem.* 1956;34:926 shows that α aryl-β-aroylpropionic acids exist in an open-chain configuration while the condensation products of these latter acids with aromatic aldehydes are lactols, refuting his previous article *Can. J. Research* 933;8:137.

Compounds of formula

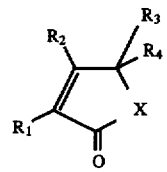

wherein:

| R₁ | R₂ | R₃ |
|---|---|---|
| phenyl | phenyl | phenyl |
| phenyl | phenyl | p-chlorophenyl |
| phenyl | phenyl | p-bromophenyl |
| piperonyl | | phenyl | p-chlorophenyl |
| phenyl | o-chlorophenyl | phenyl |
| phenyl | phenyl | p-phenylphenyl |
| anisyl (p-methoxyphenyl) | phenyl | phenyl |
| anisyl | α-furyl | phenyl |
| phenyl | piperonyl | p-chlorophenyl |
| anisyl | o-chlorophenyl | phenyl |
| anisyl | o-methoxyphenyl | phenyl |
| phenyl | phenyl | mesityl |
| phenyl | phenyl | p-methylphenyl |
| phenyl | o-chlorophenyl | p-chlorophenyl |
| phenyl | phenyl | p-methoxyphenyl |
| anisyl | o-methylphenyl | phenyl |
| phenyl | piperonyl | p-bromophenyl |
| phenyl | piperonyl | p-methoxyphenyl | are all known from the above four literature references. However, the methods of using 2(5H)-furanone, 3-(1,3-benzodioxol-5-yl)- 5-(4-chlorophenyl)-5-hydroxy-4-(phenylmethyl)—(hereinafter Compound A) and a pharmaceutical composition containing it are new.

SUMMARY OF THE INVENTION

The present invention includes compounds of Formula I or a pharmaceutically acceptable salt thereof wherein:
R₁ is cycloalkyl substituted or unsubstituted of from 3 to 12 carbon atoms,
phenyl substituted with from 1 to 5 substituents, naphthyl unsubstituted or substituted with from 1 to 5 substituents, or heteroaryl unsubstituted or substituted with from 1 to 5 substituents;

$R_2$ is alkyl substituted or unsubstituted straight, or branched, of from 1 to 12 carbon atoms, cycloalkyl substituted or unsubstituted of from 3 to 12 carbon atoms, aryl which is unsubstituted or substituted with from 1 to 5 substituents, heteroaryl which is unsubstituted or substituted with from 1 to 3 substituents, $R_3$ is alkyl substituted or unsubstituted straight, or branched, of from 1 to 12 carbon atoms, cycloalkyl substituted or unsubstituted of from 3 to 12 carbon atoms, aryl which is unsubstituted or substituted with from 1 to 5 substituents, heteroaryl which is unsubstituted or substituted with from 1 to 3 substituents;

$R_4$ is hydroxy or $OR_5$, $SR_5$, wherein $R_5$ is alkyl or substituted alkyl of from 1 to 7 carbon atoms, or $(CH_2)_n OR_5$ wherein n is an integer of from 1 to 3; X is O or S;

with the proviso that when $R_1$ is monosubstituted phenyl and the substituent is p-methoxy, $R_3$ is not unsubstituted phenyl, monosubstituted phenyl, or mesityl and with the further proviso when $R_2$ is alkyl substituted, the substituent is not oxygen at the α-position to the furanone ring.

Preferred compounds of the instant invention are those of Formula I wherein $R_1$ is phenyl substituted with from 1 to 5 substituents, naphthyl unsubstituted or substituted with from 1 to 5 substituents, or heteroaryl unsubstituted or substituted with from 1 to 5 substituents;

$R_2$ is alkyl substituted or unsubstituted straight, or branched, of from 1 to 7 carbon atoms, $R_3$ is aryl substituted or unsubstituted, heteroaryl substituted or unsubstituted;

$R_4$ is hydroxy,
$OR_5$, or
$SR_5$;

X is O or S;

with the proviso that when $R_1$ is monosubstituted phenyl and the substituent is p-methoxy, $R_3$ is not unsubstituted phenyl, monosubstituted phenyl, or mesityl and with the further proviso that when $R_2$ is alkyl substituted, the substituent is not oxygen at the α-position to the furanone.

Preferred compounds of the instant invention are those of Formula I wherein $R_1$ is 4-piperonyl,
3,4-dichlorophenyl,
3-methoxyphenyl,
3,5-dimethoxyphenyl, or

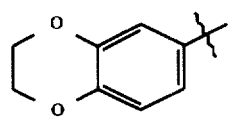

3-methoxy-4,5-methylenedioxyphenyl $R_2$ is benzyl,
4-piperonylmethyl,
4-isopropylbenzyl,
1-naphthylmethyl,
2-naphthylmethyl,
3-thiophenylmethyl,
2-thiophenylmethyl,
3,4-dichlorobenzyl,
3(N-Me) indolylmethyl,
3,4-dimethoxybenzyl,
4-Me$_2$aminobenzyl,
4-isopropylbenzyl,
4-chlorobenzyl,
4-methoxybenzyl,
4-methylbenzyl,
3-methylbenzyl,
4-isopropoxybenzyl,
4-acetamidobenzyl,
4-methylsulfonylbenzyl,
3-methyl-4-methoxybenzyl,
3-allyloxy-4-methoxybenzyl,
3,4,5-trimethoxybenzyl,
3-n-propoxybenzyl,
4-thiomethylbenzyl,
3-carbethoxybenzyl,
4-carbethoxybenzyl,
3-methoxybenzyl,
2-methoxybenzyl, or
3-chlorobenzyl;

$R_3$ is phenyl,
4-methylphenyl,
4-methoxyphenyl,
2-methylphenyl,
3-methylphenyl,
3-methoxyphenyl,
3-methyl-4-methoxyphenyl,
3,4-dimethoxyphenyl, or
2,4-dimethoxyphenyl;

$R_4$ is hydroxy,
$OCH_3$,
$OCH_2CHO$,
$OCH_2COOH$,
$OCH_2CH(OH)CH_2OH$, or
$OCH_2$(m-OH-phenyl), and X is oxygen.

More preferred compounds of the instant invention are those of Formula I wherein $R_1$ is 4-piperonyl,
3,5-dimethoxyphenyl, or
3-methoxy-4,5-methylenedioxyphenyl;

$R_2$ is 4-piperonylmethyl,
4-isopropylbenzyl,
2-naphthylmethyl,
1-naphthylmethyl,
benzyl,
2-thiophenylmethyl,
3-thiophenylmethyl,
3-(N-Me)indolylmethyl,
4-chlorophenyl,
4-methoxyphenyl,
4-methylphenyl,
4-isopropoxybenzyl,
4-acetamidobenzyl,
4-methylsulfonylbenzyl,
3-methyl-4-methoxybenzyl,
3- allyloxy-4-methoxybenzyl,
3,4,5- trimethoxybenzyl,
3-n-propoxybenzyl,
4-thiomethylbenzyl,
3-carbethoxybenzyl, 4-carbethoxybenzyl,
2-methoxybenzyl,
3-methoxybenzyl, or
3-chlorobenzyl;

$R_3$ is 4-methoxyphenyl,
3,4-dimethoxyphenyl,
3-methyl-4-methoxyphenyl, or
2,4-dimethoxyphenyl;

$R_4$ is OH; and

X is oxygen.

Still more preferred compounds of the instant invention are selected from:

2(5H)-furanone, 5-(4-chlorophenyl)-5-hydroxy-3-[4-(1-methylethyl)phenyl]-4-(phenylmethyl)-, (±)-, (±)-3-(1,3-benzodioxol-5-yl)-5-(4-chlorophenyl)-4-(phenylmethyl)-5-(2-propenyloxy)-2(5H)-furanone, acetaldehyde, [[4-(1,3-benzodioxol-5-yl)-2-(4-chlorophenyl)-2,5-dihydro-5-oxo-3-(phenylmethyl)-2-furanyl]oxo]-, (±)-, 2(5H)-furanone, 3-(1,3-benzodioxol-5-yl)-5-(4-chlorophenyl)-5-(2,3-dihydroxypropoxy)-4-(phenylmethyl)-, (±)-, acetic acid, [[4-(1,3-benzodioxol-5-yl)-2-(4-chlorophenyl)-2,5-dihydro-3-(phenylmethyl)-5-oxo-2-furanyl]-oxy]-, (±)-, 2(5H)-furanone, 3-(1,3-benzodioxol-5-yl)-5-(4-chlorophenyl)-5-[(3-hydroxyphenyl)methoxy]-4-(phenylmethyl)-, (±)-, 2(5H)-furanone, 3-(1,3-benzodioxol-5-yl)-5-hydroxy-5-(4-methylphenyl)-4-(phenylmethyl)-, 2(5H)-furanone, 3-(1,3-benzodioxol-5-yl)-5-hydroxy-5-phenyl-4-(phenylmethyl)-, 2(5H)-furanone, 3-(1,3-benzodioxol-5-yl)-5-hydroxy-5-phenyl-4-(2-thienylmethyl)-, 2(5H)-furanone, 3-(1,3-benzodioxol-5-yl)-5-hydroxy-5-phenyl-4-(3-thienylmethyl)-, 2(5H)-furanone, 5-(4-chlorophenyl)-3-(2,3-dihydro-1,4-benzodioxin-6-yl)-5-hydroxy-4-(phenylmethyl)-, 2(5H)-furanone, 3-(1,3-benzodioxol-5-yl)-5-(4-chlorophenyl)-4-[(4-chlorophenyl)methyl]-5-hydroxy-, 2(5H)-furanone, 3-(1,3-benzodioxol-5-yl)-5-(4-chlorophenyl)-5-hydroxy-4-[(4-methoxyphenyl)methyl]-, 2(5H)-furanone, 3-(1,3-benzodioxol-5-yl)-5-(4-chlorophenyl)-5-hydroxy-4-[(4-methylphenyl)methyl]-, 2(5H)-furanone, 3-(1,3-benzodioxol-5-yl)-5-(4-chlorophenyl)-5-hydroxy-4-[(3-methylphenyl)methyl]-, 2(5H)-furanone, 3-(1,3-benzodioxol-5-yl)-5-(4-chlorophenyl)-5-hydroxy-4-(2-thienylmethyl)-, 2(5H)-furanone, 5-(4-chlorophenyl)-5-hydroxy-3-[4-(1-methylethyl)phenyl]-4-(1-naphthalenylmethyl)-, (±)-, 2(5H)-furanone, 5-(4-chlorophenyl)-5-hydroxy-3-[4-(1-methylethyl)phenyl]-4-(2-naphthalenylmethyl)-, (±)-, 2(5H)-furanone, 4-(1,3-benzodioxol-5-ylmethyl)-5-(4-chlorophenyl)-5-hydroxy-3-[4-(1-methylethyl)phenyl]-, (±)-, 2(5H)-furanone, 3-(1,3-benzodioxol-5-yl)-5-(4-chlorophenyl)-5-hydroxy-4-(2-naphthalenylmethyl)-, (±)-, 2(5H)-furanone, 3-(1,3-benzodioxol-5-yl)-5-(4-chlorophenyl)-5-hydroxy-4-(1-naphthalenylmethyl)-, (±)-, 2(5H)-furanone, 3-(1,3-benzodioxol-5-yl)-5-(4-chlorophenyl)-5-hydroxy-4-[[4-(1-methylethyl)phenyl]methyl]-, (±)-, 2(5H)-furanone, 3-(1,3-benzodioxol-5-yl)-4-(1,3-benzodioxol-5-ylmethyl)-5-(4-chlorophenyl)-5-hydroxy-, (±)-, 2(5H)-furanone, 3-(1,3-benzodioxol-5-yl)-5-hydroxy-5-(4-methoxyphenyl)-4-(phenylmethyl)-, 2(5H)-furanone, 3-(1,3-benzodioxol-5-yl)-5-(4-chlorophenyl)-5-hydroxy-4-[(3-methoxyphenyl)methyl]-, 2(5H)-furanone, 3-(1,3-benzodioxol-5-yl)-5-(4-chlorophenyl)-5-hydroxy-4-(3-thienylmethyl)-, 2(5H)-furanone, 5-(4-chlorophenyl)-3[4-(dimethylamino)phenyl]-5-hydroxy-4-(phenylmethyl)-, (±)-, 2(5H)-furanone, 5-(4-chlorophenyl)-4-[(3,4-dichlorophenyl)methyl]-3-[(4-dimethylamino)phenyl]-5-hydroxy, (±)-, 2(5H)-furanone, 4-(1,3-benzodioxol-5-ylmethyl)-5-(4-chlorophenyl)-3-[4-(dimethylamino)phenyl]-5-hydroxy-, (±)-, 2(5H)-furanone, 5-(4-chlorophenyl)-3-[4-(dimethylamino)phenyl]-4-[[4-(dimethylamino)phenyl]methyl]-5-hydroxy-, (±)-, 2(5H)-furanone, 5-(4-chlorophenyl)-4-[(3,4-dimethoxyphenyl)methyl]-3-[4-(dimethylamino)phenyl]-5-hydroxy-, (±)-, 2(5H)-furanone, 5-(4-chlorophenyl)-3-[(4-(dimethylamino)phenyl]-5-hydroxy-4-[[4-(1-methylethyl)phenyl]methyl]-, (±)-, 2(5H)-furanone, 5-(4-chlorophenyl)-3-(3,4-dichlorophenyl)-5-hydroxy-4-(phenylmethyl)-, (±)-, 2(5H)-furanone, 4-(1,3-benzodioxol-5-ylmethyl)-5-(4-chlorophenyl)-3-)3,4-dimethoxyphenyl)-5-hydroxy, (±)-, 2(5H)-furanone, 3-(1,3-benzodioxol-5-yl)-5-(4-chlorophenyl)-5-hydroxy-4-[(1-methyl-1H-indol-3-yl)methyl], (±)-, 2(5H)-furanone, 5-(4-chlorophenyl)-3-(3,4-dimethoxyphenyl)-5-hydroxy-4-(phenylmethyl)-, (±)-, 2(5H)-furanone, 5-(4-chlorophenyl)-3-(3,4-dimethoxyphenyl)-4-[(3,4-dimethoxyphenyl)methyl]-5-hydroxy-, (±)-, 2(5H)-furanone, 4-(1,3-benzodioxol-5-ylmethyl)-5-(4-chlorophenyl)-3-(3,4-dichlorophenyl)-5-hydroxy-, (±)-, 2(5H)-furanone, 5-(4-chlorophenyl)-3-(3,4-dimethoxyphenyl)-5-hydroxy-4-[[4-(1-methylethyl)phenyl]methyl]-, (±)-, 2(5H)-furanone, 5-(4-chlorophenyl)-3-(3,4-dimethoxyphenyl)-4-[[4-(dimethylamino)phenyl]methyl]-5-hydroxy-, (±)-

2(5H)-furanone, 3-(1,3-benzodioxol-5-yl)-5-(4-chlorophenyl)-4-(phenylmethyl)-5-propoxy-, (±)-, 2(5H)-furanone, 5-(4-chlorophenyl)-4-[(3,4-dichlorophenyl)methyl]-3-(3,4-dimethoxyphenyl)-5-hydroxy-, (±)-, 2(5H)-furanone, 3-(1,3-benzodioxol-5-yl)-5-(4-chlorophenyl)-4-[(3-chlorophenyl)methyl]-5-hydroxy, 3-benzo[1,3]dioxol-5-yl-4-(4-tert-butyl-benzyl)-5-hydroxy-5-(4-methoxy-phenyl)-5H-furan-2-one, 3-benzo[1,3]dioxol-5-yl-5-hydroxy-5-(4-methoxyphenyl)-4-(4-methyl-benzyl)-5H-furan-2-one, 3-benzo[1,3]dioxol-5-yl-4-(4-chloro-benzyl)-5-hydroxy-5-(4-methoxy-phenyl)-5H-furan-2-one, 3-benzo[1,3]dioxol-5-yl-5-hydroxy-5-(4-methoxyphenyl)-4-(3-trifluoromethyl-benzyl)-5H-furan-2-one, 3-benzo[1,3]dioxol-5-yl-4-(4-bromo-benzyl)-5-hydroxy-5-(4-methoxy-phenyl)-5H-furan-2-one, 3-benzo[1,3]dioxol-5-yl-5-hydroxy-4-(isopropoxybenzyl)-5-benzyl-5-(4-methoxy-phenyl)-5H-furan-2-one, 3-benzo[1,3]dioxol-5-yl-4-(4-dimethylaminobenzyl)-5-hydroxy-5-(4-methoxy-phenyl)-5H-furan-2-one, 3-benzo[1,3]dioxol-5-yl-4-(4-benzyloxy-benzyl)-5-hydroxy-5-(4-methoxy-phenyl)-5H-furan-2-one, 3-benzo[1,3]dioxol-5-yl-4-benzo[1,3]dioxol-5-ylmethyl-5-hydroxy-5-(4-methoxy-phenyl)-5H-furan-2-one, 3-benzo[1,3]dioxol-5-yl-5-hydroxy-5-(4-methoxyphenyl)-4-(4-trifluoromethyl-benzyl)-5H-furan-2-one, 3-benzo[1,3]dioxol-5-yl-5-hydroxy-4-(4-methoxy-3-methyl-benzyl)-5-(4-methoxy-phenyl)-5H-furan-2-one, 3-benzo[1,3]dioxol-5-yl-5-hydroxy-5-(4-methoxyphenyl)-4-(3-methyl-benzyl)-5H-furan-2-one, 3-benzo[1,3]dioxol-5-yl-4-ethyl-5-hydroxy-5-(4-methoxy-phenyl)-5H-furan-2-one, 3-Benzo[2,3]dioxol-5-yl-4-(3-chloro-4-methoxybenzyl)-5-hydroxy-5-(4-methoxy-phenyl)-5H-furan-2-one, 3-benzo[1,3]dioxol-5-yl-4-(4-butoxy-benzyl)-5-hydroxy-5-(4-methoxy-phenyl)-5H-furan-2-one, 3-(4-chloro-phenyl)-5-hydroxy-4-(4-methoxybenzyl)-5-(4-methoxy-phenyl)-5H-furan-2-one, 5-hydroxy-4-(4-methoxy-benzyl)-5-(4-methoxyphenyl)-3-p-tolyl-5H-furan-2-one, 4-benzyl-3-(2,4-dimethoxy-phenyl)-5-hydroxy-5-(4-methoxy-phenyl)-5H-furan-2-one, 3-(3,4-dichloro-phenyl)-5-hydroxy-4-(4-methoxybenzyl)-5-(4-methoxy-phenyl)-5H-furan-2-one, 5-(4-chloro-phenyl)-3-(3,4-dichloro-phenyl)-5-hydroxy-4-(4-isopropyl-benzyl)-5H-furan-2-one, 5-(4-chloro-phenyl)-3-(3,4-dichloro-phenyl)-4-(4-dimethylamino-benzyl)-5-hydroxy-5H-furan-2-one, 4-benzyl-3-(3,4-dichloro-phenyl)-5-hydroxy-5-(4-methoxy-phenyl)-5H-furan-2-one, 3-(3,4-dichloro-phenyl)-5-hydroxy-4-(4-isopropylbenzyl)-5-(4-methoxy-phenyl)-5H-furan-2-one, 4-benzyl-3-(3,5-dimethoxy-phenyl)-5-hydroxy-5-(4-methoxy-phenyl)-5H-furan-2-one, 3-(3,5-dimethoxy-phenyl)-5-hydroxy-5-(4-methoxyphenyl)-4-(3-propoxy-benzyl)-5H-furan-2-one, 4-(3-chloro-benzyl)-3-(3,5-dimethoxy-phenyl)-5-hydroxy-5-(4-methoxy-phenyl)-5H-furan-2-one, 3-(3,5-dimethoxy-phenyl)-5-hydroxy-5-(4-methoxyphenyl)-4-(3-trifluoromethyl-benzyl)-5H-furan-2-one, 3-(3,5-dimethoxy-phenyl)-4-(3-fluoro-benzyl)-5-hydroxy-5-(4-methoxy-phenyl)-5H-furan-2-one, 3-(3,5-dimethoxy-phenyl)-5-hydroxy-4-(3-methoxybenzyl)-5-(4-methoxy-phenyl)-5H-furan-2-one, 3-(3,5-dimethoxy-phenyl)-5-hydroxy-4-(4-methoxybenzyl)-5-(4-methoxy-phenyl)-5H-furan-2-one, 4-(3,5-dichloro-benzyl)-3-(3,5-dimethoxy-phenyl)-5-hydroxy-5-(4-methoxy-phenyl)-5H-furan-2-one, 3-(3,5-dimethoxy-phenyl)-5-hydroxy-5-(4-methoxyphenyl)-4-pyridin-3-ylmethyl-5H-furan-2-one, 3-[4-(3,5-dimethoxy-phenyl)-2-hydroxy-2-(4-methoxy-phenyl)-5-oxo-2,5-dihydro-furan-3-ylmethyl]-benzaldehyde, 4-(3-allyloxy-4-methoxy-benzyl)-3-(3,5-dimethoxyphenyl)-5-hydroxy-5-(4-methoxy-phenyl)-5H-furan-2-one, 4-benzyl-5-hydroxy-5-(4-methoxy-phenyl)-5-(2,3,4,5,6-pentafluoro-phenyl)-5H-furan-2-one, 4-benzyl-3-(3,4-difluoro-phenyl)-5-hydroxy-5-(4-methoxy-phenyl)-5H-furan-2-one, 3-(3,4-difluoro-phenyl)-5-hydroxy-4-(4-isopropylbenzyl)-5-(4-methoxy-phenyl)-5H-furan-2-one, 3-(3,4-difluoro-phenyl)-4-(4-dimethylaminobenzyl)-5-hydroxy-5-(4-methoxy-phenyl)-5H-furan-2-one, 4-benzyl-3-(3,5-dichloro-phenyl)-5-hydroxy-5-(4-methoxy-phenyl)-5H-furan-2-one, 4-benzyl-5-hydroxy-5-(4-methoxy-phenyl)-3-(3-methoxy-phenyl)-5H-furan-2-one, 5-hydroxy-5-(4-methoxy-phenyl)-3-(3-methoxyphenyl)-4-(3-propoxy-benzyl)-5H-furan-2-one, 3-benzo[1,3]dioxol-5-yl-4-benzyl-5-(2,6-difluorophenyl)-5-hydroxy-5H-furan-2-one, 3-benzo[1,3]dioxol-5-yl-5-hydroxy-5-(4-methoxyphenyl)-4-(3-propoxy-benzyl)-5H-furan-2-one, 3-benzo[1,3]dioxol-5-yl-5-hydroxy-5-(4-methoxyphenyl)-4-pyridin-3-ylmethyl-5H-furan-2-one, 3-benzo[1,3]dioxol-5-yl-5-hydroxy-4-isoquinolin-4-ylmethyl-5-(4-methoxy-phenyl)-5H-furan-2-one, 3-benzo[1,3]dioxol-5-yl-4-biphenyl-4-ylmethyl-5-hydroxy-5-(4-methoxy-phenyl)-5H-furan-2-one, 4-(3-allyloxy-4-methoxy-benzyl)-3-benzo[1,3]dioxol-5-yl-5-hydroxy-5-(4-methoxy-phenyl)-5H-furan-2-one, 2(5H)-furanone, 3-(1,3-benzodioxol-5-yl)-5-hydroxy-4-(4-isoquinolinyl)-5-(4-methoxyphenyl)-, (±)-, monohydrochloride, 2(5H)-furanone, 3-(1,3-benzodioxol-5-yl)-5-hydroxy-5-(4-methoxyphenyl)-4-(3-pyridinylmethyl)-, (±)-, monohydrochloride, 2(5H)-furanone, 3-(3,5-dimethoxyphenyl)-5-hydroxy-5-(4-methoxyphenyl)-4-(3-pyridinylmethyl)-, (±)-, monohydrochloride, 4-benzyl-5-hydroxy-5-(4-methoxy-phenyl)-3-(1-methyl)-1H-indol-3-yl)-5H-furan-2-one, 2-butenoic acid, 2-(1,3-benzodioxol-5-yl)-4-(4-methoxyphenyl)-4-oxo-3-(phenylmethyl)-, (Z)-, ion (1-) compd. with 2-hydroxy-N,N,N-triethanaminium (1:1), 2-butenoic acid, 2-(1,3-benzodioxol-4-yl)-3-[(4-methoxy-3-methylphenyl)methyl]-4-(4-methoxyphenyl)-4-oxo, (Z)-, ion(1-) compound with 2-hydroxy-N,N,N-trimethylethanaminum (1:1), 2-butenoic acid, 2-(1,3-benzodioxol-5-yl)-4-(4-methoxyphenyl)-4-oxo-3-[[4-(trifluoromethyl)phenyl]

methyl]-, (Z)-, ion(1-) compound with 2-hydroxy-N,N,N-trimethylethanaminium 1:1), 4'-benzyl-5'-hydroxy-5'-(4-methoxy-phenyl)-5'H-[2,3'] bifuranyl-2'-one, 4-benzyl-5-hydroxy-5-(4-methoxy-phenyl)-3-thiophen-2-yl-5H-furan-2-one, 4-benzyl-5-hydroxy-5-(4-methoxy-phenyl)-5H-[3,3'] bifuranyl-2-one, 3-benzo[1,3]dioxol-5-yl-4-benzyl-5-(3,4-dimethoxyphenyl)-5-hydroxy-5H-furan-2-one, 3-benzo[1,3]dioxol-5-yl-4-benzyl-5-(3,4-dichlorophenyl)-5-hydroxy-5H-furan-2-one, 4-(4-benzo[1,3]dioxol-5-yl-3-benzyl-2-hydroxy-5-oxo-2,5-dihydro-furan-2-yl)-benzoic acid methyl ester, 4-[4-benzo[1,3]dioxol-5-yl-3-benzyl-2-hydroxy-5-oxo-2,5-dihydro-furan-2-yl)-benzoic acid, 3-benzo[1,3]dioxol-5-yl-4-benzyl-5-hydroxy-5-(4-isopropoxy-phenyl)-5H-furan-2-one, 3-benzo[1,3]dioxol-5-yl-4-benzyl-5-(4-benzyloxyphenyl)-5-hydroxy-5H-furan-2-one, 3-benzo[1,3]dioxol-5-yl-4-benzyl-5-(3,4-dimethylphenyl)-5-hydroxy-5H-furan-2-one, 3-benzo[1,3]dioxol-5-yl-4-benzyl-5-hydroxy-5-o-tolyl-5H-furan-2-one, 3-benzo[1,3]dioxol-5-yl-4-benzyl-5-hydroxy-5-(3-methoxy-phenyl)-5H-furan-2-one, 3-benzo[1,3]dioxol-5-yl-4-cyclohexylmethyl-5-hydroxy-5-(4-methoxy-phenyl)-5H-furan-2-one, 3-benzo[1,3]dioxol-5-yl-4-benzyl-5-methoxy-5-(4-methoxy-phenyl)-5H-furan-2-one, 3-benzo[1, 3]dioxol-5-yl-4-benzyl-5-hydroxy-5-m-tolyl-5H-furan-2-one, 4-benzyl-5-hydroxy-5-(4-methoxy-phenyl)-3-(3,4,5-trimethoxy-phenyl)-5H-furan-2-one, 3-benzo[1,3]dioxol-5-yl-4-benzyl-5-(3-chlorophenyl)-5-hydroxy-5H-furan-2-one, 3-benzo[1,3]dioxol-5-yl-5-hydroxy-5-(4-methoxyphenyl)-4-(4-methylsulfanyl-benzyl)-5H-furan-2-one, 3-benzo[1,3]dioxol-5-yl-5-hydroxy-4-(4-methanesulfonyl-benzyl)-5-(4-methoxy-phenyl)-5H-furan-2-one, 3-benzo[1,3]dioxol-5-yl-4-benzyl-5-(2,4-dimethoxyphenyl)-5-hydroxy-5H-furan-2-one, 3,5-bis -benzo[1,3]dioxol-5-yl-4-benzyl-5-hydroxy-5H-furan-2-one, 3-benzo[1,3]dioxol-5-yl-4-benzyl-5-hydroxy-5-(2-methoxy-phenyl)-5H-furan-2-one, 3-benzo[1,3]dioxol-5-yl-5-hydroxy-5-(4-methoxyphenyl)-4-naphthalen-1-ylmethyl-5H-furan-2-one, 3-benzo[1,3]dioxol-5-yl-5-hydroxy-4-(4-methoxy-2,5-dimethyl-benzyl)-5-(4-methoxy-phenyl)-5H-furan-2-one, 2-butenoic acid, 2-(1,3-benzodioxol-5-yl)-4-(4-methoxyphenyl)-4-oxo-3-[(3-propoxyphenyl)methyl]-, (Z)-, ion(1-) compd. with 2-hydroxy-N,N,N-trimethylethanaminium (1:1), 3-benzo[1,3]dioxol-5-yl-5-hydroxy-4-(4-methoxy-2,3-dimethyl-benzyl)-5-(4-methoxy-phenyl)-5H-furan-2-one, 4-(3-allyloxy-4-methoxy-benzyl)-3-benzo[1,3]dioxol-5-yl-5-(2,4-dimethoxy-phenyl)-5-hydroxy-5H-furan-2-one, 3-benzo[1,3]dioxol-5-yl-5-hydroxy-5-(4-methoxyphenyl)-4-(2-phenoxybenzyl)-5H-furan-2-one, 4-benzyl-3-(3,4-dimethoxy-phenyl)-5-hydroxy-5-(4-methoxy-phenyl)-5H-furan-2-one, 3-benzo[1,3]dioxol-5-yl-4-benzyl-5-(4- ethylphenyl)-5-hydroxy-5H-furan-2-one, 3-[4-(3,5-dimethoxy-phenyl)-2-hydroxy-2-(4-methoxy-phenyl)-5-oxo-2,5-dihydro-furan-3ylmethyl]benzoic acid 4-[4-benzo[1,3]dioxol-5-yl-2-hydroxy-2-(4-methoxyphenyl)-5-oxo-2,5-dihydro-furan-3-ylmethyl]-benzoic acid, 3-(3,5-Dimethoxyphenyl)-5-hydroxy-4-(4-methoxy-3-methylbenzyl)-5-(4-methoxyphenyl)-5H-furan-2-one, 3-(3,5-Dimethoxyphenyl)-5-hydroxy-5-(4-methoxyphenyl)-4-(4-methylbenzyl)-5H-furan-2-one, 4-(4- Chlorobenzyl)-3-(3,5-dimethoxyphenyl)-5-hydroxy-5-(4-methoxyphenyl)-5H-furan-2-one, 2(5H)-Furanone, 4-(cyclohexylmethyl)-3-(3,5-dimethoxyphenyl)-5-hydroxy-5-(4-methoxyphenyl)-, 3-(3,5-Dimethoxyphenyl)-5-hydroxy-4-(2-methoxybenzyl)-5-(4-methoxyphenyl)-5H-furan-2-one, 3-(3,5-Dimethoxyphenyl)-5-hydroxy-5-(4-methoxyphenyl)-4-(2-methylbenzyl)-5H-furan-2-one, 4-(2- Chlorobenzyl)-3-(3,5-dimethoxyphenyl)-5-hydroxy-5-(4-methoxyphenyl)-5H-furan-2-one, 4-(4-Benzo[1,3]dioxol-5-yl-2-hydroxy-2-(4-methoxyphenyl)-5-oxo-2,5-dihydrofuran-3-ylmethyl] benzoic acid, 1,3-Benzodioxol-5-acetic acid, α-[2-[(4-carboxyphenyl)methyl]-2-(4-methoxybenzoyl)ethylidene]-, disodium salt, 3-benzo[1,3]dioxol-5-yl-5-hydroxy-5-(4-methoxyphenyl)-4-(3,4,5-trimethoxy-benzyl)-5H-furan-2-one, 3-benzo[1,3]dioxol-5-yl-4-(2-chloro-benzyl)-5-hydroxy-5-(4-methoxy-phenyl)-5H-furan-2-one, 3-benzo[1,3]dioxol-5-yl-5-hydroxy-5-(4-methoxyphenyl)-4-(2-methyl-benzyl)-5H-furan-2-one, 3-benzo[1,3]dioxol-5-yl-5-hydroxy-4-(2-methoxybenzyl-5-(4-methyoxy-phenyl)-5H-furan-2-one, 3-benzo[1,3]dioxol-5-yl-5-hydroxy-4,5-bis(4-methoxyphenyl)-5H-furan-2-one, Benzoic acid, 3-[[4-(1,3-benzodioxol-5-yl)-2,5-dihydro-2-hydroxy-2-(4-methoxyphenyl)-5-oxo-3-furanyl] methyl]-, methyl ester 2(5H)-Furanone, 3-(1,3-benzodioxol-5-yl)-5-hydroxy-5-(4-methoxy-3-methylphenyl)-4-(phenylmethyl)-, (±)-, {4-[4-Benzo[1,3]dioxol-5-yl-2-hydroxy-2-(4-methoxyphenyl)-5-oxo-2,5 -dihydro-furan-3-ylmethyl]-phenyl}-acetic acid methyl ester, {3-[4-Benzo[1,3]dioxol-5-yl-2-hydroxy-2-(4-methoxyphenyl)-5-oxo-2,5-dihydro-furan-3-ylmethyl] phenyl}-acetic acid methyl ester, 3-Benzo[1,3]dioxol-5-yl-5-hydroxy-4-(4-methoxy-3,5-dimethyl-benzyl)-5-(4-methoxyphenyl)-5 H-furan-2-one, 4-Benzyl-5-hydroxy-3-(7-methoxybenzo[1,3]dioxol-5-yl)-5-(4-methoxyphenyl)-5H-furan-2-one, 3-Benzo[1,3]dioxol-5-yl-4-(3,5-dimethoxybenzyl)-5-hydroxy-5-(4-methoxyphenyl)-5H-furan-2-one, 3-Benzo[1,3]dioxol-5-yl-4-(3,4-dimethoxybenzyl)-5-hydroxy-5-(4-methoxyphenyl)-5H-furan-2-one, 3-Benzo[1,3]dioxol-5-yl-5-hydroxy-5-(4-methoxyphenyl)-4-(2,3,4-trimethoxybenzyl)-5H-furan-2-one, 3-Benzo[1,3]dioxol-5-yl-5-hydroxy-5-(4-methoxyphenyl)-4-(2,4,5-trimethoxybenzyl)-5H-furan-2-one, 3-Benzo[1,3]dioxol-5-yl-4-(2,5-dimethoxybenzyl)-5-hydroxy-5-(4-methoxyphenyl)-5H-furan-2-one, 3-Benzo[1,3]dioxol-5-yl-4-(2,3-dimethoxybenzyl)-5-hydroxy-5-(4-methoxyphenyl)-5H-furan-2-one, 3-Benzo[1,3]dioxol-5-yl-4-(4-benzyloxy-3-methoxybenzyl)-5-hydroxy-5-(4-methoxyphenyl)-5H-furan-2-one, 3-Benzo[1,3]dioxol-5-yl-4-cyclopentylmethyl-5-hydroxy-5-(4-methoxyphenyl)-5H-furan-2-one, 3-Benzo[1,3]dioxol-5-yl-4-cyclohex-3-enylmethyl-5-hydroxy-5-(4-methoxyphenyl)-5H-furan-2-one, 3-Benzo[1,3]dioxol-5-yl-4-(2-cyclopentyl-2-phenylethyl)-5-hydroxy-5-(4-methoxyphenyl)-5H-furan-2-one, 3-Benzo[1,3]dioxol-5-yl-4-[2-(benzo[1,3]dioxol-5-yloxy)-benzyl]-5-hydroxy-5-(4-methoxyphenyl)-5H-furan-2-one, 4-(2-Allyloxy-4-methoxybenzyl)-3-benzo[1,3]dioxol-5-yl-5-hydroxy-5-(4-methoxyphenyl)-5H-furan-2-one, Sodium 2-benzo[1,3]dioxol-5-yl-3-benzyl-4-(4-methoxyphenyl)-4-oxo-but-2-enoate, 1,3-Benzodioxol-5-acetic acid, α-[2-(4-methoxyphenyl)-1-[[4-(1-methylethoxy)phenyl]methyl]-2-oxoethylene]-, (Z)-, choline salt, Sodium 2-benzo[1,3]dioxol-5-yl-3-(4-isopropoxybenzyl)-4-(4-methoxyphenyl)-4-oxo-but-2-enoate, Sodium 2-Benzo[1,3]dioxol-5-yl-3-benzyl-4-(4-methoxy-3-methylphenyl)-4-oxo-but-2-enoate 5-Hydroxy-3-(7-methoxybenzo[1,3]dioxol-5-yl)-5-(4-methoxyphenyl)-4-(3,4,5-trimethoxybenzyl)-5H-furan-2-one, 4-Benzyl-5-hydroxy-3-(7-methoxy-benzo[1,3]dioxol-5-yl)-5-(4-methoxy-3-methylphenyl)-5H-furan-2-one, 5-Hydroxy-3-(7-methoxy-benzo[1,3]dioxol-5-yl)-5-(4-methoxy-3-methyl-phenyl)-4-(3,4,5-trimethoxybenzyl)-5H-furan-2-one, {4-[4-Benzo[1,3]dioxol-5-yl-2-hydroxy-2-(4-methoxyphenyl)-5-oxo-2,5-dihydro-furan-3-ylmethyl]-2,6-dimethoxyphenoxy}-acetic acid ethyl ester, {5-[4-Benzo[1,3]dioxol-5-yl-2-hydroxy-2-(4-methoxyphenyl)-5-oxo-2,5-dihydro-furan-3-ylmethyl]-2,3-dimethoxyphenoxy}-acetic acid ethyl ester, {4-[4-Benzo[1,3]dioxol-5-yl-2-hydroxy-2-(4-methoxyphenyl)-5-oxo-2,5-dihydrofuran-3-ylmethyl]-2,3-dimethoxyphenoxy}-acetic acid, {5-[4-Benzo[1,3]dioxol-5-yl-2-hydroxy-2-(4-methoxyphenyl)-5-oxo-2,5-dihydrofuran-3-ylmethyl]-2,3-dimethoxyphenoxy}-acetic acid, Potassium 3-(4-acetylamino-benzyl)-2-benzo[1,3]dioxol-5-yl-4-(4-methoxy-phenyl)-4- oxobut-2-enoate, Sodium 2-benzo[1,3]dioxol-5-yl-3-(4-methoxybenzoyl)-4-(4-methoxy-2,5-dimethylphenyl)but-2-enoate, Sodium 3-benzyl-2-(7-methoxybenzo[1,3]dioxol-5-yl)-4-(4-methoxyphenyl)-4-oxo-but-2-enoate, Sodium 2-(7-methoxybenzo-[1,3]dioxol-5-yl)-3-(4-methoxy-3-methylbenzoyl-4-(3,4,5-trimethoxyphenyl)-but-2-enoate, Sodium 3-benzyl-2-(7-methoxybenzo[1,3]dioxol-5-yl)-4-(4-methoxy-3-methylphenyl)-4-oxobut-2-enoate, Sodium 2-(7-methoxybenzo-[1,3]dioxol-5-yl)-4-(4-methoxyphenyl)-4-oxo-3-(3,4,5-trimethoxybenzyl)-but-2-enoate, Sodium 3-cyclohexylmethyl-2-(3,5-dimethoxyphenyl)-4-(4-methoxyphenyl)-4-oxobut-2-enoate, Sodium 2-Benzo[1,3]dioxol-5-yl-3-(4-methoxybenzyl)-4-(4-methoxyphenyl)-4-oxobut -2-enoate, 3-(3,5-Dimethoxy-phenyl)-5-hydroxy-4-(3-methoxy-4-octyloxybenzyl)-5-(4-methoxyphenyl)-5H-furan-2-one, 3-(3,5-Dimethoxyphenyl)-5-hydroxy-5-(4-methoxy-3-methylphenyl)-4-(3,4,5-trimethoxybenzyl)-5H-furan-2-one, 3-Benzo[1,3]dioxol-5-yl-5-hydroxy-5-(4-methoxy-3-methylphenyl)-4-(3,4,5-trimethoxybenzyl)-5H-furan-2-one, N-{4-[4-Benzo[1,3]dioxol-5-yl-2-hydroxy-2-(4-methoxy-3-methylphenyl)-5-oxo-2,5-dihydrofuran-3-ylmethyl]-phenyl}-acetamide, N-{4-[4-(3,5-Dimethoxyphenyl)-2-hydroxy-2-(4-methoxy-3-methylphenyl)-5-oxo-2,5-dihydrofuran-3-ylmethyl]phenyl}-acetamide, Potassium 3-(4-acetylaminobenzyl)-2-(3,5-dimethoxyphenyl)-4-(4-methoxy-3-methylphenyl)-4-oxobut-2-enoate, Sodium 2-Benzo[1,3]dioxol-5-yl-4-(4-methoxy-3-methyl-phenyl)-4-oxo-3-(3,4,5-trimethoxy-benzyl)-but-2-enoate, 3-(3,5-Dimethoxyphenyl)-5-hydroxy-5-(4-methoxyphenyl)-4-(3,4,5-trimethoxybenzyl)-5H-furan-2-one, 3-(3,5-Dimethoxyphenyl)-5-hydroxy-4-(4-isopropoxy-3-methoxybenzyl)-5-(4-methoxyphenyl)-5H-furan-2-one, 3-(3,5-Dimethoxyphenyl)-5-hydroxy-4-(4-isopropoxy-3-methoxybenzyl)-5-(4-methoxy-3-methylphenyl)-5H-furan-2-one 3-Benzo[1,3]dioxol-5-yl-5-hydroxy-4-(4-isopropoxy-3-methoxybenzyl)-5-(4-methoxy-3-methylphenyl)-5H-furan-2-one, 3-Benzo[1,3]dioxol-5-yl-5-hydroxy-4-(4-isopropoxy-3-methylbenzyl)-5-(4-methoxy-3-methylphenyl)-5H-furan-2-one, 3-(3,5-Dimethoxy-phenyl)-5-hydroxy-4-(4-isopropoxy-3-methyl-benzyl)-5-(4-methoxy-3-methyl-phenyl)-5H-furan-2-one, 3-Benzo[1,3]dioxol-5-yl-4-(4-cyclohexyloxy-3-methylbenzyl)-5-hydroxy-5-(4-methoxy-phenyl)-5H-furan-2-one, 3-Benzo[1,3]dioxol-5-yl-5-hydroxy-5-(4-methoxyphenyl)-4-(1,2,3,4-tetrahydro-naphthalen-1-ylmethyl)-5H-furan-2-one, 3-[4-Benzo[1,3]dioxol-5-yl-2-hydroxy-2-(4-methoxyphenyl)-5-oxo-2,5-dihydrofuran-3-ylmethyl] cyclohexanecarboxylic acid methyl ester, 3-Benzo[1,3]dioxol-5-yl-4-cyclopropylmethyl-5-hydroxy-5-(4-methoxyphenyl)-5H-furan-2-one, 1,3-Benzodioxol-5-acetic acid, α-[1-[[3-(methoxycarbonyl)phenyl]methyl]-2-(4-methoxyphenyl)-2-oxoethylene]-, monopotassium salt, 4-Benzyl-3-(2,5-dimethoxy-phenyl)-5-hydroxy-5-(4-methoxy-phenyl)-5H-furan-2-one, 3-(2,5-Dimethoxy-phenyl)-5-hydroxy-5-(4-methoxyphenyl)-4-(3,4,5-trimethoxy-benzyl)-5H-furan-2-one, 3-[4-Benzo[1,3]dioxol-5-yl-2-hydroxy-2-(4-methoxyphenyl)-5-oxo-2,5-dihydro-furan-3-ylmethyl] cyclohexanecarboxylic acid, 3-Benzo[1,3]dioxol-5-yl-5-hydroxy-4-(4-isopropylbenzyl)-5-(4-methoxy-phenyl)-5H-furan-2-one, 4-Cyclohexylmethyl-5-hydroxy-3-(7-methoxybenzo[1,3]dioxol-5-yl)-5-(4-methoxy-3-methyl-phenyl)-5H-furan-2-one, 4-Cyclohexylmethyl-5-hydroxy-3-(7-methoxybenzo[1,3]dioxol-5-yl)-5-(4-methoxy-phenyl)-5H-furan-2-one, 3-Benzo[1,3]dioxol-5-yl-5-hydroxy-4-(4-iodobenzyl)-5-(4-methoxy-phenyl)-5H-furan-2-one, 3-Benzo[1,3]dioxol-5-yl-4-(3,5-dimethoxy-4-pentyloxybenzyl)-5-hydroxy-5-(4-methoxy-phenyl)-5H-furan-2-one, 3-Benzo[1,3]dioxol-5-yl-4-(4-butoxy-3,5-dimethoxybenzyl)-5-hydroxy-5-(4-methoxy-phenyl)-5H-furan-2-one, 3-Benzo[1,3]dioxol-5-yl-4-(3-benzyloxy-4,5-dimethoxy-benzyl)-5-hydroxy-5-(4-methoxy-phenyl)-5H-furan-2-one, 4-(3-Alkyloxy-4,5-dimethoxy-benzyl)-3-benzo[1,3]dioxol-5-yl-5-hydroxy-5-(4-methoxy-phenyl)-5H-furan-2-one, 3-Benzo[1,3]dioxol-5-yl-4-(2,4-dimethoxy-benzyl)-5-hydroxy-5-(4-methoxy-phenyl)-5H-furan-2-one, 3-Benzo[1,3]dioxol-5-yl-5-hydroxy-4-(3-isopropoxy-4,5-dimethoxy-benzyl)-5-(4-methoxy-phenyl)-5H-furan-2-one, 4-Cyclopentylmethyl-5-hydroxy-3-(7-methoxybenzo[1,3]dioxol-5-yl)-5-(4-methoxy-3-methyl-phenyl)-5H-furan-2-one, 3-Benzo[1,3]dioxol-5-yl-4-[2-cyclopentyl-2-(4-methoxyphenyl)-ethyl]-5-hydroxy-5-(4-methoxyphenyl)-5H-furan-2-one, 5-Benzo[1,3]dioxol-5-yl-4-cyclopentylmethyl-5-hydroxy-3-(7-methoxy-benzo[1,3]dioxyl-5-yl)-5H-furan-2-one, 5-Benzo[1,3]dioxol-5-yl-4-cyclohexylmethyl-5-hydroxy-3-(7-methoxy-benzo[1,3]dioxol-5-yl)-5H-furan-2-one, 5-Benzo[1,3]dioxol-5-yl-5-hydroxy-3-(7-methoxybenzo[1,3]dioxol-5-yl)-4-[4-methoxy-2-(2-methoxyethoxy)-benzyl]-5H-furan-2-one, 4-Cyclopentylmethyl-5-hydroxy-3-(7-methoxybenzo[1,3]dioxol-5-yl)-5-(4-methoxy-phenyl)-5H-furan-2-one, 4-Cyclohexylmethyl-5-hydroxy-5-(7-methoxybenzo[1,3]dioxol-5-yl)-3-(4-methoxy-phenyl)-5H-furan-2-one, 4-Cyclohexylmethyl-5-(2,3-dihydro-benzo[1,4]-dioxin-6-yl)-5-hydroxy-3-(7-methoxy-benzo[1,3]dioxol-5-yl)-5H-furan-2-one, 3-Benzo[1,3]dioxol-5-yl-5-hydroxy-4-(3-methoxymethyl-benzyl)-5-(4-methoxy-phenyl)-5H-furan-2-one, 4-Cyclopentylmethyl-5-(2,3-dihydro-benzo[1,4]-dioxin-6-yl)-5-hydroxy-3-(7-methoxy-benzo[1,3]dioxol-5-yl)-5H-furan-2-one, 4-Cyclopentylmethyl-5-hydroxy-3,5-bis-(7-methoxybenzo[1,3]dioxol-5-yl)-5H-furan-2-one, 3-Benzo[1,3]dioxol-5-yl-4-(3-chlorobenzyl)-5-hydroxy-5-(4-methoxyphenyl)-5H-furan-2-one, 3-Benzo[1,3]dioxol-5-yl-5-hydroxy-4-(4-methoxybenzyl)-5-(4-methoxyphenyl)-5H-furan-2-one, 3-Benzo[1,3]dioxol-5-yl-4-(3,4-dichlorobenzyl)-5-hydroxy-5-(4-methoxyphenyl)-5H-furan-2-one, N-{4-[4-Benzo[1,3]dioxol-5-yl-2-hydroxy-2-(4-methoxyphenyl)-5-oxo-2,5-dihydro-furan-3-ylmethyl]-phenyl}-acetamide, 3-Benzo[1,3]dioxol-5-yl-4-benzyl-5-hydroxy-5-(4-methylsulfanylphenyl)-5H-furan-2-one, 3-[4-Benzo[1,3]dioxol-5-yl-2-hydroxy-2-(4-methoxyphenyl)-5-oxo-2,5-dihydro-furan-3-ylmethyl]-benzoic acid, {4-[4-Benzo[1,3]dioxol-5-yl-2-hydroxy-2-(4-methoxyphenyl)-5-oxo-2,5-dihydro-furan-3-ylmethyl]phenyl}-acetic acid, {3-[4-Benzo[1,3]dioxol-5-yl-2-hydroxy-2-(4-methoxyphenyl)-5-oxo-2,5-dihydro-furan-3-ylmethyl]-phenyl}-acetic acid, 3-Benzo[1,3]dioxol-5-yl-4-(3,5-dimethyl-4-isopropoxybenzyl)-5-hydroxy-5-(4-methoxy-phenyl)-5H-furan-2-one, 3-Benzo[1,3]dioxol-5-yl-4-(3,5-dimethyl-4-octyloxybenzyl)-5-hydroxy-5-(4-methoxyphenyl)-5H-furan-2-one, 3-Benzo[1,3]dioxol-5-yl-4-(6,6-dimethylbicyclo[3.1.1]-hept-2-en-2-ylmethyl)-5-hydroxy-5-(4-methoxyphenyl)-5H-furan-2-one, 3-Benzo[1,3]dioxol-5-yl-5-hydroxy-5-(4-methoxyphenyl)-4-(2-phenoxy-benzyl)-5H-furan-2-one, 3-Benzo[1,3]dioxol-5-yl-4-(2-cyclohexyl-ethyl)-5-hydroxy-5-(4-methoxy-phenyl)-5H-furan-2-one, 3-Benzo[1,3]dioxol-5-yl-5-hydroxy-5-(2-allyloxy-4-methoxy-phenyl)-4-benzyl-5H-furan-2-one, 3-Benzo[1,3]dioxol-5-yl-4-(3,4,5-dimethoxybenzyl)-5-methoxy-5-(4-methoxyphenyl)-5H-furan-2-one, 3-Benzo[1,3]dioxol-5-yl-4-(2-cyclohexyl-2-phenylethyl)-5-hydroxy-5-(4-methoxy-phenyl)-5H-furan-2-one, 3-(2-Allyloxy-5-methoxy-phenyl)-4-benzyl-5-hydroxy-5-(4-methoxy-phenyl)-5H-furan-2-one, {2-[4-Benzyl-5-hydroxy-5-(4-methoxy-phenyl)-2-oxo-2,5-dihydro-furan-3-yl]-4-methoxy-phenoxy}-acetic acid, 3-Benzo[1,3]dioxol-5-yl-4-cycloheptylmethyl-5-hydroxy-5-(4-methoxy-phenyl)-5H-furan-2-one, 3-Benzo[1,3]dioxol-5-yl-5-hydroxy-5-(4-methoxyphenyl)-4-pentyl-5H-furan-2-one,

[2-(4-Benzo[1,3]dioxol-5-yl-3-benzyl-2-hydroxy-5-oxo-2,5-dihydro-furan-2-yl)-5-methoxy-phenoxy]-acetic acid, {2-[4-Benzo[1,3]dioxol-5-yl-2-hydroxy-2-(4-methoxyphenyl)-5-oxo-2,5-dihydro-furan-3-ylmethyl]-5-methoxy-phenoxy}-acetic acid, 2-Butenoic acid, 2-(1,3-benzodioxol-5-yl)-4-[4-(1H-imidazol-1-yl) phenyl]4-oxo-3-(phenylmethyl)-, 2-Benzo[1,3]dioxol-5-yl-4-(4-methoxy-phenyl)-3-[4-(2-morpholin-4-yl-ethylcarbamoyl)-benzyl]-4-oxo-but-2-enoic acid, Benzamide, 4-[[4-(1,3-benzodioxol-5-yl)-2,5-dihydro-2-hydroxy-2-(4-methoxyphenyl)-5-oxo-3-furanyl]

methyl]-N-[2-(4-morpholinyl) ethyl]-, monohydrochloride, (±)-,

Sodium 2-Benzo[1,3]dioxol-5-yl-4-(4-methoxyphenyl)-4-oxo-3-(3,4,5-trimethoxy-benzyl)-but -2-enoate, Sodium 2-Benzo[1,3]dioxol-5-yl-3-cyclohexylmethyl-4-(4-methoxy-phenyl)-4-oxo-but -2-enoate, 2-(3,5-Dimethoxy-phenyl)-3-(4-methoxy-3-methylbenzoyl-carbonyl)-4-(2,4,6-trimethoxy-phenyl)-but-2-enoic acid, 3-(3,5-Dimethoxy-phenyl)-5-hydroxy-5-(4-methoxy-3-methyl-phenyl)-4-(3-methoxy-4-octyloxy-benzyl)-5 H-furan-2-one, 3-Benzo[1,3]dioxol-5-yl-5-hydroxy-5-(4-methoxy-3-methyl-phenyl)-4-(3-methoxy-4-octyloxy-benzyl)-5 H-furan-2-one 1,3-Benzodioxole-5-acetic acid, α-[1-(4-methoxybenzoyl)-2-(2-methoxyphenyl)ethylidene]-, monosodium salt, (Z)-.

Elevated levels of endothelin have been postulated to be involved in a number of pathophysiological states including diseases associated with the cardiovascular system as well as various metabolic and endocrinological disorders. As antagonists of endothelin, the compounds of Formula I are useful in the treatment of hypertension, myocardial infarction, diabetes, cerebral vasospasm, cirrhosis, septic shock, congestive heart failure, endotoxic shock, subarachnoid hemorrhage, arrhythmias, asthma, chronic and acute renal failure, preeclampsia, atherosclerotic disorders including Raynaud's disease and restenosis, angina, cancer, pulmonary hypertension, ischemic disease, gastric mucosal damage, hemorrhagic shock, stroke, head injury, and ischemic bowel disease.

The compound of Formula 1A wherein $R_1$ is piperonyl, $R_2$ is benzyl, and $R_4$ is p-chlorophenyl will also be useful in the above treatments. (See Allen references cited hereinbefore.)

A still further embodiment of the present invention is a pharmaceutical composition for administering a therapeutically effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, allyl, n-pentyl, n-hexyl, n-heptyl, n-octyl, n-nonyl, n-decyl, undecyl, and dodecyl. The alkyl group is unsubstituted or substituted by from 1 to 3 substituents selected from alkyl, alkoxy, thioalkoxy all as defined herein, hydroxy, thiol, nitro, halogen, amino, formyl, cycloalkyl, carboxyl, nitrile,

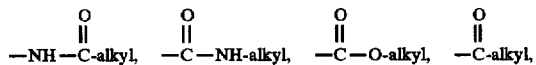

aryl, or heteroaryl wherein alkyl, aryl, and heteroaryl are defined as herein.

The term "cycloalkyl" means a saturated hydrocarbon ring which contains from 3 to 12 carbon atoms unless otherwise specified, for example, cyclopropyl, cyclobutyl, cyclopentyl, cyclohexyl, cycloheptyl, and adamantyl. The cycloalkyl ring may be unsubstituted or substituted by from 1 to 3 substituents selected from alkyl, cycloalkyl, cycloalkoxy, alkoxy, thioalkoxy all as defined herein, hydroxy, thiol, nitro, halogen, amino, formyl, carboxyl, nitrile, alkylsulfoxyl, arylsulfoxyl, alkylsulfonyl, arylsulfonyl,

aryl, or heteroaryl wherein alkyl, aryl, and heteroaryl are defined as herein.

The terms "alkoxy" and "thioalkoxy" are O-alkyl or S-alkyl as defined above for alkyl.

Two alkoxy or thioalkoxy groups can be taken together to form a cyclic group such as

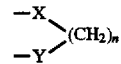

where X and Y are independently either O or S and n=1, 2, 3, or 4.

The term "aryl" means an aromatic radical which is a phenyl group, a benzyl group, a naphthyl group, a biphenyl group, a pyrenyl group, an anthracenyl group, or a fluorenyl group and the like, unsubstituted or substituted by 1 to 5 substituents selected from alkyl as defined above, alkoxy as defined above, thioalkoxy as defined above, hydroxy, thiol, nitro, halogen, amino, formyl, carboxy, nitrile, arylsulfoxyl, alkylsulfoxyl, arylsulfonyl, alkylsulfonyl,

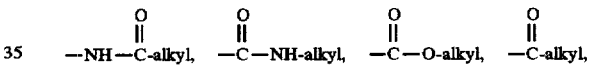

aryl or heteroaryl wherein alkyl, aryl, and heteroaryl are defined as above.

The term "heteroaryl" means a heteroaromatic radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 3 substituents selected from alkyl as defined above, aryl as defined above, alkoxy as defined above, thioalkoxy as defined above, hydroxy, thiol, nitro, halogen, formyl, amino, carboxyl,

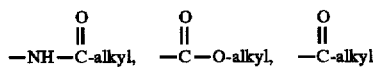

wherein alkyl is as defined above or phenyl.

"Halogen" is fluorine, chlorine, bromine or iodine.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al., "Pharmaceutical Salts," *Journal of Pharmaceutical Science* 1977;66:1–19).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts," *Journal of Pharmaceutical Science* 1977;66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. In addition, some of the cyclic lactones of Formula I and Compound A may exist in a tautomeric open chain keto-acid form, Formula II below, depending on the substitution pattern present at $R_1$, $R_2$, and $R_3$, or pH.

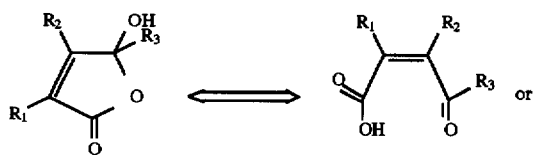

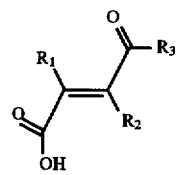

In such cases, the rate of equilibration may vary and activity may thus reside with either tautomer.

The compounds of Formula I and Compound A are valuable antagonists of endothelin. The tests employed indicate that compounds of the invention possess endothelin antagonist activity. Thus, the compounds were tested for their ability to inhibit $[^{125}I]$-ET-1($[^{125}I]$-Endothelin-1) binding in a receptor assay. Selected compounds were also tested for antagonist activity by inhibition of ET-1 stimulated arachidonic acid release and ET-1 stimulated vasoconstriction. The following testing procedures were used (Doherty, A. M., et al., "Design of C-Terminal Peptide Antagonists of Endothelin: Structure-Activity Relationships of ET-1 [16–21, D-His[16]]", *Bioorganic and Medicinal Chemistry Letters* 1993;3:497–502).

ENDOTHELIN RECEPTOR BINDING ASSAY-A (ERBA-A) INTACT CELL BINDING OF $[^{125}I]$-ET-1

Materials and Terms Use

Cells

The cells used were rabbit renal artery vascular smooth muscle cells grown in a 48-well dish (1 cm$^2$) (confluent cells).

Growth Media

The growth media was Dulbecco's Modified Eagles/Ham's F12 which contained 10% fetal bovine serum and antibiotics (penicillin/streptomycin/fungizone).

Assay Buffer

The assay buffer was a medium 199 containing Hanks salts and 25 mM Hepes buffer (Gibco 380-2350AJ), supplemented with penicillin/streptomycin/fungizone (0.5%) and bovine serum albumin (1 mg/mL).

$[^{125}I]$-ET-1

Amersham radioiodinated endothelin-1 $[^{125}I]$-ET-1 was used at final concentration of 20,000 cpm/0.25 mL (25 pM).

Protocol

First, add 0.5 mL warm assay buffer (described above) to the aspirated growth media and preincubate for 2 to 3 hours in a 37° C. water bath (do not put back in the 5% carbon dioxide). Second, remove the assay buffers, place the dish on ice, and add 150 μL of cold assay buffer described above to each well. Third, add 50 mL each of cold $[^{125}I]$-ET-1 and competing ligand to the solution (at the same time if possible). Next, place dish in a 37° C., water bath for about 2 hours and gently agitate the dish every 15 minutes. Discard the radioactive incubation mixture in the sink and wash wells 3 times with 1 mL of cold phosphate buffered saline. Last, add 250 mL of 0.25 molar sodium hydroxide, agitate for 1 hour on a rotator, and then transfer the sodium hydroxide extract to gamma counting tubes and count the radioactivity.

ENDOTHELIN RECEPTOR BINDING ASSAY-B (ERBA-B) $[^{125}I]$-ET-1 BINDING IN RAT CEREBELLAR MEMBRANES

Materials and Terms Used

Tissue Buffer

The tissue is made up of 20 mM tris(hydroxymethyl) aminomethane hydrochloride (Trizma) buffer, 2 mM ethylenediaminetetra acetate, 100 μM phenylmethylsulfonyl fluoride.

Tissue Preparation

First, thaw one aliquot of frozen rat cerebellar membranes (2 mg protein in 0.5 mL). Next, add 0.5 mL membrane aliquot to 4.5 mL cold tissue buffer, polytron at 7,500 revolutions per minute for 10 seconds. Finally, dilute tissue suspension 1/100 (0.1 mL suspension+9.9 mL tissue buffer), polytron again, and place ice.

Dilution Buffer

Medium 199 with Hank's salts plus 25 mM Hepes+1 mg/mL bovine serum albumin.

[$^{125}$I]-ET-1

Amersham [$^{125}$I]-ET-1 (aliquots of 2×10$^6$ cpm per 100 mL aliquot of [$^{125}$I]-ET-1 with 5.2 mL dilution buffer, place on ice until use (final concentration will be 20,000 cpm per tube, or 25 pM).

Protocol

Add 50 μL each of cold [$^{125}$I]-ET-1 and competing ligand to tubes on ice. Mix in 150 μL of tissue to each tube, vortex briefly, then tap to force all liquids to bottom (total assay volume=250 μL). Then place the tubes in a 37° C. water bath for 2 hours.

Add 2.5 mL cold wash buffer (50 mM Trizma buffer) to each tube, filter, and then wash tube with additional 2.5 mL wash buffer and add to filter. Finally, wash filters with an additional 2.5 mL of cold wash buffer.

Count filters for radioactivity in gamma counter.

The above process has also been modified by using human recombinant CHO-K1 cells.

The tissue used for human ETB was recombinant human ETB receptor expressed in CHO-K1 cells (chinese hamster ovary cells). The gene for human ETB receptor was cloned and inserted into the pRc-CMW expression vector, then transfected into CHO-K1 cells by electroporation. For binding assays, membranes (0.7 mg protein) of CHO-K1 cells expressing recombinant human ETB receptor were used.

IN VITRO INHIBITION OF ET-1 STIMULATED ARACHIDONIC ACID RELEASE (AAR) IN CULTURED RABBIT VASCULAR SMOOTH MUSCLE CELLS (ET$_A$) BY THE COMPOUNDS OF THE INVENTION

Antagonist activity is measured by the ability of added compounds to reduce endothelin-stimulated arachidonic acid release in cultured vascular smooth muscle cells as arachidonic acid release (AAR). [$^3$H] Arachidonic Acid Loading Media (LM) is DME/F12+0.5% FCS×0.25 mCi/mL [$^3$H] arachidonic acid (Amersham). Confluent monolayers of cultured rabbit renal artery vascular smooth muscle cells were incubated in 0.5 mL of the LM over 18 hours, at 37° C., in 5% CO$_2$. The LM was aspirated and the cells were washed once with the assay buffer (Hank's BSS+10 mM HEPES+fatty acid-free BSA (1 mg/mL)), and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 μL of the test compound (1 nM to 1 μM) and 10 μL ET-1 (0.3 nM) and the incubation was extended for 30 minutes. This solution was then collected, 10 μL of scintillation cocktail was added, and the amount of [$^3$H] arachidonic acid was determined in a liquid scintillation counter.

IN VITRO ANTAGONISM OF ET-1 STIMULATED VASOCONSTRICTION (VERA-A) IN THE RABBIT FEMORAL ARTERY (ET$_A$) AND SARAFOTOXIN 6c STIMULATED VASOCONSTRICTION IN THE RABBIT PULMONARY ARTERY (ET$_B$)

Male New Zealand rabbits were killed by cervical dislocation and exsanguination. Femoral and pulmonary arteries were isolated, cleaned of connective tissue, and cut into 4-mm rings. The endothelium was denuded by placing the rings over hypodermic tubing (32 gauge for femoral rings and 28 gauge for pulmonary rings, Small Parts, Inc, Miami, Fla.) and gently rolling them. Denuded rings were mounted in 20 mL organ baths containing Krebs-bicarbonate buffer (composition in mM: NaCl, 118.2; NaHCO$_3$, 24.8; KCl, 4.6; MgSO$_4$ 7.H$_2$O, 1.2; KH$_2$PO$_4$, 1.2; CaCl$_2$.2H$_2$O; Ca-Na$_2$ EDTA, 0.026; dextrose, 10.0), that was maintained at 37° C. and gassed continuously with 5% CO$_2$ in oxygen (pH 7.4). Resting tension was adjusted to 3.0 g for femoral and 4.0 g pulmonary arteries; the rings were left for 90 minutes to equilibrate. Vascular rings were tested for lack of functional endothelium (i.e., lack of an endothelium-dependent relaxation response to carbachol (1.0 μM) in norepinephrine (0.03 μM) contracted rings. Agonist peptides, ET-1 (femoral), and S6c (pulmonary), were cumulatively added at 10-minute intervals. The ET antagonists were added 30 minutes prior to adding the agonist and pA$_2$ values were calculated (Table II).

The data in Table II below show the endothelin receptor binding and antagonist activity of representative compounds of the instant invention.

TABLE II

| Example | ERBA-A* | ERBA-B* | AAR-A$^c$ | VERA-A$^b$ |
|---|---|---|---|---|
| 4 | 34% | 52% | | |
| 16 | 1.2 | 4.55 | | |
| 20 | 0.05 | 0.5 | 0.15 | 6.4 |
| 24 | 1.3 | 26 | | |
| 25 | 1.7 | 15.6 | | |
| 26 | 0.79 | 15.5 | | |
| 30 | 7.9 | 13 | | |
| 31 | 9.9 | 9.1 | | |
| 32 | 1.0 | 6.3 | | |
| 33 | 3.5 | 5.7 | | |
| 34 | 1.3 | 7 | | |
| 35 | 1.1 | 3.3 | | |
| 39 | 2.2 | 4.2 | 3.8 | |
| 40 | 10% | 22% | | |
| 41 | 37% | 9 | | |
| 42 | 36% | 54% | | |
| 43 | 2.7 | 7 | | |
| 44 | 2.8 | 35% | | |
| 45 | 1.5 | 9.1 | | |
| 46 | 3.6 | 6.4 | | |
| 47 | 3.9 | 7.8 | | |
| 48 | 1.2 | 6.2 | | |
| 54 | | 18 | | |
| 55 | | 21 | | |
| 56 | 14 | | | |
| 57 | 11 | | | |
| 61 | 11 | 11 | | |
| 65 | 9.3 | 6.0 | | |
| 66 | 2.4 | 7.4 | | |
| 67 | 7.1 | 6.3 | | |
| 68 | 1.7 | 9.8 | | |
| 69 | 9.1 | 8.4 | | |
| 70 | 9.3 | 15 | | |
| 71 | | 4.2 | | |
| 73 | 21 | 13 | | |
| 74 | 2.5 | 12 | | |
| 75 | 0.016 | 1.2 | 0.071 | |

TABLE II-continued

| Example | ERBA-A[a] | ERBA-B[a] | AAR-A[c] | VERA-A[b] |
|---|---|---|---|---|
| 76 | 0.05 | 0.39 | 0.52 | |
| 77 | 0.009 | 0.22 | 0.031 | 6.2 |
| 78 | 0.24 | 0.89 | | |
| 79 | 0.084 | 0.52 | | |
| 80 | 0.0014 | 0.88[d] | | 7.2 |
| 81 | 0.14 | 0.72 | | |
| 82 | 0.02 | 1.3 | 0.14 | 5.6 |
| 83 | 0.071 | 0.5 | | |
| 84 | 0.0033 | 1.4[d] | | 6.8 |
| 85 | 0.023 | 1.6[d] | 0.20 | 6.4 |
| 86 | 0.31 | | | |
| 87 | 0.063 | 1.5[d] | | |
| 88 | 0.25 | | | |
| 89 | 0.006 | 1.14[d] | 0.039 | 6.3 |
| 90 | 0.02 | 3.5[d] | 0.088 | |
| 91 | 0.53 | 15[d] | | |
| 92 | 0.004 | 1.4[d] | | 6.6 |
| 93 | 0.0052 | 0.22[d] | | 6.0 |
| 97 | 0.97 | | | |
| 101 | 0.31 | | | |
| 105 | 0.75 | | | |
| 113 | 0.3 | 25[d] | | |
| 117 | 0.31 | 2.7[d] | | |
| 118 | 0.54 | 13 | | |
| 119 | 5.8 | 4.1 | | |
| 120 | 0.85 | | | |
| 121 | 0.074 | | | |
| 125 | 0.029 | 0.2 | | |
| 126 | 0.01 | 1.5[d] | 0.086 | 6.7 |
| 127 | 0.013 | 1.2[d] | 0.150 | 6.2 |
| 128 | 0.023 | 1.6[d] | 0.210 | 5.9 |
| 129 | 0.072 | 2.3[d] | | |
| 130 | 0.097 | 1.2[d] | 0.030 | 6.7 |
| 131 | 0.015 | 1.35[d] | | 6.3 |
| 132 | 0.07 | 2.75[d] | | |
| 133 | 0.03 | 6.8[d] | 0.076 | |
| 134 | 0.024 | 1.2 | | |
| 135 | 0.009 | 0.33 | | 6.9 |
| 143 | 1.9 | | | |
| 144 | 0.29 | | | |
| 145 | 1.7 | | | |
| 149 | 0.6 | | | |
| 153 | 0.36 | 2 | | |
| 154 | 0.1 | 2.1 | | |
| 158 | 2.3 | 21 | | |
| 159 | 0.012 | 0.56 | 0.036 | 7.0 |
| 160 | 0.35 | | 0.055 | |
| 161 | 0.04 | 3.2[d] | | |
| 162 | 0.39 | 1.9[d] | | |
| 163 | 0.02 | 0.88[d] | | 6.9 |
| 164 | 0.05 | 4[d] | | |
| 165 | 0.04 | 25[d] | | |
| 166 | 0.04 | >2.5[d] | | |
| 170 | 1.3 | 0.9 | | |
| 171 | 0.039 | 2.2 | | 6.2 |
| 172 | 7.2 | >2.5[d] | | |
| 182 | 0.016 | 2[d] | 0.050 | |
| 190 | 0.065 | 0.75 | 0.78 | |
| 194 | 0.56 | | | |
| 198 | 0.41 | | | |
| 204 | 1.05 | 10[d] | | |
| 208 | 1.2 | 5.4[d] | | |
| 212 | 1.3 | | | |
| 216 | 0.29 | 8 | | |
| 220 | 0.3 | 1.5 | | |
| 221 | 0.02 | 0.24[d] | 0.120 | 6.4 |
| 235 | 0.67 | >2.5[d] | | |
| 236 | 0.23 | >2.5[d] | | 6.5 |
| 237 | 0.011 | >2.5[d] | | 6.2 |
| 241 | 0.035 | >2.5[d] | | 6.2 |
| 245 | 0.11 | 2.0[d] | | |
| 249 | 0.5 | >2.5[d] | | |
| 250 | 0.013 | >2.5[d] | | |
| 251 | 0.006 | >2.5[d] | | |
| 253 | 0.017 | 0.9[d] | | 7.0 |
| 254 | 0.017 | 2.9[d] | | 6.7 |
| 255 | 0.0083 | 1.4[d] | | |
| 261 | 0.16 | 3.9[d] | | |
| 266 | 0.6 | >2.5[d] | | |
| 267 | 0.71 | >2.5[d] | | |
| 271 | 0.39 | >2.5[d] | | |
| 272 | 0.0064 | 0.76[d] | | |
| 273 | | | | |
| 274 | 0.14 | >2.5[d] | | |
| 275 | 0.012 | | | |
| 281 | 0.0006 | | | 7.7 |
| 286 | 0.0046 | 6[d] | | |
| 290 | 0.012 | 1.75[d] | | |
| 291 | 0.04 | 1.4[d] | | |
| 292 | 0.083 | >2.5[d] | | |
| 293 | >2.5 | >2.5[d] | | |
| 294 | 0.0034 | 0.78[d] | | |
| 295 | 0.13 | >2.5[d] | | |
| 296 | 0.006 | 0.58[d] | | |
| 297 | 0.064 | 0.87[d] | | |
| 301 | 0.0056 | 0.66[d] | | 7.0 |
| 302 | 2.3 | 2[d] | | |
| 303 | 0.0027 | 0.76[d] | | |
| 304 | 0.0048 | 0.95[d] | | |
| 305 | 0.033 | 2[d] | | |
| 306 | 0.002 | 0.85[d] | | |
| 307 | 0.0059 | 1[d] | | |
| 308 | 0.016 | 2.2[d] | | |
| 309 | 0.018 | 0.86[d] | | |
| 310 | 0.54 | 8.8[d] | | |
| 313 | 0.099 | >2.5[d] | | |
| 314 | 0.0084 | 0.64[d] | | |
| 315 | 0.04 | 11.76[d] | | |
| 316 | 0.0081 | 0.69[d] | | |
| 319 | 0.0056 | 0.18[d] | | |
| 322 | 3.3 | 4[d] | | |
| 324 | 0.0084 | 5.3[d] | | 329 |
| 329 | 0.11 | 0.11 | | |
| 337 | 2.5 | >25[d] | | |
| 339 | 0.24 | 1.3[d] | | |
| 340 | 0.069 | 0.63[d] | | |
| 341 | 0.08 | >2.5[d] | | |
| 343 | 0.01 | 2.2[d] | | |
| 344 | 0.38 | >25[d] | | |
| 348 | 7.1 | >25[d] | | |
| 349 | 0.51 | 25[d] | | |
| 350 | 0.29 | >2.5[d] | | |
| 351 | 0.016 | >0.25[d] | 0.049 | 6.2 |
| 352 | 0.005 | 1.25[d] | | 7.2 |
| 353 | 0.0044 | >0.25[d] | | |
| 354 | 0.0008 | 0.91[d] | <0.001 | 7.5 |
| 355 | 0.042 | 1.6[d] | | |
| 356 | 0.00025 | 0.34[d] | | 7.7 |
| 360 | 0.0099 | 1.35[d] | | 7.0 |
| 361 | 0.002 | 0.22[d] | | 7.4 |
| 362 | 0.026 | 1.2[d] | | |
| 363 | <0.0025 | 1.1[d] | | |
| 366 | 0.0073 | 4.9[d] | | |
| 367 | | | | |
| 368 | <0.025 | 0.96[d] | | |
| 369 | | 0.328[d] | | |
| 370 | 0.01 | 1.53[d] | | |
| 371 | 0.00039 | 0.328[d] | | |
| 380 | 0.024 | 2[d] | | |
| 381 | 0.068 | 0.57[d] | | |
| 382 | 0.0009 | >0.25[d] | | 6.8 |
| 383 | 0.0005 | 0.29[d] | 7.4 | |
| 384 | 0.001 | 0.76[d] | 0.00021 | 7.3 |
| 385 | 0.0008 | 0.69[d] | | |
| 386 | 0.005 | 2.1[d] | | 6.9 |
| 388 | 0.0014 | 1.1[d] | 0.00026 | 7.0 |
| 389 | 0.0036 | 1.1[d] | 0.0024 | |
| 390 | 0.007 | 0.82[d] | | |
| 391 | 0.0018 | >0.25[d] | | |
| 392 | 3.8 | 14[d] | | |
| 393 | 0.24 | 0.83[d] | | |
| 394 | 0.068 | 0.42[d] | | |
| 395 | 0.013 | 0.84[d] | | |
| 396 | 0.047 | 1.2[d] | | |

TABLE II-continued

| Example | ERBA-A[a] | ERBA-B[a] | AAR-A[c] | VERA-A[b] |
|---|---|---|---|---|
| 397 | 0.61 | 2.6[d] | | |
| 398 | 0.83 | >2.5[d] | | |
| 399 | 0.02 | 1.1[d] | | |
| 400 | 0.039 | >2.5[d] | | |
| 403 | 0.25 | 3[d] | | |
| 404 | 0.058 | >2.5[d] | | |
| 405 | 0.0074 | 2.7[d] | | 6.6 |
| 406 | | | | 6.6 |

[a]IC$_{50}$ values in μM or % inhibitor at $10^{-5}$M
[b]pA2 values
[c]μM
[d]Human cloned receptor data As can be seen in Table II above, the compounds of Formula I bind to the endothelin receptors $ET_A$ (ERBA-A) and $ET_B$ (ERBA-B) in the μM to nM range.

IN VIVO STUDIES

Relative potencies of 171 and 253 at inhibiting ET-1 (1.0 nmol/kg, IV bolus) induced depressor and pressor responses were determined in anesthetized (Inactin 120 mg/kg, IP), ganglionic blocked rats (male 300–500 g, Sprague Dawley). Antagonists were administered IV bolus (3, 10, 30, 100 μmol/kg, IV bolus) in separate groups of rats (5 minutes before ET-1 challenge [see Haleen, et al., J. Cardiovasc, Pharm., 22(Suppl. 8):598–5102 (1993)]). Duration of action of the antagonist was determined in conscious, chronically prepared normotensive rats. Rats were challenged with ET-1 (1.0 nmol/kg, IV bolus) on 5 consecutive days; Day =b 1 =1 control and on Days 2–5 at 5, 20, 60, and 120 minutes following treatment with the antagonist. Separate groups of rats were used for each antagonist treatment. The results are shown in Table III.

TABLE III

In Vivo Activity of Nonpeptide ET Antagonists

| Example Number | % Inhibition on ET-1 (1 nm/kg, IV) Induced Pressor Response at Dose of X (μmol/kg, IV) | | | |
|---|---|---|---|---|
| | 3 | 10 | 30 | 100 |
| 171 | 21 | 26 | 35 | 57 |
| 253 | 22 | 42 | 53 | — |

The said compounds also reduce endothelin-stimulated arachoidonic acid release (AAR) and therefore are antagonists.

Furthermore, in vitro activity is demonstrated by the antagonism of endothelin-stimulated vasoconstriction of rabbit femoral artery.

GENERAL SYNTHETIC APPROACHES

The compounds of Formula I and Compound A may be prepared by several methods. In Scheme I, condensation of an aldehyde with an acetophenone-type compound in basic solution such as alcoholic sodium hydroxide. This gives a chalcone derivative which is treated with HCN in a solvent such as aqueous alcohol to give the nitrile. The nitrile is hydrolyzed to the ester with an acidic solution such as HCl/MeOH/H$_2$O. The ester is then condensed and cyclized with another aldehyde in a solvent such as methanol using a base such as sodium methoxide.

Further derivatization of the alcohol can be made by chlorination of the hydroxyl with a chlorinating agent such as SOCl$_2$. Even further derivatization can be accomplished with displacement of the chloride with nucleophiles, such as alcohols, other halogens, amines, and thiols.

In Scheme II the chalcone from Scheme I is treated with the anion of triphenylorthothioformate in an organic solvent such as THF. This compound is then converted to a keto ester with a mix of mercury salts by warming in an alcoholic solvent such as ethanol. The keto ester can then be converted to compound, of Formula I and Compound A as in Scheme I.

SCHEME I

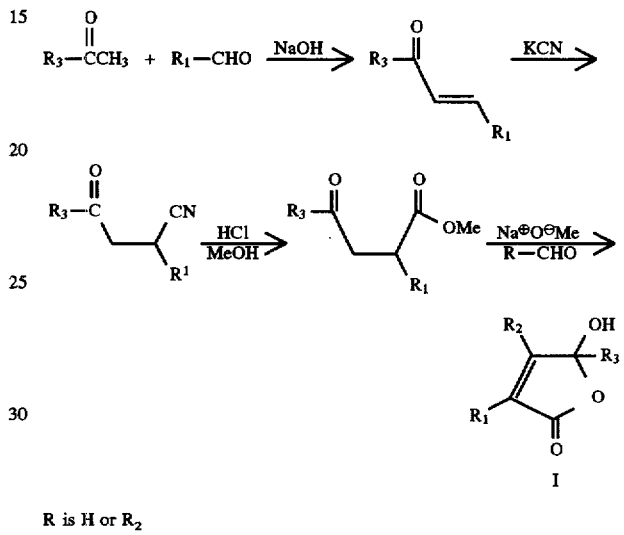

R is H or R$_2$

SCHEME II

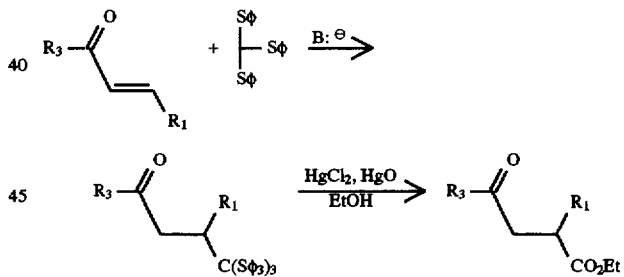

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/k g daily. A daily dose range of about 0.01 mg to about 10 mg/k g is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the preferred methods for preparing the compounds of the invention. Examples 1–3, 5, 13–15, 17–19, 21–23, 27–29, 36–38, 49–51, 58–60, 62–64, 94–96, 98–100, 102–104, 106–108, 110–112, 114–116, 122–124, 136–138, 140–142, 146–148, 150–152, 155–157, 167–169, 174–176, 178–180, 183–185, 187–189, 191–193, 195–197, 200–203, 205–207, 209–211, 213–215, 217–219, 224–226, 228–230, 232–234, 238–240, 242–244, 246–248, 258–260, 263–265, 268–270, 287–289, 298–300, 311–312, 317–318, 320–321, 323, 325–328, 331–332, 334–336, 342, 345–347, 357–359, 372–377, 417–419, 421–423, 429–433, 435–437, 439–443, and 446–448 are intermediates useful in making the final products.

EXAMPLE 1

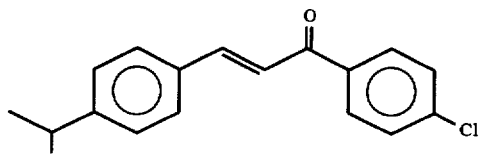

To 4-Chloroacetophenone 18.3 g (118 mmol) in an Erlenmeyer flask in absolute ethanol was added 4-isopropylbenzaldehyde 25.0 mL (165 mmol). This solution was cooled to 10° C. and 10% sodium hydroxide in water, 7.8 mL, was added slowly. The solution was swirled continuously for 10 minutes, during which time an oil separated. Scratching the side of the flask with a glass rod caused crystallization. After 2 hours of intermittent mixing of the solid, it was collected by filtration and washed with 80% ethanol (50 mL). The solid was air dried giving 33.5 g (99%) of a light yellow solid which was identified by $^1$H NMR, IR, MS.

EXAMPLE 2

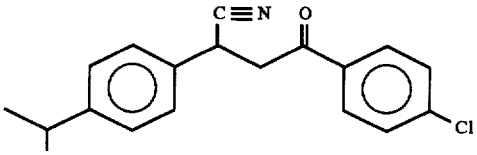

To the chalcone, 1, 33.5 g (188 mmol) in absolute ethanol (425 mL) at 55° C. was added acetic acid 14 mL (236 mmol) followed by slow addition of potassium cyanide 20 g (308 mmol) in water (60 mL). After 6 hours, thin layer analysis indicated that no starting chalcone remained; water (50 mL) was then added and the solution was cooled to 0° C. After 2 hours, a solid had precipitated and it was collected by filtration, washed with 75% ethanol (2×50 mL), and the solid was first air dried then dried at 0.5 mm Hg giving the nitrile as a colorless solid 29.0 g (79%); identified by ¹H NMR, IR, MS.

EXAMPLE 3

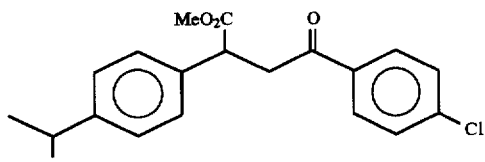

To the nitrile, 2, 29 g (93 mmol) powdered in a mortar and pestle was added methanol (150 mL). This mixture was saturated with hydrogen chloride gas and heated to 45° C. until no starting nitrile remained upon thin layer analysis, water (30 mL) was then added, and the reaction was cooled in an ice bath. The solid that formed was removed by filtration and washed with 75% methanol (50 mL) followed by drying at 0.5 mm Hg. The ester, a colorless solid 20.5 g (64%), was identified by ¹H NMR, IR, MS.

EXAMPLE 4

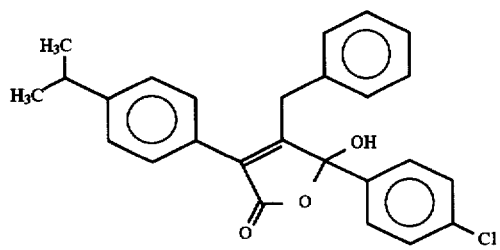

2(5H)-Furanone, 5-(4-chlorophenyl)-5-hydroxy-3-[4-(1-methylethyl)phenyl]-4-(phenylmethyl)-, (±)-

To sodium metal 70 mg, (3.05 mmol) in methanol, (5 mL) was added benzaldehyde 0.325 mL (3.20 mmol) then the ester, 3, 1.0 g (2.90 mmol). The resulting mixture was heated to reflux until the ester was consumed as determined by thin layer analysis. Acetic acid was added and the reflux was continued for 16 hours. The solvent was evaporated; flash chromatography of the residue 4:1 hexane/ethyl acetate provided the product 4 as a foam 816 mg (67%) that was identified by ¹H NMR, IR, [M+H]⁺=419 Da.

EXAMPLE 5

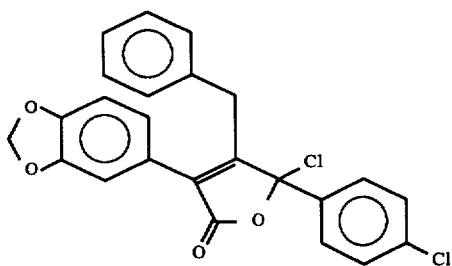

The alcohol 39 (1.0 g 2.37 mmol) in thionylchloride was heated at 55° C. for 16 hours. The excess thionyl chloride was removed under reduced pressure to give an oil. This oil was taken up in a small volume of diethyl ether and hexane was added resulting in precipitation of the product as a tan solid. The solvent was decanted and the product was dried under a stream of nitrogen to give about 1 g (95%) of product that was utilized in crude form.

EXAMPLE 6

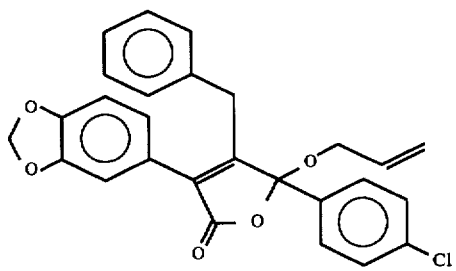

(±)-3-(1,3-benzodioxol-5-yl)-5-(4-chlorophenyl)-4-(phenylmethyl)-5-(2-propenyloxy)-2(5H)-furanone The chloride (750 mg), formed in a manner similar to Example 5, was heated at reflux with allyl alcohol (5 mL) for 2 hours, excess alcohol was removed under reduced pressure, and the residue was chromatographed on SIO₂ 4:1 hex/ethyl acetate giving a colorless oil 783 mg (95%) that was identified by ¹H NMR.

EXAMPLE 7

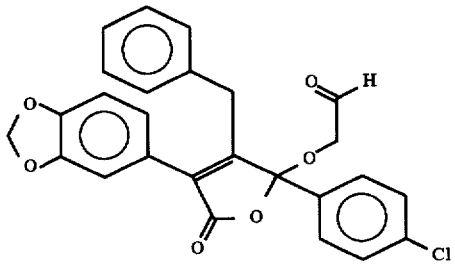

Acetaldehyde, [[4-(1,3-benzodioxol-5-yl)-2-(4-chlorophenyl)-2,5-dihydro-5-oxo-3-(phenylmethyl)-2-furanyl]oxo]-, (±)-

The vinyl ether 6 516 mg (1.11 mmol) in dioxane/water 4:1 (5 mL) was treated with osmium tetroxide 2% (0.022 mmol) and sodium metaperiodate 502 mg (2.31 mmol). After 6 hours, thin layer analysis indicated no starting ether remained. Ethyl acetate was added, the mixture was washed with water and then brine, followed by drying over magnesium sulfate. The solvent was evaporated under reduced pressure to give an oil that was chromatographed on silica gel 10% ethyl acetate/dichloromethane to give a colorless oil 324 mg (63%) that was identified by ¹H NMR, IR, [M+H]⁺=463 Da.

EXAMPLE 8

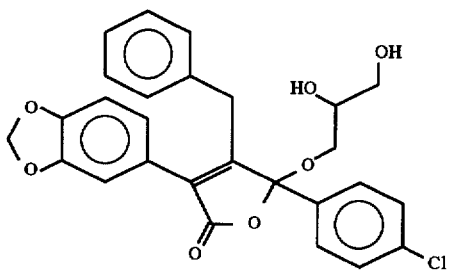

2(5H)-Furanone, 3-(1,3-benzodioxol-5-yl)-5-(4-Chlorophenyl)-5-(2,3-dihydroxypropoxy)-4-(phenylmethyl)-, (±)-

To the vinyl ether 6 259 mg (0.56 mmol) in dioxane/water 8:1 (9 mL) was added osmium tetroxide 5% (0.028 mmol) and N-methylmorpholine-N-oxide (132 mg) (1.12 mmol). After 4 hours, thin layer analysis indicated no starting ether remained; ethyl acetate was added, and the solution was washed with 10% $H_2SO_4$, brine, and then dried over magnesium sulfate to give an oil. Chromatography on silica gel 30% ethyl acetate/dichloromethane provided a colorless foam 176 mg (63%) that was identified by $^1$H NMR, IR, [M+H]$^+$=494 Da.

EXAMPLE 9

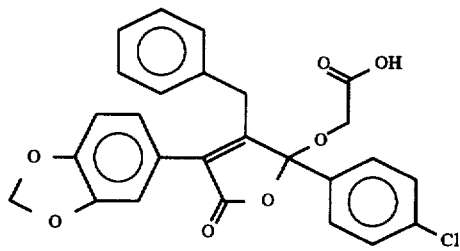

Acetic acid, [[4-(1,3-benzodioxol-5-yl)-2-(4-chlorophenyl)-2,5-dihydro-3-(phenylmethyl)-5-oxo-2-furanyl]oxy]-, (±)-

The aldehyde 7 220 mg (0.47 mmol) in acetone at 0° C. was treated with Jones Reagent until a brown color persisted for 10 minutes, excess oxidant was removed by the addition of methanol. Ethyl acetate was then added, the solution was washed with water, brine, and then dried over magnesium sulfate to give a yellow oil 114 mg (51%) that was identified by $^1$H NMR, IR, [M+H]$^+$=478 Da.

EXAMPLE 10

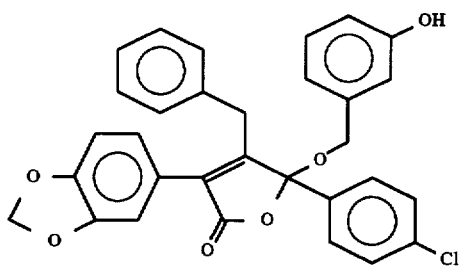

2(5H)-Furanone, 3-(1,3-benzodioxol-5-yl)-5-(4-chlorophenyl)-5-[(3-hydroxyphenyl)methoxy]-4-(phenylmethyl)-, (±)-

To the chloride 500 mg (1.1 mmol), formed as in Example 5, in dichloroethane (5 mL) was added 3-hydroxybenzyl alcohol and the solution was heated to reflux. After 16 hours, the solution was cooled and evaporated under reduced pressure. The residue was chromatographed on silica gel 7:3 hexane:ethyl acetate to give a colorless foam 471 mg (81%) that was identified by $^1$H NMR, IR, [M+H]$^+$=526 Da.

EXAMPLE 11

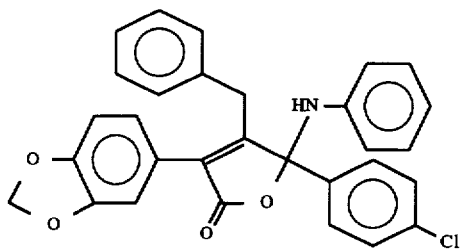

2(5H)-Furanone, 3-(1,3-benzodioxol-5-yl)-5-(4-chlorophenyl)-5-(phenylamino)-4-(phenylmethyl)-, (±)-

To the chloride 350 mg (0.79 mmol), prepared as in Example 5, in toluene (7 mL) was added aniline (145 μL, 1.6 mmol). The solution was heated at 90° C. for 16 hours cooled, and the solvent was evaporated under reduced pressure. Chromatography of the residue on silica gel 70:30 hexane/ether provided a foam 310 mg (79%) that was identified by $^1$H NMR, IR, [M+H]$^+$=496 Da.

EXAMPLE 12

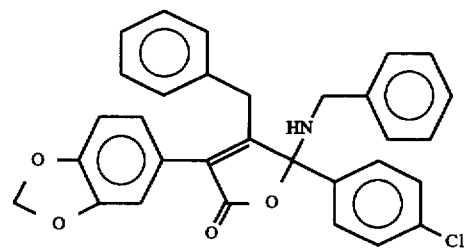

2(5H)-Furanone, 3-(1,3-benzodioxol-5-yl)-5-(4-chlorophenyl)-4-(phenylmethyl)-5-[(phenylmethyl)amino]-, (±)-

To alcohol 39 420 mg (1.0 mmol) in toluene (10 mL) was added benzylamine (0.5 mL). The solution was heated to reflux for 24 hours, cooled, and the solvent was evaporated to give an oil. The residue was chromatographed on silica gel 3:1 hexane/ether, providing a colorless solid 123 mg (24%) that was identified by $^1$H NMR, IR, [M+H]$^+$=510 Da.

EXAMPLE 13

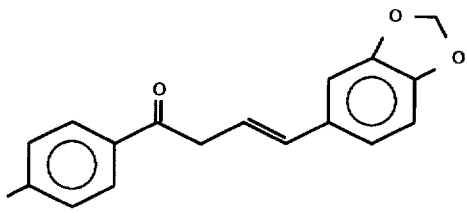

Following the procedure of Example 1 instead employing 4-methylacetophenone (14.76 g) and piperonal (23.1 g), provided a solid 26.1 g (89%) that was identified by $^1$H NMR, IR, MS, and microanalysis.

EXAMPLE 14

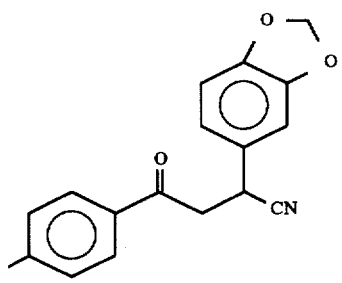

Following the procedure described in Example 2 instead employing 13 (25.5 g), provided the nitrile as a dark solid 17.6 g (63%) that was identified by $^1$H NMR, IR, MS, and microanalysis.

EXAMPLE 15

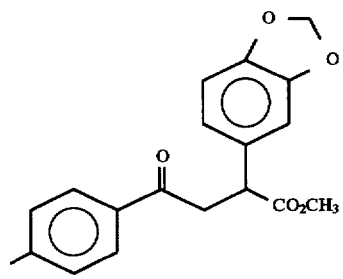

Following the procedure described in Example 3 instead employing nitrile 14 (17.4 g), provided the methyl ester as a solid 18.7 g (96%) that was identified by $^1$H NMR, IR, MS, and microanalysis.

EXAMPLE 16

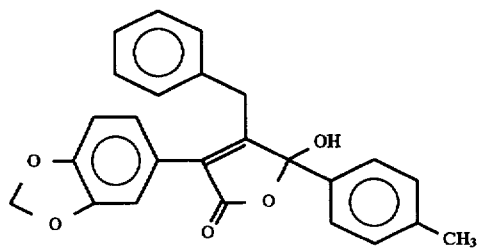

2(5H)-Furanone, 3-(1,3-benzodioxol-5-yl)-5-hydroxy-5-(4-methylphenyl)-4-(phenylmethyl)-

Following the procedure described in Example 4 instead employing the methyl ester 15 (1.30 g), Na (97 mg) and benzaldehyde (467 mg) as the aldehyde, provide the lactone as a solid 0.85 g (53%) that was identified by $^1$H NMR, IR, [M+H]$^+$=400 Da., and microanalysis.

EXAMPLE 17

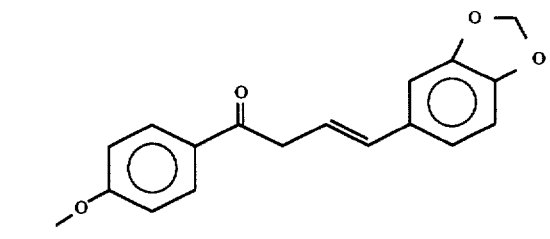

Following the procedure of Example 1 instead employing 4-methoxyacetophenone (16.5 g) and piperonal (23.12 g), provided a solid 31.1 g (99%) that was identified by $^1$H NMR, IR, MS, and microanalysis.

EXAMPLE 18

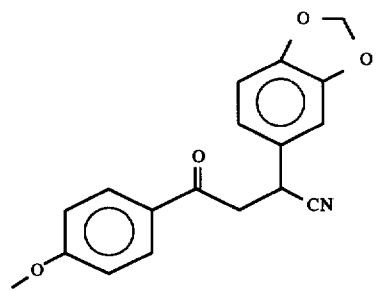

Following the procedure described in Example 2 instead employing 17 (31 g), provided the nitrile as a dark solid 31.9 g (94%) that was identified by $^1$H NMR, IR, MS, and microanalysis.

EXAMPLE 19

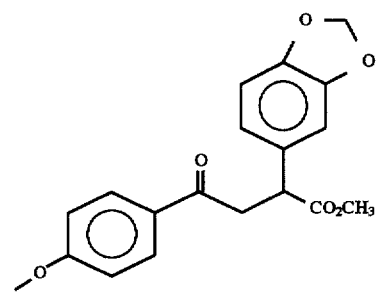

Following the procedure described in Example 3 instead employing nitrile 18 (27.6 g), provided the methyl ester as a solid 28.1 g (92%) that was identified by $^1$H NMR, IR, MS, and microanalysis.

EXAMPLE 20

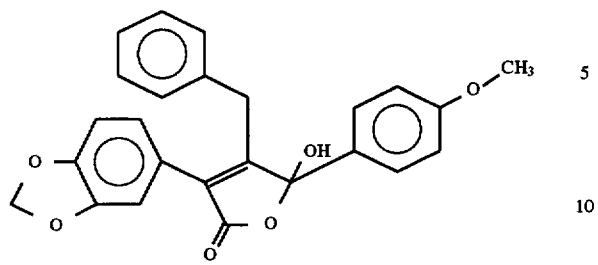

2(5H)-Furanone, 3-(1,3-benzodioxol-5-yl)-5-hydroxy-5-(4-methoxyphenyl)-4-(phenylmethyl)-

Following the procedure described in Example 4 instead employing the methyl ester 19 (1.36 g), Na (97 mg), and benzaldehyde (467 mg) as the aldehyde, provide the lactone as a foam 0.850 g (51%) that was identified by $^1$H NMR, IR, [M+H]$^+$=416 Da., and microanalysis.

EXAMPLE 21

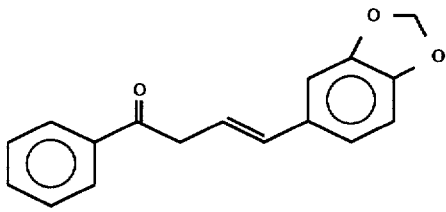

Following the procedure of Example 1 instead employing acetophenone (13.2 g) and piperonal (23.12 g), provided a light yellow solid 27.2 g (98%) that was identified $^1$H NMR, IR, MS, and microanalysis.

EXAMPLE 22

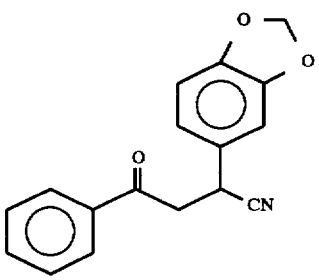

Following the procedure described in Example 2 instead employing 21 (26.1 g), provided the nitrile as a colorless solid 26.9 g (94%) that was identified by $^1$H NMR, IR, MS, and microanalysis.

EXAMPLE 23

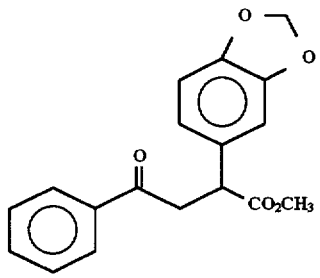

Following the procedure described in Example 3 instead employing nitrile 22 (24.09 g), provided the methyl ester as a tan solid 19.9 g (74%) that was identified by $^1$H NMR, IR, MS, and microanalysis.

EXAMPLE 24

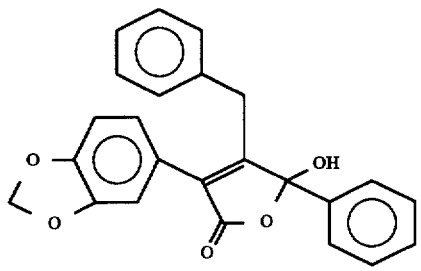

2(5H)-Furanone, 3-(1,3-benzodioxol-5-yl)-5-hydroxy-5-phenyl-4-(phenylmethyl)-

Following the procedure described in Example 4 instead employing the methyl ester 23 (1.25 g), Na (97 mg), and benzaldehyde (467 mg) as the aldehyde, provide the lactone as a foam 1.516 g (98%) that was identified by $^1$H NMR, IR, [M+H]$^+$=386 Da., and microanalysis.

EXAMPLE 25

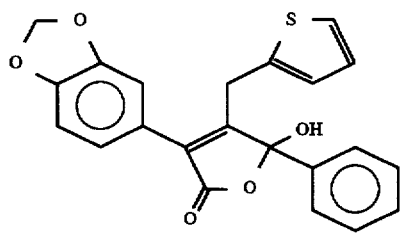

2(5H)-Furanone, 3-(1,3-benzodioxol-5-yl)-5-hydroxy-5-phenyl-4-(2-thienylmethyl)-

Following the procedure described in Example 4 instead employing the methyl ester 23 (1.25 g), Na (97 mg), and 2-thiophenecarboxaldehyde (493 mg) as the aldehyde, provide the lactone as a foam 1.15 g (73%) that was identified $^1$H NMR, IR, [M+H]$^+$=392 Da., and microanalysis.

EXAMPLE 26

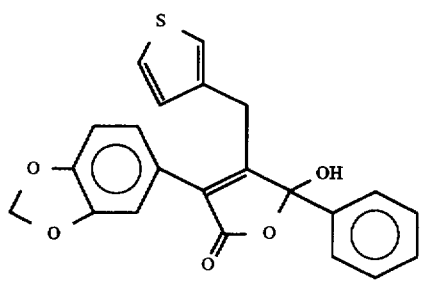

2(5H)-Furanone, 3-(1,3-benzodioxol-5-yl)-5-hydroxy-5-phenyl-4-(3-thienylmethyl)-

Following the procedure described in Example 4 instead employing the methyl ester 23 (1.25 g), Na (97 mg), and 3-thiophene carboxaldehyde (493 mg) as the aldehyde, provide the lactone as a foam 0.800 (51%) that was identified by $^1$H NMR, IR, [M+H]$^+$=392 Da., and microanalysis.

EXAMPLE 27

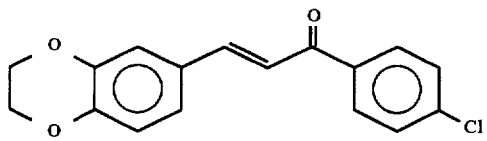

Following the procedure of Example 1 instead employing 4-chloroacetophenone (10.4 g) and 1,4-benzodioxan-6-carboxaldehyde (15.49 g), provided a colorless solid 18.9 g (82%) that was identified by $^1$H NMR, IR, MS, and microanalysis.

EXAMPLE 28

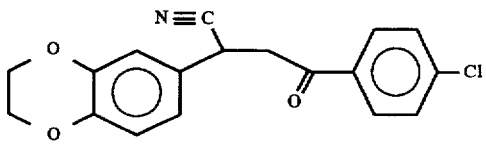

Following the procedure described in Example 2 instead employing 27 (12.25 g), provided the nitrile as a colorless solid 11.9 g (89%) that was identified by $^1$H NMR, IR, MS.

EXAMPLE 29

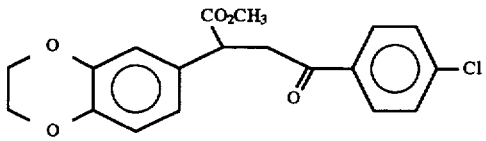

Following the procedure described in Example 3 instead employing nitrile 28 (10 g), provided the methyl ester as a solid 10.1 g (92%) that was identified by $^1$H NMR, IR, MS.

EXAMPLE 30

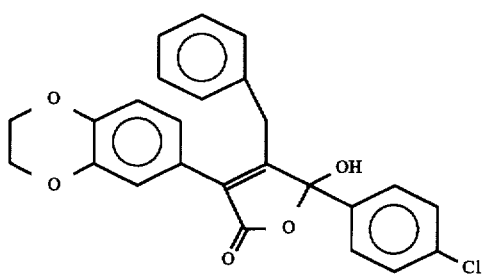

2(5H)-Furanone, 5-(4-chlorophenyl)-3-(2,3-dihydro-1,4-benzodioxin-6-yl)-5-hydroxy-4-(phenylmethyl)-

Following the procedure described in Example 4 instead employing the methyl ester 29 (1.44 g), Na (97 mg), and benzaldehyde (467 mg) as the aldehyde, provide the lactone as a foam 0.495 g (28%) that was identified by $^1$H NMR, IR, [M+H]$^+$=434 Da., and microanalysis.

EXAMPLE 31

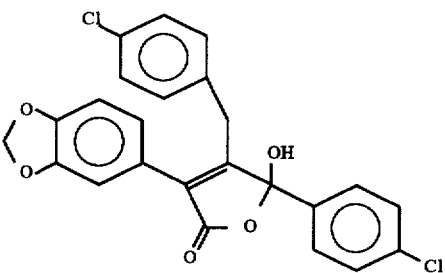

2(5H)-Furanone, 3-(1,3-benzodioxol-5-yl)-5-(4-chlorophenyl)-4-[(4-chlorophenyl)methyl]-5-hydroxy- Following the procedure described in Example 4 only employing the methyl ester 37 (1.39 g), Na (97 mg), and p-chlorobenzaldehyde (0.619 g) as the aldehyde, provide the lactone as a tan solid 0.865 g (48%) that was identified by $^1$H NMR, IR, [M+H]$^+$=454 Da.

EXAMPLE 32

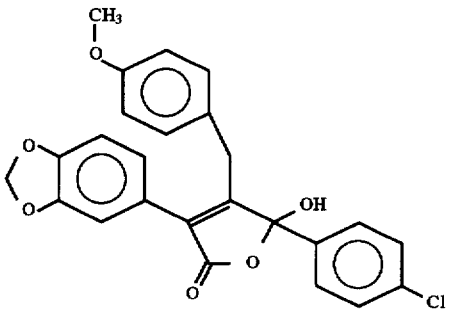

2(5H)-Furanone, 3-(1,3-benzodioxol-5-yl)-5-(4-chlorophenyl)-5-hydroxy-4-[(4-methoxyphenyl)methyl]-

Following the procedure described in Example 4 only employing the methyl ester 37 (1.39 g), Na (97 mg), and p-anisaldehyde (0.60 g) as the aldehyde, provide the lactone as a tan solid 0.410 g (23%) that was identified by $^1$H NMR, IR, [M+]$^+$=450 Da.

EXAMPLE 33

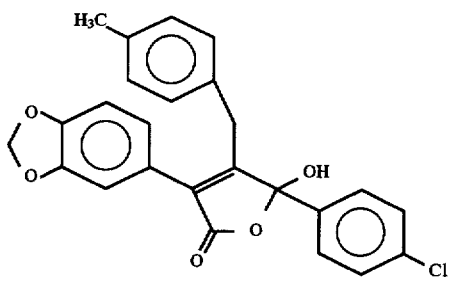

2(5H)-Furanone, 3-(1,3-benzodioxol-5-yl)-5-(4-chlorophenyl)-5-hydroxy-4-[(4-methylphenyl)methyl]-

Following the procedure described in Example 4 only employing the methyl ester 37 (1.39 g), Na (97 mg), and p-tolylaldehyde (528 mg) as the aldehyde, provide the lactone as a foam 0.50 g (29%) that was identified by $^1$H NMR, IR, [M+H]$^+$=434 Da.

EXAMPLE 34

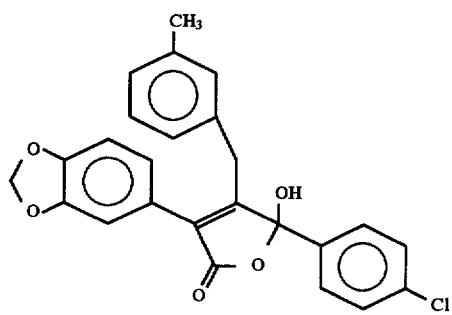

2(5H)-Furanone, 3-(1,3-benzodioxol-5-yl)-5-(4-chlorophenyl)-5-hydroxy-4-[(3-methylphenyl)methyl]-

Following the procedure described in Example 4 only employing the methyl ester 37 (1.39 g), Na (97 mg), and m-tolylaldehyde (529 mg) as the aldehyde, provide the lactone as a foam 1.19 g (68%) that was identified by $^1$H NMR, IR, [M+H]$^+$=434 Da.

EXAMPLE 35

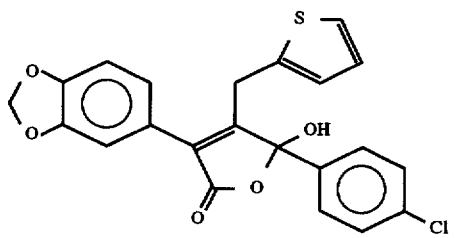

2(5H)-Furanone, 3-(1,3-benzodioxol-5-yl)-5-(4-chlorophenyl)-5-hydroxy-4-(2-thienylmethyl)-

Following the procedure described in Example 4 only employing the methyl ester 37 (1.39 g), Na (97 mg), and 2-thiophenecarboxaldehyde (493 mg) as the aldehyde, provide the lactone as a foam 0.730 g (43%) that was identified by $^1$H NMR, IR, [M+H]$^+$=426 Da.

EXAMPLE 36

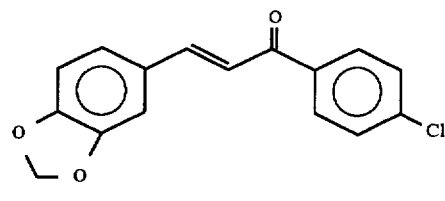

Following the procedure of Example 1 instead employing piperonal, provided a colorless solid 35.25 g (104%) that was identified by $^1$H NMR, IR, MS, and found to contain traces of ethanol.

EXAMPLE 37

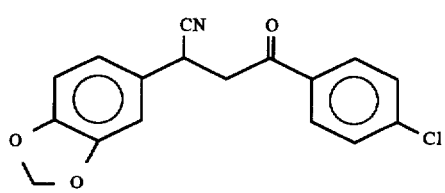

Following the procedure described in Example 2 instead employing 36, provided the nitrile as a colorless solid 30 g (81%) that was identified by $^1$H NMR.

EXAMPLE 38

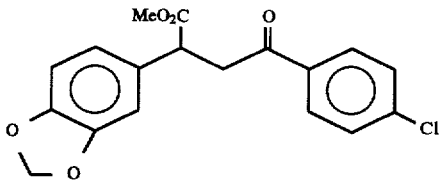

Following the procedure described in Example 3 only employing 37, provided the nitrile as a colorless solid 12 g (36%) that was identified by $^1$H NMR.

EXAMPLE 39

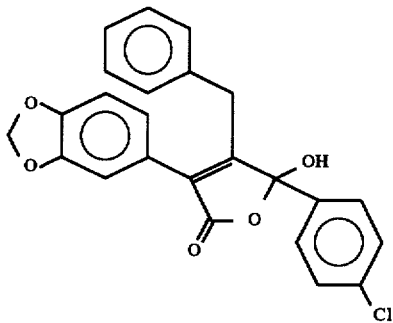

2(5H)-Furanone, 3-(1,3-benzodioxol-5-yl)-5-(4-chlorophenyl)-5-hydroxy-4-(phenylmehyl)-

Following the procedure described in Example 4 only employing the methyl ester 38, and benzaldehyde as the aldehyde, provide the lactone as a foam 4.29 g (59%) that was identified by $^1$H NMR, IR, MS.

EXAMPLE 40

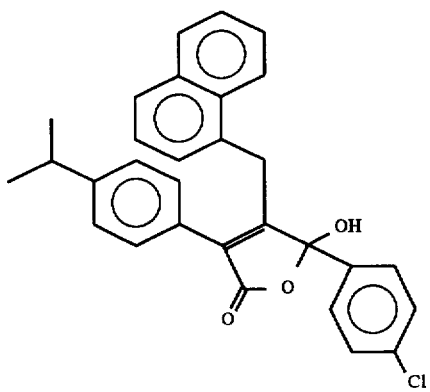

2(5H)- Furanone, 5-(4-chlorophenyl)-5-hydroxy-3-[4-(1-methylethyl)phenyl]-4-(1-naphthalenylmethyl)-, (±)-

Following the procedure described in Example 4 only employing the methyl ester 3, and 1-naphthaldehyde as the aldehyde, provide the lactone as a foam 816 mg (60%) that was identified by $^1$H NMR, IR, [M+H]$^+$=468 Da.

EXAMPLE 41

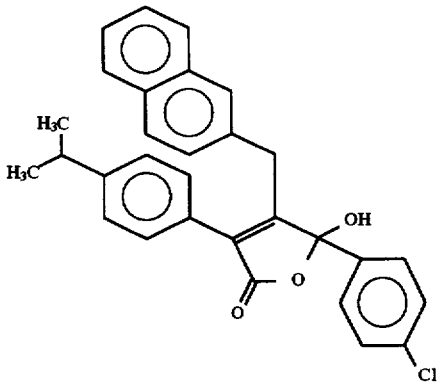

2(5H)-Furanone, 5-(4-chlorophenyl)-5-hydroxy-3-[4-(1-methylethyl)phenyl]-4-(2-naphthalenylmethyl)-, (±)-

Following the procedure described in Example 4 only employing the methyl ester 3, and 2-naphthaldehyde as the aldehyde, provide the lactone as a foam 784 mg (58%) that was identified by $^1$H NMR, IR, [M+H]$^+$=468 Da.

EXAMPLE 42

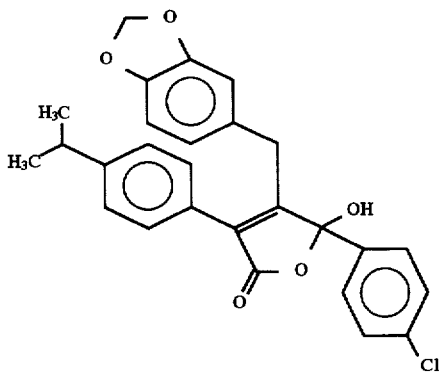

2(5H)-Furanone, 4-(1,3-benzodioxol-5-ylmethyl)-5-(4-chlorophenyl)-5-hydroxy-3-[4-(1-methylethyl)phenyl]-, (±)-

Following the procedure described in Example 4 only employing the methyl ester 3, and piperonal as the aldehyde, provide the lactone as a solid 687 mg (51%) that was identified by $^1$H NMR, IR, [M+H]$^+$=462 Da.

EXAMPLE 43

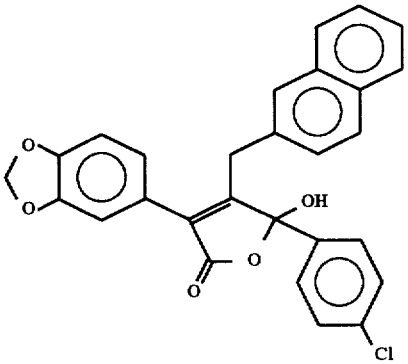

2(5H)-Furanone, 3-(1,3-benzodioxol-5-yl)-5-(4-chlorophenyl)-5-hydroxy-4-(2-naphthalenylmethyl)-, (±)-

Following the procedure described in Example 4 only employing the methyl ester 38, and 2-naphthaldehyde as the aldehyde, provide the lactone as a solid 861 mg (63%) that was identified by $^1$H NMR, IR, [M+H]$^+$=462 Da.

EXAMPLE 44

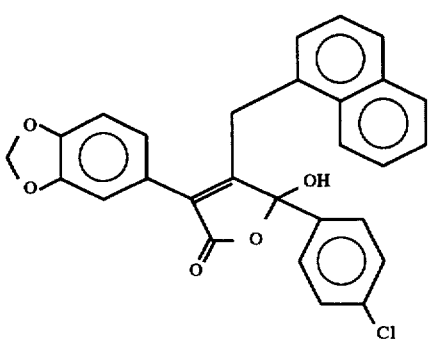

2(5H)-Furanone) 3-(1,3-benzodioxol-5-yl)-5-(4-chlorophenyl)-5-hydroxy-4-(1-naphthalenylmethyl)-, (±)-

Following the procedure described in Example 4 only employing the methyl ester 38, and 1-naphthaldehyde as the aldehyde, provide the lactone as a foam 1.02 g (75%) that was identified by $^1$H NMR, IR, [M+H]$^+$=470 Da.

EXAMPLE 45

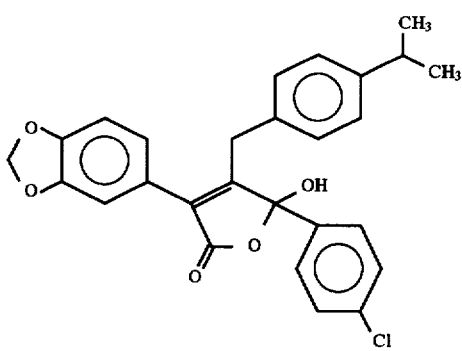

2(5H)-Furanone, 3-(1,3-benzodioxol-5-yl)-5-(4-chlorophenyl)-5-hydroxy-4-[[4-(1-methylethyl)phenyl]methyl]-, (3S)-

Following the procedure described in Example 4 only employing the methyl ester 38, and 4-isopropylbenzaldehyde as the aldehyde, provide the lactone as a foam 743 mg (56%) that was identified by $^1$H NMR, IR, [M+H]$^+$=463 Da.

EXAMPLE 46

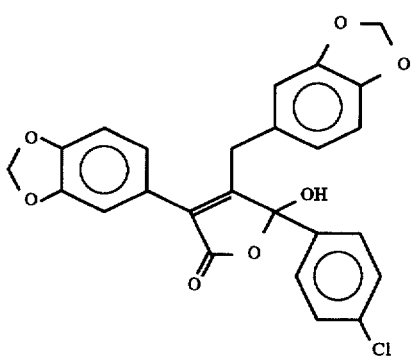

2(5H)-Furanone, 3-(1,3-benzodioxol-5-yl)-4-(1,3-benzodioxol-5-ylmethyl)-5-(4-chlorophenyl)-5-hydroxy-, (±)-

Following the procedure described in Example 4 only employing the methyl ester 38 and, piperonal as the aldehyde, provide the lactone as a foam 815 mg (61%) that was identified by $^1$H NMR, IR, MS.

EXAMPLE 47

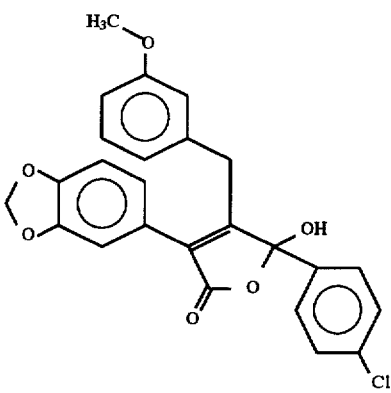

2(5H)-Furanone, 3-(1,3-benzodioxol-5-yl)-5-(4-chlorophenyl)-5-hydroxy-4-[(3-methoxyphenyl)methyl]-

Following the procedure described in Example 4 only employing the methyl ester 37 (1.39 g), Na (97 mg), and m-anisaldehyde (0.60 g) as the aldehyde, provide the lactone as a light yellow solid 1.21 g (67%) that was identified by $^1$H NMR, IR, [M+H]$^+$=450 Da.

EXAMPLE 48

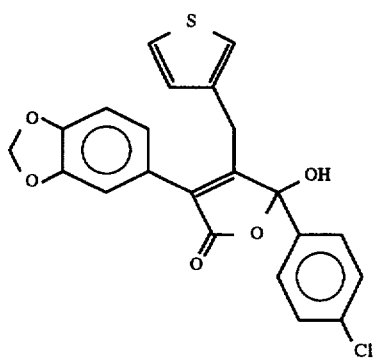

2(5H)-Furanone, 3-(1,3-benzodioxol-5-yl)-5-(4-chlorophenyl)-5-hydroxy-4-(3-thienylmethyl)-

Following the procedure described in Example 4 only employing the methyl ester 37 (1.39 g), Na (97 mg), and 3-thiophenylaldehyde (493 mg) as the aldehyde, provide the lactone as a pale pink solid 0.690 g (40%) that was identified by $^1$H NMR, IR, [M+H]$^+$=426 Da.

EXAMPLE 49

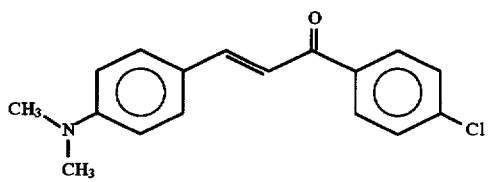

Following the procedure of Example 1 only employing 4-(dimethylamino)benzaldehyde, provided a yellow solid 7.60 g (83%) that was identified by $^1$H NMR, IR, MS.

EXAMPLE 50

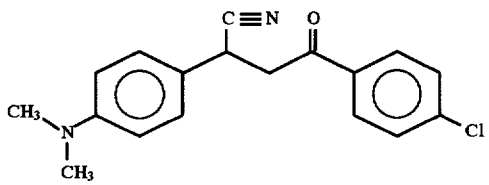

Following the procedure described in Example 2 only employing 49, provided the nitrile as a light brown solid 7.10 g (87%) that was identified by $^1$H NMR, IR, MS.

EXAMPLE 51

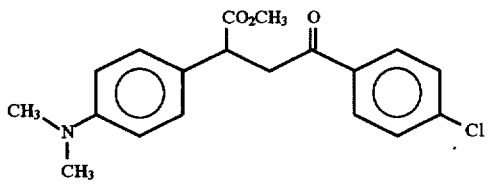

Following the procedure described in Example 3 only employing nitrile 50, provided the methyl ester as a yellow solid 5.67 g (72%) that was identified by $^1$H NMR, IR, MS.

EXAMPLE 52

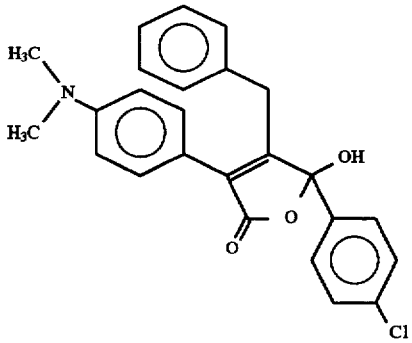

2(5H)-Furanone, 5-(4-chlorophenyl)-3[4-(dimethylamino)phenyl]-5-hydroxy-4-(phenylmethyl)-, (±)-

Following the procedure described in Example 4 only employing the methyl ester 51, and benzaldehyde as the aldehyde, provide the lactone as a pale yellow solid 0.300 g (26%) after purification by chromatography on silica gel using 1:9, ethyl acetate:hexane followed by crystallization from diethyl ether, and was identified by $^1$H NMR, IR, [M+H]$^+$=420 Da.

EXAMPLE 53

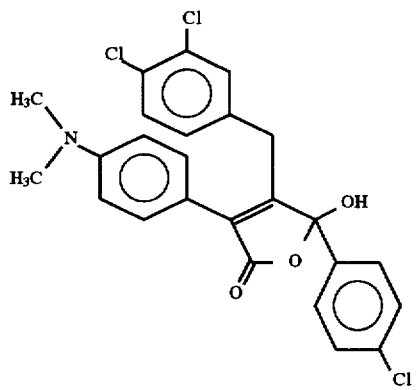

2(5H)-Furanone, 5-(4-chlorophenyl)-4-[(3,4-dichlorophenyl)methyl]-3-[(4-dimethylamino)phenyl]-5-hydroxy, (±)-

Following the procedure described in Example 4 only employing the methyl ester 51, and 3,4-dichlorobenzaldehyde as the aldehyde, provide the lactone as a yellow solid 0.150 g (30%) after purification by chromatography on silica gel using 3:7, ethyl acetate:hexane followed by crystallization from diethyl ether and was identified by $^1$H NMR, IR, [M+H]$^+$=488 Da.

EXAMPLE 54

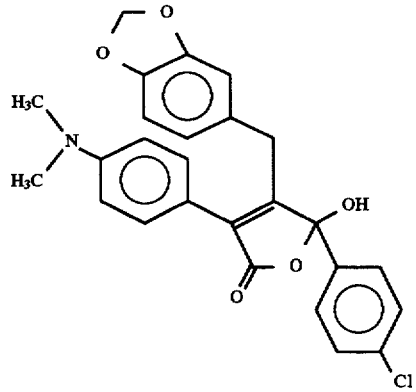

2(5H)-Furanone, 4-(1,3-benzodioxol-5-ylmethyl)-5-(4-chlorophenyl)-3-[4-(dimethylamino)phenyl]-5-hydroxy-, (±)-

Following the procedure described in Example 4 only employing the methyl ester 51, and piperonal as the aldehyde, provide the lactone as a yellow solid 0.18 g (43%) after purification by chromatography on silica gel using 1:4, ethyl acetate:hexane followed by crystallization from diethyl ether and was identified by $^1$H NMR, IR, [M+H]$^+$=464 Da.

EXAMPLE 55

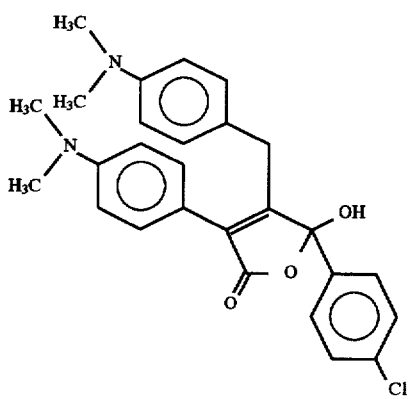

2(5H)-Furanone, 5-(4-chlorophenyl)-3-[4-(dimethylamino)phenyl]-4-[[4-(dimethylamino)phenyl]methyl]-5-hydroxy-, (±)-

Following the procedure described in Example 4 only employing the methyl ester 51, and p-dimethylaminobenzaldehyde as the aldehyde, provide the lactone as a yellow solid 0.40 g (59%) after purification by chromatography on silica gel using 1:4, ethyl acetate:hexane followed by crystallization from diethyl ether and was identified by $^1$H NMR, IR, [M+H]$^+$=463 Da.

EXAMPLE 56

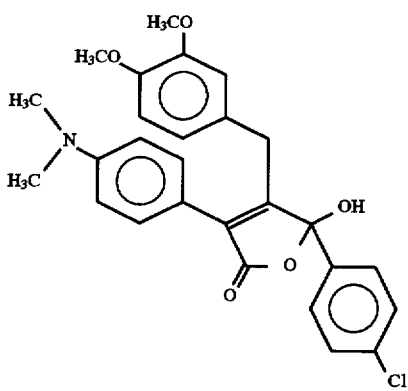

2(5H)-Furanone, 5-(4-chlorophenyl)-4-[(3,4-dimethoxyphenyl)methyl]-3-[4-(dimethylamino)phenyl]-5-hydroxy-, (±)-

Following the procedure described in Example 4 only employing the methyl ester 51, and 3,4-dimethoxybenzaldehyde as the aldehyde, provide the lactone as a yellow foam 0.300 g (43%) after purification by chromatography on silic gel using 1:9, ethyl acetate:hexane followed by crystallization from diethyl ether, and was identified by $^1$H NMR, IR, [M+H]$^+$=480 Da.

EXAMPLE 57

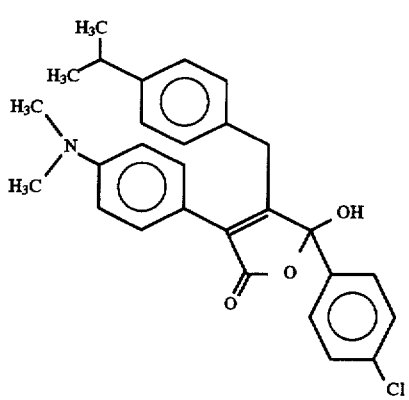

2(5H)-Furanone, 5-(4-chlorophenyl)-3-[(4-(dimethylamino)phenyl]-5-hydroxy-4-[[4-(1-methylethyl)phenyl]methyl]-, (±)-

Following the procedure described in Example 4 only employing the methyl ester 51, and 4-isopropylbenzaldehyde as the aldehyde, provide the lactone as a yellow solid 0.150 g (27%) after purification on silica gel using 3:7, ethyl acetate:hexane followed by crystallization from diethyl ether and was identified by $^1$H NMR, IR, [M+H]$^+$=462 Da.

EXAMPLE 58

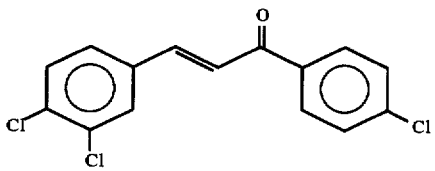

Following the procedure of Example 1 only employing 3,4-dichlorobenzaldehyde, provided a colorless solid 35.9 g (80%) that was identified by $^1$H NMR, IR, MS.

EXAMPLE 59

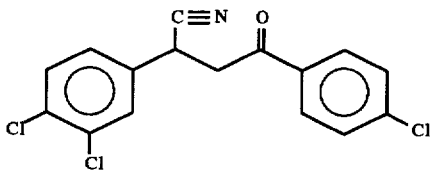

Following the procedure described in Example 2 only employing 58, provided the nitrile as a colorless solid 16.2 g (42%) that was identified by $^1$H NMR, IR, MS.

EXAMPLE 60

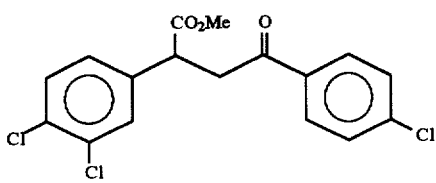

Following the procedure described in Example 3 only employing nitrile 59, provided the methyl ester after chromatography on silica gel 4:1 $CH_2Cl_2$:hexane as a light brown oil 8.0 g (44%) that was identified by $^1$H NMR, IR, MS.

EXAMPLE 61

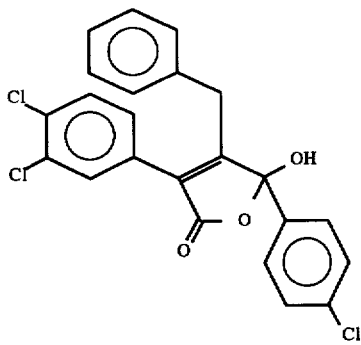

2(5H)-Furanone, 5-(4-chlorophenyl)-3-(3,4-dichlorophenyl)-5-hydroxy-4-(phenylmethyl)-, (±)-

Following the procedure in Example 4 only employing the methyl ester 60, and benzaldehyde as the aldehyde, provide the lactone as solid 948 mg (78%) that was identified by $^1$H NMR, IR, [M+H]$^+$=445 Da.

EXAMPLE 62

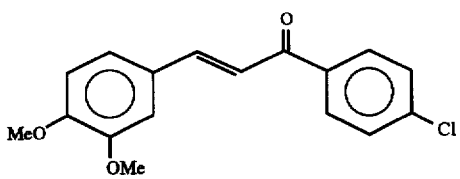

Following the procedure of Example 1 only employing 3,4-dimethoxybenzaldehyde, provided a colorless solid 31 g (86%) that was identified by $^1$H NMR, IR, MS.

EXAMPLE 63

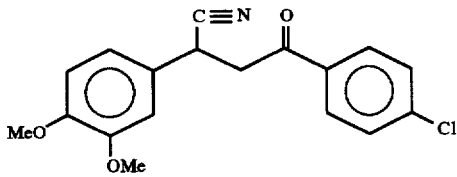

Following the procedure described in Example 2 only employing 62, provided the nitrile as a colorless solid 32.0 g (95%) that was identified by $^1$H NMR, IR, MS.

EXAMPLE 64

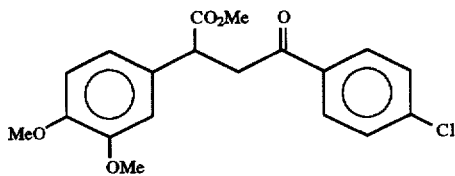

Following the procedure described in Example 3 only employing nitrile 63, provided the methyl ester as a light green solid 18.8 g (53%) that was identified by $^1$H NMR, IR, MS.

EXAMPLE 65

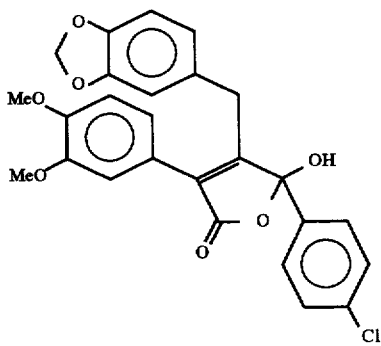

2(5H)-Furanone, 4-(1,3-benzodioxol-5-ylmethy)-5-(4-chlorophenyl)-3-(3,4-dimethoxyphenyl)-5-hydroxy, (±)-

Following the procedure described in Example 4 only employing the methyl ester 64, and piperonal as the aldehyde, provide the lactone as a foam 663 mg (46%) that crystalizes from diethyl ether and was identified by $^1$H NMR, IR, [M+H]$^+$=480 Da.

EXAMPLE 66

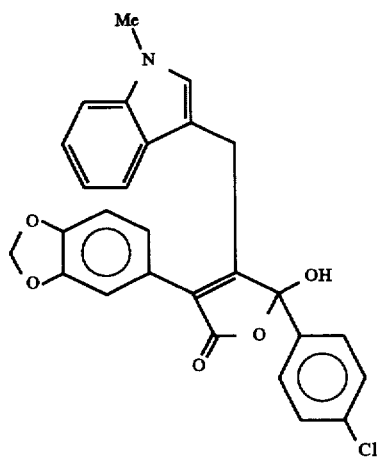

2 (5H)-Furanone, 3-(1,3-benzodioxol-5-yl)-5-(4-chlorophenyl)-5-hydroxy-4-[(1-methyl-1H-indol-3-yl)methyl], (±)-

Following the procedure described in Example 4 only employing the methyl ester 37, and 1-methylindole-3-carboxaldehyde as the aldehyde, provide the lactone as a foam 276 mg (20%) that was identified by $^1$H NMR, IR, [M+H]$^+$=474 Da.

EXAMPLE 67

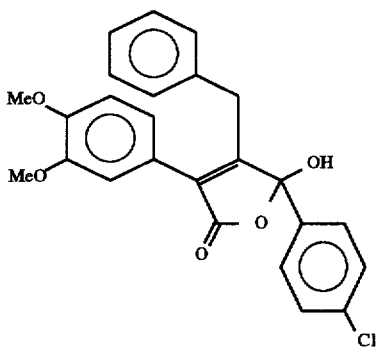

2(5H)-Furanone, 5-(4-chlorophenyl)-3-(3,4-dimethoxyphenyl)-5-hydroxy-4-(phenylmethyl)-, (±)-

Following the procedure described in Example 4 only employing the methyl ester 64, and benzaldehyde as the aldehyde, provide the lactone as a foam 692 mg (53%) that crystalizes from diethyl ether and was identified by $^1$H NMR, IR, [M+H]$^+$=436 Da.

EXAMPLE 68

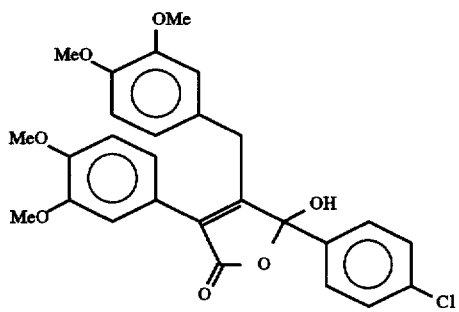

2(5H)-Furanone, 5-(4-chlorophenyl)-3-(3,4-dimethoxyphenyl)-4-[(3,4-dimethoxyphenyl)methyl]-5-hydroxy-, (±)-

Following the procedure described in Example 4 only employing the methyl ester 64, and 3,4-dimethoxybenzaldehyde as the aldehyde, provide the lactone as a foam 810 mg (54%) that was identified by $^1$H NMR, IR, [M+H]$^+$=496 Da.

EXAMPLE 69

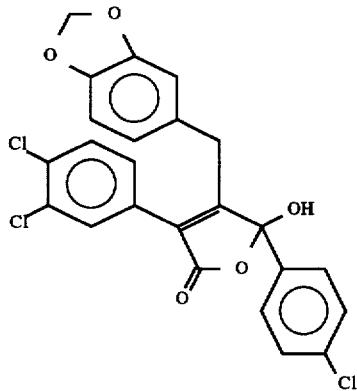

2(5H)-Furanone, 4-(1,3-benzodioxol-5-ylmethyl)-5-(4-chlorophenyl)-3-(3,4-dichlorophenyl)-5-hydroxy-, (±)-

Following the procedure described in Example 4 only employing the methyl ester 60, and piperonal as the aldehyde, provide the lactone as a foam 1.11 g (85%) that crystalizes from diethyl ether and was identified by $^1$H NMR, IR, [M+H]$^+$=488 Da.

EXAMPLE 70

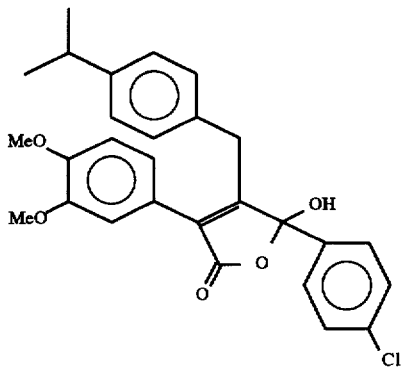

2(5H)-Furanone, 5-(4-chlorophenyl)-3-(3,4-dimethoxyphenyl)-5-hydroxy-4-[[4-(1-methylethyl)phenyl]methyl]-, (±)-

Following the procedure described in Example 4 only employing the methyl ester 64, and 4-isopropylbenzaldehyde as the aldehyde, provide the lactone as a foam 635 mg (44%) that crystalizes from diethyl ether and was identified by $^1$H NMR, IR, [M+H]$^+$=478 Da.

EXAMPLE 71

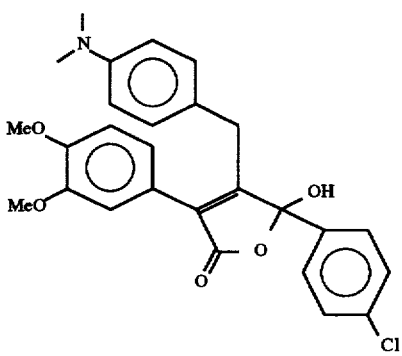

2(5H)-Furanone, 5-(4-Chlorophenyl)-3-(3,4-dimethoxyphenyl)-4-[[4-(dimethylamino)phenyl]methyl]-5-hydroxy-, (±)-

Following the procedure described in Example 4 only employing the methyl ester 64, and 4-(dimethylamino) benzaldehyde as the aldehyde, provide the lactone as a foam 511 mg (34%) that crystalizes from diethyl ether and was identified by $^1$H NMR, IR, [M+H]$^+$=480 Da.

EXAMPLE 72

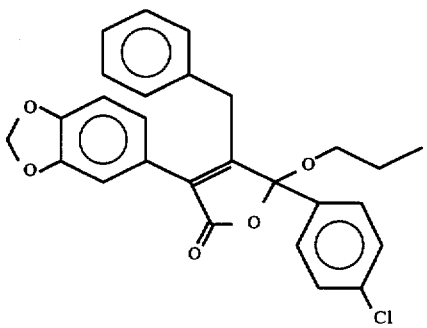

2(5H)-Furanone, 3-(1,3-benzodioxol-5-yl)-5-(4-chlorophenyl)-4-(phenylmethyl)-5-propoxy-, (±)-

To a solution of 39 (50 mg, 0.12 mmol) in propanol (15 mL) was added HCl(g) until the solution was saturated. After 18 hours toluene was added and the solvent was evaporated to give an orange oil. Chromatography on silica gel (4:1 hexane:ethyl acetate) gave 34 mg (62%) as a colorless oil that was identified by $^1$H NMR and [M+H]$^+$= 463 Da.

EXAMPLE 73

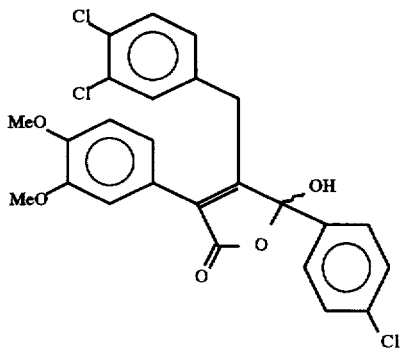

2(5H)-Furanone, 5-(4-chlorophenyl)-4-[(3,4-dichlorophenyl)methyl]-3-(3,4-dimethoxyphenyl)-5-hydroxy-, (±)-

Following the procedure described in Example 4 only employing the methyl ester from 64, and 3,4-dichlorobenzaldehyde as the aldehyde, provide the lactone as a solid 0.517 g (34%) after chromatography on silica gel (6% ethyl acetate in dichloromethane) followed by crystallization from diethyl ether, that was identified by $^1$H NMR, IR, [M+H]$^+$=507 Da.

EXAMPLE 74

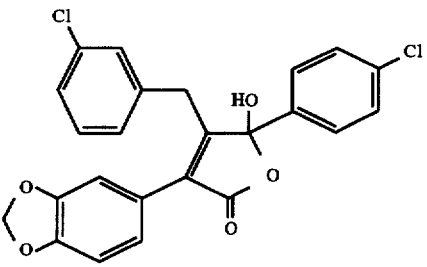

2(5H)-Furanone, 3-(1,3-benzodioxol-5)-5-(4-chlorophenyl) -4-[(3-chlorophenyl)methyl]-5-hydroxy Following the procedure described in Example 4 only employing the methyl ester 37 (1.387 g), Na (97 mg), and m-chlorobenzaldehyde (0.619 g) as the aldehyde, provide the lactone as a light yellow solid 1.16 g (64%) that was identified by $^1$H NMR, IR, [M+H]$^+$=439 Da.

EXAMPLE 75

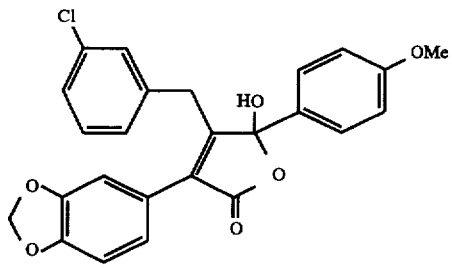

3-Benzo[1,3]dioxol-5-yl-4-(3-chlorobenzyl)-5-hydroxy-5-(4-methoxyphenyl)-5H-furan-2-one To methanol (2 mL) was added sodium methoxide (37 mg, 0.685 mmol) and stirred to dissolve. To this was added the ester, 19, (0.2 g, 0.585 mmol) then 3-chlorobenzaldehyde (95 mg, 0.685 mmol). The mixture was heated to reflux for 4 hours. The solution was then treated with acetic acid (2 mL) and refluxed an additional 16 hours. The solvents were removed by evaporation and the residue was partitioned between ethyl acetate (300 mL) and water (100 mL). The organic phase was separated and dried over magnesium sulfate and evaporated to dryness. The crude product was then purified by flash chromatography (100 g silica gel, 4:1 hexane:ethyl acetate). The butenolide was isolated by evaporation of the appropriate fractions to give 179 mg (65%) as a foam. The butenolide was identified by $^1$H NMR, IR, MS, [M+H]$^+$=451 Da., and microanalysis.

EXAMPLE 76

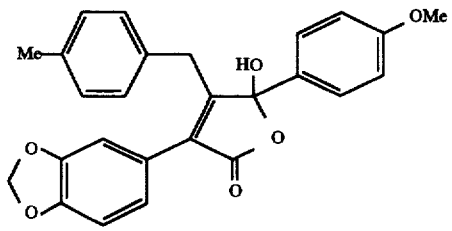

3-Benzo[1,3]dioxol-5-yl-5-(4-methoxyphenyl)-4-(4-methylbenzyl)-5H-furan-2-one

To a solution of sodium methoxide (37 mg, 0.685 mmol) in methanol (2 mL) was added the ester 19 (0.2 g, 585 mmol) then 4-tolualdehyde (0.07 mL, 0.685 mmol). The resulting mixture was heated to reflux for 4 hours. Acetic acid (0.5 mL) was added and the reflux continued for 16 hours. The solvent was evaporated. Dissolved residue in ethyl acetate (100 mL). Washed the organic phase with aqueous hydrochloric acid (1N, 80 mL), then aqueous sodium chloride (saturated, 80 mL). Dried the organic phase over magnesium sulfate. The solvent was evaporated. Flash chromatography of the residue, eluted with 4:1 hexane:ethyl acetate provided the product as a foam (120 mg, 48%) that was identified by $^1$H NMR, [M+H]$^+$=431 Da., IR, and elemental analysis.

EXAMPLE 77

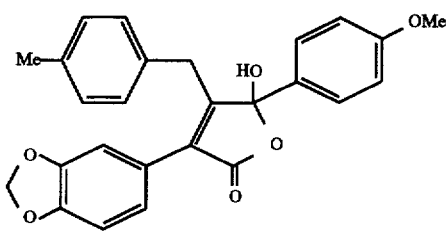

3-Benzo[1,3]dioxol-5-yl-5-hydroxy-4-(4-methoxybenzyl)-5-(4-methoxyphenyl)-5H-furan-2-one To a solution of sodium methoxide (122 mg, 2.26 mmol) in methanol (7 mL) was added the ester 19 (0.7 g, 2.05 mmol) then 4-methoxybenzaldehyde (0.3 mL, 2.26 mmol). The resulting mixture was heated to reflux for 4 hours. Acetic acid (2 mL) was added and the reflux continued for 16 hours. The solvent was evaporated. Dissolved residue in ethyl acetate (300 mL). Washed the organic phase with aqueous hydrochloric acid (1N, 100 mL), then aqueous sodium chloride (saturated, 100 mL). Dried the organic phase over magnesium sulfate. The solvent was evaporated. Flash chromatography of the residue, eluted with 4:1 hexane:ethyl acetate provided the product as a foam (255 mg, 28%) that was identified by $^1$H NMR, [M+H]$^+$=447 Da., IR, and elemental analysis.

EXAMPLE 78

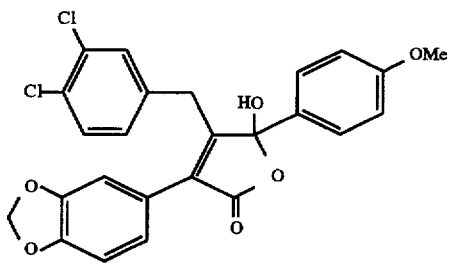

3-Benzo[1,3]dioxol-5-yl-4-(3,4-dichlorobenzyl)-5-hydroxy-5-(4-methoxyphenyl)-5H-furan-2-one To a solution of sodium methoxide (174 mg, 3.22 mmol) in methanol (10 mL) was added the ester 19 (1.0 g, 2.924 mmol) then 3,4-dichlorobenzaldehyde (563 mg, 3.22 mmol). The resulting mixture was heated to reflux for 4 hours. Acetic acid (2 mL) was added and the reflux continued for 16 hours. The solvent was evaporated. Dissolved residue in ethyl acetate (300 mL). Washed the organic phase with aqueous hydrochloric acid (1N, 100 mL), then aqueous sodium chloride (saturated, 100 mL). Dried the organic phase over magnesium sulfate. The solvent was evaporated. Flash chromatography of the residue, eluted with 4:1 hexane:ethyl acetate provided the product as a foam (838 mg, 60%) that was identified by $^1$H NMR, [M+H]$^+$=485 Da., IR, and elemental analysis.

EXAMPLE 79

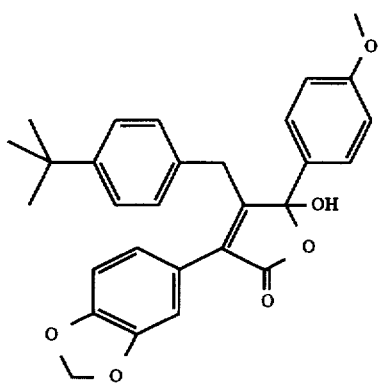

3-Benzo[1,3]dioxol-5-yl-4-(4-tert-butylbenzyl)-5-hydroxy-5-(4-methoxyphenyl)-5H-furan-2-one To methanol (7 mL) was added sodium methoxide (0.122 g, 2.26 mmol) and stirred to dissolve. To this was added 4-tertbutyl-benzaldehyde (0.365 g, 2.26 mmol) then the ester, 19, (0.7 g, 2.05 mmol). The mixture was heated to reflux for 4 hours. The solution was then treated with acetic acid (2 mL) and refluxed for an additional 16 hours. The solvents were removed by evaporation and the residue was partitioned between ethyl acetate (300 mL) and 1N HCl (100 mL). The organic layer was washed with brine (100 mL). The organic layer was then dried over MgSO$_4$ and evaporated to dryness. The crude material was purified by flash chromatography (25 g silica gel, 25% ethyl acetate/hexane). The butenolide was isolated by evaporation of the appropriate fractions 0.2 g (20%) as a white foam. The butenolide was identified by $^1$H NMR, IR, MS, [M+H]$^+$=474 Da.

EXAMPLE 80

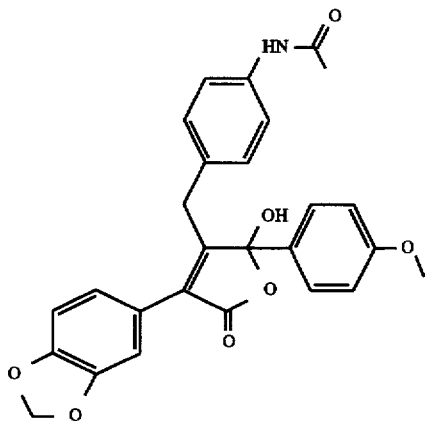

N-{4-[4-Benzo[1,3]dioxol-5-yl-2-hydroxy-2-(4-methoxyphenyl)-5-oxo-2,5-dihydro-furan-3-ylmethyl]-phenyl}-acetamide To methanol (15 mL) was added sodium metal (253 mg, 11 mmol) and stirred to dissolve. To this was added the ester, 19, (3.42 g, 10 mmol) then 4-acetamidobenzaldehyde (1.63 g, 10 mmol). The mixture was heated to reflux for 20 hours. The solution was then treated with acetic acid (3 mL) and refluxed an additional 24 hours. The solvents were removed by evaporation and the residue was partitioned between ethyl acetate (120 mL) and water (100 mL). The organic phase was separated and dried over magnesium sulfate and evaporated to dryness. The crude product was then purified by flash chromatography (500 g silica gel, 1:1, ethyl acetate-:methylene chloride). The butenolide was isolated by evaporation of the appropriate fractions to give 2.90 g (61%) as a yellow foam. The butenolide was identified by $^1$H NMR, IR, MS, [M+H]$^+$=474 Da., and microanalysis.

EXAMPLE 81

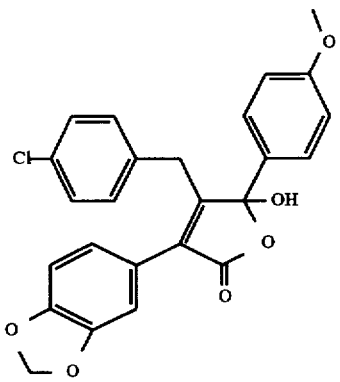

3-Benzo[1,3]dioxol-5-yl-4-(4-chlorobenzyl)-5-hydroxy-5-(4-methoxophenyl)-5H-furan-2-one To methanol (2 mL) was added sodium methoxide (0.037 g, 0.685 mmol) and stirred to dissolve. To this was added 4-chlorobenzaldehyde (0.095 g, 0.685 mmol) then the ester, 19, (0.2 g, 0.585 mmol). This mixture was heated to reflux for 4 hours. The solution was then treated with acetic acid (2 mL) and refluxed for an additional 16 hours. The solvents were removed by evaporation and the residue was partitioned between ethyl acetate (300 mL) and 1N HCl (100 mL). The organic layer was then dried over MgSO$_4$ and evaporated to dryness. The crude material was purified by flash chromatography (25 g silica gel, 25% ethyl acetate/hexane). The butenolide was isolated by evaporation of the appropriate fractions and crystallized from isopropyl ether-methylene chloride to give 0.179 g (65%) as a light yellow foam. The butenolide was identified by $^1$H NM R, IR, MS, [M+H]$^+$=451 Da., and microanalysis.

EXAMPLE 82

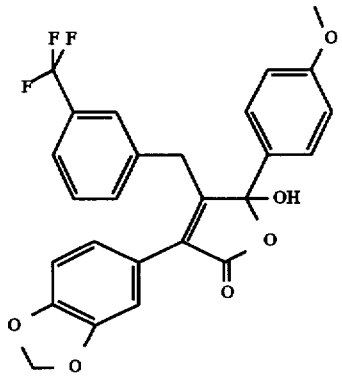

3-Benzo[1,3]dioxol-5-yl-5-hydroxy-5-(4-methoxyphenyl)-4-(3-trifluoromethylbenzyl)-5H-furan-2-one To dimethoxyethane (7 mL) was added potassium-tert-butoxide (0.252 g, 2.25 mmol) and stirred to dissolve. To this was added 3-trifluoromethylbenzaldehyde (0.39 g, 2.24 mmol) then the ester, 19, (0.7 g, 2.0 mmol). The mixture was heated to reflux for 4.5 hours. The solution was then treated with acetic acid (2 mL) and refluxed for an additional 18 hours. The solvents were removed by evaporation and the residue was partitioned between ethyl acetate (150 mL) and 1N HCl (90 mL), then brine (100 mL). The organic layer was then dried over MgSO$_4$ and evaporated to dryness. The crude material was purified by flash chromatography (40 g silica gel, 25% ethyl acetate/hexane). The butenolide was isolated by evaporation of the appropriate fractions and crystallized from isopropyl ether-methylene chloride to give 0.184 g (19%) as a yellow foam. The butenolide was identified by $^1$H NMR, IR, MS, [M+H]$^+$=485 Da.

EXAMPLE 83

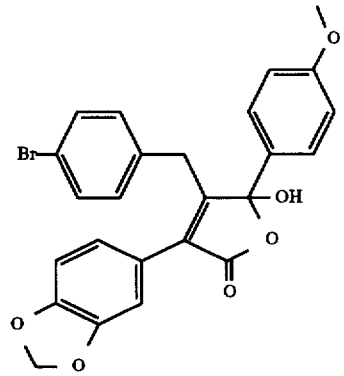

3-Benzo[1,3]dioxol-5-yl-4-(4-bromobenzyl)-5-hydroxy-5-(4-methoxyphenyl)-5H-furan-2-one To methanol (7 mL) was added sodium metal (0.122 g, 2.26 mmol) and stirred to dissolve. To this was added 4-bromobenzaldehyde (0.416 g, 2.2 mmol) then the ester, 19, (0.7 g, 2.0 mmol). The mixture was heated to reflux for 4 hours. The solution was then treated with acetic acid (2 mL) and refluxed for an additional 16 hours. The solvents were removed by evaporation and the residue was partitioned between ethyl acetate (300 mL) and 1N HCl (100 mL). The organic layer was washed with brine (100 mL). The organic layer was then dried over MgSO$_4$ and evaporated to dryness. The crude material was purified by flash chromatography (50 g silica gel, 25% ethyl acetate/hexane). The butenolide was isolated by evaporation of the appropriate fractions and crystallized from isopropyl ether-methylene chloride to give 0.28 g (28%) as white crystals. The butenolide was identified by $^1$H NMR, IR, MS, [M+H]$^+$=496 Da.

EXAMPLE 84

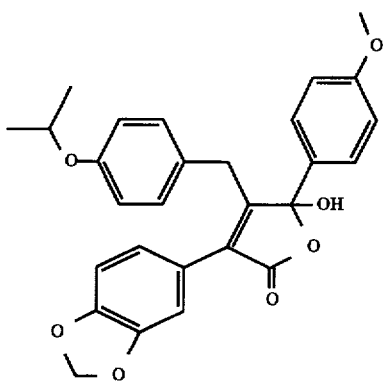

3-Benzo[1,3]dioxol-5-yl-5-hydroxy-4-(isopropoxybenzyl)-5-(4-methoxyphenyl)-5H-furan-2-one To methanol (10 mL) was added sodium metal (0.22 g, 9.6 mmol) and stirred to dissolve. To this was added 4-isoproxybenzaldehyde (1.59 g, 9.6 mmol) then the ester, 19, (3 g, 8.77 mmol). The mixture was heated to reflux for 18 hours. The solution was then treated with acetic acid (6 mL) and refluxed for an additional 24 hours. The solvents were removed by evaporation and the residue was partitioned between ethyl acetate (300 mL) and an aqueous saturated sodium bicarbonate (150 mL). The organic layer was washed with aqueous saturated sodium bicarbonate (150 mL), then brine (100 mL). The organic layer was then dried over MgSO$_4$ and evaporated to dryness. The crude material was purified by flash chromatography (120 g silica gel, 25% ethyl acetate/hexane). The butenolide was isolated by evaporation of the appropriate fractions 1.6 g (38%) as a white foam. The butenolide was identified by $^1$H NMR, IR, MS, [M+H]$^+$=475 Da., and microanalysis.

EXAMPLE 85

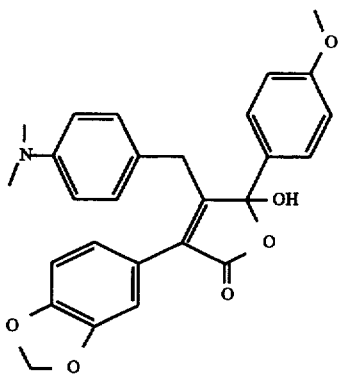

3-Benzo[1,3]dioxol-5-yl-4-(4-dimethylaminobenzyl)-5-hydroxy-5-(4-methoxyphenyl)-5H-furan-2-one To methanol (5 mL) was added sodium metal (0.12 g, 5.2 mmol) and stirred to dissolve. To this was added 4-dimethylaminobenzaldehyde (0.48 g, 3.2 mmol) then the ester, 19, (1 g, 2.9 mmol). The mixture was heated to reflux for 16 hours. The solution was then treated with acetic acid (2 mL) and refluxed for an additional 18 hours. The solvents were removed by evaporation and the residue was partitioned between ethyl acetate (200 mL) and an aqueous saturated sodium bicarbonate (100 mL). The organic layer was washed with brine (100 mL). The organic layer was then dried over MgSO$_4$ and evaporated to dryness. The crude material was purified by flash chromatography (80 g silica gel, 22% ethyl acetate/hexane). The butenolide was isolated by evaporation of the appropriate fraction to give 0.38 g (28%) as a yellow foam. The butenolide was identified by $^1$H NMR, IR, MS, [M+H]$^+$=460 Da.

EXAMPLE 86

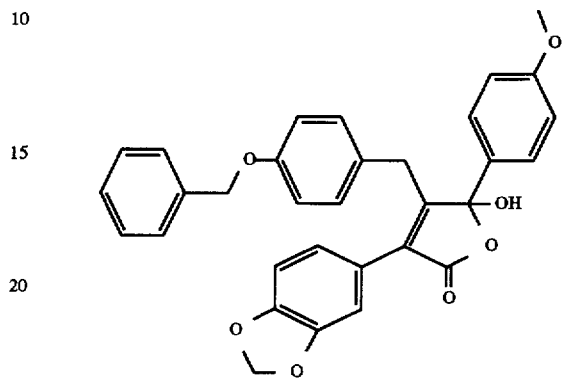

3-Benzo[1,3]dioxol-5-yl-4-(4-benzyloxybenzyl)-5-hydroxy-5-(4-methoxyphenyl)-5H-furan-2-one To methanol (15 mL) was added sodium metal (0.22 g, 9.6 mmol) and stirred to dissolve. To this was added 4-benzyloxybenzaldehyde (2.05 g, 9.6 mmol) then the ester, 19, (3 g, 8.8 mmol). The mixture was heated to reflux for 8 hours. The solution was then treated with acetic acid (6 mL) and refluxed for an additional 18 hours. The solvents were removed by evaporation and the residue was partitioned between ethyl acetate (200 mL) and water (50 mL). The organic layer was washed with brine (50 mL). The organic layer was then dried over MgSO$_4$ and evaporated to dryness. The crude material was purified by flash chromatography (100 g silica gel, 25% ethyl acetate hexane). The butenolide was isolated by evaporation of the appropriate fractions and crystallized from isopropyl ether to give 2.4 g (22%) as a light blue solid. The butenolide was identified by $^1$H NMR, IR, MS, [M+H]$^+$=523 Da., and microanalysis.

EXAMPLE 87

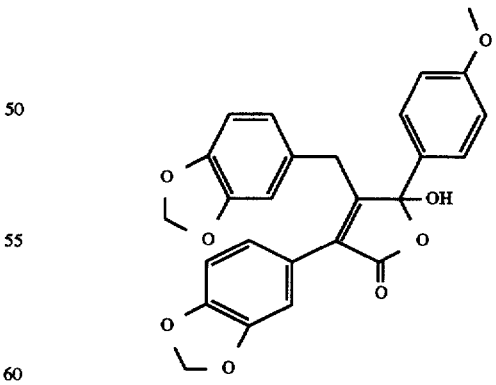

3-Benzo[1,3]dioxol-5-yl-4-benzo[1,3]dioxol-5-ylmethyl-5-hydroxy-5-(4-methoxyphenyl)-5H-furan-2-one To isopropanol (5 mL) was added sodium metal (0.078 g, 3.4 mmol) and stirred to dissolve. To this was added piperonal (0.483 g, 3.2 mmol) then the ester, 19, (1 g, 2.9 mmol). The mixture was heated to reflux for 8 hours. The solution was then treated with acetic acid (2 mL) and refluxed for an additional 18 hours. The solvents were removed by evaporation and the residue was partitioned between ethyl acetate (200 mL) and an aqueous saturated sodium bicarbonate (100 mL). The organic layer was washed with aqueous saturated sodium bicarbonate (2×100 mL), then brine (100 mL). The organic layer was then dried over MgSO₄ and evaporated to dryness. The crude material was purified by flash chromatography (70 g silica gel, 25% ethyl acetate/hexane). The butenolide was isolated by evaporation of the appropriate fractions and crystallized from isopropyl ether-methylene chloride to give 0.28 g (21%) as white crystals. The butenolide was identified by ¹H NMR, IR, MS, [M+H]⁺=461 Da.

EXAMPLE 88

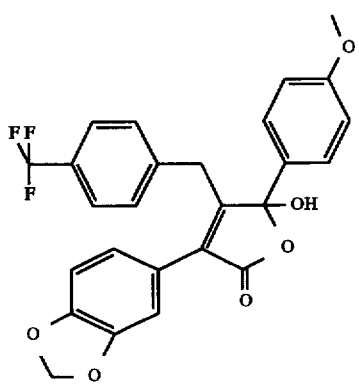

3-Benzo[1,3]dioxol-5-yl-5-hydroxy-5-(4-methoxyphenyl)-4-(4-trifluoromethylbenzyl)-5H-furan-2-one To methanol (10 mL) was added sodium metal (0.164 g, 7.1 mmol) and stirred to dissolve. To this was added 4-trifluoromethylbenzaldehyde (1.475 g, 6.6 mmol) then the ester, 19, (2 g, 5.8 mmol). The mixture was heated to reflux for 18 hours. The solution was then treated with acetic acid (4 mL) and refluxed for an additional 18 hours. The solvents were removed by evaporation and the residue was partitioned between ethyl acetate (500 mL) and an aqueous saturated sodium bicarbonate (200 mL). The organic layer was washed with aqueous saturated sodium bicarbonate (2×200 mL), then brine (100 mL). The organic layer was then dried over MgSO₄ and evaporated to dryness. The crude material was purified by flash chromatography (100 g silica gel, 25% ethyl acetate/hexane). The butenolide was isolated by evaporation of the appropriate fractions and crystallized from isopropyl ether-methylene chloride to give 2.25 g (80%) as a white solid. The butenolide was identified by ¹H NMR, IR, MS, [M+H]⁺=485 Da., and microanalysis.

EXAMPLE 89

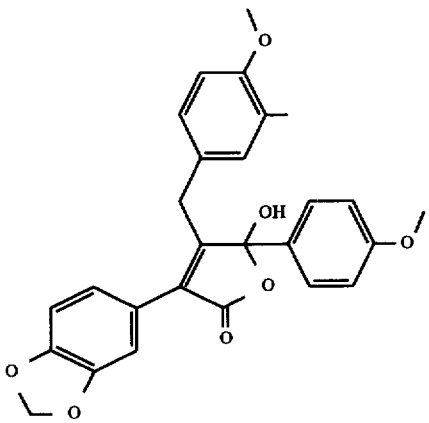

3-Benzo[1,3]dioxol-5-yl-5-hydroxy-4-(4-methoxy-3-methylbenzyl)-5-(4-methoxyphenyl)-5H-furan-2-one To methanol (15 mL) was added sodium metal (0.37 g, 16 mmol) and stirred to dissolve. To this was added 3-methyl-p-anisaldehyde (2.46 g, 16.4 mmol) then the ester, 19, (5 g, 14.6 mmol). The mixture was heated to reflux for 16 hours. The solution was then treated with acetic acid (6 mL) and refluxed for an additional 24 hours. The solvents were removed by evaporation and the residue was partitioned between ethyl acetate (300 mL) and an aqueous saturated sodium bicarbonate (200 mL). The organic layer was washed with aqueous saturated sodium bicarbonate (2×200 mL), then brine (100 mL). The organic layer was then dried over MgSO₄ and evaporated to dryness. The crude material was purified by flash chromatography (150 g silica gel, 25% ethyl acetate/hexane). The butenolide was isolated by evaporation of the appropriate fractions and crystallized from isopropyl ethermethylene chloride to give 3.2 g (47%) as white crystals. The butenolide was identified by ¹H NMR, IR, MS, [M+H]⁺=444 Da., and microanalysis.

EXAMPLE 90

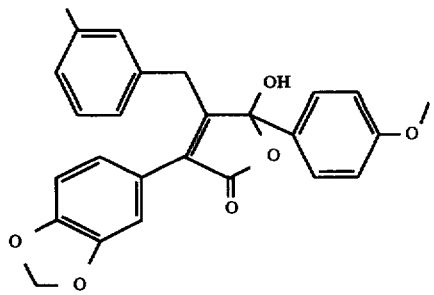

3-Benzo[1,3]dioxol-5-yl-5-hydroxy-5-(4-methoxyphenyl)-4-(3-methylbenzyl)-5H-furan-2-one To t-butanol (3 mL) was added potassium-t-butoxide (0.36 g, 3.2 mmol) and stirred to dissolve. To this was added m-tolualdehyde (0.386 g, 3.2 mmol) then the ester, 19, (1 g, 2.9 mmol). The mixture was heated to 63° C. for 5 hours. The solution was then treated with acetic acid (2 mL) and heated at 63° C. for an additional 18 hours. The solvents were removed by evaporation and the residue was partitioned between ethyl acetate (200 mL) and brine (100 mL). The organic layer was washed with brine (100 mL). The organic layer was dried over $MgSO_4$ and evaporated to dryness. The crude material was purified by flash chromatography (35 g silica gel, 25% ethyl acetate/hexane). The butenolide was isolated by evaporation of the appropriate fractions 0.489 g (39%) as a white foam. The butenolide was identified by $^1H$ NMR, IR, MS, $[M+H]^+=431$ Da., and microanalysis.

EXAMPLE 91

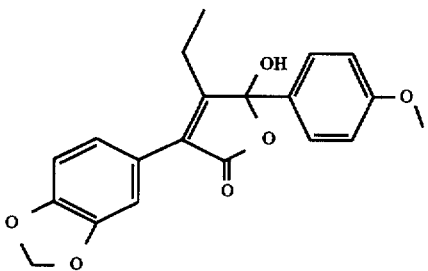

3-Benzo[1,3]dioxol-5-yl-4-ethyl-5-hydroxy-5-(4-methoxyphenyl)-5H-furan-2-one

To DMF (5 mL) and methanol (1 mL) was added sodium methoxide (0.157 g, 2.9 mmol) and stirred to dissolve. To this was added acetaldehyde (2.5 g, 62.5 mmol) then the ester, 19, (1 g, 2.9 mmol). The mixture was stirred at 0° C. for 4 hours, then warmed to room temperature for 16 hours. The solution was then treated with acetic acid (2 mL) and refluxed for an additional 18 hours. The solvents were removed by evaporation and the residue was partitioned between ethyl acetate (200 mL) and 1N HCl (100 mL), washed with brine (100 mL). The organic layer was then dried over $MgSO_4$ and evaporated to dryness. The crude material was purified by flash chromatography (30 g silica gel, 22% ethyl acetate/hexane). The butenolide was isolated by evaporation of the appropriate fractions to give 0.1 g (10%) as a yellow foam. The butenolide was identified by $^1H$ NMR, IR, MS, $[M+H]^+=355$ Da.

EXAMPLE 92

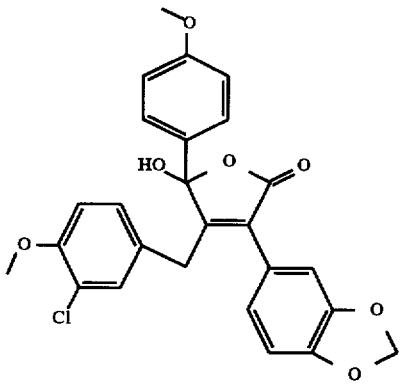

3-Benzo[1,3]dioxol-5-yl-4-(3-chloro-4-methoxybenzyl)-5-hydroxy-5-(4-methoxyphenyl)-5H-furan-2-one To methanol was added sodium metal (0.2 g, 8.7 mmol) and stirred to dissolve. To this was added 3-chloro-4-methoxybenzaldehyde (1.65 g, 8.8 mmol) then the ester, 19, (3 g, 8.8 mmol). The mixture was heated to reflux for 16 hours. The solution was then treated with acetic acid (2 mL) and refluxed for an additional 24 hours. The solvents were removed by evaporation and the residue was partitioned between ethyl acetate (200 mL) and an aqueous saturated sodium bicarbonate (150 mL). The organic layer was washed with aqueous saturated sodium bicarbonate (150 mL), then brine (100 mL). The organic layer was then dried over $MgSO_4$ and evaporated to dryness. The crude material was purified by flash chromatography (40 g silica gel, 25% ethyl acetate/hexane). The butenolide was isolated by evaporation of the appropriate fractions and crystallized from isopropyl ether-methylene chloride to give 1.71 g (41%) as white crystals. The butenolide was identified by $^1H$ NMR, IR, MS, $[M+H]^+=481$ Da., and microanalysis.

EXAMPLE 93

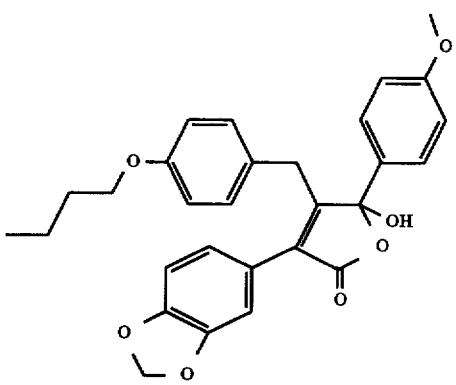

3-Benzo[1,3]dioxol-5-yl-4-(4-butoxybenzyl)-5-hydroxy-5-(4-methoxyphenyl)-5H-furan-2-one To methanol (10 mL) was added sodium metal (0.22 g, 9.6 mmol) and stirred to dissolve. To this was added 4-butoxybenzaldehyde (1.7 g, 9.6 mmol) then the ester, 19, (3 g, 8.8 mmol). The mixture was heated to reflux for 24 hours. The solution was then treated with acetic acid (3 mL) and refluxed for an additional 24 hours. The solvents were removed by evaporation and the residue was partitioned between ethyl acetate (300 mL) and an aqueous saturated sodium bicarbonate (200 mL). The organic layer was washed with aqueous saturated sodium bicarbonate (200 mL), then brine (100 mL). The organic layer was then dried over $MgSO_4$ and evaporated to dryness. The crude material was purified by flash chromatography (40 g silica gel, 25% ethyl acetate/hexane). The butenolide was isolated by evaporation of the appropriate fractions and crystallized from isopropyl ether-methylene chloride to give 2 g (46%) as white crystals. The butenolide was identified by $^1H$ NMR, IR, MS, $[M+H]^+=489$ Da., and microanalysis.

EXAMPLE 94

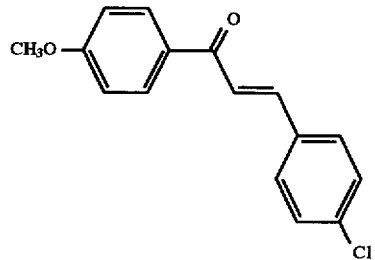

To 4-methoxyacetophenone (21.4 g, 142 mmol) in absolute ethanol (35 mL) in an erlenmeyer was added 4-chlorobenzaldehyde (20 g, 142 mmol). The solution swirled while 10% sodium hydroxide (6 mL) added. The mixture swirled for 1 hour and allowed to stand to precipitate. The solid was collected by filtration and washed with 80% ethanol (100 mL). The solid was dried in vacuo giving 35 g (90%) of a yellow solid which was identified by $^1$H NMR, IR, MS, and microanalysis.

EXAMPLE 95

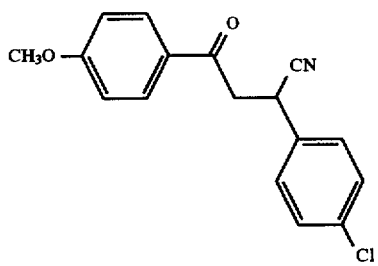

To the chalcone, 94, (35 g, 129 mmol) in 2-ethoxyethanol (200 mL) at 105° C. was added acetic acid (8.1 mL) followed by slow addition of potassium cyanide (12.53 g, 193 mmol) in water (25 mL). The solution was stirred at 105° C. for 0.25 hour. The solution was cooled. Product crystallized. Filtered to collect the solid. The solid was washed repeatedly with 70% ethanol (200 mL), air dried, and then dried in vacuo to give the nitrile, 29.62 g (77%). The nitrile was identified by $^1$H NMR, IR, MS, and microanalysis.

EXAMPLE 96

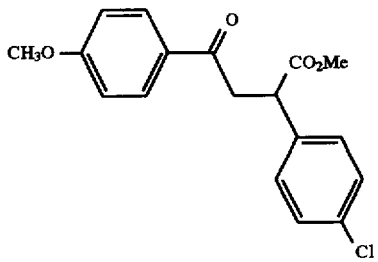

To the nitrile, 95, (5 g, 16.7 mmol) was added methanol (180 mL). The mixture was saturated with HCl (g) and stirred at room temperature until no nitrile remained by thin-layer chromatography. The solvent was removed at reduced pressure and the residue was partitioned between ethyl acetate (200 mL) and water (100 mL). The organic phase was washed with brine (100 mL) and dried over MgSO$_4$. The solvent was removed at reduced pressure and the residue was dissolved with hot methanol. This solution was treated with charcoal and filtered. The ester, 96, 4.2 g (76%) crystallized upon cooling the filtrate to room temperature. The ester was identified by $^1$H NMR, IR, MS, and microanalysis.

EXAMPLE 97

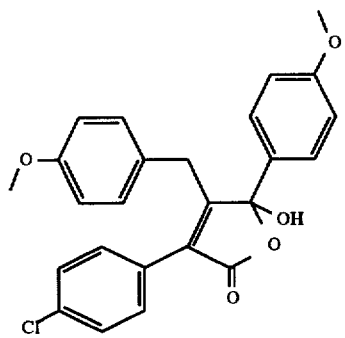

3-(4-Chlorophenyl)-5-hydroxy-4-(4-methoxybenzyl)-5-(4-methoxyphenyl)-5H-furan-2-one To methanol (10 mL) was added sodium metal (0.15 g, 6.6 mmol) and stirred to dissolve. To this was added p-anisaldehyde (0.9 g, 6.6 mmol) then the ester, 96, (2 g, 6 mmol). The mixture was heated to reflux for 24 hours. The solution was then treated with acetic acid (4 mL) and refluxed for an additional 24 hours. The solvents were removed by evaporation and the residue was partitioned between ethyl acetate (300 mL) and an aqueous saturated sodium bicarbonate (150 mL). The organic layer was washed with aqueous saturated sodium bicarbonate (150 mL), then brine (100 mL). The organic layer was then dried over MgSO$_4$ and evaporated to dryness. The crude material was purified by flash chromatography (40 g silica gel, 25% ethyl acetate/hexane). The butenolide was isolated by evaporation of the appropriate fractions and crystallized from isopropyl ether-methylene chloride to give 1.5 g (60%) as white crystals. The butenolide was identified by $^1$H NMR, IR, MS, [M+H]$^+$=437 Da., and microanalysis.

EXAMPLE 98

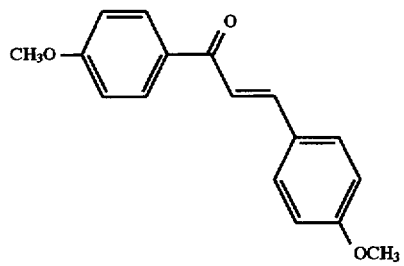

To 4-methoxyacetophenone (13 g, 86 mmol) in absolute ethanol (70 mL) in an erlenmeyer was added p-anisaldehyde (11.78 g, 86 mmol). The solution swirled while 10% sodium hydroxide (8 mL) added. The mixture swirled for 10 minutes and allowed to stand to precipitate. The solid was collected by filtration and washed with 80% ethanol (100 mL). The solid was dried in vacuo giving 14.66 g (63%) of a solid which was identified by $^1$H NMR, IR, MS, and microanalysis.

EXAMPLE 99

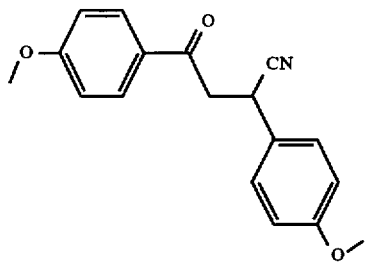

To the chalcone, 98, (14.66 g, 54.7 mmol) in 2-ethoxyethanol (90 mL) at 55° C. was added acetic acid (3.3 mL) followed by slow addition of potassium cyanide (5.34 g, 82 mmol) in water (15 mL). The solution was stirred at 105° C. for 0.25 hour. The solution was cooled, product crystallized. The mixture was then filtered to collect the solid. The solid was washed repeatedly with 70% ethanol (200 mL), air dried, and then dried in vacuo to give the nitrile 14.42 g (89%). The nitrile was identified by $^1$H NMR, IR, MS, and microanalysis.

EXAMPLE 100

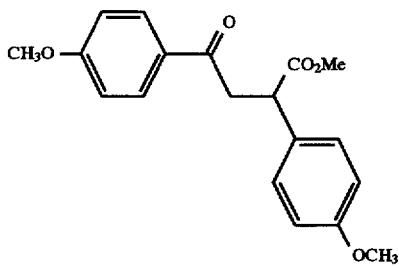

To the nitrile, 99, (10.1 g, 34.2 mmol) was added methanol (200 mL). The mixture was saturated with HCl (g) and stirred at room temperature until no nitrile remained by thin-layer chromatography. The solvent was removed at reduced pressure and the residue was partitioned between ethyl acetate (200 mL) and water (100 mL). The organic phase was washed with brine (100 mL) and dried over MgSO$_4$. The solvent was removed at reduced pressure and the residue was dissolved with hot methanol. This solution was treated with charcoal and filtered. The ester, 100, 1.76 g (16%) crystallized upon cooling the filtrate to room temperature. The ester was identified by $^1$H NMR, IR, MS, and microanalysis.

EXAMPLE 101

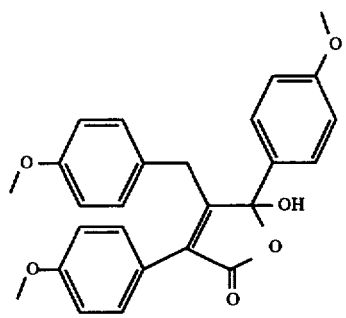

5-Hydroxy-4-(4-methoxybenzyl)-3,5-bis-(4-methoxyphenyl)-5H-furan-2-one

To methanol (5 mL) was added sodium metal (0.12 g, 5.2 mmol) and stirred to dissolve. To this was added p-anisaldehyde (0.72 g, 5.3 mmol) then the ester, 100, (1.5 g, 4.6 mmol). The mixture was heated to reflux for 18 hours. The solution was then treated with acetic acid (2 mL) and refluxed for an additional 24 hours. The solvents were removed by evaporation and the residue was partitioned between ethyl acetate (200 mL) and an aqueous saturate sodium bicarbonate (200 mL). The organic layer was washed with aqueous saturated sodium bicarbonate (200 mL), then brine (100 mL). The organic layer was then dried over MgSO$_4$ and evaporated to dryness. The crude material was purified by flash chromatography (40 g silica gel, 25% ethyl acetate/hexane). The butenolide was isolated by evaporation of the appropriate fractions and crystallized from isopropyl ether-methylene chloride to give 0.63 g (32%) as white crystals. The butenolide was identified by $^1$H NMR, IR, MS, [M+H]$^+$=433 Da., and microanalysis.

EXAMPLE 102

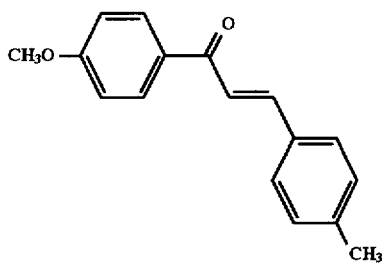

To 4-methoxyacetophenone (12.23 g, 80 mmol) in absolute ethanol (40 mL) in an erlenmeyer was added tolualdehyde (9.6 g, 80 mmol). The solution swirled while 10% sodium hydroxide (8 mL) added. The mixture swirled for 1 hour and allowed to stand to precipitate. The solid was collected by filtration and washed with 80% ethanol (100 mL). The solid was dried in vacuo giving 19 g (92%) solid which was identified by $^1$H NMR, IR, MS, and microanalysis.

EXAMPLE 103

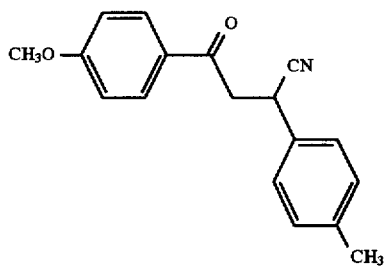

To the chalcone, 102, (25.4 g, 100 mmol) in 2-ethoxyethanol (90 mL) at 105° C. was added acetic acid (6.4 mL) followed by slow addition of potassium cyanide (9.83 g, 150 mmol) in water (20 mL). The solution was stirred at 105° C. for 0.25 hour. The solution was cooled, product crystallized out. The mixture was then filtered to collect the solid. The solid was washed repeatedly with 70% ethanol (200 mL), air dried, and then dried in vacuo to give the nitrile 24 g (85%). The nitrile was identified by $^1$H NMR, IR, MS, and microanalysis.

EXAMPLE 104

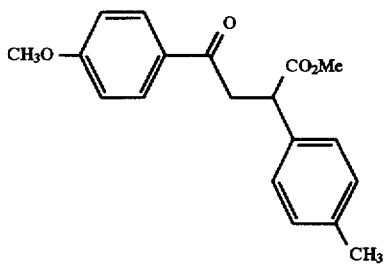

To the nitrile, 103, (10.7 g, 38.4 mmol) was added methanol (200 mL). The mixture was saturated with HCl (g) and stirred at room temperature until no nitrile remained by thin-layer chromatography. The solvent was removed at reduced pressure and the residue was partitioned between ethyl acetate (200 mL) and water (100 mL). The organic phase was washed with brine (100 mL) and dried over MgSO$_4$. The solvent was removed at reduced pressure and the residue was dissolved with hot methanol. This solution was treated with charcoal and filtered. The ester, 104, 6.25 g (52%) crystallized upon cooling the filtrate to room temperature. The ester was identified by $^1$H NMR, IR, MS, and microanalysis.

EXAMPLE 105

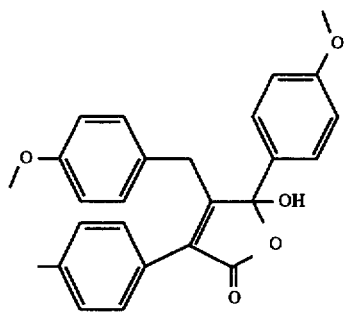

5-Hydroxy-4-(4-methoxybenzyl)-5-(4-methoxyphenyl)-3-p-tolyl-5H-furan-2-one

To methanol (8 mL) was added sodium metal (0.16 g, 7 mmol) and stirred to dissolve. To this was added p-anisaldehyde (0.96 g, 7 mmol) then the ester, 104, (2 g, 6.4 mmol). The mixture was heated to reflux for 18 hours. The solution was then treated with acetic acid 4 mL and refluxed for an additional 24 hours. The solvents were removed by evaporation and the residue was partitioned between ethyl acetate (200 mL) and an aqueous saturated sodium bicarbonate (100 mL). The organic layer was washed with aqueous saturated sodium bicarbonate (100 mL), then brine (100 mL). The organic layer was then dried over MgSO$_4$ and evaporated to dryness. The crude material was purified by flash chromatography (40 g silica gel, 25% ethyl acetate/hexane). The butenolide was isolated by evaporation of the appropriate fraction and crystallized from isopropyl ether-methylene chloride to give 1 g (37.5%) as white crystals. The butenolide was identified by $^1$H NMR, IR, MS, [M+H]$^+$=417 Da., and microanalysis.

EXAMPLE 106

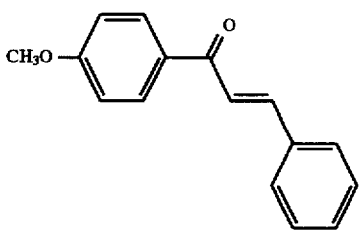

To 4-methoxyacetophenone (12 g, 80 mmol) in absolute ethanol (40 mL) in an erlenmeyer was added benzaldehyde (8.13 g, 80 mmol). The solution swirled while 10% sodium hydroxide (5 mL) added. The mixture swirled for 10 minutes and allowed to stand to precipitate. The solid was collected by filtration and washed with 80% ethanol (100 mL). The solid was dried in vacuo giving 15.34 g (80%) of a white solid which was identified by $^1$H NMR, IR, MS, and microanalysis.

EXAMPLE 107

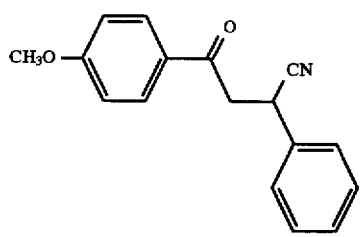

To the chalcone, 106, (15.34 g, 64 mmol) in 2-ethoxyethanol (90 mL) at 105° C. was added acetic acid (4.1 mL) followed by slow addition of potassium cyanide (6.3 g, 96.6 mmol) in water (15 mL). The solution was stirred at 105° C. for 0.25 hour. The solution was cooled, product crystallized. The mixture was then filtered to collect the solid. The solid was washed repeatedly with 70% ethanol (200 mL), air dried, and then dried in vacuo to give the nitrile 11.6 g (66%). The nitrile was identified by $^1$H NMR, IR, MS, and microanalysis.

EXAMPLE 108

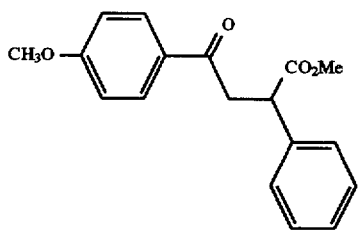

To the nitrile, 107, (10.5 g, 39.6 mmol) was added methanol (200 mL). The mixture was saturated with HCl (g) and stirred at room temperature until no nitrile remained by thin-layer chromatography. The solvent was removed at reduced pressure and the residue was partitioned between ethyl acetate (200 mL) and water (200 mL). The organic phase was washed with brine (100 mL) and dried over MgSO$_4$. The solvent was removed at reduced pressure and the residue was dissolved with hot methanol. This solution was treated with charcoal and filtered. The ester, 108, 4.8 g (40%) crystallized upon cooling the filtrate to room temperature. The ester was identified by $^1$H NMR, IR, MS, and microanalysis.

EXAMPLE 109

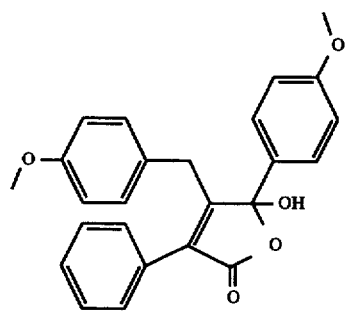

5-Hydroxy-4-(4-methoxybenzyl)-5-(4-methoxyphenyl)-3-phenyl-5H-furan-2-one

To methanol (8 mL) was added sodium metal (0.18 g, 8.2 mmol) and stirred to dissolve. To this was added p-anisaldehyde (0.96 g, 8.2 mmol) then the ester, 108, (1.9 g, 6.3 mmol). The mixture was heated to reflux for 18 hours. The solution was then treated with acetic acid (4 mL) and refluxed for an additional 24 hours. The solvents were removed by evaporation and the residue was partitioned between ethyl acetate (300 mL) and an aqueous saturated sodium bicarbonate (150 mL). The organic layer was washed with aqueous saturated sodium bicarbonate (150 mL), then brine (100 mL). The organic layer was then dried over MgSO$_4$ and evaporated to dryness. The crude material was purified by flash chromatography (40 g silica gel, 25% ethyl acetate/hexane). The butenolide was isolated by evaporation of the appropriate fractions and crystallized from isopropyl ether-methylene chloride to give 1.03 g (40%) as a yellow foam. The butenolide was identified by $^1$H NMR, IR, MS, [M+H]$^+$=403 Da., and microanalysis.

EXAMPLE 110

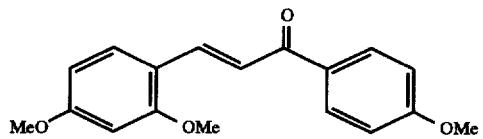

To 2,4-dimethoxybenzaldehyde (12.17 g, 72 mmol) in absolute ethanol (30 mL) in an erlenmeyer was added 4-methoxyacetophenone (10.0 g, 66.6 mmol). The solution swirled while 10% sodium hydroxide (4.5 mL) added. The mixture swirled for 10 minutes and allowed to stand to precipitate. The solid was collected by filtration and washed with 80% ethanol (70 mL). The solid was dried in vacuo giving 17.1 g (86%) of a yellow solid which was identified by $^1$H NMR, IR, and MS.

EXAMPLE 111

To the chalcone, 110, (17.0 g, 57 mmol) in ethanol:chloroform 5:1 (240 mL) at 55° C. was added acetic acid (6.5 mL) followed by slow addition of potassium cyanide (9.26 g, 143 mmol) in water (20 mL). The solution was stirred at 55° C. for 48 hours. The chloroform was evaporated and the solution was allowed to stand 14 hours during which time a solid was deposited. The solid was collected by filtration, then dissolved in ethyl acetate/dichloromethane and decolorized with norite. Filtration and evaporation gave a tan solid 13.0 g (70%). The nitrile was identified by $^1$H NMR, IR, and MS.

EXAMPLE 112

To the nitrile, 111, (2.0 g, 5.6 mmol) was added methanol (20 mL). The mixture was saturated with HCl (g) and heated to 45° C. until no nitrile remained, by thin-layer chromatography. The solution was cooled and water was added. Extraction with ethyl acetate provided a green oil that was chromatographed on silica gel (2:1, hexane/ethyl acetate) to give the ester, 945 mg (47%), as a colorless solid.

EXAMPLE 113

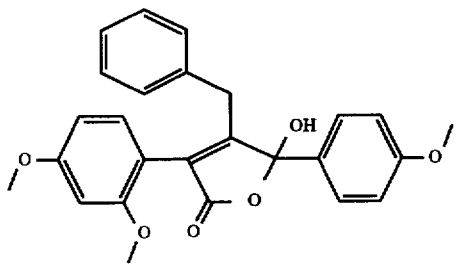

4-Benzyl-3-(2,4-dimethoxyphenyl)-5-hydroxy-5-(4-mehoxyphenyl)-5H-furan-2-one

To methanol (5 mL) was added sodium metal (67 mg, 2.9 mmol) and stirred to dissolve. To this was added benzaldehyde (300 mg, 2.9 mmol) then the ester, 112, (950 mg, 2.65 mmol). The mixture was heated to reflux for 10 hours. The solution was split, and half then treated with acetic acid (5 mL) and refluxed for an additional 30 hours. The solvents were removed by evaporation. The crude product was then purified by flash chromatography (200 g silica gel, 3% methanol/dichloromethane). The butenolide was isolated by evaporation of the appropriate fractions to give 118 mg (10%) as a solid. The butenolide was identified by $^1$H NMR, IR, MS, [M+H]$^+$=433 Da., and microanalysis.

EXAMPLE 114

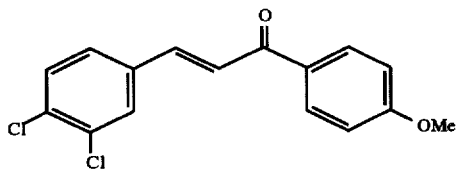

To 3,4-dichlorobenzaldehyde (18.3 g, 105 mmol) in absolute ethanol (40 mL) in an erlenmeyer was added 4-methoxyacetophenone (15.0 g, 100 mmol). The solution swirled while 10% sodium hydroxide (7 mL) added. The mixture swirled for 10 minutes and allowed to stand to precipitate. The solid was collected by filtration and washed with 80% ethanol (70 mL). The solid was dried in vacuo giving 31.7 g (103%) of a light yellow solid which was identified by $^1$H NMR, IR, and MS.

EXAMPLE 115

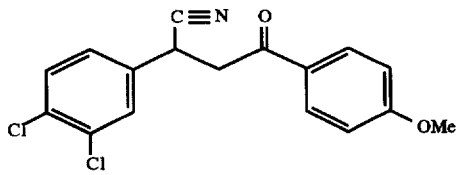

To the chalcone, 114, (31.7 g, 103 mmol) in ethanol:chloroform 5:1 (420 mL) at 55° C. was added acetic acid (11.8 mL) followed by slow addition of potassium cyanide (16.8 g, 255 mmol) in water (50 mL). The solution was stirred at 60° C. for 6 hours. The solution was cooled and the chloroform removed on a rotovap, water (100 mL) was added, and the solution was cooled to 0° C. The resulting precipitate was collected by filtration, air dried, and then dried in vacuo to give the nitrile 33.6 g (98%) as a light brown solid. The nitrile was identified by $^1$H NMR, IR, and MS.

EXAMPLE 116

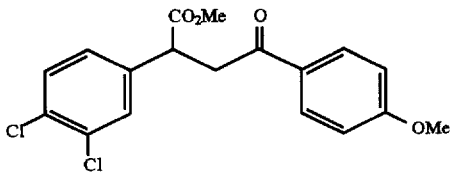

To the nitrile, 115, (16.0 g, 47.9 mmol) was added methanol (300 mL). The mixture was saturated with HCl (g) and heated to 45° C. until no nitrile remained, by thin-layer chromatography. The solution was cooled and treated with water (60 mL). The gummy precipitate was taken up in dichloromethane and washed with water and brine. After drying over magnesium sulfate, the solvent was evaporated to give a brown foam. Chromatography SiO$_2$ (4:1, dichloromethane:hexane) gave a solid, the ester 8.75 g (49%) which was identified by $^1$H NMR, IR, and MS.

EXAMPLE 117

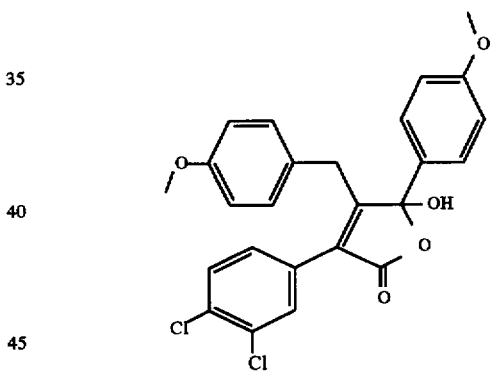

3-(3,4-Dichlorophenyl)-5-hydroxy-4-(4-methoxybenzyl)-5-(4-methoxyphenyl)-5H-furan-2-one To methanol (10 mL) was added sodium metal (0.14 g, 6.1 mmol) and stirred to dissolve. To this was added p-anisaldehyde (0.84 g, 6.1 mmol) then the ester, 116, (2 g, 5.5 mmol). The mixture was heated to reflux for 20 hours. The solution was then treated with acetic acid (4 mL) and refluxed for an additional 24 hours. The solvents were removed by evaporation and the residue was partitioned between ethyl acetate (200 mL) and an aqueous saturated sodium bicarbonate (100 mL). The organic layer was washed with aqueous saturated sodium bicarbonate (100 mL), then brine (100 mL). The organic layer was then dried over MgSO$_4$ and evaporated to dryness. The crude material was purified by flash chromatography (40 g silica gel, 25% ethyl acetate/hexane). The butenolide was isolated by evaporation of the appropriate fractions and crystallized from isopropyl ether-methylene chloride to give 1.4 g (55%) as white crystals. The butenolide was identified by $^1$H NMR, IR, MS, [M+H]$^+$=472 Da., and microanalysis.

EXAMPLE 118

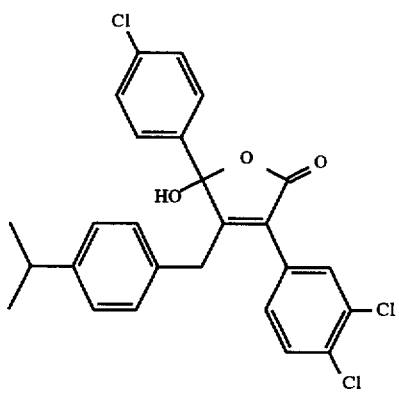

5-(4-Chlorophenyl)-3-(3,4-dichlorophenyl)-5-hydroxy-4-(4-isopropylbenzyl)-5H-furan-2-one

To methanol (5 mL) was added sodium metal (68 mg, 2.9 mmol) and stirred to dissolve. To this was added cuminaldehyde (0.45 mL, 2.9 mmol) then the ester, 60, (1.0 g, 2.7 mmol). The mixture was heated to reflux for 16 hours. The solution was then treated with acetic acid (7 mL) and refluxed for an additional 6 hours. The solvents were removed by evaporation. The crude product was then purified by flash chromatography (250 g silica gel, 2% ethyl acetate/dichloromethane). The butenolide was isolated by evaporation of the appropriate fractions to give 840 mg (65%) as a colorless foam. The butenolide was identified by $^1$H NMR, IR, MS, [M+H]$^+$=488 Da., and microanalysis.

EXAMPLE 119

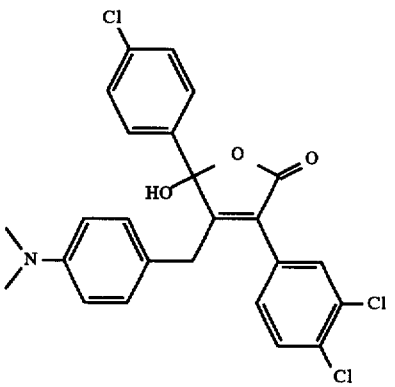

5-(4-Chlorophenyl)-3-(3,4-dichlorophenyl)-4-(4-dimethylaminobenzyl)-5-hydroxy-5H-furan-2-one

To methanol (5 mL) was added sodium metal (68 g, 2.9 mmol) and stirred to dissolve. To this was added 4-(dimethylamino)benzaldehyde (440 mg, 2.9 mmol) then the ester, 60, (1.0 g, 2.7 mmol). The mixture was heated to reflux for 16 hours. The solution was then treated with acetic acid (7 mL) and refluxed an additional 6 hours. The solvents were removed by evaporation. The crude product was then purified by flash chromatography (250 g silica gel, 4% ethyl acetate/dichloromethane). The butenolide was isolated by evaporation of the appropriate fractions to give 290 mg (22%) as a light yellow foam. The butenolide was identified by $^1$H NMR, IR, MS, [M+H]$^+$=489 Da., and microanalysis.

EXAMPLE 120

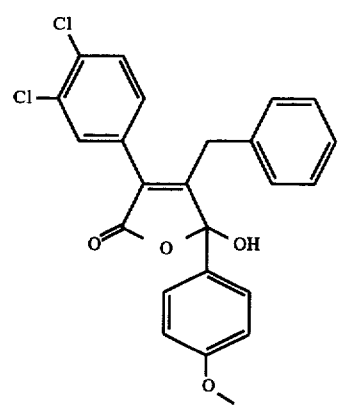

4-Benzyl-3-(3,4-dichlorophenyl)-5-hydroxy-5-(4-methoxyphenyl)-5H-furan-2-one

To methanol (5 mL) was added sodium metal (35 mg, 1.5 mmol) and stirred to dissolve. To this was added benzaldehyde (152 μL, 1.5 mmol) then the ester, 115, (500 mg, 1.36 mmol). The mixture was heated to reflux for 4 hours. The solution was then treated with acetic acid (7 mL) and refluxed an additional 16 hours. The solvents were removed by evaporation. The crude product was then purified by flash chromatography (250 g silica gel, 4% ethyl acetate/dichloromethane). The butenolide was isolated by evaporation of the appropriate fractions to give 479 mg (80%) as a colorless foam. The butenolide was identified by $^1$H NMR, IR, MS, [M +H]$^+$=442 Da., and microanalysis.

EXAMPLE 121

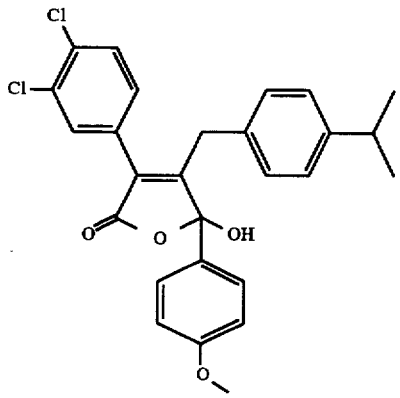

3-(3,4-Dichlorophenyl)-5-hydroxy-4-(4-isopropylbenzyl)-5-(4-methoxyphenyl)-5H-furan-2-one

To methanol (5 mL) was added sodium metal (35 mg, 1.5 mmol) and stirred to dissolve. To this was added cuminaldehyde (228 μL, 1.5 mmol) then the ester, (500 mg, 1.36 mmol). The mixture was heated to reflux for 4 hours. The solution was then treated with acetic acid (7 mL) and refluxed an additional 16 hours. The solvents were removed by evaporation. The crude product was then purified by flash chromatography (250 g silica gel, 4% ethyl acetate/dichloromethane). The butenolide was isolated by evaporation of the appropriate fractions to give 489 mg (74%) as a colorless foam. The butenolide was identified by $^1$H NMR, IR, MS, [M+H]$^+$=484 Da., and microanalysis.

EXAMPLE 122

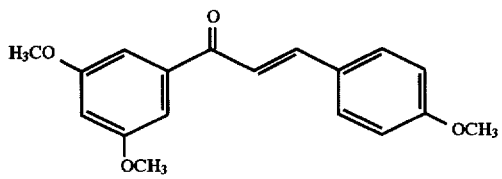

To 3,5-dimethoxyacetophenone (15.0 g, 99.88 mmol) in absolute ethanol (70 mL) in an erlenmeyer was added 4-methoxybenzaldehyde (23.24 g, 139.83 mmol). The solution swirled while 10% sodium hydroxide (10 mL) added. The mixture swirled for 1 hour and allowed to stand to precipitate. The solid was collected by filtration and washed with 80% ethanol (2×200 mL). The solid was dried in vacuo giving 28.5 g (95%) of a pale yellow solid which was identified by $^1$H NMR.

EXAMPLE 123

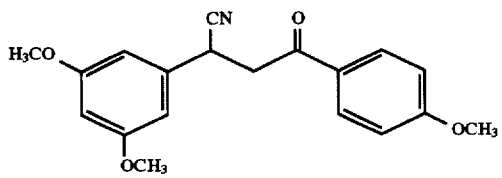

To the chalcone, 122, (10 g, 33.52 mmol) in 2-ethoxyethanol (50 mL) at 55° C. was added acetic acid (3.80 mL) followed by slow addition of potassium cyanide (5.45 g, 83.80 mmol) in water (10 mL). The solution was stirred at 105° C. for 10 hours. The solution was cooled and evaporated to dryness. The crude product was then purified by flash chromatography (500 g silica gel eluent, 20% ethyl acetate/hexane). Dried in vacuo to give the nitrile, 7.60 g (69%) as a dark green solid. The nitrile was identified by $^1$H NMR.

EXAMPLE 124

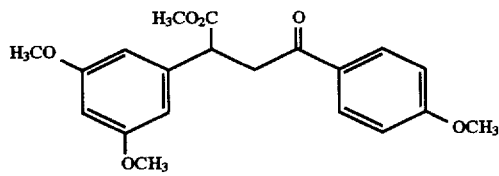

To the nitrile, 123, (3 g, 9.22 mmol) was added methanol (30 mL). The mixture was saturated with HCl (g) and heated to 80° C. until no nitrile remained, by thin-layer chromatography. The solution was cooled. The solution was evaporated to dryness, then purified on 300 g SiO$_2$ eluent 15% ethyl acetate/hexane. This gave the ester 1.10 g (33%) as a light brown semisolid which was identified by $^1$H NMR, IR, MS, and microanalysis.

EXAMPLE 125

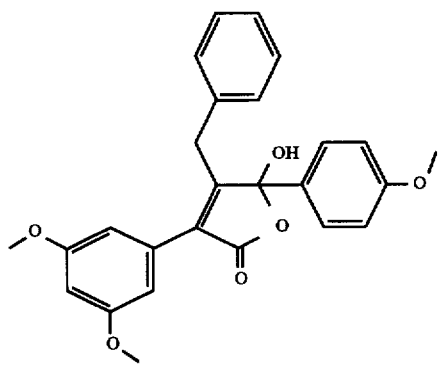

4-Benzyl-3-(3,5-dimethoxyphenyl)-5-hydroxy-5-(4-methoxyphenyl)-5H-furan-2-one

To methanol (5 mL) was added sodium metal (0.021 g, 0.92 mmol) and stirred to dissolve. To this was added benzaldehyde (0.10 g, 0.92 mmol) then the ester, 124, (0.3 g, 0.84 mmol). The mixture was heated to reflux for 3 hours. The solution was then treated with acetic acid (5 mL) and refluxed an additional 12 hours. The solvents were removed by evaporation. The crude product was then purified by flash chromatography (170 g silica gel, 20% ethyl acetate/hexane). The butenolide was isolated by evaporation of the appropriate fractions to give 0.20 g (55%) as a light brown solid. The butenolide was identified by $^1$H NMR, IR, MS, [M+H]$^+$=433 Da., and microanalysis.

EXAMPLE 126

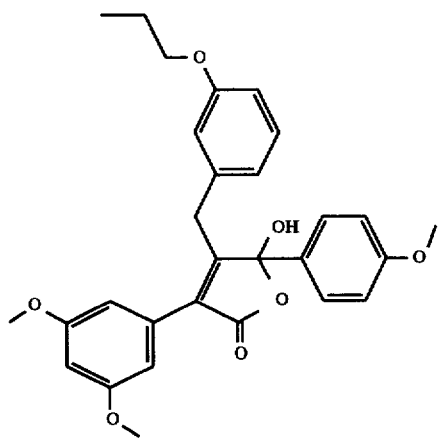

3-(3,5-Dimethoxyphenyl)-5-hydroxy-5-(4-methoxyphenyl)-4-(3-propoxybenzyl)-5H-furan-2-one To methanol (5 mL) was added sodium metal (0.03 g, 1.20 mmol) and stirred to dissolve. To this was added 3-O-propylbenzaldehyde (0.18 g, 1.10 mmol) then the ester, 124, (0.35 g, 0.98 mmol). The mixture was heated to reflux for 10 hours. The solution was then treated with acetic acid (5 mL) and refluxed an additional 5 hours. The solvents were removed by evaporation. The crude product was then purified by flash chromatography (170 g silica gel, 15% ethyl acetate/hexane). The butenolide was isolated by evaporation of the appropriate fractions to give 0.26 g (54%) as an amorphous glass. The butenolide was identified by $^1$H NMR, IR, MS, [M+H]$^+$=491 Da., and HPLC=97.97%.

EXAMPLE 127

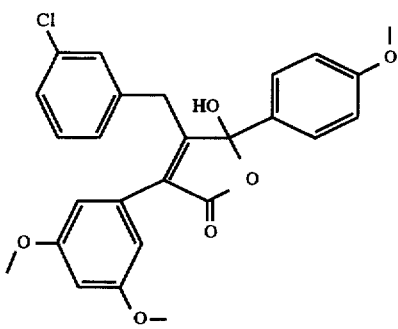

4-(3-Chlorobenzyl)-3-(3,5-dimethoxyphenyl)-5-hydroxy-5-(4-methoxyphenyl)-5H-furan-2-one To methanol (5 mL) was added sodium metal (0.017 g, 0.75 mmol) and stirred to dissolve. To this was added 3-chlorobenzaldehyde (0.078 g, 0.55 mmol) then the ester, 124, (0.18 g, 0.5 mmol). The mixture was heated to reflux for 10 hours. The solution was then treated with acetic acid (5 mL) and refluxed an additional 8 hours. The solvents were removed by evaporation. The crude product was then purified by flash chromatography (170 g silica gel, 15% ethyl acetate/hexane). The butenolide was isolated by evaporation of the appropriate fractions to give 0.13 g (55%) as a solid. The butenolide was identified by $^1$H NMR, IR, MS, $[M+H]^+$=467 Da., and HPLC=98.76%.

EXAMPLE 128

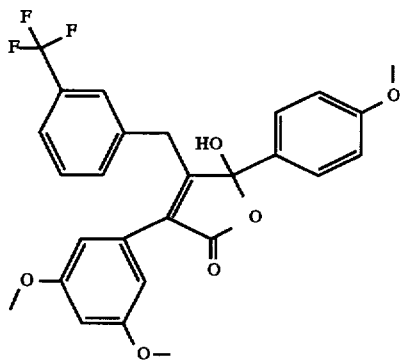

3-(3,5-Dimethoxyphenyl)-5-hydroxy-5-(4-methoxyphenyl)-4-(3-trifluoromethylbenzyl)-5H-furan-2-one To methanol (5 mL) was added sodium metal (0.014 g, 0.614 mmol) and stirred to dissolve. To this was added 3-trifluoromethylbenzaldehyde (0.107 g, 0.614 mmol) then the ester, 124, (0.20 g, 0.56 mmol). The mixture was heated to reflux for 10 hours. The solution was then treated with acetic acid (5 mL) and refluxed an additional 8 hours. The solvents were removed by evaporation. The crude product was then purified by flash chromatography (170 g silica gel, 15% ethyl acetate/hexane). The butenolide was isolated by evaporation of the appropriate fractions to give 0.15 g (53%) as a solid. The butenolide was identified by $^1$H NMR, IR, MS, $[M+H]^+$=501 Da., and HPLC=99.5%.

EXAMPLE 129

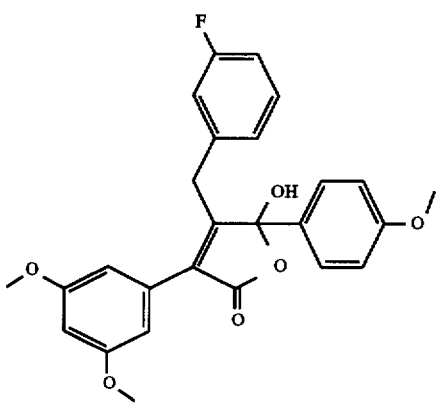

3-(3,5-Dimethoxphenyl)-4-(3-fluorobenzyl)-5-hydroxy-5-(4-methoxyphenyl)-5H-furan-2-one To methanol (5 mL) was added sodium metal (0.023 g, 1.00 mmol) and stirred to dissolve. To this was added 3-fluorobenzaldehyde (0.114 g, 0.92 mmol) then the ester, 124, (0.30 g, 0.837 mmol). The mixture was heated to reflux for 10 hours. The solution was then treated with acetic acid (5 mL) and refluxed an additional 12 hours. The solvents were removed by evaporation and the residue was partitioned between ethyl acetate and water. The organic phase was separated and dried over magnesium sulfate and evaporated to dryness. The crude product was then purified by flash chromatography (170 g silica gel, eluent 20% ethyl acetate/hexane). The butenolide was isolated by evaporation of the appropriate fractions to give 0.24 g (63%) as a white solid. The butenolide was identified by $^1$H NMR, IR, MS, $[M+H]^+$=451 Da., and microanalysis.

EXAMPLE 130

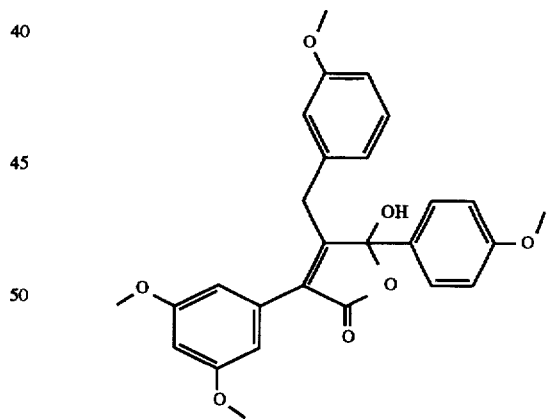

3-(3,5-Dimethoxyphenyl)-5-hydroxy-4-(3-methoxybenzyl)-5-(4-methoxyphenyl)-5H-furan-2-one To methanol (5 mL) was added sodium metal (0.023 g, 1.0 mmol) and stirred to dissolve. To this was added 3-methoxybenzaldehyde (0.125 g, 0.92 mmol) then the ester, 124, (0.30 g, 0.834 mmol). The mixture was heated to reflux for 10 hours. The solution was then treated with acetic acid (5 mL) and refluxed an additional 12 hours. The solvents were removed by evaporation and the residue was partitioned between ethyl acetate and water. The organic phase was separated and dried over magnesium sulfate and evaporated to dryness. The crude product was then purified by flash chromatography (170 g silica gel, 20% ethyl acetate/hexane). The butenolide was isolated by evaporation of the appropriate fractions to give 0.30 g (77%) as a solid. The butenolide was identified by ¹H NMR, IR, MS, [M+H]⁺=463 Da., and microanalysis.

EXAMPLE 131

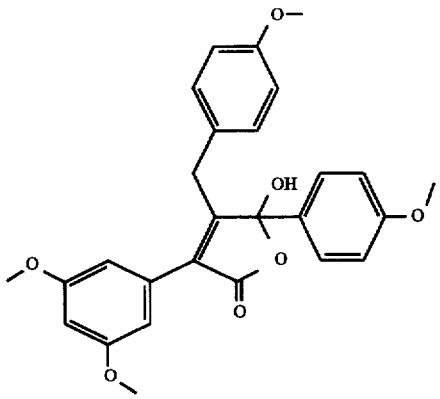

3-(3,5-Dimethoxyphenyl)-5-hydroxy-4-(4-methoxybenzyl)-5-(4-methoxyphenyl)-5H-furan-2-one To methanol (5 mL) was added sodium metal (0.023 g, 1.0 mmol) and stirred to dissolve. To this was added 4-methoxybenzaldehyde) 0.125 g, 0.92 mmol) then the ester, 124, (0.3 g, 0.837 mmol). The mixture was heated to reflux for 72 hours. The solution was then treated with acetic acid and refluxed an additional 24 hours. The solvents were removed by evaporation. The crude product was then purified by flash chromatography (170 g silica gel, 15% ethyl acetate/hexane). The butenolide was isolated by evaporation of the appropriate fractions to give 0.10 g (26%) as a solid. The butenolide was identified by ¹H NMR, IR, MS, [M+H]⁺=463 Da., and HPLC=95%.

EXAMPLE 132

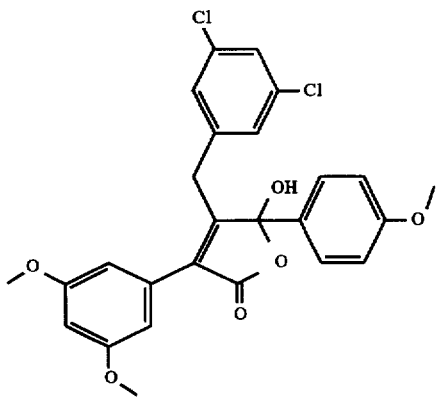

4-(3,5-Dichlorobenzyl)-3-(3,5-dimethoxyphenyl)-5-hydroxy-5-(4-methoxyphenyl)-5H-furan-2-one To methanol (5 mL) was added sodium metal (0.03 g, 1.0 mmol) and stirred to dissolve. To this was added 3,5-dichlorobenzaldehyde (0.161 g, 0.92 mmol) then the ester, 124, (0.3 g, 0.837 mmol). The mixture was heated to reflux for 3 hours. The solution was then treated with acetic acid (5 mL) and refluxed an additional 3 hours. The solvents were removed by evaporation. The crude product was then purified by flash chromatography (170 g silica gel, 20% ethyl acetate/hexane). The butenolide was isolated by evaporation of the appropriate fractions to give 0.24 g (57%) as a solid. The butenolide was identified by ¹H NMR, IR, MS, [M+H]⁺=501 Da., and microanalysis.

EXAMPLE 133

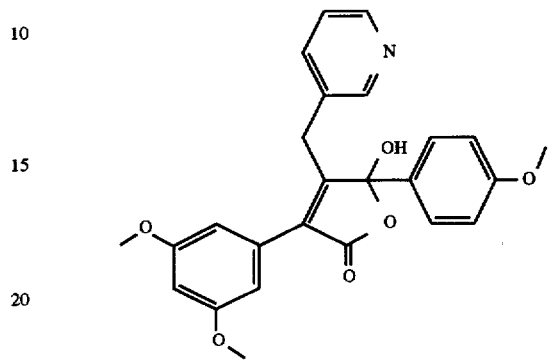

3-(3,5-Dimethoxyphenyl)-5-hydroxy-5-(4-methoxyphenyl)-4-pyridin-3methyl-5H-furan-2-one To methanol (5 mL) was added sodium metal (0.038 g, 1.68 mmol) and stirred to dissolve. To this was added 3-pyridylcarboxaldehyde (0.164 g, 1.53 mmol) then the ester, 124, (0.5 g, 1.40 mmol). The mixture was heated to reflux for 2 hours. The solution was then treated with acetic acid (5 mL) and refluxed an additional 5 hours. The solvents were removed by evaporation. The crude product was then purified by flash chromatography (170 g silica gel, 25% ethyl acetate/hexane). The butenolide was isolated by evaporation of the appropriate fractions to give 0.50 g (82%) as a solid. The butenolide was identified by ¹H NMR, IR, MS, [M+H]⁺=434 Da., and HPLC=98.74%.

EXAMPLE 134

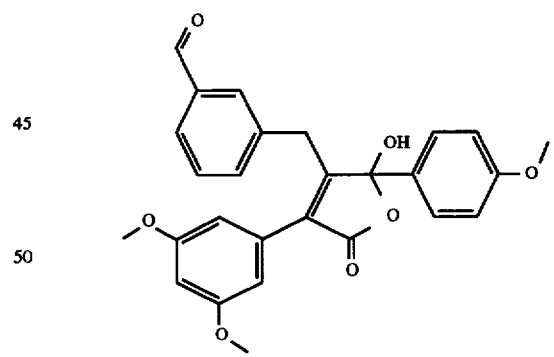

3-[4-(3,5-Dimethoxyphenyl)-2-hydroxy-2-(4-methoxyphenyl)-5-oxo-2,5-dihydrofuran-3-ylmethyl] benzaldehyde To methanol (5 mL) was added sodium metal (0.023 g, 1.00 mmol) and stirred to dissolve. To this was added 3-formylbenzaldehyde (0.225 g, 1.67 mmol) then the ester, 124, (0.30 g, 0.837 mmol). The mixture was heated to reflux for 1 hour. The solution was then treated with acetic acid (5 mL) and refluxed an additional 8 hours. The solvents were removed by evaporation. The crude product was then purified by flash chromatography (170 g silica gel, 20% ethyl acetate/hexane). The butenolide was isolated by evaporation of the appropriate fractions to give 0.28 g (72%) as a solid. The butenolide was identified by $^1$H NMR, IR, MS, [M+H]$^+$=461 Da., and microanalysis.

EXAMPLE 135

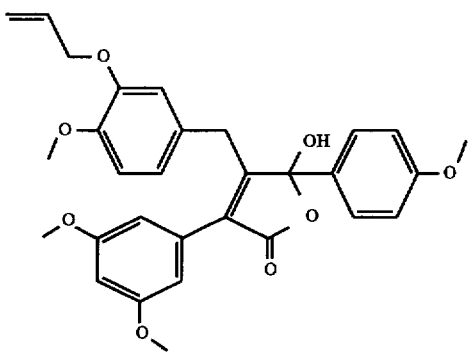

4-(3-Allyloxy-4-methoxybenzyl)-3-(3,5-dimethoxyphenyl)-5-hydroxy-5-(4-methoxyphenyl)-5H-furan-2-one To methanol (5 mL) was added sodium metal (0.023 g, 1.0 mmol) and stirred to dissolve. To this was added 3-alloxy-p-anisaldehyde (0.295 g, 1.53 mmol) then the ester, 124, (0.5 g, 1.40 mmol). The mixture was heated to reflux for 12 hours. The solution was then treated with acetic acid (5 mL) and refluxed an additional 12 hours. The solvents were removed by evaporation. The crude product was then purified by flash chromatography (170 g silica gel, 20% ethyl acetate/hexane). The butenolide was isolated by evaporation of the appropriate fractions to give 0.30 g (41%) as a solid. The butenolide was identified by $^1$H NMR, IR, MS, [M+H]$^+$=519 Da., and microanalysis.

EXAMPLE 136

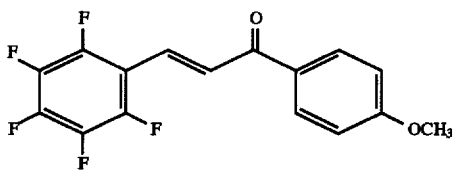

To p-methoxyacetophenone (2.74 g, 18.22 mmol) in THF (60 mL) in an erlenmeyer was added pentafluorobenzaldehyde (5.0 g, 25.50 mmol). The solution swirled while 10% sodium hydroxide (20 mL) added. The mixture swirled for 10 minutes and allowed to stand to precipitate. The solid was collected by filtration and washed with 80% ethanol (100 ml). The solid was dried in vacuo giving 2.61 g (31%) of a light brown solid which was identified by $^1$H NMR.

EXAMPLE 137

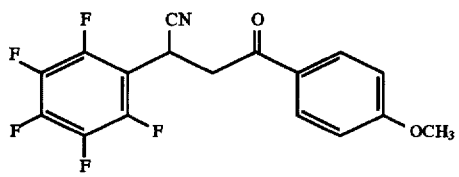

To the chalcone, 136, (2.61 g, 7.35 mmol) in 2-ethoxyethanol (30 mL) at 55° C. was added acetic acid (5 mL) followed by slow addition of potassium cyanide (1.19 g, 18.37 mmol) in water (5 mL). The solution was stirred at 105° C. for 12 hours. The solution was cooled. The solution was evaporated. The crude product was purified on 170 g of SiO$_2$ 10% ethyl acetate/hexane to give the nitrile 0.4 g (15%) as a solid. The nitrile was identified by $^1$H NMR.

EXAMPLE 138

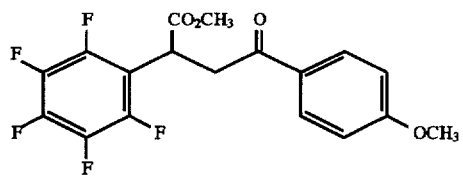

To the nitrile, 137, (0.4 g, 1.12 mmol) was added methanol (1.0 mL). The mixture was saturated with HCl (g) and heated to 45° C. until no nitrile remained, by thin-layer chromatography. The solution was cooled and treated with water (5 mL). The resultant gummy stuff oiled out, decanted the solvent, and the residue dried in vacuo. This gave the ester 0.37 g (85%) as a light brown solid which was identified by $^1$H NMR.

EXAMPLE 139

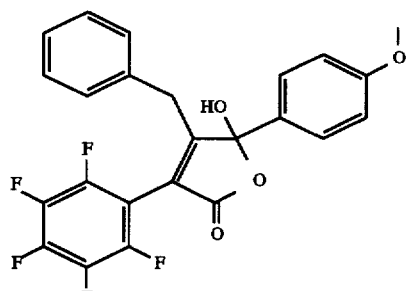

4-Benzyl-5-hydroxy-5-(4-methoxyphenyl)-3-(2,3,4,5,6-pentafluorophenyl)-5H-furan-2-one To methanol (5 mL) was added sodium metal (0.026 g, 1.14 mmol) and stirred to dissolve. To this was added benzaldehyde (0.111 g, 1.05 mmol) then the ester, 138, (0.37 g, 0.953 mmol). The mixture was heated to reflux for 12 hours. The solution was then treated with acetic acid (5 mL) and refluxed an additional 12 hours. The solvents were removed by evaporation. The crude product was then purified by flash chromatography (170 g silica gel, 20% ethyl acetate/hexane). The butenolide was isolated by evaporation of the appropriate fractions to give 0.10 g (22%) as a purple color solid. The butenolide was identified by $^1$H NMR, IR, MS, [M+H]$^+$=463 Da., and microanalysis.

EXAMPLE 140

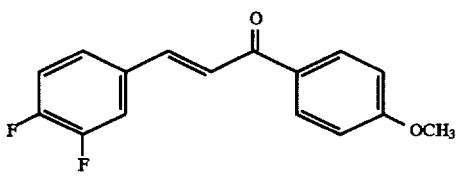

To 4-methoxyacetophenone (7.0 g, 41.13 mmol) in absolute ethanol (40 mL) in an erlenmeyer was added 3,4- difluorobenzaldehyde (8.18 g, 57.6 mmol). The solution swirled while 10% sodium hydroxide (4 mL) added. The mixture swirled for 10 minutes and allowed to stand to precipitate. The solid was collected by filtration and washed with 80% ethanol (100 mL). The solid was dried in vacuo giving 10.50 g (93%) of a pale yellow solid which was identified by $^1$H NMR.

EXAMPLE 141

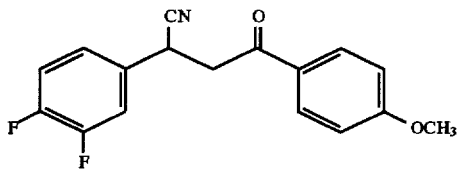

To the chalcone, 140, (5.05 g, 18.23 mmol) in 2-ethoxyethanol (40 mL) at 55° C. was added acetic acid (2.10 mL) followed by slow addition of potassium cyanide (3.0 g, 45.6 mmol) in water (5.0 mL). The solution was stirred at 105° C. for 12 hours. The solution was cooled and treated with water (5 mL). The mixture was then filtered to collect the solid. The solid was washed repeatedly with 70% ethanol (2'100 mL), air dried, and then dried in vacuo to give the nitrile 4.2 g (76%) as an off-white solid. The nitrile was identified by $^1$H NMR.

EXAMPLE 142

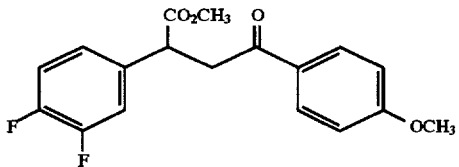

To the nitrile, 141, (1.57 g, 5.20 mmol) was added methanol (40 mL). The mixture was saturated with HCl (g) and heated to 45° C. until no nitrile remained, by thin-layer chromatography. The solution was cooled and treated with water (5 mL). The resultant solid was filtered to collect, washed with 80% methanol (2×250 mL), and dried in vacuo. This gave the ester 1.5 g (86%) as a solid which was identified by $^1$H NMR.

EXAMPLE 143

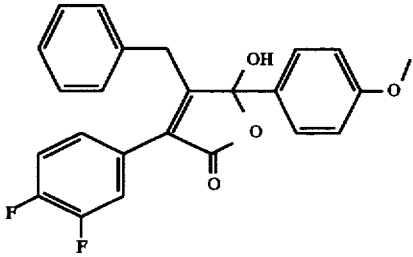

4-Benzyl-3-(3,4-difluorophenyl)-5-hydroxy-5-(4-methoxyphenyl)-5H-furan-2-one

To methanol (5 mL) was added sodium metal (0.024 g, 1.04 mmol) and stirred to dissolve. To this was added benzaldehyde (0.105 g, 0.987 mmol) then the ester, 142, (0.3 g, 0.90 mmol). The mixture was heated to reflux for 4 hours.

The solution was then treated with acetic acid (5 mL) and refluxed an additional 12 hours. The solvents were removed by evaporation. The crude product was then purified by flash chromatography (170 g silica gel, 15% ethyl acetate/hexane). The butenolide was isolated by evaporation of the appropriate fractions to give 0.25 g (68%) as a light brown solid. The butenolide was identified by $^1$H NMR, IR, MS, [M+H]$^+$=409 Da., and microanalysis.

EXAMPLE 144

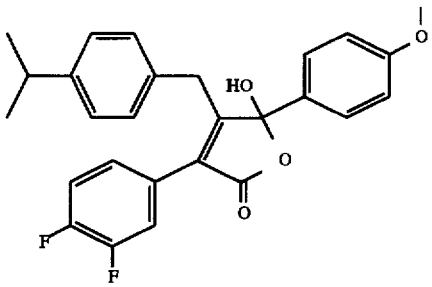

3-(3,4-Difluorophenyl)-5-hydroxy-4-(4-isopropylbenzyl)-5-(4-methoxyphenyl)-5H-furan-2-one To methanol (5 mL) was added sodium metal (0.024 g, 1.04 mmol) and stirred to dissolve. To this was added cuminaldehyde (0.146 g, 0.987 mmol) then the ester, 142, (0.3 g, 0.897 mmol). The mixture was heated to reflux for 8 hours. The solution was then treated with acetic acid (5 mL) and refluxed an additional 12 hours. The solvents were removed by evaporation. The crude product was then purified by flash chromatography (170 g silica gel, 15% ethyl acetate/hexane). The butenolide was isolated by evaporation of the appropriate fractions to give 0.20 g (49%) as an off-white solid. The butenolide was identified by $^1$H NMR, IR, MS, [M+H]$^+$=451 Da., and microanalysis.

EXAMPLE 145

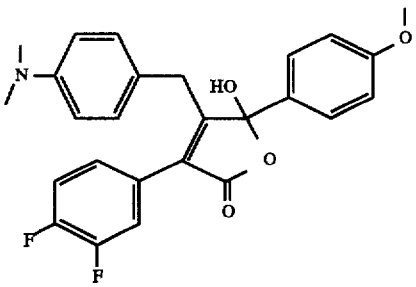

3-(3,4-Difluorophenyl)-4-(4-dimethylaminobenzyl)-5-hydroxy-5-(4-methoxyphenyl)-5H-furan-2-one To methanol (5 mL) was added sodium metal (0.016 g, 0.72 mmol) and stirred to dissolve. To this was added 4-dimethylaminobenzaldehyde (0.10 g, 0.66 mmol) then the ester, 142, (0.2 g, 0.60 mmol). The mixture was heated to reflux for 12 hours. The solution was then treated with acetic acid (5 mL) and refluxed an additional 12 hours. The solvents were removed by evaporation. The crude product was then purified by flash chromatography (170 g silica gel, 15% ethyl acetate/hexane). The butenolide was isolated by evaporation of the appropriate fractions to give 0.06 g (22%) as a solid. The butenolide was identified by $^1$H NMR, IR, MS, [M+H]$^+$=452 Da., and HPLC=90%.

EXAMPLE 146

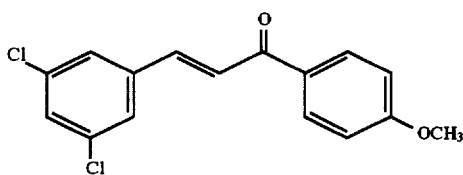

To 4-methoxyacetophenone (3.064 g, 20.40 mmol) in absolute ethanol (40 mL) in an erlenmeyer was added 3,5-dichlorobenzaldehyde (5.0 g, 28.57 mmol). The solution swirled while 10% sodium hydroxide (5 mL) added. The mixture swirled for 10 minutes and allowed to stand to precipitate. The solid was collected by filtration and washed with 80% ethanol (100 mL). The solid was dried in vacuo giving 6.44 g (73%) of a pale yellow solid which was identified by $^1$H NMR.

EXAMPLE 147

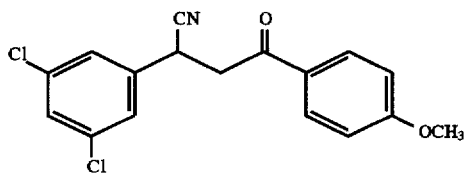

To the chalcone, 146, (6.44 g, 20.96 mmol) in 2-ethoxyethanol (50 mL) at 55° C. was added acetic acid (1.33 mL) followed by slow addition of potassium cyanide (2.044 g, 31.44 mmol) in water (5.0 mL). The solution was stirred at 105° C. for 12 hours. The solution was cooled and treated with water. The mixture was then filtered to collect the solid. The solid was washed repeatedly with 70% ethanol (2×100 mL), air dried, and then dried in vacuo to give the nitrile 6.51 g (92%) as a dark green solid. The nitrile was identified by $^1$H NMR.

EXAMPLE 148

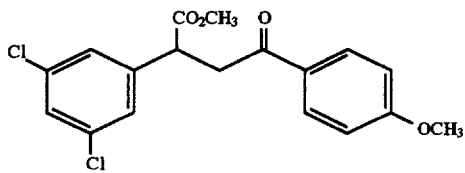

To the nitrile, 147, (2.2 g, 6.60 mmol) was added methanol (70 mL). The mixture was saturated with HCl (g) and heated to 80° C. until no nitrile remained, by thin-layer chromatography. The solution was cooled. The solution was evaporated to dryness. The crude product was purified on SiO$_2$ 170 g (15% ethyl acetate/hexane). This gave the ester 0.35 g (15%) as a solid which was identified by $^1$H NMR, IR, MS, and microanalysis.

EXAMPLE 149

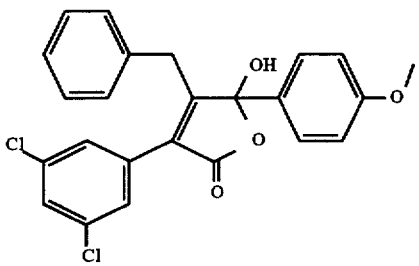

4-Benzyl-3-(3,5-dichloro-phenyl)-5-hydroxy-5-(4-methoxy-phenyl)-5H-furan-2-one

To methanol (5 mL) was added sodium metal (0.015 g, 0.65 mmol) and stirred to dissolve. To this was added benzaldehyde (0.064 g, 0.60 mmol) then the ester, 148, (0.2 g, 0.544 mmol). The mixture was heated to reflux for 3 hours. The solution was then treated with acetic acid (5 mL) and refluxed an additional 12 hours. The solvents were removed by evaporation. The crude product was then purified by flash chromatography (170 g silica gel, 10% ethyl acetate/hexane). The butenolide was isolated by evaporation of the appropriate fractions to give 0.12 g (50%) as a solid. The butenolide was identified by $^1$H NMR, IR, MS, [M+H]$^+$=441 Da., and microanalysis.

EXAMPLE 150

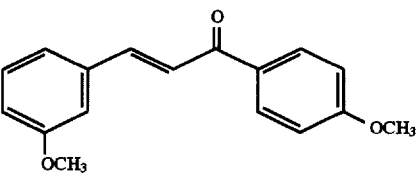

To 4-methoxyacetophenone (15 g, 97.88 mmol) in absolute ethanol (70 mL) in an erlenmeyer was added aldehyde (19.10 g, 139.84 mmol). The solution swirled while 10% sodium hydroxide (10 mL) added. The mixture swirled for 10 minutes and allowed to stand to precipitate. The solid was collected by filtration and washed with 80% ethanol (2'100 mL). The solid was dried in vacuo giving 24.70 g (92%) of a pale yellow solid which was identified by $^1$H NMR.

EXAMPLE 151

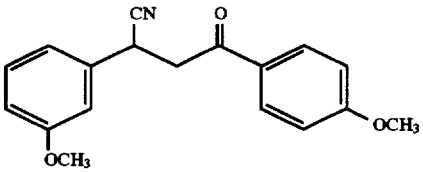

To the chalcone, 150, (10.0 g, 37.27 mmol) in 2-ethoxyethanol (50 mL) at 55° C. was added acetic acid (2.35 mL) followed by slow addition of potassium cyanide (3.64 g, 55.90 mmol) in water (1.0 mL). The solution was stirred at 105° C. for 12 hours. The solution was cooled. The solution was evaporated to dryness, purified on SiO$_2$ (400 g) (30% ethyl acetate/hexane) to give the nitrile 9.48 g (86%) as a dark green oil. The nitrile was identified by $^1$H NMR.

EXAMPLE 152

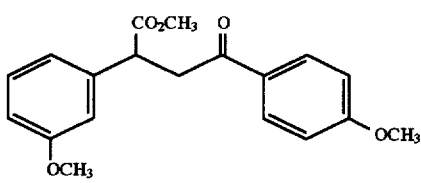

To the nitrile, 151, (3 g, 10.16 mmol) was added methanol (20 mL). The mixture was saturated with HCl (g) and heated to 80° C. until no nitrile remained, by thin-layer chromatography. The solution was cooled and treated with water (10 mL). The resultant solid was filtered to collect, washed with 80% methanol (2×20 mL), and dried in vacuo. This gave the ester 3.10 g (92%) as a gray solid which was identified by $^1$H NMR.

EXAMPLE 153

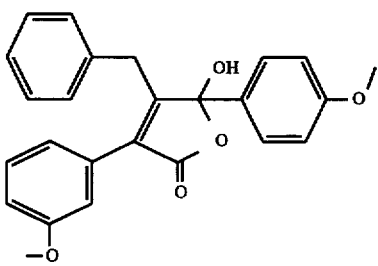

4-Benzyl-5-hydroxy-5-(4-methoxyphenyl)-3-(3-methoxyphenyl)-5H-furan-2-one

To methanol (5 mL) was added sodium metal (0.042 g, 1.82 mmol) and stirred to dissolve. To this was added benzaldehyde (0.177 g, 1.70 mmol) then the ester, 152, (0.5 g, 1.52 mmol). The mixture was heated to reflux for 12 hours. The solution was then treated with acetic acid (5 mL) and refluxed an additional 12 hours. The solvents were removed by evaporation. The crude product was then purified by flash chromatography (170 g silica gel, eluent 20% ethyl acetate/hexane). The butenolide was isolated by evaporation of the appropriate fractions to give 0.35 g as a dark orange semi-solid. The butenolide was identified by $^1$H NMR, IR, MS, [M+H]$^+$=403 Da., and microanalysis.

EXAMPLE 154

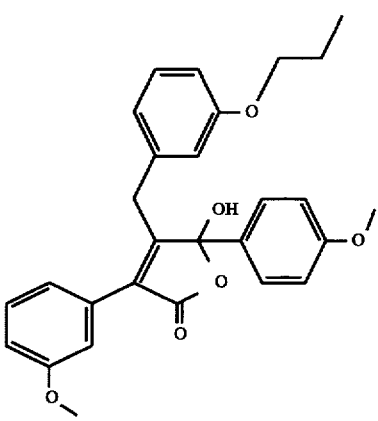

5-Hydroxy-5-(4-methoxyphenyl)-3-(3-methoxyphenyl)-4-(3-propoxybenzyl)-5H-furan-2-one To methanol (5 mL) was added sodium metal (0.03 g, 1.28 mmol) and stirred to dissolve. To this was added benzaldehyde (0.193 g, 1.20 mmol) then the ester, 152, (0.35 g, 1.066 mmol). The mixture was heated to reflux for 4 hours. The solution was then treated with acetic acid (5 mL) and refluxed an additional 5 hours. The solvents were removed by evaporation. The crude product was then purified by flash chromatography (170 g silica gel, 20% ethyl acetate/hexane). The butenolide was isolated by evaporation of the appropriate fractions to give 0.27 g (55%) as a brown semi-solid. The butenolide was identified by $^1$H NMR, IR, MS, [M+H]$^+$=461 Da., and microanalysis.

EXAMPLE 155

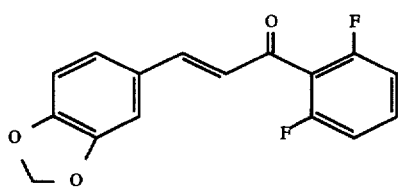

To 2,6-difluoroacetophenone (10.0 g, 64 mmol) in absolute ethanol (40 mL) in an erlenmeyer was added aldehyde (13.46 g, 89.66 mmol). The solution swirled while 10% sodium hydroxide (5 mL) added. The mixture swirled for 10 minutes and allowed to stand to precipitate. The solid was collected by filtration and washed with 80% ethanol (100 mL). The solid was dried in vacuo giving 18.27 g (99%) of an off-white solid which was identified by $^1$H NMR.

EXAMPLE 156

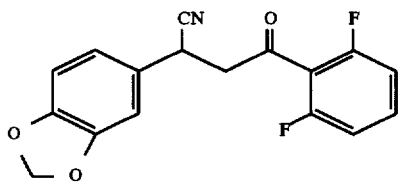

To the chalcone, 155, (10.0 g, 34.70 mmol) in absolute ethanol (40 mL) at 55° C. was added acetic acid (4.0 mL) followed by slow addition of potassium cyanide (5.64 g, 86.73 mmol) in water (13 mL). The solution was stirred at 100° C. for 12 hours. The solution was cooled and treated with water (20 mL). A gummy solid precipitated, and the solvent decanted off. The gummy residue was dissolved in ethyl acetate (100 mL), washed with water (20 mL), dried over MgSO$_4$ filter, evaporated, purified on 400 g of SiO$_2$ (20% ethyl acetate/hexane) to give the nitrile 1.5 g (14%) as a brownish solid. The nitrile was identified by $^1$H NMR, IR, MS, and microanalysis.

EXAMPLE 157

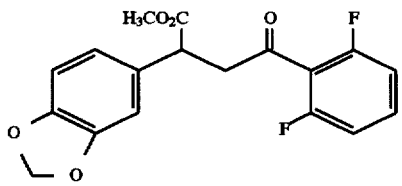

To the nitrile, 156, (1.5 g, 4.75 mmol) was added methanol (20 mL). The mixture was saturated with HCl (g) and heated to 45° C. until no nitrile remained, by thin-layer chromatography. The solution was cooled. The solution was evaporated to dryness, added ether (20 mL), precipitated out, filtered to collect, and dried. Purified on 200 g of SiO₂ (15% ethyl acetate/hexane). This gave the ester 1.0 g (54%) as an off-white solid which was identified by ¹H NMR.

EXAMPLE 158

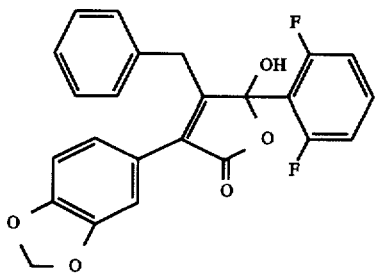

3-Benzo[1,3]dioxol-5-yl-4-benzyl-5-(2,6-difluorophenyl)-5-hydroxy-5H-furan-2-one To methanol (5 mL) was added sodium metal (0.022 g, 0.94 mmol) and stirred to dissolve. To this was added benzaldehyde (0.091 g, 0.86 mmol) then the ester, 157, (0.3 g, 0.78 mmol). The mixture was heated to reflux for 5 hours. The solution was then treated with acetic acid (5 mL) and refluxed an additional 12 hours. The solvents were removed by evaporation. The crude product was then purified by flash chromatography (170 g silica gel, 15% ethyl acetate/hexane). The butenolide was isolated by evaporation of the appropriate fractions to give 0.20 g (60%) as an off-white solid. The butenolide was identified by ¹H NMR, IR, MS, [M+H]⁺=422 Da., and microanalysis.

EXAMPLE 159

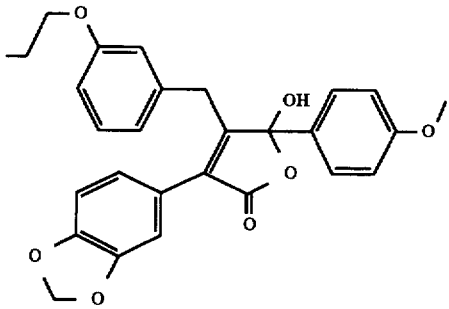

3-Benzo[1,3]dioxol-5-yl-5-hydroxy-5-(4-methoxyphenyl)-4-(3-propoxybenzyl)-5H-furan-2-one To methanol (5 mL) was added sodium metal (0.030 g, 1.227 mmol) and stirred to dissolve. To this was added 3-O-propoxybenzaldehyde (0.184 g, 1.124 mmol) then the ester, 15, (0.35 g, 1.022 mmol). The mixture was heated to reflux for 12 hours. The solution was then treated with acetic acid (6 mL) and refluxed an additional 12 hours. The solvents were removed by evaporation. The crude product was then purified by flash chromatography (170 g silica gel, 15% ethyl acetate/hexane). The butenolide was isolated by evaporation of the appropriate fractions to give 0.20 g (41%) as an off-white solid. The butenolide was identified by ¹H NMR, IR, MS, [M+H]⁺=475 Da., and microanalysis.

EXAMPLE 160

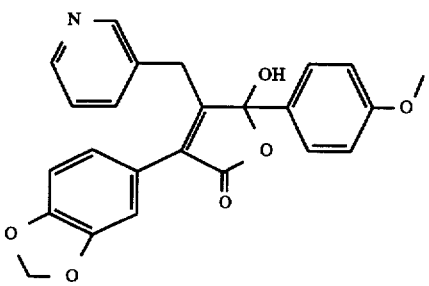

3-Benzo[1,3]dioxol-5-yl-5-hydroxy-5-(4-methoxyphenyl)-4-pyridin-3-ylmethyl-5H-furan-2-one To methanol (5 mL) was added sodium metal (0.024 g, 1.05 mmol) and stirred to dissolve. To this was added 3-pyridylcarboxaldehyde (0.103 g, 0.964 mmol) then the ester, 15, (0.30 g, 0.876 mmol). The mixture was heated to reflux for 2 hours. The solution was then treated with acetic acid (5 mL) and refluxed an additional 12 hours. The solvents were removed by evaporation. The crude product was then purified by flash chromatography (170 g silica gel, 20% ethyl acetate/hexane). The butenolide was isolated by evaporation of the appropriate fractions to give 0.16 g (43%) as an off-white solid. The butenolide was identified by ¹H NMR, IR, MS, [M+H]⁺=418 Da., and HPLC=97%.

EXAMPLE 161

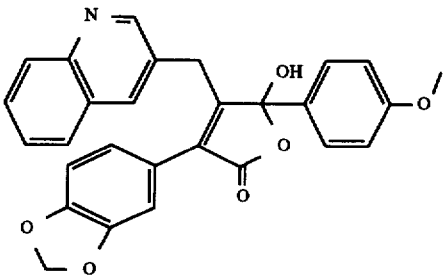

3-Benzo[1,3]dioxol-5-yl-5-hydroxy-4-isoquinolin-4-ylmethyl-5-(4-methoxyphenyl)-5H-furan-2-one To methanol (5 mL) was added sodium metal (0.024 g, 1.05 mmol) and stirred to dissolve. To this was added 3-isoquinolinylcarboxaldehyde (0.15 g, 0.964 mmol) then the ester, 15, (0.30 g, 0.876 mmol). The mixture was heated to reflux for 12 hours. The solution was then treated with acetic acid (5 mL) and refluxed an additional 8 hours. The solvents were removed by evaporation. The crude product was then purified by flash chromatography (170 g silica gel, 20% ethyl acetate/hexane). The butenolide was isolated by evaporation of the appropriate fractions to give 0.12 g (29%) as an off-white solid. The butenolide was identified by ¹H NMR, IR, MS, [M+H]⁺=468 Da., and HPLC=99%.

EXAMPLE 162

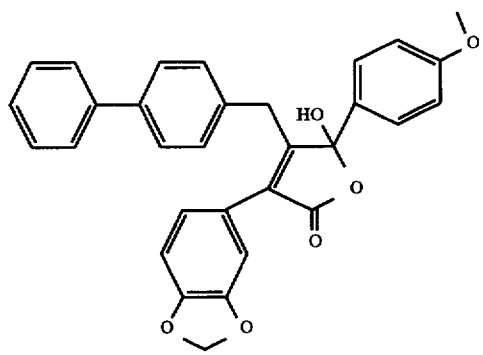

3-Benzo[1,3]dioxol-5-yl-4-biphenyl-4-ylmethyl-5-hydroxy-5-(4-methoxyphenyl)-5H-furan-2-one To methanol (5 mL) was added sodium metal (0.024 g, 1.05 mmol) and stirred to dissolve. To this was added 4-phenylbenzaldehyde (0.176 g, 0.964 then the ester, 15, (0.30 g, 0.876 mmol). The mixture was heated to reflux for 12 hours. The solution was then treated with acetic acid (5 mL) and refluxed an additional 8 hours. The solvents were removed by evaporation. The crude product was then purified by flash chromatography (170 g silica gel, 20% ethyl acetate/hexane). The butenolide was isolated by evaporation of the appropriate fractions to give 0.18 (41%) as an off-white solid. The butenolide was identified by $^1$H NMR, IR, MS, [M+H]$^+$=493 Da., and HPLC=97%.

EXAMPLE 163

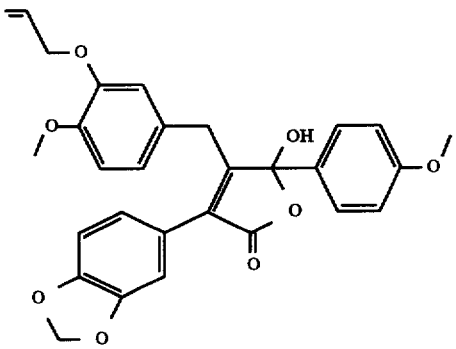

4-(3-Allyloxy-4-methoxybenzyl)-3-benzo[1,3]dioxol-5-yl-5-hydroxy-5-(4-methoxyphenyl)-5H-furan-2-one To methanol (5 mL) was added sodium metal (0.04 g, 1.75 mmol) and stirred to dissolve. To this was added 3-allyloxy-4-methoxybenzaldehyde (0.30 g, 1.60 mmol) then the ester, 15, (0.50 g, 1.46 mmol). The mixture was heated to reflux for 12 hours. The solution was then treated with acetic acid (5 mL) and refluxed an additional 12 hours. The solvents were removed by evaporation. The crude product was then purified by flash chromatography (170 g silica gel, 20% ethyl acetate/hexane). The butenolide was isolated by evaporation of the appropriate fractions to give 0.20 g (27%) as an off-white solid. The butenolide was identified by $^1$H NMR, IR, MS, [M+H]$^+$=503 Da., and microanalysis.

EXAMPLE 164

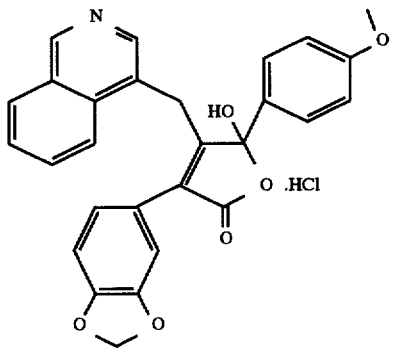

2(5H)-Furanone, 3-(1,3-benzodioxol-5-yl)-5-hydroxy-4-(4-isoquinolinyl)-5-(4-methoxyphenyl)-, (±)-, monohydrochloride To 161 (0.050 g, 0.107 mmol) in dioxane (1 mL) at 50° C. was added 0.026 mL of 4N HCl in dioxane (0.97 eq, 0.1036 mmol). The solution stirred for 2 minutes then evaporated to dryness, dried in vacuo 15 minutes to give 0.06 g solid. The salt was identified by $^1$H NMR, MS, [M+H]$^+$=468 Da.

EXAMPLE 165

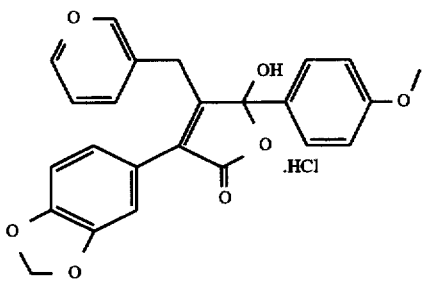

2(5H)-Furanone, 3-(1,3-benzodioxol-5-yl)-5-hydroxy-5-(4-methoxyphenyl)-4-(3-pyridinylmethyl)-, (±)-, monohydrochloride To 160 (0.05 g, 0.12 mmol) in dioxane (1 mL) was added 4N HCl in dioxane (0.029 mL) (0.97 g, 0.1161 mmol). Stirred for 2 minutes then evaporated to dryness, dried in vacuo for 15 minutes to give 0.055 g (100%) of a solid. The salt was identified by MS, [M+H]$^+$=418 Da.

EXAMPLE 166

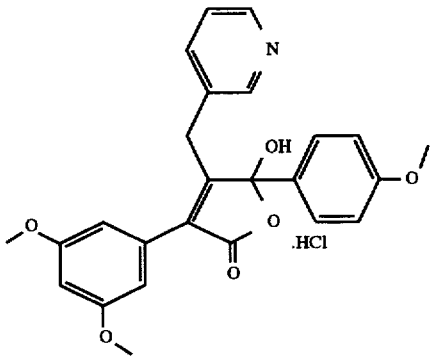

2(5H)-Furanone, 3-(3,5-dimethoxyphenyl)-5-hydroxy-5-(4-methoxyphenyl)-4-(3-pyridinylmethyl)-, (±)-, monohydrochloride To 133 (0.0524 g, 0.1208 mmol) in dioxane was added 4N HCl in dioxane (0.029 mL) (0.970 g, 0.1171 mmol). Stirred for 2 minutes then evaporated to dryness, dried in vacuo to give 0.055 g (100%) of a solid which was identified by $^1$H NMR, MS, [M+H]$^+$=434 Da.

EXAMPLE 167

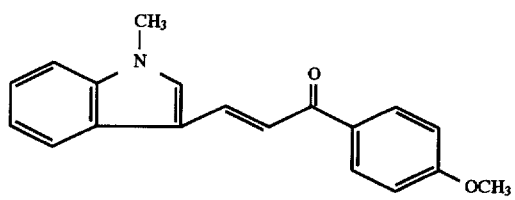

To 4-methoxyacetophenone (14.84 g, 98.82 mmol) in absolute ethanol (40 mL) in an erlenmeyer was added N-methylindolyl-3-carboxaldehyde (20 g, 125.66 mmol). The solution swirled while 10% sodium hydroxide (8 mL) added. The mixture swirled for 10 minutes and allowed to stand to precipitate. The solid was collected by filtration and washed with 80% ethanol (2×100 mL). The solid was dried in vacuo giving 17.58 g (62%) of an off-white solid which was identified by $^1$H NMR.

EXAMPLE 168

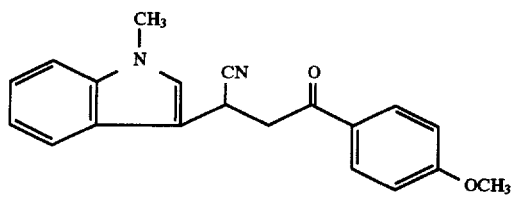

To the chalcone, 157, (7.00 g, 24.0 mmol) in absolute ethanol (15 mL) at 55° C. was added acetic acid (2.75 mL) followed by slow addition of potassium cyanide (3.90 g, 60.0 mmol) in water (15 mL). The solution was stirred at 70° C. for 12 hours. The solution was cooled and treated with water (30 mL). The mixture was then filtered to collect the solid. The solid was washed repeatedly with 70% ethanol (2×50 mL), air dried, and then dried in vacuo to give the nitrile 5.22 g (68%) as a brownish solid. The nitrile was identified by $^1$H NMR.

EXAMPLE 169

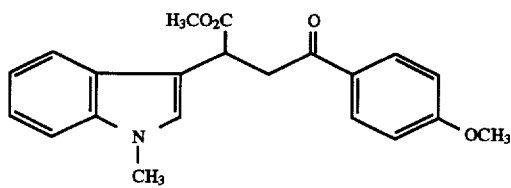

To the nitrile, 168, (5.22 g, 16.40 mmol) was added methanol (40 mL). The mixture was saturated with HCl (g) and heated to 80° C. until no nitrile remained, by thin-layer chromatography. The solution was cooled and treated with water (20 mL). The resultant solid was filtered to collect, washed with 80% methanol (100 mL), purified on 3.00 g of SiO$_2$, (30% ethyl acetate/hexane), and dried in vacuo. This gave the ester 1.0 g (17%) as a white solid which was identified by $^1$H NMR, IR, MS, and microanalysis.

EXAMPLE 170

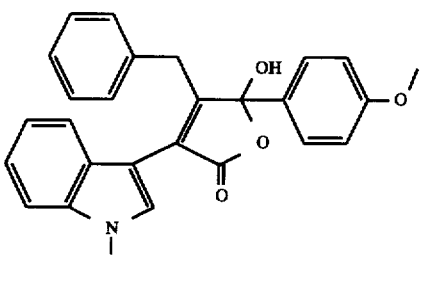

4-Benzyl-5-hydroxy-5-(4-methoxyphenyl)-3-(1-methyl)-1H-indol-3-yl)-5H-furan-2-one To methanol (5 mL) was added sodium metal (0.029 g, 1.25 mmol) and stirred to dissolve. To this was added aldehyde (0.133 g, 1.25 mmol) then the ester, 169, (0.4 g, 1.14 mmol). The mixture was heated to reflux for 5 hours. The solution was then treated with acetic acid 8 mL and refluxed an additional 12 hours. The solvents were removed by evaporation. The crude product was then purified by flash chromatography (170 g silica gel, 20% ethyl acetate/hexane). The butenolide was isolated by evaporation of the appropriate fractions to give 0.24 g (49%) as an off-white solid. The butenolide was identified by $^1$H NMR, IR, MS, [M+H]$^+$=425 Da., and microanalysis.

EXAMPLE 171

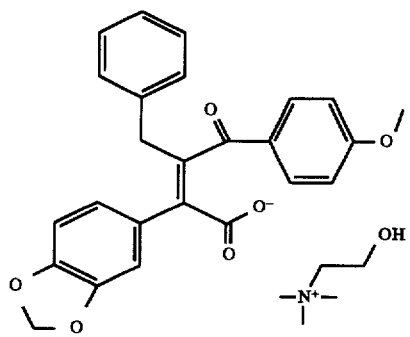

2-Butenoic acid, 2-(1,3-benzodioxol-5-yl)-4-(4-methoxyphenyl)-4-oxo-3-(phenylmethyl)-, (Z)-, ion(1-) compd. with 2-hydroxy-N,N,N-triethanaminium (1:1)

Compound 20 (0.61g, 1.59 mmol) was dissolved in methanol (20 mn). Choline hydroxide 45% solution in methanol (0.43 mL, 1.55 mmol) was added, stirred for 5 minutes, then evaporated in vacuo. The oil was dissolved in water (20 mL) and lyophilized to afford (4) as a yellow powder 0.66 g (80%). The salt was identified by $^1$H NMR, IR, MS, [M+H]$^+$=417 Da.

EXAMPLE 172

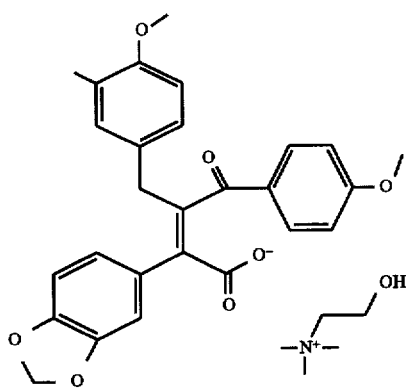

2-Butenoic acid, 2-(1,3-benzodioxol-5-yl)-3-[(4-methoxy-3-methylphenyl)methyl]-4-(4-methoxyphenyl)-4-oxo-, (Z)-, ion(1-) compd. with 2-hydroxy-N,N,N-trimethylethanaminium (1:1)

To a solution of 89, (1.147 g, 2.50 mmol) in methanol (20 mL) and THF (4 mL) was added choline hydroxide in methanol (45%, by weight) (0.68 mL, 2.45 mmol), stirred for 5 minutes, then evaporated in vacuo. This oil was dissolved in water (200 mL) and washed with ether (50 mL). Lyophilization of the aqueous layer afforded the salt 1.27 g (90%). The salt was identified by $^1$H NMR, MS [M+H]$^+$= 417 Da.

EXAMPLE 173

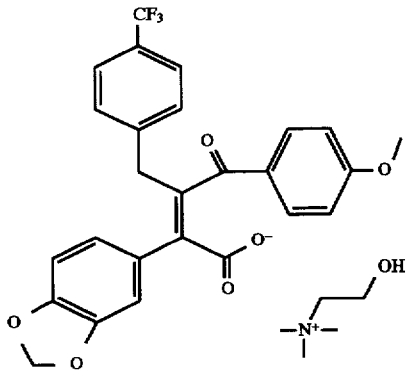

2-Butenoic acid, 2-(1,3-benzodioxol-5-yl)-4-(methoxyphenyl)-4-oxo-3-[[4-(trifluoromethyl)phenyl]methyl]-, (Z)-, ion(1- ) comp. with 2-hydroxy-N,N,N-trimethylethanaminium (1:1)

To a solution of 88, (0.048 g, 0.1 mmol) in methanol (2 mL) was added choline hydroxide in methanol (45%, by weight) (0.025 mL, 0.09 mmol). This solution was evaporated to afford a colorless viscous oil. This oil crystallized from methanol (0.5 mL) and ether (3 mL). The product (2) was collected and washed with ether (2×10 mL). Yield (0.046 g, 78%) mp 150–158 dec. The salt was identified by $^1$H NMR, MS, [M+H]$^+$=441 Da.

EXAMPLE 174

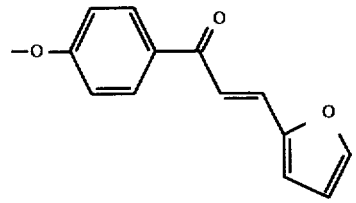

To p-methoxyacetophenone (5.0 g, 33 mmol) in absolute ethanol (9 mL) in an erlenmeyer was added 2-furaldehyde (2.73 mL) (33 mmol). The solution swirled while 10% sodium hydroxide (1.5 mL) added. The mixture swirled for 10 minutes and allowed to stand to precipitate. The solid was collected by filtration and washed with 80% ethanol. The solid was dried in vacuo giving 5.52 g (73%) of a solid which was identified by $^1$H NM R, IR, MS, and microanalysis.

EXAMPLE 175

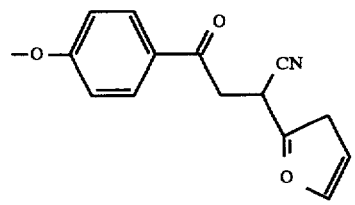

To the chalcone, 174, (5.52 g, 24 mmol) in ethanol (50 mL) at 55° C. was added acetic acid (1.92 mL) followed by slow addition of potassium cyanide (3.84 g, 59 mmol) in water (10 mL). The solution was stirred at reflux for 1 hour. The solution was cooled and treated with water. The mixture was then filtered to collect the solid. The solid was washed repeatedly with 70% ethanol, air dried, and then dried in vacuo to give the nitrile 3.61 g (59%). The nitrile was identified by $^1$H NMR, IR, and MS.

EXAMPLE 176

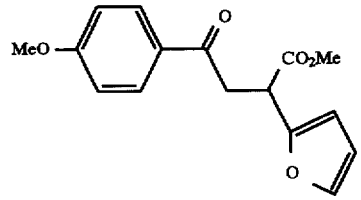

A mixture of 175 (1.0 g, 3.9 mmol), p-toluenesulfonic acid monohydrate (0.74 g, 3.9 mmol) in 20 mL MeOH was heated at reflux for 6 hours. No precipitate was formed. The reaction mixture was concentrated and the residue was partitioned between ethyl acetate and water. The organic layer was washed with water, saturated sodium chloride, dried MgSO$_4$, filtered, and concentrated. The crude product was purified by flash chromatography (silica gel 60, 7:3 hexane:ethyl acetate) to give a light yellow viscous oil 0.52 g (46%). The product was identified by $^1$H NMR, MS, and $^{13}$C NMR.

EXAMPLE 177

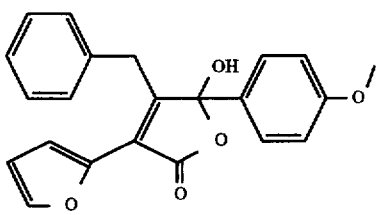

4'-Benzyl-5'-hydroxy-5'-(4-methoxyphenyl)-5'H-[2,3'] bifuranyl-2'-one

To methanol (5 mL) was added sodium metal (44 mg, 1.9 mmol) and stirred to dissolve. To this was added benzaldehyde (0.20 mL, 2.0 mmol) then the ester, 175, (051 g, 1.8 mmol). The mixture was heated to reflux for 4 hours. The solution was then treated with acetic acid (5.0 mL) and refluxed for an additional 18 hours. The solvents were removed by evaporation and the residue was partitioned between ethyl acetate and water. The organic phase was separated and dried over magnesium sulfate and evaporated to dryness. The crude product was then purified by flash chromatography (silica gel, 7:3 hexane:ethyl acetate). The butenolide was isolated by evaporation of the appropriate fractions to give 0.46 g (71%) as a solid. The butenolide was identified by $^1$H NMR, IR, MS, [M+H]$^+$=363 Da., and microanalysis.

EXAMPLE 178

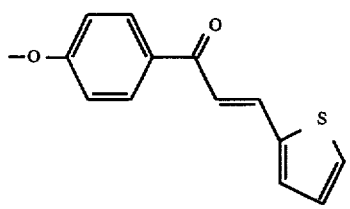

To 4-methoxyacetophenone (5.0 g, 33 mmol) in absolute ethanol (15 mL) in an erlenmeyer was added 2-thiophenecarboxaldehyde (3.08 mL, 33 mmol). The solution swirled while 10% sodium hydroxide (15 mL) added. The mixture swirled for 10 minutes and allowed to stand to precipitate. The solid was collected by filtration and washed with 80% ethanol. The solid was dried in vacuo giving 5.34 g (66%) of a solid which was identified by $^1$H NMR, IR, and MS.

EXAMPLE 179

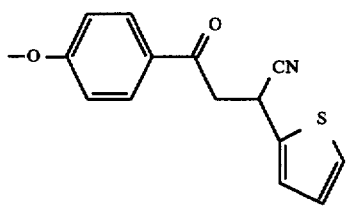

To the chalcone, 178, (5.34 g, 22 mmol) in ethanol (50 mL) at 55° C. was added acetic acid (1.74 mL) followed by slow addition of potassium cyanide (3.51 g, 54 mmol) in water (8 mL). The solution was stirred at reflux for 1 hour. The mixture was concentrated in vacuo and partitioned between ethyl acetate and water. The organic layer was washed thoroughly with water, brine, and dried over MgSO$_4$. The crude material was purified by silica gel chromatography (7:3 ethyl acetate:hexane) to give an oil 4.38 g (73%). The nitrile was identified by $^1$H NMR, MS, and IR.

EXAMPLE 180

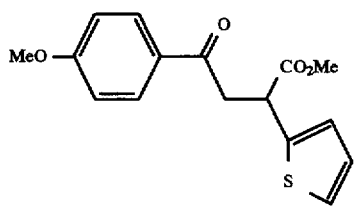

A solution of 179 (4.33 g, 16 mmol), p-toluenesulfonic acid monohydrate (3.04 g, 0.016 mmol) in 80 mL MeOH was heated at reflux for 6 hours. The reaction mixture was concentrated and the residue was partitioned between ethyl acetate and water. The organic layer was washed with water, saturated salt solution, dried (MgSO$_4$), filtered, and concentrated. The crude product was purified by flash chromatography (silica gel 60, 7:3 hexane:ethyl acetate) to give a yellow viscous oil 3.18 g (65%). The product was identified by $^1$H NMR and MS.

EXAMPLE 181

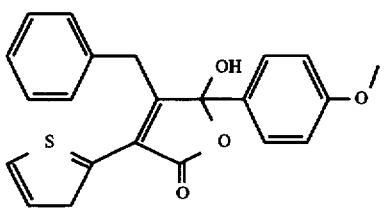

4-Benzyl-5-hydroxy-5-(4-methoxyphenyl)-3-thiophen-2-yl-5H-furan-2-one

To methanol (15 mL) was added sodium metal (250 mg, 11 mmol) and stirred to dissolve. To this was added benzaldehyde (1.16 mL, 11.6 mmol) then the ester, 180, (3.18 g, 10.4 mmol). The mixture was heated to reflux for 3.5 hours. The solution was then treated with acetic acid (10 mL) and refluxed for an additional 18 hours. The solvents were removed by evaporation and the residue was partitioned between ethyl acetate and water. The organic phase was separated and dried over magnesium sulfate and evaporated to dryness. The crude product was then purified by flash chromatography (silica gel, 7:3 hexane:ethyl acetate). The butenolide was isolated by evaporation of the appropriate fractions to give 0.65 g (16.5%) as a solid. The butenolide was identified by $^1$H NMR, IR, MS, [M+H]$^+$= 379 Da., and microanalysis.

EXAMPLE 182

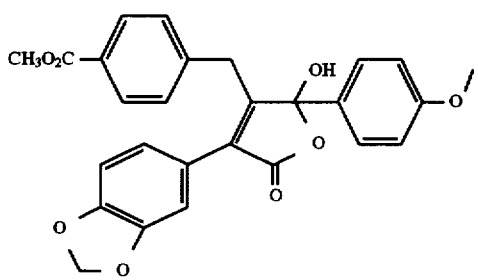

4-[4-Benzo[1,3]dioxol-5-yl-2-hydroxy-2-(4-methoxyphenyl)-5-oxo-2,5-dihydrofuran-3-ylmethyl]benzoic acid methyl ester To methanol (5 mL) was added sodium metal (56 g, 2.4 mmol) and stirred to dissolve. To this was added methyl-4-formylbenzoate (415 mg, 2.5 mmol) then the ester, 19, (0.8 g, 2.3 mmol). The mixture was heated to reflux for 1.5 hours. The solution was then treated with acetic acid (5 mL) and refluxed an additional 18 hours. The solvents were removed by evaporation and the residue was partitioned between ethyl acetate and water. The organic phase was separated and dried over magnesium sulfate and evaporated to dryness. The crude product was then purified by flash chromatography (silica gel, 3:2 hexane:ethyl acetate). The butenolide was isolated by evaporation of the appropriate fractions to give 0.63 g (57%) as a solid. The butenolide was identified by $^1$H NMR, IR, MS, [M+H]$^+$=475 Da., and microanalysis.

EXAMPLE 183

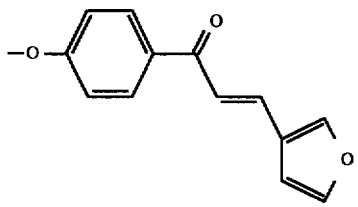

To 4-methoxyacetophenone (5.0 g, 33 mmol) in absolute ethanol (9 mL) in an erlenmeyer was added 3-furaldehyde (2.9 mL, 33 mmol). The solution swirled while 10% sodium hydroxide (15 mL) added. The mixture swirled for 10 minutes and allowed to stand to precipitate. The solid was collected by filtration and washed with 80% ethanol. The solid was dried in vacuo giving 5.52 g (73%) of a solid which was identified by $^1$H NMR and MS.

EXAMPLE 184

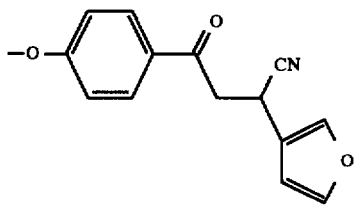

To the chalcone, 183, (5.52 g, 2.4 mmol) in ethanol (50 mL) at 55° C. was added acetic acid (1.92 mL) followed by slow addition of potassium cyanide (3.84 g, 59 mmol) in water (10 mL). The solution was stirred at reflux for 1 hour.

The mixture was concentrated in vacuo and the residue partitioned between ethyl acetate and water. The organic layer was washed thoroughly with water, brine, and dried over MgSO$_4$. The organic layer evaporated and the material purified by recrystallization from ethyl acetate\hexane to give the nitrile 3.60 g (59%). The product identified by $^1$H NMR, IR, MS, and microanalysis.

EXAMPLE 185

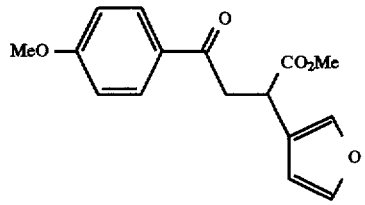

A solution of 184 (3.0 g, 0.012 mmol), p-toluenesulfonic acid monohydrate (2.82 g, 0.012 mmol) in 60 mL MeOH was heated at reflux for 6 hours. The reaction mixture was concentrated and the residue was partitioned between ethyl acetate and water. The organic layer was washed with water, brine, dried (MgSO$_4$), filtered, and concentrated. The crude product was purified by flash chromatography (silica gel 60, 7:3 hexane:ethyl acetate) to give a light yellow oil which crystallized on standing, 2.18 g (63%). The product was identified by $^1$H NMR and MS.

EXAMPLE 186

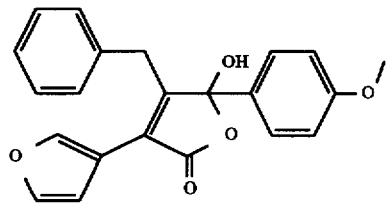

4-Benzyl-5-hydroxy-5-(4-methoxyphenyl-5H-[3,3']-bifuranyl-2-one

To methanol (20 mL) was added sodium metal (175 mg, 7.6 mmol) and stirred to dissolve. To this was added benzaldehyde (0.80 g 8.0 mmol) then the ester, 185, (2.07 g, 7.2 mmol). The mixture was heated to reflux for 2 hours. The solution was then treated with acetic acid (20 mL) and refluxed an additional 18 hours. The solvents were removed by evaporation and the residue was partitioned between ethyl acetate and water. The organic phase was separated and dried over magnesium sulfate and evaporated to dryness. The crude product was then purified by flash chromatography (silica gel, 4:1 hexane:ethyl acetate). The butenolide was isolated by evaporation of the appropriate fractions to give 0.64 g (25%) as a solid. The butenolide was identified by $^1$H NMR, IR, MS, [M+H]$^+$=363 Da., and microanalysis.

EXAMPLE 187

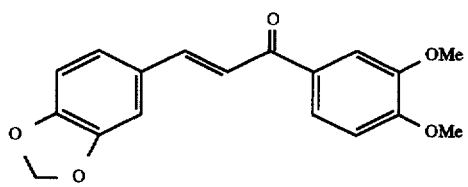

To 3',4'-dimethoxyacetophenone (12.5 g, 69 mmol) in absolute ethanol (200 mL) in an erlenmeyer was added piperonal (10 g, 67 mmol). The solution was swirled while 10% sodium hydroxide (35 mL) added. The mixture swirled for 10 minutes and allowed to stand to precipitate. The solid was collected by filtration and washed with 80% ethanol (50 mL). The solid was dried in vacuo giving 18.3 g (87%) of a yellow solid which was identified by $^1$H NMR, IR, MS, and microanalysis.

EXAMPLE 188

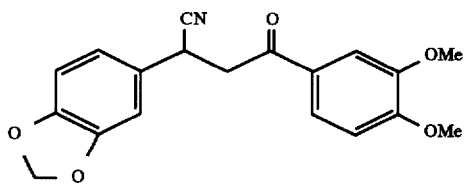

To the chalcone, 157, (17.95 g, 54.7) mmol) in 2-ethoxyethanol (150 mL) at 55° C. was added acetic acid (4 mL) followed by slow addition of potassium cyanide (5.3 g, 81 mmol) in water. The solution was stirred at 105° C. for 0.25 hour. The solution was cooled and treated with water (25 mL). The mixture was filtered to collect the solid. The solid was washed repeatedly with 70% ethanol (50 mL), air dried, and then dried in vacuo to give the nitrile 12.7 g (68%) as a yellow solid. The nitrile was identified by $^1$H NMR, IR, MS, and microanalysis.

EXAMPLE 189

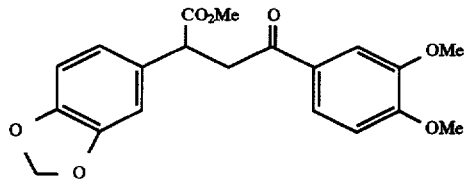

To the nitrile, 188, (10 g, 29.4 mmol) was added methanol (150 mL). The mixture was saturated with HCl (g) and heated to 45° C. until no nitrile remained, by thin-layer chromatography. The solution was cooled and treated with water (200 mL). The resultant solid was filtered to collect, washed with 80% methanol (50 mL), and dried in vacuo. This gave the ester 8.9 g (81%) as a white solid which was identified by $^1$H NMR, IR, MS, and microanalysis.

EXAMPLE 190

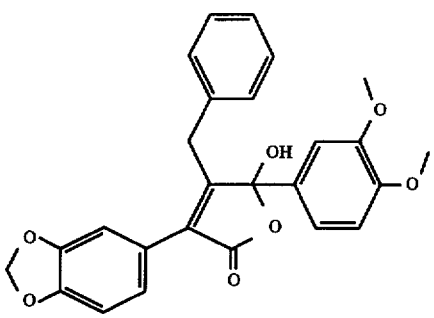

3-Benzo[1,3]dioxol-5-yl-4-benzyl-5-(3,4-dimethoxyphenyl)-5-hydroxy-5H-furan-2-one To methanol (100 mL) was added sodium metal (0.9 g, 39 mmol) and stirred to dissolve. To this was added benzaldehyde (4 g, 37 mmol) then the ester, 189, (8.3 g, 22.3 mmol). The mixture was heated to reflux for 4 hours. The solution was then treated with acetic acid (18 mL) and refluxed an additional 16 hours. The solvents were removed by evaporation and the residue was partitioned between ethyl acetate (150 mL) and water (25 mL). The organic phase was separated and dried over magnesium sulfate and evaporated to dryness. The crude product was then purified by flash chromatography (1000 g silica gel, (10:1) CHCl$_3$/ethyl acetate). The butenolide was isolated by evaporation of the appropriate fractions to give 4.7 g (47%) as a white solid. The butenolide was identified by $^1$H NMR, IR, MS, [M+H]$^+$=447 Da., and microanalysis.

EXAMPLE 191

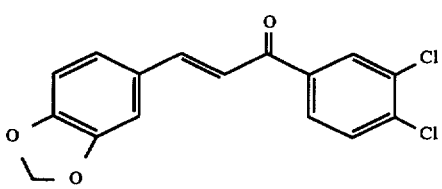

To 3',4'-dichloroactophenone (12.6 g, 69 mmol) in absolute ethanol (200 mL) in an erlenmeyer was added piperonal (10 g, 67 mmol). The solution swirled while 10% sodium hydroxide (35 mL) added. The mixture swirled for 10 minutes and allowed to stand to precipitate. The solid was collected by filtration and washed with 80% ethanol (50 mL). The solid was dried in vacuo giving 17.8 g (86%) of a yellow solid which was identified by $^1$H NMR and MS.

EXAMPLE 192

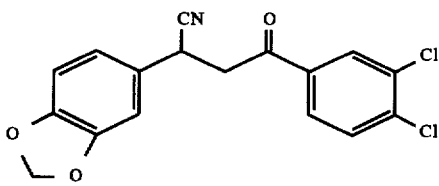

To the chalcone, 191, (17.3 g, 54 mmol) in 2-ethoxyethanol (150 mL) at 55° C. was added acetic acid (3.5 mL) followed by slow addition of potassium cyanide (5.3 g, 81 mmol) in water (5 mL). The solution was stirred at 105° C. for 0.25 hour. The solution was cooled and treated with water (15 mL). The mixture was then filtered to collect the solid. The solid was washed repeatedly with 70% ethanol (50 mL), air dried, and then dried in vacuo to give the nitrile 16.7 g (89%) as a yellow solid. The nitrile was identified by $^1$H NMR.

EXAMPLE 193

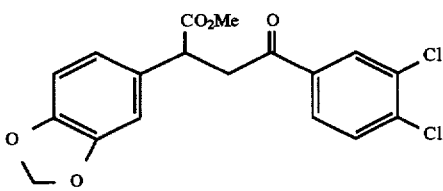

To the nitrile, 192, (10 g, 28.8 mmol) was added methanol (200 mL). The mixture was saturated with HCl (g) and heated to 45° C. until no nitrile remained, by thin-layer chromatography. The solution was cooled and removed the solvent. This gave the ester 10.2 g (98%) as a brown oil which was identified by $^1$H NMR.

EXAMPLE 194

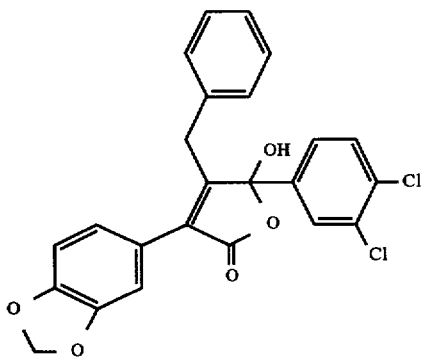

3-Benzo[1,3]dioxol-5-yl-4-benzyl-5-(3,4-dichlorophenyl)-5-hydroxy-5H-furan-2-one To methanol (100 mL) was added sodium metal (0.65 g, 28 mmol) and stirred to dissolve. To this was added benzaldehyde (3 g, 28 mmol) then the ester, 193, (8.6 g, 22.5 mmol). The mixture was heated to reflux for 4 hours. The solution was then treated with acetic acid (20 mL) and refluxed an additional 12 hours. The solvents were removed by evaporation and the residue was partitioned between ethyl acetate (150 mL) and water (25 mL). The organic phase was separated and dried over magnesium sulfate and evaporated to dryness. The crude product was then purified by flash chromatography (1000 g silica gel, (10:1) CHCl$_3$/ethyl acetate). The butenolide was isolated by evaporation of the appropriate fractions to give 3.6 g (35%) as an orange solid. The butenolide was identified by $^1$H NMR, IR, MS, [M+H]$^+$=457 Da., and microanalysis.

EXAMPLE 195

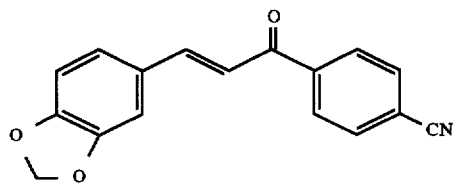

To 4'-cyanoacetophenone (9.7 g, 67 mmol) in absolute ethanol (200 mL) in an erlenmeyer was added piperonal (10 g, 67 mmol). The solution swirled while 10% sodium hydroxide (35 mL) added. The mixture swirled for 10 minutes and allowed to stand to precipitate. The solid was collected by filtration and washed with 80% ethanol (50 mL). The solid was dried in vacuo giving 13.5 g (73%) of a yellow solid which was identified by $^1$H NMR, IR, MS, and microanalysis.

EXAMPLE 196

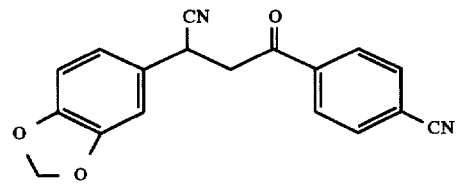

To the chalcone, 195, (12.5 g, 45.8 mmol) in 2-ethoxyethanol (50 mL) at 55° C. was added acetic acid (3.5 mL) followed by slow addition of potassium cyanide (7.5 g, 115 mmol) in water (10 mL). The solution was stirred at 105° C. for 0.25 hour. The solution was cooled and treated with water (10 mL). The mixture was then filtered to collect the solid. The solid was washed repeatedly with 70% ethanol (50 mL), air dried, and then dried in vacuo to give the nitrile 8.6 g (62%) as a yellow solid. The nitrile was identified by $^1$H NMR, IR, MS, and microanalysis.

EXAMPLE 197

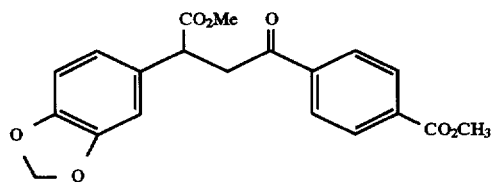

To the nitrile, 196, (6.2 g, 20.3 mmol) was added methanol (50 mL). The mixture was saturated with HCl (9) and heated to 45° C. until no nitrile remained, by thin-layer chromatography. The solution was cooled and treated with water (100 mL). The resultant solid was filtered to collect, washed with 80% methanol (50 mL), and dried in vacuo. This gave the ester 6.1 g (81%) as a light brown solid which was identified by $^1$H NMR.

EXAMPLE 198

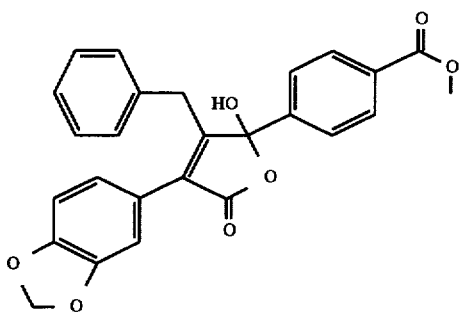

4-(4-Benzo[1,3]dioxol-5-yl-3-benzyl-2-hydroxy-5-oxo-2,5-dihydrofuran-2-yl)benzoic acid methyl ester To methanol (50 mL) was added sodium metal (0.2 g, 8.7 mmol) and stirred to dissolve. To this was added benzaldehyde (0.6 g, 5.7 mmol) then the ester, 197, (1.5 g, 4 mmol). The mixture was heated to reflux for 4 hours. The solution was then treated with acetic acid (3 mL) and refluxed an additional 12 hours. The solvents were removed by evaporation and the residue was partitioned between ethyl acetate (100 mL) and water (20 mL). The organic phase was separated and dried over magnesium sulfate and evaporated to dryness. The crude product was then purified by flash chromatography (300 g silica gel, (10:1) CHCl$_3$/ethyl acetate). The butenolide was isolated by evaporation of the appropriate fractions to give 0.85 g (48%) as a white solid. The butenolide was identified by $^1$H NMR, IR, MS, [M+H]$^+$=445 Da., and microanalysis.

EXAMPLE 199

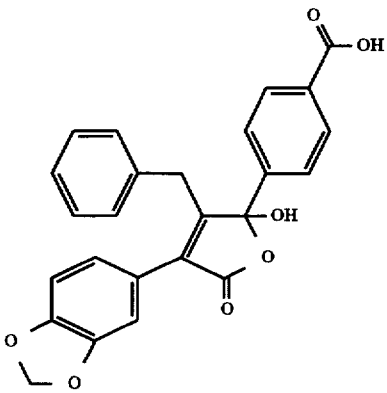

4-[4-Benzo[1,3]dioxol-5-yl-3-benzyl-2-hydroxy-5-oxo-2,5-dihydrofuran-2-yl)-benzoic acid To the butenolide, 198, (0.5 g, 1.1 mmol) was dissolved in methanol (10 mL) added 1.1 mL of 1N NaOH at 0° C., then at room temperature for 1 hour. The solvent was removed by evaporation. The residue was dissolved in water (15 mL) and acidified with 1N HCl (15 mL), filtered the solid dried under vacuo to give the acid 0.35 g (74% yield) as a white solid. The acid was identified by $^1$H NMR, IR, MS, [M+H]$^+$=431 Da., and microanalysis.

EXAMPLE 200

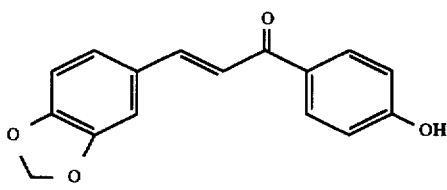

To 4'-hydroxyacetophenone (9.1 g, 69 mmol) in absolute ethanol (200 mL) in an erlenmeyer was added piperonal (10 g, 67 mmol). The solution swirled while 10% sodium hydroxide (35 mL) added. The mixture swirled for 10 minutes and allowed to stand to precipitate. The solid was collectedly filtration and washed with 80% ethanol (50 mL). The solid was dried in vacuo giving 16.5 g (91%) of a yellow solid which was identified by $^1$H NMR, IR, MS, and microanalysis.

EXAMPLE 201

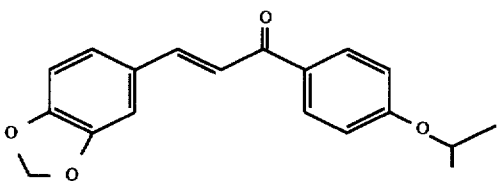

A mixture of chalcone, 200, (5.35 g, 19.7 mmol), K$_2$CO$_3$ (3 g, 20 mmol), and isopropyl bromide (3 g, 24 mmol) in 100 mL of DMF was heated to reflux for 3 hours. The solvent was removed by evaporation. The residue was purified by flash column chromatography (1000 g silica gel, (200:1) CHCl$_3$/ethyl acetate). The product was isolated by evaporation of the appropriate fraction to give 4.8 g (78.5% yield). The product was identified by $^1$H NMR, IR, MS, [M+H]$^+$=311.1 Da., and microanalysis.

EXAMPLE 202

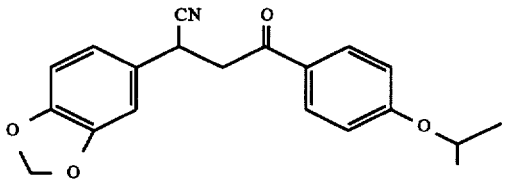

To the chalcone, 201, (4.0 g, 12.9 mmol) in 2-ethoxyethanol (50 mL) at 55° C. was added acetic acid (1 mL) followed by slow addition of potassium cyanide (1.3 g, 1.994 mmol) in water (1 mL). The solution was stirred at 105° C. for 0.25 hour. The solution was cooled and treated with water (50 mL). The mixture was then filtered to collect the solid. The solid was washed repeatedly with 70% ethanol (50 mL), air dried, and then dried in vacuo to give the nitrile 3.85 g (88.6%) as a brown solid. The nitrile was identified by $^1$H NMR and MS.

EXAMPLE 203

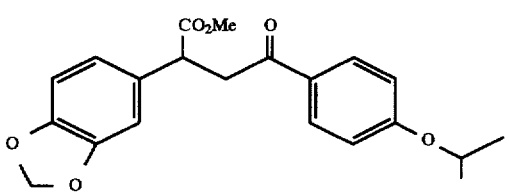

To the nitrile, 202, (3 g, 8.9 mmol) was added methanol (25 mL). The mixture was saturated with HCl (g) and heated to 45° C. until no nitrile remained, by thin-layer chromatography. The solution was cooled and treated with water (100 mL). The resultant solid was filtered to collect, washed with 80% methanol (10 mL) and dried in vacuo. This gave the ester 2.4 g (73%) as a yellow solid which was identified by $^1$H NMR, IR, MS, and microanalysis.

EXAMPLE 204

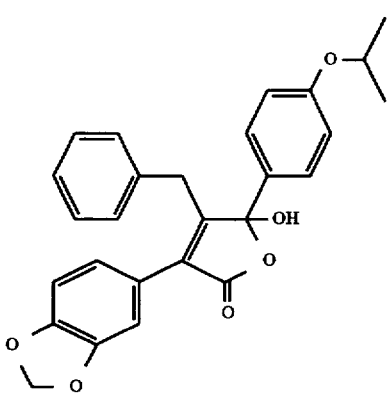

3-Benzo[1,3]dioxol-5-yl-4-benzyl-5-hydroxy-5-(4-isopropoxyphenyl)-5H-furan-2-one To methanol (60 mL) was added sodium metal (0.15 g, 4.5 mmol) and stirred to dissolve. To this was added benzaldehyde (1 g, 9.4 mmol) then the ester, 203, (1.5 g, 4 mmol). The mixture was heated to reflux for 4 hours. The solution was then treated with acetic acid (3 mL) and refluxed an additional 12 hours. The solvents were removed by evaporation and the residue was partitioned between ethyl acetate (100 mL) and water (20 mL). The organic phase was separated and dried over magnesium sulfate and evaporated to dryness. The crude product was then purified by flash chromatography (300 g silica gel, (100:1) CHCl$_3$/ethyl acetate). The butenolide was isolated by evaporation of the appropriate fractions to give 0.46 g (26%) as a white solid. The butenolide was identified by $^1$H NMR, IR, MS, [M+H]$^+$=445 Da., and microanalysis.

EXAMPLE 205

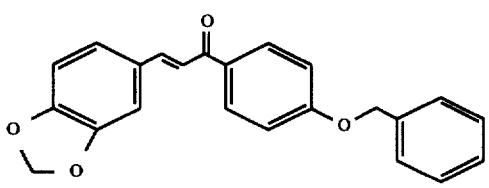

A mixture of chalcone, 200, (5.25 g, 19.6 mmol), K$_2$CO$_3$ (3 g, 20 mmol), and benzylbromide (3.4 g, 20 mmol) in 100 mL of DMF was heated to reflux for 3 hours. The solvent was removed by evaporation. The residue was purified by flash column chromatography (1000 g silica gel, (200:1) CHCl$_3$/ethyl acetate). The product was isolated by evaporation of the appropriate fractions to give 6.2 g (88% yield). The product was identified by $^1$H NMR, IR, MS, [M+H]$^+$=359.1 Da., and microanalysis.

EXAMPLE 206

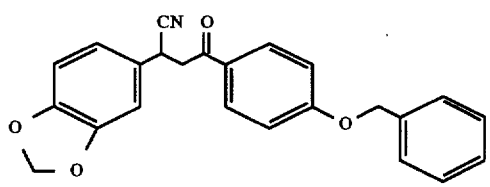

To the chalcone, 205, (5.3 g, 14.8 mmol) in 2-ethoxyethanol (100 mL) at 55° C. was added acetic acid (1.5 mL) followed by slow addition of potassium cyanide (2.7 g, 41.5 mmol) in water (1.5 mL). The solution was stirred at 105° C. for 0.25 hour. The solution was cooled and treated with water (25 mL). The mixture was then filtered to collect the solid. The solid was washed repeatedly with 70% ethanol (50 mL), air dried, and then dried in vacuo to give the nitrile 4.7 g (82.5%) as a brown solid. The nitrile was identified by $^1$H NMR and MS.

EXAMPLE 207

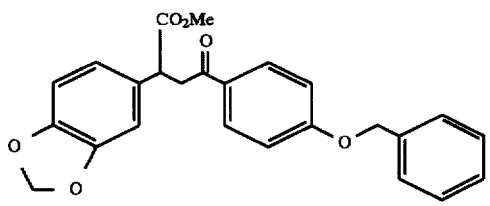

To the nitrile, 206, (3.4 g, 8.8 mmol) was added methanol (25 mL). The mixture was saturated with HCl (g) and heated to 45° C. until no nitrile remained, by thin-layer chromatography. The solution was cooled and treated with water (100 mL). The resultant solid was filtered to collect, washed with 80% methanol (20 mL) and dried in vacuo. This gave the ester 2.7 g (73%) as a white solid which was identified by $^1$H NMR, IR, MS, and microanalysis.

EXAMPLE 208

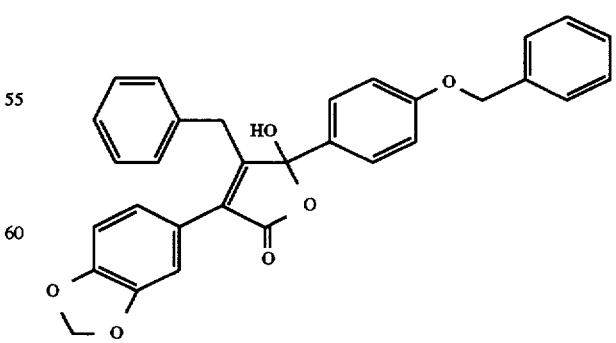

3-Benzo[1,3]dioxol-5-yl-4-benzyl-5-(4-benzyloxyphenyl)-5-hydroxy-5H-furan-2-one

To methanol (50 mL) was added sodium metal (0.15 g, 4.5 mmol) and stirred to dissolve. To this was added benzaldehyde (1 g, 9.4 mmol) then the ester, 207, (1.5 g, 3.6 mmol). The mixture was heated to reflux for 4 hours. The solution was then treated with acetic acid (3 mL) and refluxed an additional 12 hours. The solvents were removed by evaporation and the residue was partitioned between ethyl acetate (100 mL) and water (20 mL). The organic phase was separated and dried over magnesium sulfate and evaporated to dryness. The crude product was then purified by flash chromatography (300 g silica gel, (100:1) CHCl$_3$/ ethyl acetate). The butenolide was isolated by evaporation of the appropriate fractions to give 0.96 g (54%) as a white solid. The butenolide was identified by $^1$H NMR, IR, MS, [M+H]$^+$=493 Da., and microanalysis.

EXAMPLE 209

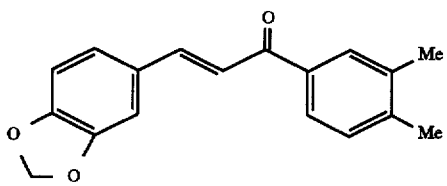

To 3'4'-dimethylacetophenone (11.5 g, 77.6 mmol) in absolute ethanol (200 mL) in an erlenmeyer was added piperonal (10 g, 67 mmol). The solution swirled while 10% sodium hydroxide (35 mL) added. The mixture swirled for 10 minutes and allowed to stand to precipitate. The solid was collected by filtration and washed with 80% ethanol (100 mL). The solid was dried in vacuo giving 18.6 g (99%) of a light yellow solid which was identified by $^1$H NMR, IR, MS, and microanalysis.

EXAMPLE 210

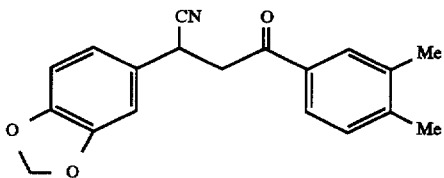

The chalcone, 209, (17.61 g, 62.9 mmol) in 2-ethoxyethanol (200 mL) at 55° C. was added acetic acid (4 mL) followed by slow addition of KCN (5.7 g, 87.7 mmol) in water (6 mL). The solution was stirred at 105° C. for 0.25 hour. The solvent was evaporated. The residue was purified by flash column chromatography (1.5 kg silica gel, CHCl$_3$). The product was isolated by evaporation of the appropriate fractions to give 19.08 g (98% yield) as a brown oil which was identified by $^1$H NMR.

EXAMPLE 211

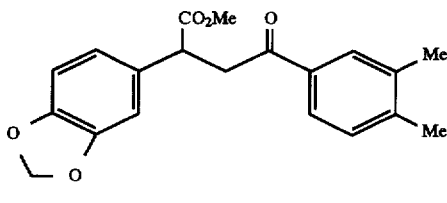

To the nitrile, 209, (12.5 g, 40.67 mmol) was added methanol (50 mL). The mixture was saturated with HCl (g) and heated to 45° C. until no nitrile remained, by thin-layer chromatography. The solution was cooled and treated with water (100 mL) and ethyl acetate (100 mL). The organic phase was separated and dried over MgSO$_4$ and evaporated. The crude product was purified by flash column chromatography (1000 g silica gel, (200:1) CHCl$_3$/ethyl acetate). The product was isolated by evaporation of the appropriate fractions to give the ester 11.2 g (81%) as a brown oil which was identified by $^1$H NMR.

EXAMPLE 212

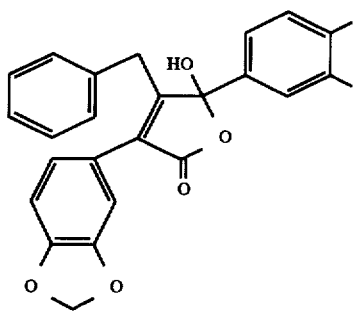

3-Benzo[1,3]dioxol-5-yl-4-benzyl-5-(3,4- dimethylphenyl)-5-hydroxy-5H-furan-2-one To methanol (60 mL) was added sodium metal (0.5 g, 22 mmol) and stirred to dissolve. To this was added benzaldehyde (2.6 g, 24.5 mmol) then the ester, 211, (5.6 g, 16.5 mmol). The mixture was heated to reflux for 4 hours. The solution was then treated with acetic acid (10 mL) and refluxed an additional 12 hours. The solvents were removed by evaporation and the residue was partitioned between ethyl acetate (200 mL) and water (25 mL). The organic phase was separated and dried over magnesium sulfate and evaporated to dryness. The crude product was then purified by flash chromatography (1000 g silica gel, (100:1) CHCl$_3$/ ethyl acetate). The butenolide was isolated by evaporation of the appropriate fractions to give 4.6 g (67%) as an orange solid. The butenolide was identified by $^1$H NMR, IR, MS, [M+H]$^+$=415 Da., and microanalysis.

EXAMPLE 213

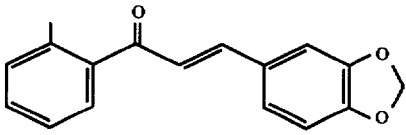

To o-methylacetophenone (10.1 g, 75 mmol) in absolute ethanol (40 mL) in an erlenmeyer was added piperonal (15 g, 100 mmol). The solution swirled while 10% sodium

EXAMPLE 214

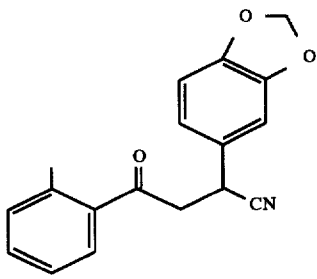

To the chalcone, 213, (24.5 g, 92 mmol) in ethanol (350 mL) at 55° C. was added acetic acid (11.4 mL) followed by slow addition of potassium cyanide (15 g, 230 mmol) in water (60 mL). The solution was stirred at 60° C. for 18 hours. The solution was cooled and treated with water (150 mL). The mixture was then filtered to collect the solid. The solid was washed repeatedly with 70% ethanol, air dried, and then dried in vacuo to give the nitrile 18.5 g (69%) as a solid. The nitrile was identified by $^1$H NMR, IR, MS, and microanalysis.

EXAMPLE 215

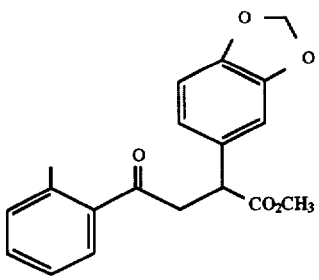

To the nitrile, 214, (3.8 g, 12.95 mmol) was added methanol (50 mL). The mixture was saturated with HCl (g) and heated to 45° C. until no nitrile remained, by thin-layer chromatography. The solution was cooled and treated with water (70 mL). The mixture was evaporated in vacuo and partitioned between water and ethyl acetate. The organic phase washed with brine and dried over magnesium sulfate. The organic phase was evaporated in vacuo. This gave the ester 3.7 g (88%) as a foam which was identified by $^1$H NMR, IR, MS, and microanalysis.

EXAMPLE 216

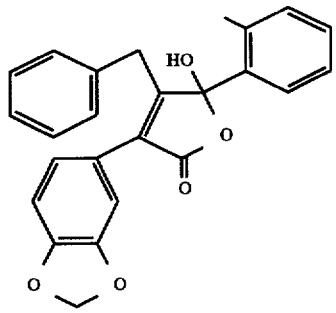

3-Benzo[1,3]dioxol-5-yl-4-benzyl-5-hydroxy-5-o-tolyl-5H-furan-2-one

To methanol (12 mL) was added sodium metal (97 mg, 4.2 mmol) and stirred to dissolve. To this was added benzaldehyde (467 mg, 4.4 mmol) then the ester, 215, (1.31 g, 4.0 mmol). The mixture was heated to reflux for 4.5 hours. The solution was then treated with acetic acid (1.5 mL) and refluxed an additional 16 hours. The solvents were removed by evaporation and the residue was partitioned between ethyl acetate (70 mL) and water (100 mL). The organic phase was separated and dried over magnesium sulfate and evaporated to dryness. The crude product was then purified by flash chromatography (200 g silica gel, 5% ethyl acetate-:methylene chloride). The butenolide was isolated by evaporation of the appropriate fractions to give 305 mg (19%) as a foam. The butenolide was identified by $^1$H NMR, IR, MS, [M+H]$^+$=401 Da., and microanalysis.

EXAMPLE 217

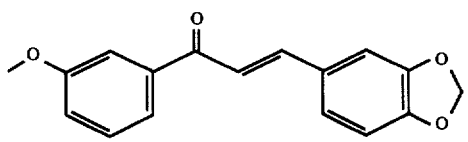

To m-methoxyacetophenone (11.3 g, 75 mmol) in absolute ethanol (30 mL) in an erlenmeyer was added piperonal (13.5 g, 90 mmol). The solution swirled while 10% sodium hydroxide (5 mL) added. The mixture swirled for 10 minutes and allowed to stand to precipitate. The solid was collected by filtration and washed with 80% ethanol. The solid was dried in vacuo giving 19.35 g (92%) of a solid which was identified by $^1$H NMR, IR, MS, and microanalysis.

EXAMPLE 218

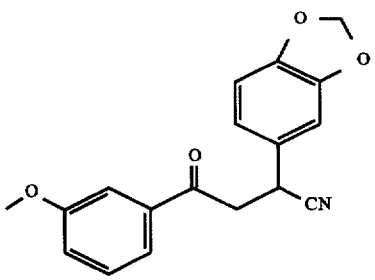

To the chalcone, 217, (17.85 g, 63.2 mmol) in ethanol (300 mL) at 55° C. was added acetic acid (7.6 mL) followed by slow addition of potassium cyanide (10.29 g, 158 mmol)

in water (50 mL). The solution was stirred at 75°–90° C. for 24 hours. The solution was cooled and treated with water (100 mL). The mixture was then filtered to collect the solid. The solid was washed repeatedly with 70% ethanol, air dried, and then dried in vacuo to give the nitrile 17.7 g (91%) as a solid. The nitrile was identified by $^1$H NMR, IR, MS, and microanalysis.

EXAMPLE 219

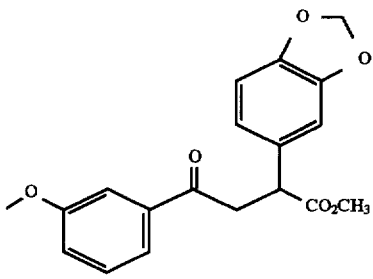

To the nitrile, 218, (17 g, 55 mmol) was added methanol (200 mL). The mixture was saturated with HCl (g) and heated to 45° C. until no nitrile remained, by thin-layer chromatography. The solution was cooled and treated with water (50 mL). The compound oiled out of solution. The liquid phase was decanted off the oil and the oil partitioned between ethyl acetate and brine. The organic phase was dried over magnesium sulfate and evaporated in vacuo to give a foam. The ester 15.1 g (80%) was identified by $^1$H NMR, IR, MS, and microanalysis.

EXAMPLE 220

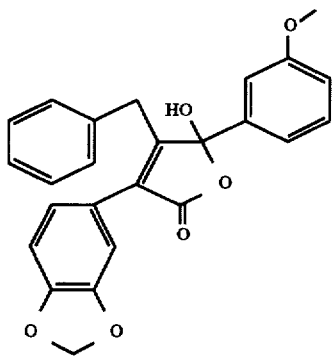

3-Benzo[1,3]dioixol-5-yl-4-benzyl-5-hydroxy-5-(3-methoxyphenyl)-5H-furan-2-one

To methanol (10 mL) was added sodium metal (97 mg, 4.2 mmol) and stirred to dissolve. To this was added benzaldehyde (467 mg, 4.4 mmol) then the ester, 219, (1.37 g, 4.0 mmol). The mixture was heated to reflux for 4 hours. The solution was then treated with acetic acid (1.0 mL) and refluxed an additional 18 hours. The solvents were removed by evaporation and the residue was partitioned between ethyl acetate (75 mL) and water (50 mL). The organic phase was separated and dried over magnesium sulfate and evaporated to dryness. The crude product was then purified by flash chromatography (250 g silica gel, 5% ethyl acetate/ methylene chloride). The butenolide was isolated by evaporation of the appropriate fractions to give 545 mg (33%) as a light yellow foam. The butenolide was identified by $^1$H NMR, IR, MS, [M+H]$^+$=417 Da., and microanalysis.

EXAMPLE 221

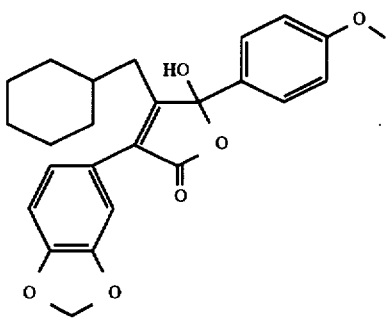

3-Benzo[1,3]dioxol-5-yl-4-cyclohexylmethyl-5-hydroxy-5-(4-methoxyphenyl)-5H-furan-2-one To ethanol (12 mL) was added sodium metal (97 mg, 4.2 mmol) and stirred to dissolve. To this was added cyclohexanecarboxaldehyde (494 mg, 4.4 mmol) then the ester, 19, (1.37 g, 4.0 mmol). The mixture was heated to reflux for 90 hours. The solution was then treated with acetic acid (1.0 mL) and refluxed an additional 24 hours. The solvents were removed by evaporation and the crude product was then purified by flash chromatography (150 g silica gel, 5–10% ethyl acetate/methylene chloride). The butenolide was isolated by evaporation of the appropriate fractions to give 190 mg (11%) as a light yellow oil. The butenolide was identified by $^1$H NMR, IR, MS, [M+]$^+$=417 Da., and microanalysis.

EXAMPLE 222

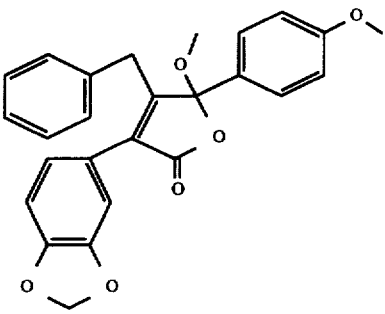

3-Benzo[1,3]dioxol-5-yl-4-benzyl-5-methoxy-5-(4-methoxyphenyl)-5H-furan-2-one

To the butenolide, 20, (205 mg, 0.5 mmol) in methanol (15 mL) was added HCl (g). The saturated solution warmed to 50° C. for 18 hours. The cooled solution was evaporated in vacuo and the product purified by chromatography (120 g silica gel, 3:1 hexane:ethyl acetate). The appropriate fractions were combined and evaporated to give the new butenolide as a clear solid, 119 mg (55%). The compound was identified by $^1$H NMR, IR, MS, [M+H]$^+$=431 Da., and microanalysis.

EXAMPLE 223

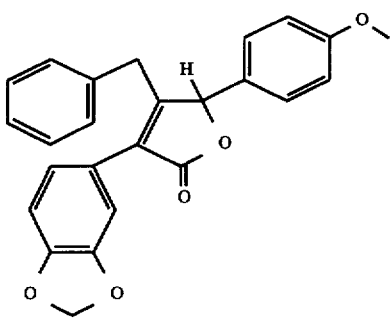

3-Benzo[1,3]dioxol-5-yl-4-benzyl-5-(4-methoxyphenyl)-5H-furan-2-one

In TFA (8 mL), at 0° C., under an $N_2$ stream was added in parts a mixture of the butenolide (416 mg, 1.0 mmol) and sodium borohydride (378 mg, 10 mmol). The resultant deep green solution was stirred for 5 minutes. The solution evaporated free of TFA and carefully treated with water (20 mL). The solution extracted with ethyl acetate (25 mL) and the organic phase separated and washed with brine. The organic phase evaporated and the crude material purified by chromatography (70 g silica gel, 5% ethyl acetate/methylene chloride). The appropriate fractions were combined and evaporated in vacuo to give the new butenolide as a yellow solid, 282 mg (70%). The butenolide was identified by $^1$H NMR, Ir, MS, $[M+H]^+$=401 Da., and microanalysis.

EXAMPLE 224

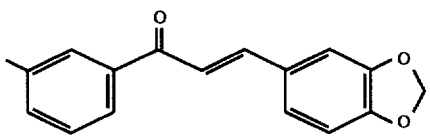

To m-methylacetophenone (10.06 g, 75 mmol) in absolute ethanol (30 mL) in an erlenmeyer was added piperonal (13.50 g, 90 mmol). The solution swirled while 10% sodium, hydroxide (5 mL) added. The mixture swirled for 10 minutes and allowed to stand to precipitate. The solid was collected by filtration and washed with 80% ethanol (2×100 mL). The solid was dried in vacuo giving 19.1 g (96%) of a solid which was identified by $^1$H NMR, IR, MS, and microanalysis.

EXAMPLE 225

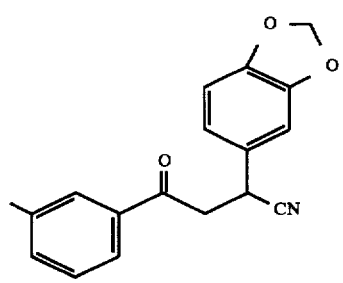

To the chalcone, 224, (16.0 g, 60 mmol) in ethanol (300 mL) at 55° C. was added acetic acid (8.1 mL) followed by slow addition of potassium cyanide (9.8 g, 150 mmol) in water (50 mL). The solution was stirred at 70° C. for 24 hours. The solution was cooled and treated with water (125 mL). The mixture was then filtered to collect the solid. The solid was washed repeatedly with 70% ethanol (200 mL), air dried, and then dried in vacuo to give the nitrile 15.1 g (86%) as a solid. The nitrile was identified by $^1$H NMR, IR, MS, and microanalysis.

EXAMPLE 226

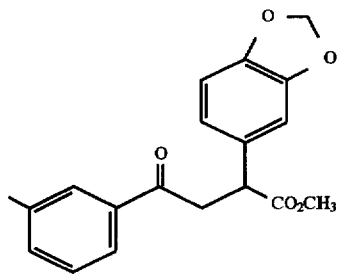

To the nitrile, 225, (10 g, 34.1 mmol) was added methanol (120 mL). The mixture was saturated with HCl (g) and heated to 45° C. until no nitrile remained, by thin-layer chromatography. The solution was cooled and treated with water (30 mL). The resultant solid was filtered to collect, washed with 80% methanol, and dried in vacuo. This gave the ester 6.7 g (60%) as a tan solid which was identified by $^1$H NMR, IR, MS, and microanalysis.

EXAMPLE 227

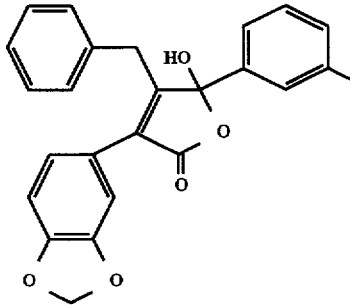

3-Benzo[1,3-dioxol-5-yl-4-benzyl-5-hydroxy-5-m-tolyl-5H-furan-2-one

To methanol (12 mL) was added sodium metal (97 mg, 4.2 mmol) and stirred to dissolve. To this was added benzaldehyde (467 mg, 4.4 mmol) then the ester, 226, (1.31 g, 4.0 mmol). The mixture was heated to reflux for 6 hours. The solution was then treated with acetic acid (2 mL) and refluxed an additional 18 hours. The solvents were removed by evaporation and the residue was partitioned between ethyl acetate (50 mL) and water (50 mL). The organic phase was separated and dried over magnesium sulfate and evaporated to dryness. The crude product was then purified by flash chromatography (150 g silica gel, 5% ethyl acetate/methylene chloride). The butenolide was isolated by evaporation of the appropriate fractions to give 980 mg (61%) as a foam. The butenolide was identified by $^1$H NMR, IR, MS, $[M+H]^+$=401 Da., and microanalysis.

EXAMPLE 228

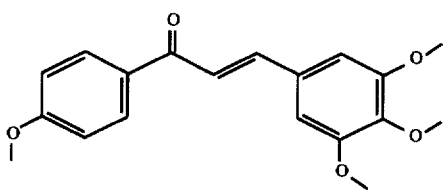

To p-methoxyacetophenone (10.5 g, 70 mmol) in absolute ethanol (65 mL) in an erlenmeyer was added 3,4,5-trimethoxybenzaldehyde (16.7 g, 85 mmol). The solution swirled while 10% sodium hydroxide (3 mL) added. The mixture swirled for 10 minutes and allowed to stand to precipitate. The solid was collected by filtration and washed with 80% ethanol. The solid was dried in vacuo giving 22.4 g (97%) of a solid which was identified by $^1$H NMR, IR, MS, and microanalysis.

EXAMPLE 229

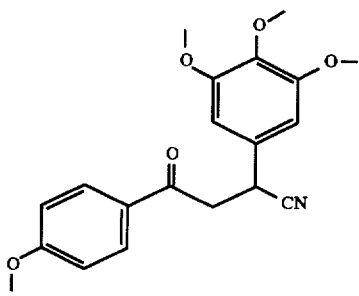

To the chalcone, 228, (13.93 g, 42.4 mmol) in ethanol (250 mL) at 55° C. was added acetic acid (5.8 mL) followed by slow addition of potassium cyanide (6.9 g, 106 mmol) in water (50 mL). The mixture treated with chloroform (50 mL). The solution was stirred at 60° C. for 24 hours. The mixture treated with an additional amount of potassium cyanide (6.9 g, 106 mmol) and acetic acid (5.8 g) and warmed to reflux, stirred 24 hours. The reaction mixture evaporated free of solvents and the aqueous extracted with ethyl acetate. The organic phase washed with 10% citric acid (75 mL), saturated sodium bicarbonate (75 mL), and brine (75 mL). The organic phase was dried over magnesium sulfate and evaporated in vacuo to give an oil, 8.6 g (57%). The nitrile was identified by $^1$H NMR, IR, MS, and microanalysis.

EXAMPLE 230

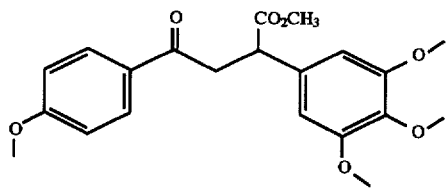

To the nitrile, 229, (8.3 g, 23.4 mmol) was added methanol (120 mL). The mixture was saturated with HCl (g) and heated to 45° C. until no nitrile remained, by thin-layer chromatography. The solution was cooled and treated with water (75 mL). The resultant solid was filtered to collect, washed with 80% methanol, and dried in vacuo. This gave the ester 3.7 g (40%) as a tan solid which was identified by $^1$H NMR, IR, MS, and microanalysis.

EXAMPLE 231

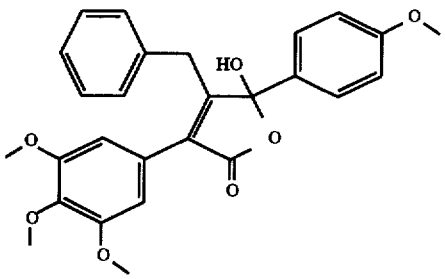

4-Benzyl-5-hydroxy-5-(4-methoxyphenyl)-3-(3,4,5-trimethoxyphenyl)-5H-furan-2-one To methanol (12 mL) was added sodium metal (97 g, 4.2 mmol) and stirred to dissolve. To this was added benzaldehyde (467 g, 4.4 mmol) then the ester, 230, (1.55 g, 4.0 mmol). The mixture was heated to reflux for 18 hours. The solution was then treated with acetic acid (2 mL) and refluxed an additional 8 hours. The solvents were removed by evaporation and the residue was partitioned between ethyl acetate (50 mL) and water (50 mL). The organic phase was separated and dried over magnesium sulfate and evaporated to dryness. The crude product was then purified by flash chromatography (150 g silica gel, (1:3) ethyl acetate: methylene chloride). The butenolide was isolated by evaporation of the appropriate fractions to give 690 mg (37%) as a white solid. The butenolide was identified by $^1$H NMR, IR, MS, [M+H]$^+$=463 Da., and microanalysis.

EXAMPLE 232

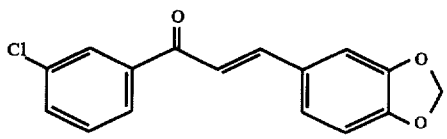

To m-chloroacetophenone (6.8 g, 50 mmol) in absolute ethanol (30 mL) in an erlenmeyer was added piperonal (10.1 g, 67.5 mmol). The solution swirled while 10% sodium hydroxide (32 mL) added. The mixture swirled for 10 minutes and allowed to stand to precipitate. The solid was collected by filtration and washed with 80% ethanol. The solid was dried in vacuo giving 12.7 g (89%) of a solid which was identified by $^1$H NMR, IR, MS, and microanalysis.

EXAMPLE 233

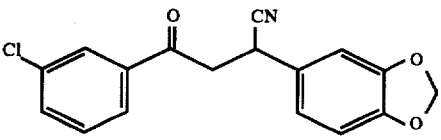

To the chalcone, 232, (11.3 g, 39.4 mmol) in ethanol (300 mL) at 55° C. was added acetic acid (4.7 mL) followed by slow addition of potassium cyanide (6.4 g, 98 mmol) in water (40 mL). The solution was stirred at 60°–70° C. for 18 hours. The solution was cooled and treated with water (100 mL). The mixture was then filtered to collect the solid. The solid was washed repeatedly with 70% ethanol, air dried, and then dried in vacuo to give the nitrile 9.95 g (80%) as a solid. The nitrile was identified by $^1$H NMR, IR, MS, and microanalysis.

EXAMPLE 234

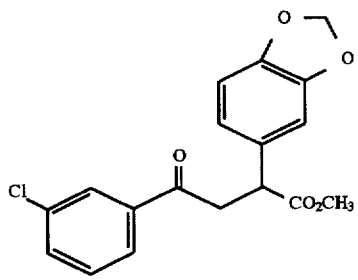

To the nitrile, 233, (9.65 g, 30.8 mmol) was added methanol (100 mL). The mixture was saturated with HCl (g) and heated to 45° C. until no nitrile remained, by thin-layer chromatography. The solution was cooled and treated with water (75 mL). The resultant solid was filtered to collect, washed with 80% methanol, and dried in vacuo. This gave the ester 7.0 g (65%) as a solid which was identified by $^1$H NMR, IR, MS, and microanalysis.

EXAMPLE 235

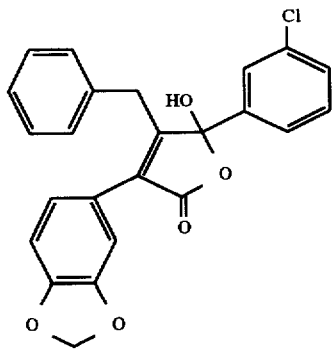

3-Benzo[1,3]dioxol-5-yl-4-benzyl-5-(3-chlorophenyl)-5-hydroxy-5H-furan-2-one

To methanol (12 mL) was added sodium metal (97 mg, 4.2 mmol) and stirred to dissolve. To this was added benzaldehyde (467 g, 4.4 mmol) then the ester, 234, (1.39 g, 4.0 mmol). The mixture was heated to reflux for 24 hours. The solution was then treated with acetic acid (1.0 mL) and refluxed an additional 7 hours. The solvents were removed by evaporation and the residue was partitioned between ethyl acetate (50 mL) and water (50 mL). The organic phase was separated and dried over magnesium sulfate and evaporated to dryness. The crude product was then purified by flash chromatography (200 g silica gel, 5% ethyl acetate/methylene chloride). The butenolide was isolated by evaporation of the appropriate fractions to give 1.1 g (65%) as a solid. The butenolide was identified by $^1$H NMR, IR, MS, [M+H]$^+$=421 Da., and microanalysis.

EXAMPLE 236

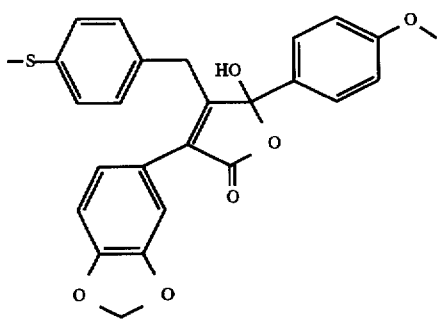

3-Benzo[1,3]dioxol-5-yl-5-hydroxy-5-(4-methoxyphenyl)-4-(4-methylsulfanylbenzyl)-5H-furan-2-one To methanol (25 mL) was added sodium metal (301 mg, 13.1 mmol) and stirred to dissolve. To this was added 4-thiomethylbenzaldehyde (2.09 g, 13.75 mmol) then the ester, 19, (4.48 g, 12.5 mmol). The mixture was heated to reflux for 24 hours. The solution was then treated with acetic acid (3 mL) and refluxed an additional 24 hours. The solvents were removed by evaporation and the residue was partitioned between ethyl acetate (75 mL) and water (75 mL). The organic phase was separated and dried over magnesium sulfate and evaporated to dryness. The crude product was then purified by flash chromatography (100 g silica gel, 5% ethyl acetate/methylene chloride). The butenolide was isolated by evaporation of the appropriate fractions to give 2.3 g (39%) as glass. The butenolide was identified by $^1$H NMR, IR, MS, [M+H]$^+$=463 Da., and microanalysis.

EXAMPLE 237

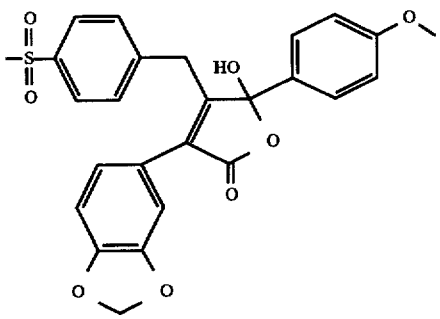

3-Benzo[1,3]dioxol-5-yl-5-hydroxy-4-(4-methanesulfonylbenzyl)-5-(4-methoxyphenyl)-5H-furan-2-one In chloroform (45 mL) was dissolved the butenolide, 236, (735 mg, 1.54 mmol) and 50% m-chloroperbenzoic acid (1.38 g, 4.0 mmol). The solution warmed to 50° C. for 24 hours. The mixture filtered free of insolubles and the organic filtrate washed successively with water (100 mL), saturated NaHCo (40 mL), and brine (40 mL). The organic phase dried over magnesium sulfate and evaporated in vacuo. The crude material was purified by chromatography (150 g silica gel, 20% ethyl acetate/methylene chloride). The appropriate fractions were combined and evaporated in vacuo to give a light yellow foam, 295 mg (38%). The butenolide was identified by $^1$H NMR, IR, MS, [M+H]$^+$=495, and microanalysis.

EXAMPLE 238

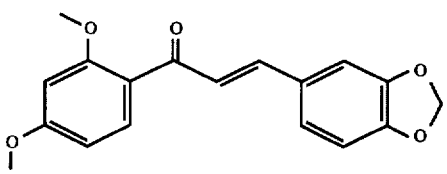

To 2,4-dimethoxyacetophenone (12.6 g, 75 mmol) in absolute ethanol (50 mL) in an erlenmeyer was added piperonal (11.26 g, 75 mmol). The solution swirled while 10% sodium hydroxide (3 mL) added. The mixture swirled for 10 minutes and allowed to stand to precipitate. The solid was collected by filtration and washed with 80% ethanol (2×100 mL). The solid was dried in vacuo giving 21.1 g (96%) of a solid which was identified by $^1$H NMR, IR, MS, and microanalysis.

EXAMPLE 239

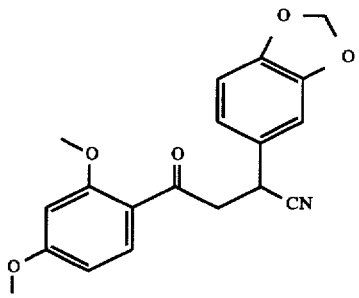

To the chalcone, 238, (15.6 g, 50 mmol) in ethanol (300 mL) at 55° C. was added acetic acid (7.0 mL) followed by slow addition of potassium cyanide (8.14 g, 128 mmol) in water (50 mL). The solution was stirred at 70° C. for 96 hours. The solution was cooled and treated with water (100 mL). The mixture was then filtered to collect the solid. The solid was washed repeatedly with 70% ethanol, air dried, and then dried in vacuo to give the nitrile 9.9 g (58%) as a solid. The nitrile was identified by $^1$H NMR, IR, and microanalysis.

EXAMPLE 240

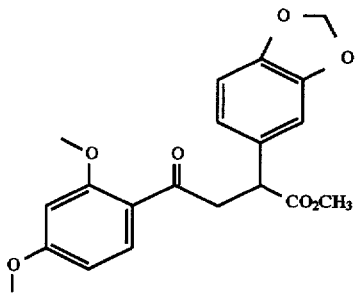

To the nitrile, 239, (9.06 g, 26.7 mmol) was added methanol (50 mL). The mixture was saturated with HCl (g) and heated to 45° C. until no nitrile remained, by thin-layer chromatography. The solution was cooled and treated with water (30 mL). The resultant solid was filtered to collect, washed with 80% methanol (2×100 mL) and dried in vacuo. This gave the ester 4.9 g (49%) as a solid which was identified by $^1$H NMR, IR, MS, and microanalysis.

EXAMPLE 241

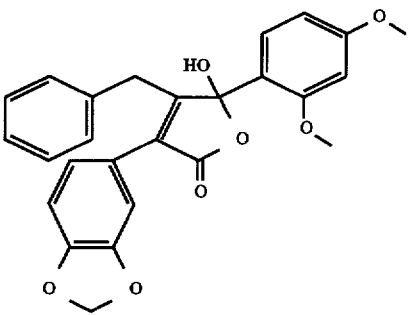

3-Benzo[1,3]dioxol-5-yl-4-benzyl-5-(2,4-dimethoxyphenyl)-5-hydroxy-5H-furan-2-one To methanol (12 mL) was added sodium metal (97 g, 4.2 mmol) and stirred to dissolve. To this was added benzaldehyde (467 g, 4.4 mmol) then the ester, 240, (1.49 g, 4.0 mmol). The mixture was heated to reflux for 24 hours. The solution was then treated with acetic acid (2 mL) and refluxed an additional 24 hours. The solvents were removed by evaporation and the residue was partitioned between ethyl acetate (50 mL) and water (50 mL). The organic phase was separated and dried over magnesium sulfate and evaporated to dryness. The crude product was then purified by flash chromatography (150 g silica gel, 5% ethyl acetate/methylene chloride). The butenolide was isolated by evaporation of the appropriate fractions to give 501 mg (28%) as a tan foam. The butenolide was identified by $^1$H NMR, IR, MS, [M+H]$^+$=447 Da., and microanalysis.

EXAMPLE 242

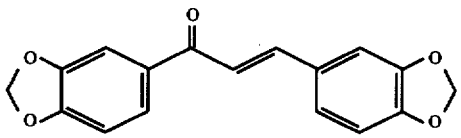

To 3,4-methylenedioxyacetophenone (16.4 g, 100 mmol) in absolute ethanol (80 mL) in an erlenmeyer was added piperonal (16.5 g, 110 mmol). The solution swirled while 10% sodium hydroxide (5 mL) added. The mixture swirled for 10 minutes and allowed to stand to precipitate. The solid was collected by filtration and washed with 80% ethanol (2×200 mL). The solid was dried in vacuo giving 21.2 g (72%) of a solid which was identified by $^1$H NMR, IR, MS, and microanalysis.

EXAMPLE 243

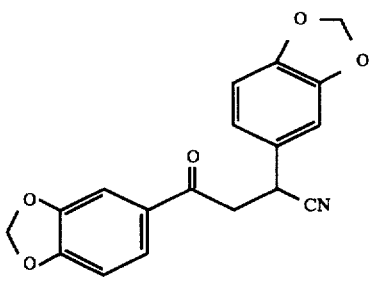

To the chalcone, 242, (20.85 g, 70.4 mmol) in ethanol (400 mL) at 55° C. was added acetic acid (9.2 mL) followed by slow addition of potassium cyanide (11.45 g, 176 mmol) in water (50 mL). The solution was stirred at reflux for 24 hours. The solution was cooled and treated with water (350 mL). The mixture was then filtered to collect the solid. The solid was washed repeatedly with 70% ethanol, air dried, and then dried in vacuo to give the nitrile 22.2 g (97%). The nitrile was identified by $^1$H NMR, IR, MS, and microanalysis.

EXAMPLE 244

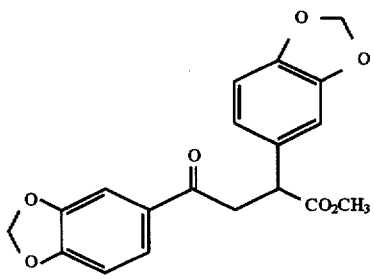

To the nitrile, 243, (21.2 g, 65.6 mmol) was added methanol (150 mL). The mixture was saturated with HCl (g) and heated to 45° C. until no nitrile remained, by thin-layer chromatography. The solution was cooled and treated with water (150 mL). The resultant solid was filtered to collect, washed with 80% methanol (100 mL), and dried in vacuo. This gave the ester 6.1 g (26%) as a solid which was identified by $^1$H NMR, IR, MS, and microanalysis.

EXAMPLE 245

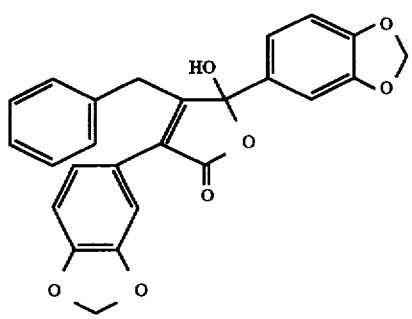

3,5-Bis-benzo[1,3]dioxol-5-yl-4-benzyl-5-hydroxy-5H-furan-2-one

To methanol (12 mL) was added sodium metal (101 mg, 4.4 mmol) and stirred to dissolve. To this was added benzaldehyde (488 mg, 4.6 mmol) then the ester, 244, (1.43 g, 4.0 mmol). The mixture was heated to reflux for 24 hours. The solution was then treated with acetic acid (2 mL) and refluxed an additional 24 hours. The solvents were removed by evaporation and the residue was partitioned between ethyl acetate (25 mL) and water (25 mL). The organic phase was separated and dried over magnesium sulfate and evaporated to dryness. The crude product was then purified by flash chromatography (150 g silica gel, 10% ethyl acetate/ methylene chloride). The butenolide was isolated by evaporation of the appropriate fractions to give 595 mg (35%) as a solid. The butenolide was identified by $^1$H NMR, IR, MS, $[M+H]^+$=431 Da., and microanalysis.

EXAMPLE 246

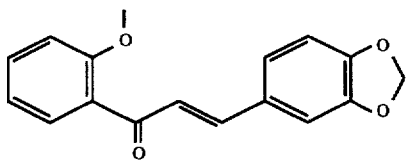

To o-methyoxyacetophenone (10.5 g, 70 mmol) in absolute ethanol (35 mL) in an erlenmeyer was added piperonal (11.26 g, 75 mmol). The solution swirled while 10% sodium hydroxide (2 mL) added. The mixture swirled for 10 minutes and allowed to stand to precipitate. The solid was collected by filtration and washed with 80% ethanol. The solid was dried in vacuo giving 19.1 g (96%) of a solid which was identified by $^1$H NMR, IR, MS, and microanalysis.

EXAMPLE 247

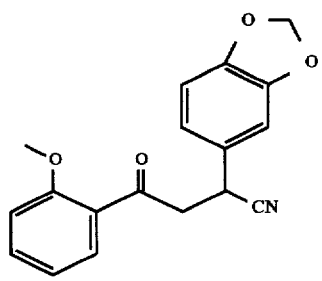

To the chalcone, 246, (18.3 g, 64.8 mmol) in ethanol (200 mL) at 55° C. was added acetic acid (8.6 mL) followed by slow addition of potassium cyanide (10.5 g, 162 mmol) in water (20 mL). The solution was stirred at 60° C. for 18 hours. The solution was cooled and treated with water (120 mL). The mixture was then filtered to collect the solid. The solid was washed repeatedly with 70% ethanol, air dried, and then dried in vacuo to give the nitrile 11.55 g (58%). The nitrile was identified by $^1$H NMR, IR, MS, and microanalysis.

EXAMPLE 248

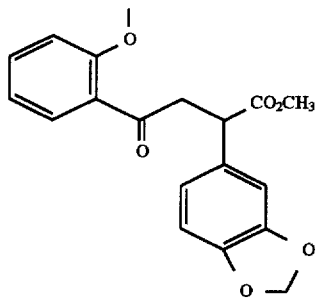

To the nitrile, 247, (11.17 g, 36.1 mmol) was added methanol (125 mL). The mixture was saturated with HCl (g) and heated to 45° C. until no nitrile remained, by thin-layer chromatography. The solution was cooled and treated with water (120 mL). The resultant solid was filtered to collect, washed with 80% methanol (2×100 mL), and dried in vacuo. This gave the ester 7.7 g (63%) as a solid which was identified by $^1$H NMR, IR, MS, and microanalysis.

EXAMPLE 249

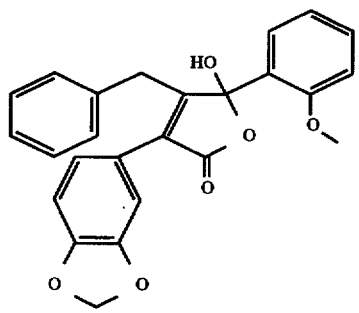

3-Benzo[1,3]dioxol-5-yl-4-benzyl-5-hydroxy-5-(2-methoxyphenyl)-5H-furan-2-one

To methanol (12 mL) was added sodium metal (97 mg, 4.2 mmol) and stirred to dissolve. To this was added benzaldehyde (467 g, 4.4 mmol) then the ester, 248, (1.37 g, 4.0 mmol). The mixture was heated to reflux for 18 hours. The solution was then treated with acetic acid (2 mL) and refluxed an additional 24 hours. The solvents were removed by evaporation and the residue was partitioned between ethyl acetate (75 mL) and water (75 mL). The organic phase was separated and dried over magnesium sulfate and evaporated to dryness. The crude product was then purified by flash chromatography (silica gel, 5% ethyl acetate/methylene chloride). The butenolide was isolated by evaporation of the appropriate fractions to give 605 mg (38%) as a white foam. The butenolide was identified by $^1$H NMR, IR, MS, [M+H]$^+$=417 Da., and microanalysis.

EXAMPLE 250

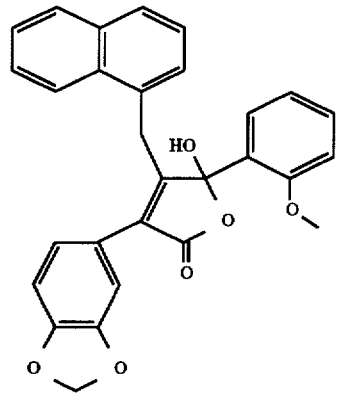

3-Benzo[1,3]dioxol-5-yl-5-hydroxy-5-(4-methoxyphenyl)-4-naphthalen-1-ylmethyl-5H-furan-2-one To methanol (10 mL) was added sodium metal (97 mg, 4.2 mmol) and stirred to dissolve. To this was added benzaldehyde (467 g, 4.4 mmol) then the ester, 19, (1.37 g, 4.0 mmol). The mixture was heated to reflux for 18 hours. The solution was then treated with acetic acid (2 mL) and refluxed an additional 24 hours. The solvents were removed by evaporation and the residue was partitioned between ethyl acetate (30 mL) and water (50 mL). The organic phase was separated and dried over magnesium sulfate and evaporated to dryness. The crude product was then purified by flash chromatography (150 g silica gel, 10% ethyl acetate/methylene chloride). The butenolide was isolated by evaporation of the appropriate fractions to give 1.50 mg (80%) as a white foam. The butenolide was identified by $^1$H NMR, IR, MS, [M+H]$^+$=467 Da., and microanalysis.

EXAMPLE 251

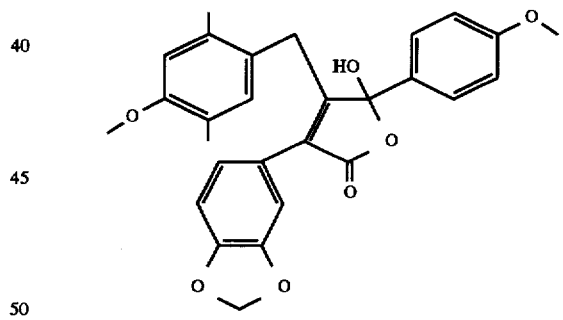

3-Benzo[1,3]dioxol-5-yl-5-hydroxy-4-(4-methoxy-2,5-dimethylbenzyl)-5-(4-methoxyphenyl)-5H-furan-2-one To methanol (12 mL) was added sodium metal (97 mg, 4.2 mmol) and stirred to dissolve. To this was added 2,5-dimethyl-4-methoxybenzaldehyde (722 mg, 4.4 mmol) then the ester, 19, (1.37 g, 4.0 mmol). The mixture was heated to reflux for 18 hours. The solution was then treated with acetic acid (1.0 mL) and refluxed an additional 24 hours. The solvents were removed by evaporation and the residue was partitioned between ethyl acetate (50 mL) and water (50 mL). The organic phase was separated and dried over magnesium sulfate and evaporated to dryness. The crude product was then purified by flash chromatography (150 g silica gel, 5% ethyl acetate/methylene chloride). The butenolide was isolated by evaporation of the appropriate fractions to give 340 mg (18%) as a white foam. The butenolide was identified by ¹H NMR, IR, MS, [M+H]⁺= 475 Da., and microanalysis.

EXAMPLE 252

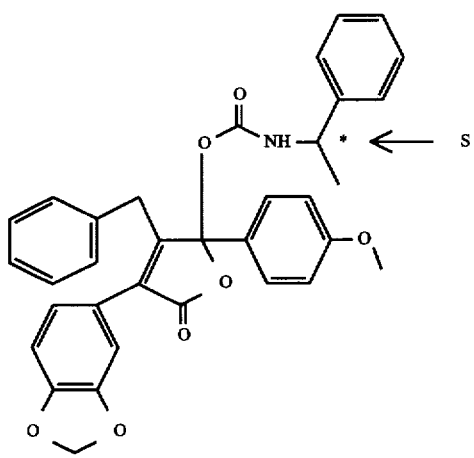

[R-(R*,S*)] and [S-(R*,R*)]carbamic acid, (1-phenylethyl)-, 4-(1,3-benzodioxol-5-yl)-2,5-dihydro-2-(4-methoxyphenyl)-5-oxo-3-(phenylmethyl)-2-furanyl ester In methylene chloride (5 mL) was dissolved the butenolide, 20, (416 mg, 1.0 mmol) and the solution treated with (S)-α-phenethylisocyanate (162 mg, 1.1 mmol) and the mix stirred at room temperature for 24 hours. The mixture treated with DMAP (15 mg) and again with (S)-α-phenethylisocyanate (162 mg, 1.1 mmol). The solution stirred for an additional 24 hours and then quenched with water (20 mL). The solution treated with ethyl acetate (10 mL) and the organic phase separated, dried over magnesium sulfate, and evaporated to give an oil. The oil was purified by flash chromatography (70 g silica gel, 2:1 hexane:ethyl acetate). The new butenolide 310 mg (55%) was identified by ¹H NMR, IR, MS, [M+H]⁺=564 Da., and microanalysis.

EXAMPLE 253

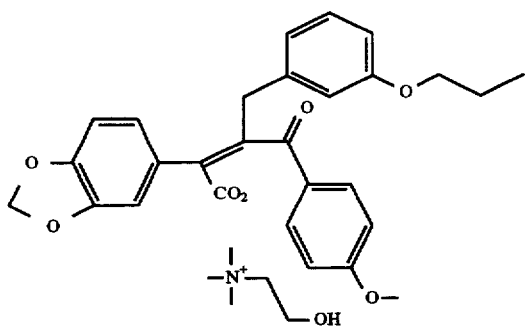

2-Butenoic acid, 2-(1,3-benzodioxol-5-yl)-4-(4-methoxyphenyl)-4-oxo-3-[(3-propoxyphenyl)methyl]-, (Z)-, ion(1-) compound with 2-hydroxy-N,N,N-trimethylethanaminium (1:1)

The butenolide, 159, (5.0 g, 10.54 mmol) was dissolved in methanol (100 mL) and the solution treated with choline hydroxide (45% solution in methanol) (1.28 g, 10.54 mmol). The solution stirred for 0.5 hour and evaporated in vacuo to give a foam. The foam was dissolved in water (150 mL) and washed once with ether (100 mL). The aqueous solution was evaporated in vacuo free of organics, frozen, and lyophilized to give 5.2 g (87%) of the salt. The salt was identified by ¹H NMR, IR, MS, [M+H]⁺=578 Da., and microanalysis.

EXAMPLE 254

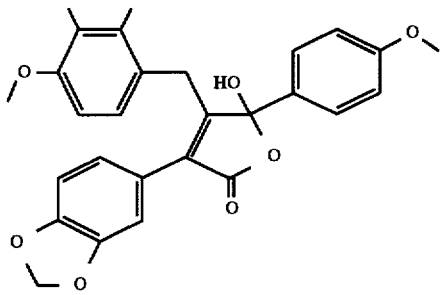

3-Benzo[1,3]dioxol-5-yl-5-hydroxy-4-(4-methoxy-2,3-dimethylbenzyl)-5-(4-methoxyphenyl)-5H-furan-2-one To methanol (10 mL) was added sodium metal (97 mg, 4.2 mmol) and stirred to dissolve. To this was added 2,3-dimethyl-4-methoxybenzaldehyde (722 mg, 4.4 mmol) then the ester, 19, (1.37 g, 4.8 mmol). The mixture was heated to reflux for 18 hours. The solution was then treated with acetic acid (2 mL) and refluxed an additional 24 hours. The solvents were removed by evaporation and the residue was partitioned between ethyl acetate (50 mL) and water (50 mL). The organic phase was separated and dried over magnesium sulfate and evaporated to dryness. The crude product was then purified by flash chromatography (100 g silica gel, 10% ethyl acetate/methylene chloride). The butenolide was isolated by evaporation of the appropriate fractions to give 198 mg (10%) as a pale yellow foam. The butenolide was identified by ¹H NMR, IR, MS, [M+H]⁺= 475 Da., and microanalysis.

EXAMPLE 255

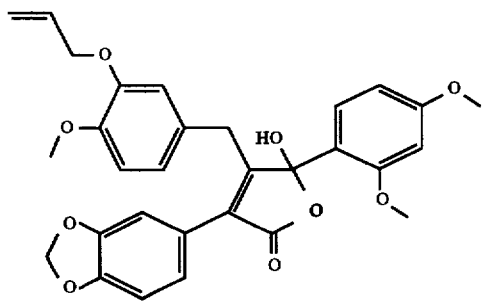

4-(3-Allyloxy-4-methoxybenzyl)-3-benzo[1,3]dioxol-5-yl-5-(2,4-dimethoxyphenyl)-5-hydroxy-5H-furan-2-one To methanol (8 mL) was added sodium metal (101 mg, 4.4 mmol) and stirred to dissolve. To this was added 3-allyloxy-4-methoxybenzaldehyde (865 mg, 4.5 mmol) then the ester, 240, (1.61 g, 4.3 mmol). The mixture was heated to reflux for 18 hours. The solution was then treated with acetic acid (2 mL) and refluxed an additional 72 hours. The solvents were removed by evaporation and the residue was partitioned between ethyl acetate (50 mL) and water (50 mL). The organic phase was separated and dried over magnesium sulfate and evaporated to dryness. The crude product was then purified by flash chromatography (150 g silica gel, 10% ethyl acetate/methylene chloride). The butenolide was isolated by evaporation of the appropriate fractions to give 185 mg (8%) as light yellow foam. The butenolide was identified by ¹H NMR, IR, MS, [M+H]⁺= 533 Da., and microanalysis.

EXAMPLE 256

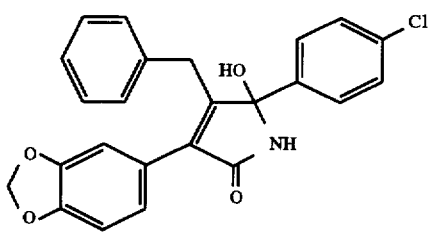

3-Benzo[1,3]dioxol-5-yl-4-benzyl-5-(4-chlorophenyl)-5-hydroxy-1,5-dihydropyrrol-2-one A solution of 39 (100 mg, 0.228 mmol) in anhydrous THF (1 mL) was treated with ammonium hydroxide (0.3 mL), and the reaction mixture stirred for 2 hours at room temperature. The solvent was evaporated, the residue taken up in ethyl acetate, dried over magnesium sulfate, and the solvent evaporated. The resulting glass was crystallized from hexane/ethyl acetate to afford the product as brown crystals (80.0 mg, 83%). The product was characterized by $^1$H NMR, MS, (M+H)=420), IR, and C NMR.

EXAMPLE 257

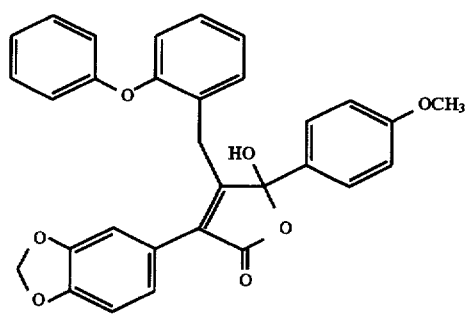

3-Benzo[1,3]dioxol-5-yl-5-hydroxy-5-(4-methoxyphenyl)-4-(2-phenoxybenzyl)-5H-furan-2-on To methanol 30 mL was added sodium metal (0.125 g, 5.46 mmol) and stirred to dissolve. To this was added O-phenoxybenzaldehyde (1.28 g, 6.4 mmol) then the ester, 19, (1.70 g, 4.96 mmol). The mixture was heated to reflux for 6 hours. The solution was then treated with acetic acid 3 mL and refluxed an additional 24 hours. The solvents were removed by evaporation and the residue was partitioned between ethyl acetate 50 mL and water 25 mL. The organic phase was separated and dried over magnesium sulfate and evaporated to dryness. The crude product was then purified by flash chromtography (50 g silica gel, EtOAc/hexane=25/75). The butenolide was isolated by evaporation of the appropriate fractions to give 1.78 g (70%) as a green foam. The butenolide was identified by $^1$H NMR, IR, M, [M+H]$^+$=509 Da., and microanalysis.

EXAMPLE 258

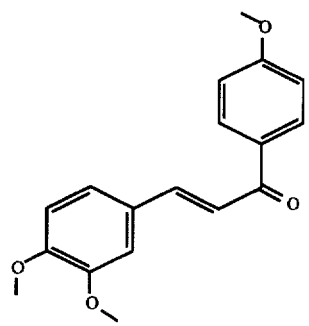

To 4-methoxyacetophenone (10.5 g, 70 mmol) in absolute ethanol (40 mL) in an erlenmeyer was added 3,4-dimethoxybenzaldehyde (14.0 g, 90 mmol). The solution swirled while 10% sodium hydroxide (4 mL) added. The mixture swirled for 10 minutes and allowed to stand. The solution evaporated to a small volume diluted with ethyl acetate (200 mL) and washed successively with 10% citric acid, saturated sodium bicarbonate (150 mL), 15% sodium bisulfite (2×150 mL), and brine (150 mL). The organic phase dried over magnesium sulfate and evaporated in vacuo to give a thick oil 21.3 g (100%), which was identified by $^1$H NMR, IR, MS, and microanalysis.

EXAMPLE 259

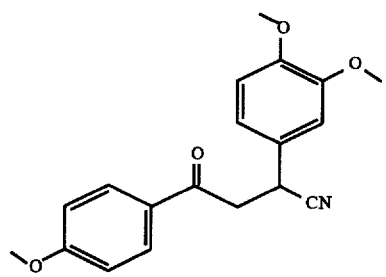

To the chalcone, 258, (16.2 g, 54.2 mmol) in ethanol (300 mL) at 55° C. was added acetic acid (7.1 mL) followed by slow addition of potassium cyanide (8.84 g, 136 mmol) in water (50 mL). The solution was stirred at 60° C. for 24 hours. The solution was cooled and treated with water (250 mL). The mixture was then filtered to collect the solid. The solid was washed repeatedly with 70% ethanol (100 mL), air dried, and then dried in vacuo to give the nitrile 11.3 g (64%) as a solid. The nitrile was identified by $^1$H NMR, IR, MS, and microanalysis.

EXAMPLE 260

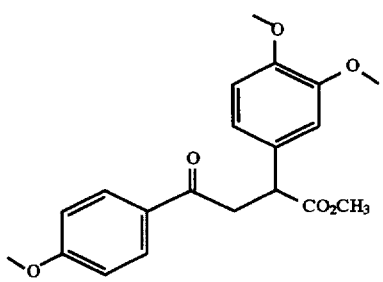

To the nitrile, 259, (8.9 g, 27.4 mmol) was added methanol (110 mL). The mixture was saturated with HCl (g) and heated to 45° C. until no nitrile remained, by thin-layer chromatography. The solution was cooled and treated with water (100 mL). The product oils out and the liquid decanted from the oil. The oil was dissolved in ethyl acetate (150 mL) and washed with 1N HCl (70 mL). The organic phase washed with saturated sodium bicarbonate (100 mL) and brine (50 mL). The organic phase dried over magnesium sulfate and evaporated in vacuo to give a thick oil 7.1 g (72%) which was identified by $^1$H NMR, IR, MS, and microanalysis.

EXAMPLE 261

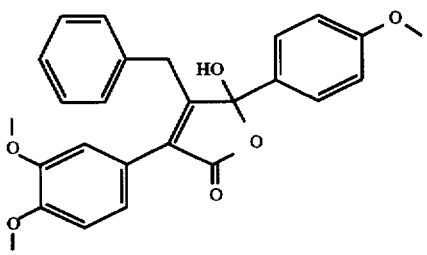

4-Benzyl-3-(3,4-dimethoxyphenyl)-5-hydroxy-5-(4-methoxyphenyl)-5H-furan-2-one

To methanol (12 mL) was added sodium metal (97 mg, 4.2 mmol) and stirred to dissolve. To this was added benzaldehyde (467 mg, 4.4 mmol) then the ester, 260, (1.43 g, 4.0 mmol). The mixture was heated to reflux for 6 hours. The solution was then treated with acetic acid (2 mL) and refluxed an additional 24 hours. The solvents were removed by evaporation and the residue was partitioned between ethyl acetate (50 mL) and water (50 mL). The organic phase was separated and dried over magnesium sulfate and evaporated to dryness. The crude product was then purified by flash chromatography (175 g silica gel, 10% ethyl acetate/methylene chloride). The butenolide was isolated by evaporation of the appropriate fractions to give 0.980 g (57%) as a light green solid. The butenolide was identified by $^1$H NMR, IR, MS, [M+H]$^+$=433 Da., and microanalysis.

EXAMPLE 262

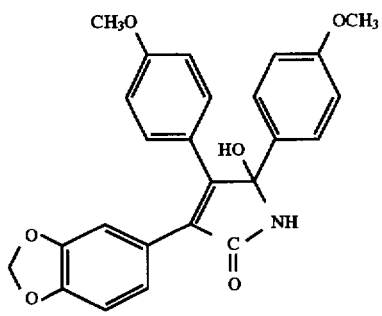

2H-Pyrrole-2-one, 3-(1,3-benzodioxol-5-yl)-1,5-dihydro-5-hydroxy-4,5-bis(4-methoxyphenyl)-, (±)-

Sixty percent sodium hydride (0.42 g, 10.5 mmol) in oil suspension was washed free of oil using dry THF. The resulting solid was suspended in 5 mL DMSO, heated briefly to 60° C., and stirred to a homogeneous brown oil over 1 hour at 25° C. This solution was diluted with 75 mL dry THF, and a solution of 3,4(methylenedioxy) phenylacetonitrile (1.61 g, 10 mmol) in 25 mL THF was added. After 3 minutes at 25° C., 4,4'-dimethoxybenzil (2.7 g, 19 mmol) was added, followed by stirring at 25° C. overnight.

The solvents were removed by evaporation giving an orange oil which was partitioned between ethyl acetate (100 mL) and saturated sodium bicarbonate solution. The organic phase was washed with brine, dried over magnesium sulfate, and evaporated to dryness. The crude product was purified by flash chromatography (450 g silica gel, ethyl acetate/CHCl$_3$=10/90). The product was isolated by evaporation of appropriate fractions followed by recrystallization from ethyl ether, giving a yellow solid 1.04 g (24%). The product was identified by $^1$H NMR, MS, and microanalysis.

EXAMPLE 263

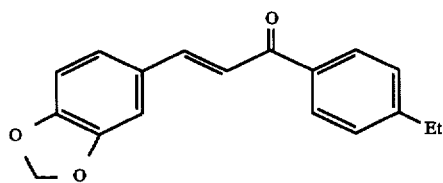

To 4'-ethylacetophenone (14 g, 94.5 mmol) in absolute ethanol (200 mL) in an erlenmeyer was added piperonal (14 g, 93.3 mmol). The solution swirled while 10% sodium hydroxide (41 mL) added. The mixture swirled for 10 minutes and allowed to stand to precipitate. The solid was collected by filtration and washed with 80% ethanol (50 mL). The solid was dried in vacuo giving 21 g (80%) of an off-white solid which was identified by $^1$H NMR, IR, MS, and microanalysis.

EXAMPLE 264

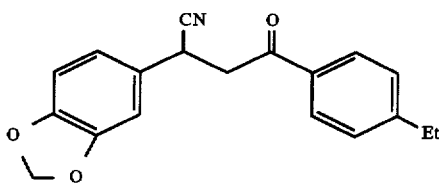

To the chalcone, 263, (10 g, 35.7 mmol) in 2-ethoxyethanol (75 mL) at 55° C. was added acetic acid (3.5 mL) followed by slow addition of potassium cyanide (6 g, 92.3 mmol) in water (10 mL). The solution was stirred at 105° C. for 0.5 hour. The solution was cooled and treated with water (200 mL). The mixture was then filtered to collect the solid. The solid was washed repeatedly with 70% ethanol (100 mL), air dried, and then dried in vacuo to give the nitrile 5.9 g (54%) as a solid. The nitrile was identified by $^1$H NMR, IR, MS, and microanalysis.

EXAMPLE 265

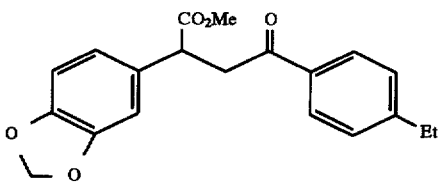

To the nitrile, 264, (5.6 g, 18.2 mmol) was added methanol (100 mL). The mixture was saturated with HCl (g) and heated to 45° C. until no nitrile remained, by thin layer chromatography. The solution was cooled and treated with water (10 mL), then removed the solvent, redissolved in CH$_2$Cl$_2$ (25 mL), filtered through a short packed column to give methyl ester as an oil. This gave the ester 6.0 g (96%) as a brown oil which was identified by $^1$H NMR.

EXAMPLE 266

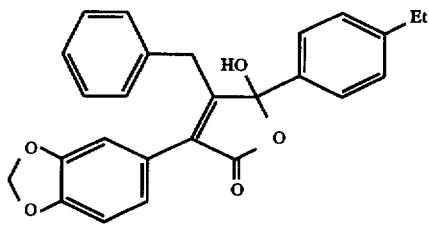

3-Benzo[1,3]dioxol-5-yl-4-benzyl-5-(4-ethylphenyl)-5-hydroxy-5H-furan-2-one

To methanol (50 mL) was added sodium metal (0.75 g, 32.6 mmol) and stirred to dissolve. To this was added benzaldehyde (3 g, 18.7 mmol) then the ester 265, (5.42 g, 15.9 mmol). The mixture was heated to reflux for 4 hours. The solution was then treated with acetic acid (4 mL) and refluxed an additional 0.5 hour. The solvents were removed by evaporation and the residue was partitioned between ethyl acetate (150 mL) and water (20 mL). The organic phase was separated and dried over magnesium sulfate and evaporated to dryness. The crude product was then purified by flash chromatography (500 g silica gel, (10:1) CH$_2$Cl$_2$:ethyl acetate). The butenolide was isolated by evaporation of the appropriate fractions to give 1.65 g (25%) as white solid. The butenolide was identified by $^1$H NMR, IR, MS, [M+H]$^+$=415 Da., and microanalysis.

EXAMPLE 267

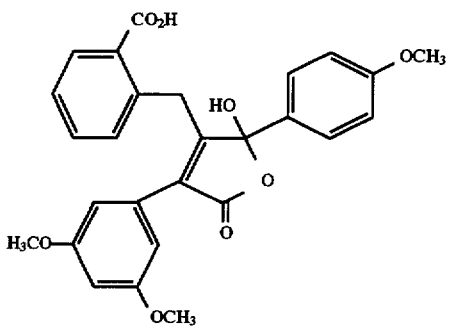

3-[4-(3,5-Dimethoxyphenyl)-2-hydroxy-2-(4-methoxyphenyl)-5-oxo-2,5-dihydrofuran-3-ylmethyl] benzoic acid To 134 (100 mg, 0.217 mmol) in Acetone (10 mL) was added at 0° C. Jones' Reagent (2.39 mmol) dropwise stirred at 0° C. and monitored by TLC (30% EtOAc/hexane). No starting material after 4 hours. The mixture was diluted with EtOAc (50 mL) then washed with H$_2$O (2×30 mL), dried over MgSO$_4$, filtered, evaporated in vacuo. Purified on SiO$_2$ (170 g) eluent (3% CH$_3$OH/CH$_2$Cl$_2$) y: 0.03 g. NMR, IR, HPLC, 81%.

EXAMPLE 268

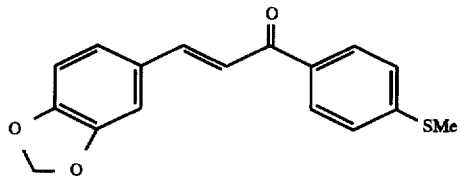

To 4'-methylthioacetophenone (15.5 g, 93.3 mmol) in absolute ethanol (250 mL) in an erlenmeyer was added piperonal (14 g, 93.3 mmol). The solution swirled while 10% sodium hydroxide (41 mL) added. The mixture swirled for 10 minutes and allowed to stand to precipitate. The solid was collected by filtration and washed with 80% ethanol (50 mL). The solid was dried in vacuo giving 27 g (97%) of a yellow solid which was identified by $^1$H NMR, IR, MS, and microanalysis.

EXAMPLE 269

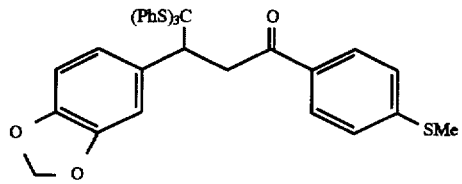

Triphenyl orthothioformate (6.8 g, 20 mmol) was treated with n-BuLi (2.1M, 10 mL) at −78° C. under nitrogen for 30 minutes, then added the chalcone 268, (5.4 g, 18.1 mmol) in 100 mL of THF, another 30 minutes at −78° C., removed the dry ice bath stirred at room temperature for 30 minutes. The

EXAMPLE 270

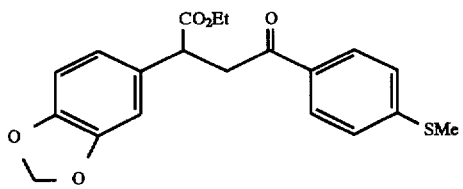

To the orthothio ester 269, (3.7 g, 5.8 mmol), HgCl₂ (7.8 g, 28.7 mmol), HgO (2.5 g, 11.5 mmol) in 150 mL of EtOH (95%) was refluxed for 7 hours under nitrogen. The mixture was filtered and the filtrate was diluted with H₂O (75 mL) and extracted with two 100 ml of CH₂Cl₂. The extracts were combined, washed with 1N HCl (200 mL), brine, dried MgSO₄. The crude product was purified by flash chromatography (500 g silica gel, (200:1) CH₂Cl₂/ethyl acetate). The ethyl ester was isolated by evaporation of the appropriate fraction to give 1.05 g (48.6% yield) which was identified by H-NMR.

EXAMPLE 271

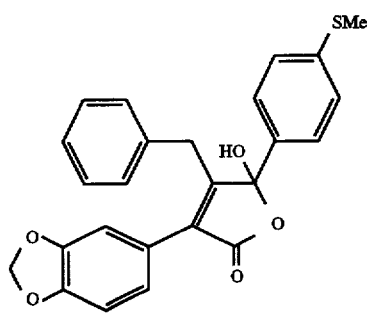

3-Benzo[1,3]dioxol-5-yl-4-benzyl-5-hydroxy-5-(4-methylsulfanylphenyl)-5H-furan-2-one To methanol (15 mL) was added sodium metal (0.2 g, 8.7 mmol) and stirred to dissolve. To this was added benzaldehyde (0.8 g, 7.5 mmol) then the ester, 270, (0.8 g, 2.1 mmol). The mixture was heated to reflux for 3 hours. The solution was then treated with acetic acid (1 mL) and refluxed an additional 12 hours. The solvents were removed by evaporation and the residue was partitioned between ethyl acetate (50 mL) and water (5 mL). The organic phase was separated and dried over magnesium sulfate and evaporated to dryness. The crude product was then purified by flash chromatography (200 g silica gel, (20:1) CH₂Cl₂/ethyl acetate). The butenolide was isolated by evaporation of the appropriate fractions to give 0.28 g (31%) as white solid. The butenolide was identified by ¹H NMR, IR, MS, [M+H]⁺=433 Da., and microanalysis.

EXAMPLE 272

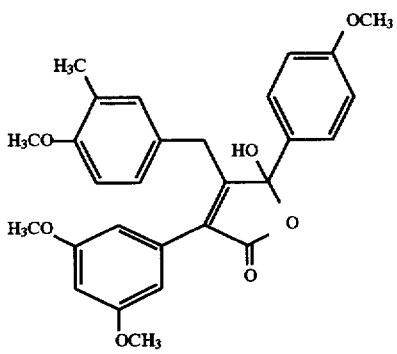

3-(3,5-Dimethoxyphenyl)-5-hydroxy-4-(4-methoxy-3-methylbenzyl)-5-(4-methoxyphenyl-5H-furan-2-one To methanol (5 mL) was added sodium metal (97 mg, 4.2 mmol) and stirred to dissolve. To this was added a solution of the ester, 124, (1.43 g, 4.0 mmol) in 10 mL MeOH; and then 661 mg (4.4 mmol) 3-methyl-4-methoxybenzaldehyde. The mixture was heated to reflux for 24 hours. The solution was then treated with acetic acid (3 mL) and refluxed an additional 24 hours. The solvents were removed by evaporation and the residue was partitioned between ethyl acetate (150 mL) and water (150 mL). The organic phase was separated and washed with brine and dried over magnesium sulfate and evaporated to dryness. The crude product was then purified by flash chromatography (150 g 230–400 mesh silica gel, eluting with 10% ethyl acetate/dichloromethane). The butenolide was isolated by evaporation of the appropriate fractions to give 550 mg (28.8%) as a tan foam. The butenolide was identified by ¹H NMR, MS, [M+H]⁺=477 Da., and microanalysis.

EXAMPLE 273

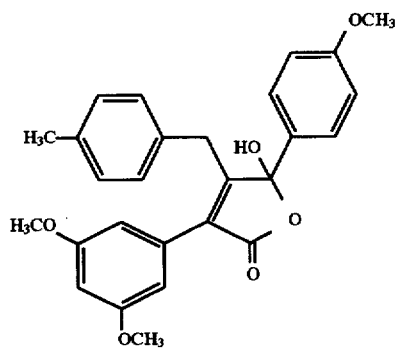

3-(3,5-Dimethoxyphenyl)-5-hydroxy-5-(4-methoxyphenyl)-4-(4-methylbenzyl)-5H-furan-2-one To methanol (5 mL) was added sodium metal (97 mg, 4.2 mmol) and stirred to dissolve. To this was added a solution of the ester, 124, (1.43 g, 4.0 mmol) in 10 mL MeOH; and then 529 mg (4.4 mmol) 4-methyl-benzaldehyde. The mixture was heated to reflux for 24 hours. The solution was then treated with acetic acid (3 mL) and refluxed an additional 6 hours. The solvents were removed by evaporation and the residue was partitioned between ethyl acetate (150 mL) and water (150 mL). The organic phase was separated and washed with brine and dried over magnesium sulfate and evaporated to dryness. The crude product was then purified by flash chromatography (150 g 230–400 mesh silica gel, eluting with 10% ethyl acetate/dichloromethane). The

EXAMPLE 274

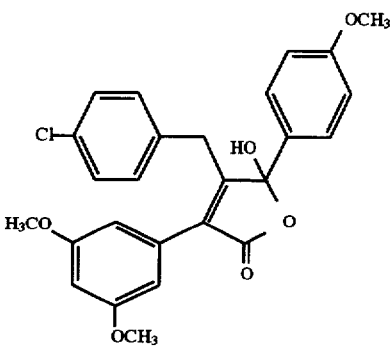

4-(4-Chlorobenzyl)-3-(3,5-dimethoxyphenyl)-5-hydroxy-5-(4-methoxyphenyl-5H-furan-2-one To methanol (5 mL) was added sodium metal (97 mg, 4.2 mmol) and stirred to dissolve. To this was added a solution of the ester, 124, (1.43 g, 4.0 mmol) in 10 mL MeOH; and then 638 mg (4.4 mmol) 4-chloro-benzaldehyde. The mixture was heated to reflux for 24 hours. The solution was then treated with acetic acid (3 mL) and refluxed an additional 6 hours. The solvents were removed by evaporation and the residue was partitioned between ethyl acetate (150 mL) and water (150 mL). The organic phase was separated and washed with brine and dried over magnesium sulfate and evaporated to dryness. The crude product was then purified by flash chromatography (150 g 230–400 mesh silica gel, eluting with 10% ethyl acetate/dichloromethane). The butenolide was isolated by evaporation of the appropriate fractions to give 900 mg (47.9%) as a tan foam. The butenolide was identified by $^1$H NMR, MS, [M+H]$^+$=470 Da., and microanalysis.

EXAMPLE 275

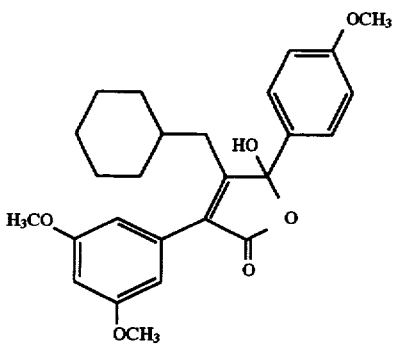

2(5H)-Furanone, 4-(cyclohexylmethyl)-3-(3,5-dimethoxyphenyl)-5-hydroxy-5-(4-methoxyphenyl)-

To methanol (5 mL) was added sodium metal (97 mg, 4.2 mmol) and stirred to dissolve. To this was added a solution of the ester, 124, (1.43 g, 4.0 mmol) in 10 mL MeOH; and then 504 mg (4.4 mmol) cyclohexanecarboxaldehyde. The mixture was heated to reflux for 24 hours. The solution was then treated with acetic acid (3 mL) and refluxed an additional 36 hours. The solvents were removed by evaporation and the residue was partitioned between ethyl acetate (150 mL) and water (150 mL). The organic phase was separated and washed with brine and dried over magnesium sulfate and evaporated to dryness. The crude product was then purified by flash chromatography (150 g 230–400 mesh silica gel, eluting with 10% ethyl acetate/dichloromethane). The butenolide was isolated by evaporation of the appropriate fractions to give 513 mg (29.0%) as a tan foam. The butenolide was identified by $^1$H NMR, MS, [M+H]$^+$=439 Da., and microanalysis.

EXAMPLE 276

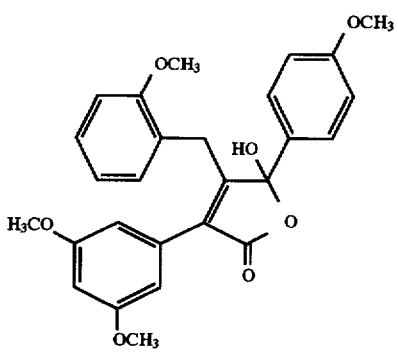

3-(3,5-Dimethoxyphenyl)-5-hydroxy-4-(2-methoxybenzyl)-5-(4-methoxyphenyl-5H-furan-2-one To methanol (5 mL) was added sodium metal (97 mg, 4.2 mmol) and stirred to dissolve. To this was added a solution of the ester, 124, (1.43 g, 4.0 mmol) in 10 mL MeOH; and then 611 mg (4.4 mmol) anisealdehyde. The mixture was heated to reflux for 36 hours. The solution was then treated with acetic acid (3 mL) and refluxed an additional 36 hours. The solvents were removed by evaporation and the residue was partitioned between ethyl acetate (150 mL) and water (150 mL). The organic phase was separated and washed with brine and dried over magnesium sulfate and evaporated to dryness. The crude product was then purified by flash chromatography (150 g 230–400 mesh silica gel, eluting with 10% ethyl acetate/dichloromethane). The butenolide was isolated by evaporation of the appropriate fractions to give 644 mg (34.8%) as a tan foam. The butenolide was identified by $^1$H NMR, MS, [M+H]$^+$=463 Da., and microanalysis.

EXAMPLE 277

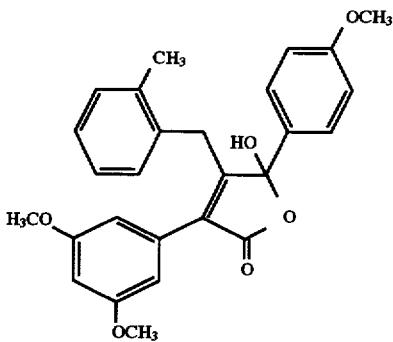

3-(3,5-Dimethoxyphenyl)-5-hydroxy-5-(4-methoxyphenyl)-4-(2-methylbenzyl)-5H-furan-2-one To methanol (5 mL) was added sodium metal (97 mg, 4.2 mmol) and stirred to dissolve. To this was added a solution of the ester, 124, (1.43 g, 4.0 mmol) in 10 mL MeOH; and then 540 mg (4.4 mmol) O-toualdehyde. The mixture was heated to reflux for 24 hours. The solution was then treated with acetic acid (3 mL) and refluxed an additional 24 hours. The solvents were removed by evaporation and the residue was partitioned between ethyl acetate (150 mL) and water (150 mL). The organic phase was separated and washed with brine and dried over magnesium sulfate and evaporated to dryness. The crude product was then purified by flash chromatography (150 g 230–400 mesh silica gel, eluting with 10% ethyl acetate/dichloromethane). The butenolide was isolated by evaporation of the appropriate fractions to give 585 mg (32.7%) as a tan foam. The butenolide was identified by $^1$H NMR, MS, [M+H]$^+$=447 Da., and microanalysis.

EXAMPLE 278

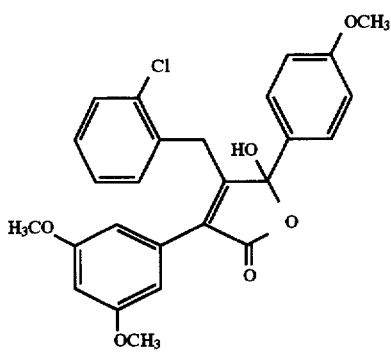

4-(2-Chlorobenzyl)-3-(3,5-dimethoxyphenyl)-5-hydroxy-5-(4-methoxyphenyl)-5H-furan-2-one To methanol (5 mL) was added sodium metal (97 mg, 4.2 mmol) and stirred to dissolve. To this was added a solution of the ester, 124, (1.43 g, 4.0 mmol) in 10 mL MeOH; and then 620 mg (4.4 mmol) O-chlorobenzaldehyde. The mixture was heated to reflux for 24 hours. The solution was then treated with acetic acid (3 mL) and refluxed an additional 24 hours. The solvents were removed by evaporation and the residue was partitioned between ethyl acetate (150 mL) and water (150 mL). The organic phase was separated and washed with brine and dried over magnesium sulfate and evaporated to dryness. The crude product was then purified by flash chromatography (150 g 230–400 mesh silica gel, eluting with 10% ethyl acetate/dichloromethane). The butenolide was isolated by evaporation of the appropriate fractions to give 782 mg (41.6%) as a tan foam. The butenolide was identified by $^1$H NMR, MS, [M+H]$^+$=470 Da., and microanalysis.

EXAMPLE 279

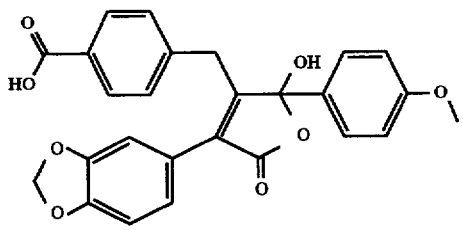

4-[4-Benzo[1,3]dioxol-5-yl-2-hydroxy-2-(4-methoxyphenyl)-5-oxo-2,5-dihydrofuran-3-ylmethyl] benzoic acid To a suspension of 182, 2.31 g (4.9 mmol) in methanol (30 mL) was added 9.8 mL of NaOH solution (1.0N) and the mixture warmed to reflux for 19 hours. The mixture diluted with water and washed once with ethyl acetate. The aqueous phase made acidic (pH=2) with 1.0N HCl. The aqueous then extracted with ethyl acetate. The organic phase dried over magnesium sulfate, filtered, and evaporated to give an off white solid, 2.31 g (100%). The product was identified by $^1$H NMR, IR, MS, [M+H]$^+$=461 and microanalysis.

EXAMPLE 280

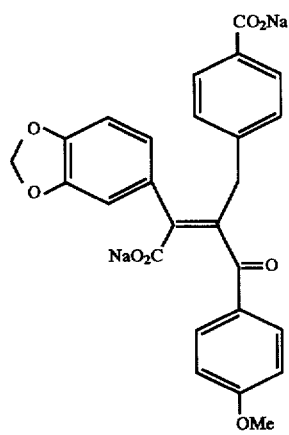

1,3-Benzodioxol-5-acetic acid, α-[2-[(4-carboxyphenyl)methyl]-2-(4-methoxybenzoyl)ethylidene]-, disodium salt To a solution of 279 0.27 g (0.59 mmol) in 5.0 mL MeOH was added dropwise 2.34 mL (1.17 mmol) 0.5017N NaOH solution in H$_2$O. After addition was complete, the reaction mixture was stored overnight at room temperature. The reaction mixture was concentrated and the residue was lyophilized. Yield=~300 mg. The compound was identified by $^1$H NMR, IR, MS, [M+H]$^+$=460 Da., and microanalysis.

EXAMPLE 281

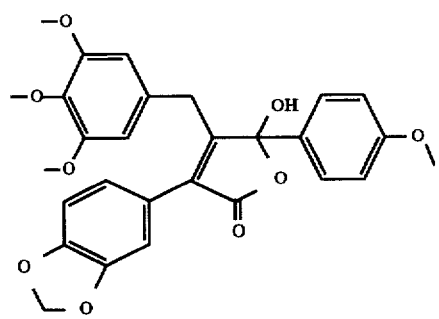

3-benzo[1,3]dioxol-5-yl-5-hydroxy-5-(4-methoxyphenyl)-4-(3,4,5-trimethoxybenzyl)-5H-furan-2-one To methanol 6 mL was added sodium metal 57 mg (2.5 mmol) and stirred to dissolve. To this was added 3,4,5-trimethoxybenzaldehyde 0.50 g (2.5 mmol) then the ester, 19, 0.822 g (2.4 mmol). The mixture was heated to reflux for 16 hours. The solution was then treated with acetic acid 1.5 mL and refluxed for additional 6 hours. The solvents were removed by evaporation and the residue was partitioned between ethyl acetate 20 mL and water 20 mL. The organic phase was separated and dried over magnesium sulfate and evaporated to dryness. The crude product was then purified by flash chromatography (150 g silica gel, 20% ethyl acetate: methylene chloride). The butenolide was isolated by evaporation of the appropriate fractions to give 0.719 g (59%) as a foam. The butenolide was identified by ¹H NMR, IR, MS, [M+H]⁺=507 Da., and microanalysis.

EXAMPLE 282

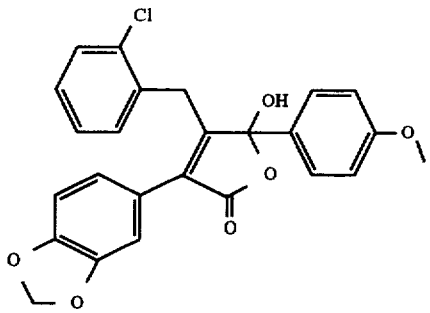

3-Benzo[1,3]dioxol-5-yl-4-(2-chlorobenzyl)-5-hydroxy-5-(4-methoxyphenyl)-5H-furan-2-one To methanol 8 mL was added sodium metal 97 mg (4.2 mmol) and stirred to dissolve. To this was added 2-chlorobenzaldehyde 0.619 g (4.4 mmol) then the ester, 19, 1.37 g (4.0 mmol). The mixture was heated to reflux for 18 hours. The solution was then treated with acetic acid 1.0 mL and refluxed an additional 24 hours. The solvents were removed by evaporation and the residue was partitioned between ethyl acetate 25 mL and water 25 mL. The organic phase was separated and dried over magnesium sulfate and evaporated to dryness. The crude product was then purified by flash chromatography (150 g silica gel, 10% ethyl acetate: methylene chloride). The butenolide was isolated by evaporation of the appropriate fractions to give 0.925 g (51%) as a light yellow foam. The butenolide was identified by ¹H NMR, IR, MS, [M+H]⁺=451 Da., and microanalysis.

EXAMPLE 283

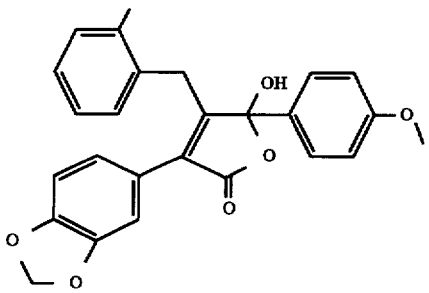

3-Benzo[1,3]dioxol-5-yl-5-hydroxy-5-(4-methoxyphenyl)-4-(2-methylbenzyl)-5H-furan-2-one To methanol 15 mL was added sodium metal 97 mg (4.2 mmol) and stirred to dissolve. To this added 2-methylbenzaldehyde 529 mg (4.4 mmol) then the ester, 19, 1.37 g (4.0 mmol). The mixture was heated to reflux for 18 hours. The solution was then treated with acetic acid 1.0 mL and refluxed an additional 24 hours. The solvents were removed by evaporation and the residue was partitioned between ethyl acetate 50 mL and water 50 mL. The organic phase was separated and dried over magnesium sulfate and evaporated to dryness. The crude product was then purified by flash chromatography (150 g silica gel, 10% ethyl acetate: methylene chloride). The butenolide was isolated by evaporation of the appropriate fractions to give 1.30 g (76%) as a white foam. The butenolide was identified by ¹H NMR, IR, MS, [M+H]⁺=431 Da., and microanalysis.

EXAMPLE 284

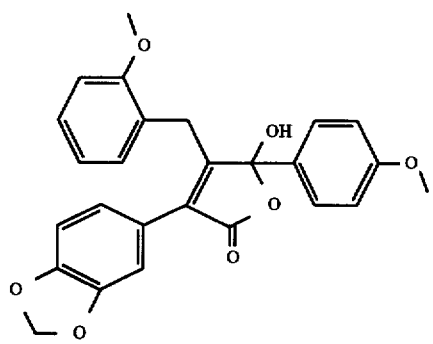

3-Benzo[1,3]dioxol-5-yl-5-hydroxy-4-(2-methoxybenzyl)-5-(4-methoxyphenyl)-5H-furan-2-one To methanol 8 mL was added sodium metal 97 mg (4.2 mmol) and stirred to dissolve. To this was added 2-methoxybenzaldehyde 0.599 g (4.4 mmol) then the ester, 19, 1.37 g (4.0 mmol). The mixture was heated to reflux for 18 hours. The solution was then treated with acetic acid 1.0 mL and refluxed an additional 24 hours. The solvents were removed by evaporation and the residue was partitioned between ethyl acetate 25 mL and water 25 mL. The organic phase was separated and dried over magnesium sulfate and evaporated to dryness. The crude product was then purified by flash chromatography (150 g silica gel, 10% ethyl acetate: methylene chloride). The butenolide was isolated by evaporation of the appropriate fractions to give 0.730 g (40%) as a tan solid. The butenolide was identified by ¹H NMR, IR, MS, [M+S]⁺=447 Da. for microanalysis.

EXAMPLE 285

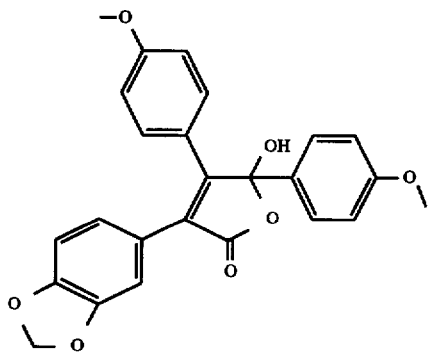

3-Benzo[1,3]dioxol-5-yl-5-hydroxy-4,5-bis-(4-methoxyphenyl)-5H-furan-2-one

Butyllithium in hexane (1.6M, 6.25 mL, 10 mmol) was added to 50 mL dry tetrahydrofuran and cooled to –60° C. Diisopropylamine (1.4 mL, 10 mmol) was added, and the mixture was stirred for 30 minutes. 3,4-(Methylenedioxy) phenyl acetic acid (0.9 g, 5.0 mmol) dissolved in 20 mL dry tetrahydrofuran was added to the mixture was followed by stirred for 1 hour at 25° C. 4,4'-Dimethoxybenzil (1.35 g, 5.0 mmol) was added, followed by stirring at 25° C. for 16 hours.

The solvents were removed by evaporation giving a solid residue which was partitioned between ethyl acetate (75 mL) and 1N citric acid. The organic phase was washed with brine, dried over magnesium sulfate, and evaporated to dryness. The crude product was purified by flash chromatography (50 g silica gel, ethyl acetate:hexane=10:90). The

147 product was isolated by evaporation of appropriate fractions giving a yellow solid 1.0 g. The solid was recrystallized from ethyl ether and pentane repeatedly, giving a yellow solid, 50 mg.

This solid was further purified by flash chromatography (15 g silica gel, ethyl acetate:hexane=10:90). The product was isolated by evaporation of appropriate fractions giving a yellow solid 21.3 mg (0.98%). The product was identified by $^1$H NMR, MS, and microanalysis.

EXAMPLE 286

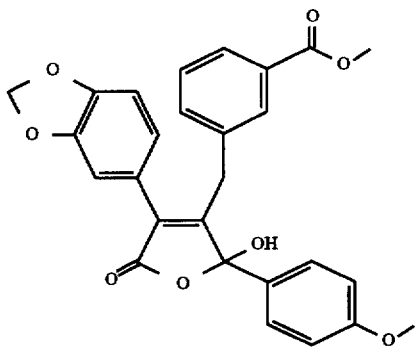

Benzoic acid, 3-[[4-(1,3-benzodioxol-5-yl)-2,5-dihydro-2-hydroxy-2-(4-methoxyphenyl)-5-oxo-3-furanyl]methyl]-, methyl ester To methanol (30 mL) was added sodium metal (0.3 g, 14.3 mmol) and stirred to dissolve. To this was added the ester, 19, (4.69 g, 13.7 mmol) then methyl-3-formylbenzoate (2.45 g, 14.9 mmol). The mixture was heated to reflux for 3 hours. The solution was then treated with acetic acid (30 mL) and refluxed an additional 23 hours. The solvents were removed by evaporation, and the residue was partitioned between ethyl acetate and water. The organic phase was separated and dried over magnesium sulfate and evaporated to dryness. The crude product was then purified by flash chromatography (silica gel, 7:3 (hexane:ethyl acetate)). The butenolide was isolated by evaporation of the appropriate fractions to give 4.90 g (75%) as a foam. The butenolide was identified by $^1$H NMR, IR, MS, [M+H]$^+$=475 Da., and microanalysis.

EXAMPLE 287

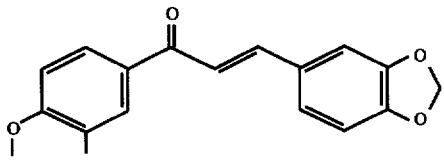

To 3-methyl-4-methoxyacetophenone (7.2 g, 43.8 mmol) in absolute ethanol (30 mL) in an erlenmeyer was added piperonal (6.76 g, 45 mmol). The solution swirled while 10% sodium hydroxide (2 mL) added. The mixture swirled for 10 minutes and allowed to stand to precipitate. The solid was collected by filtration and washed with 80% ethanol. The solid was dried in vacuo giving 11.9 g (92%) of a yellow solid which was identified by $^1$H NMR, IR, MS, and microanalysis.

148

EXAMPLE 288

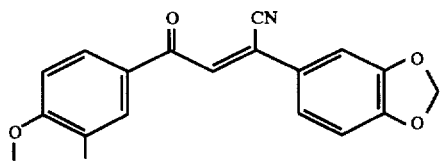

To the chalcone, 287, (5.77 g, 19.5 mmol) in ethanol (200 mL) at 55° C. was added acetic acid (2.6 mL) followed by slow addition of potassium cyanide (3.17 g, 48.7 mmol) in water (30 mL). The solution was stirred at reflux for 42 hours. The solution was cooled and treated with water (200 mL). The mixture was then filtered to collect the solid. The solid was washed repeatedly with 70% ethanol, air dried, and then dried in vacuo to give the nitrile 6.0 g (95%) as a dark solid. The nitrile was identified by $^1$H NMR, IR, MS, and microanalysis.

EXAMPLE 289

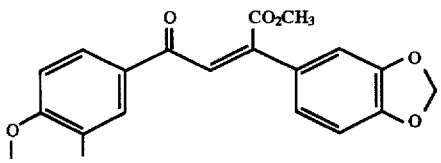

To the nitrile, 298, (5.75 g, 17.8 mmol) was added methanol (70 mL). The mixture was saturated with HCl (g) and heated to 45° C. until no nitrile remained, by thin layer chromatography. The solution was cooled and the liquid decanted from a thick oil. The oil was dissolved in ethyl acetate (100 mL) and washed with 1N HCl (100 mL), water (100 mL), and brine (100 mL). The organic phase dried over magnesium sulfate and evaporated in vacuo. The resultant oil was purified by Prep 500A chromatography (1 column, 8:3 (hexane:ethyl acetate), 100 mL/min). Evaporation of the correct fraction gave the ester 3.71 g (59%) as a thick oil which was identified by $^1$H NMR, IR, MS, and microanalysis.

EXAMPLE 290

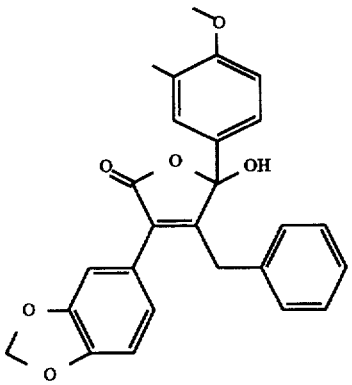

2(5H)-Furanone, 3-(1,3-benzodioxol-5-yl)-5hydroxy-5-(4-methoxy-3-methylphenyl)-4-(phenylmethyl)-, (±)-

To methanol (8 mL) was added sodium metal (97 mg, 4.2 mmol) and stirred to dissolve. To this was added the ester, 289, (1.4 g, 4.0 mmol) then benzaldehyde (467 mg, 4.4 mmol). The mixture was heated to reflux for 18 hours. The solution was then treated with acetic acid (1 mL) and refluxed an additional 24 hours. The solvents were removed by evaporation, and the residue was partitioned between ethyl acetate (25 mL) and water (20 mL). The organic phase was separated and dried over magnesium sulfate and evaporated to dryness. The crude product was then purified by flash chromatography (150 g silica gel, 5% ethyl acetate: methylene chloride). The butenolide was isolated by evaporation of the appropriate fractions to give 595 mg (35%) as a white foam. The butenolide was identified by $^1$H NMR, IR, MS, [M+H]$^+$=431 Da., and microanalysis.

EXAMPLE 291

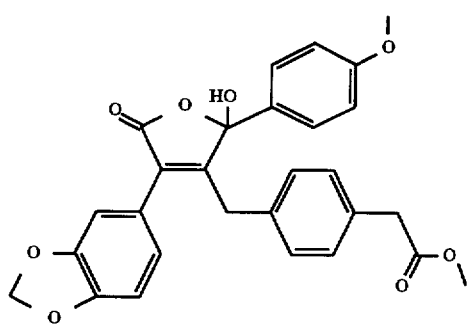

{4-[4-Benzo[1,3]dioxol-5-yl-2-hydroxy-2-(4-methoxyphenyl)-5-oxo-2,5-dihydro-furan-3-ylmethyl]-phenyl}-acetic acid methyl ester To methanol (30 mL) was added sodium metal (0.19 g, 8.2 mmol) and stirred to dissolve. To this was added the ester, 19, (2.67 g, 7.8 mmol) then methyl-(4-formylphenyl) acetate (1.8 g, 10.1 mmol). The mixture was heated to reflux for 2 hours. The solution was then treated with acetic acid (25 mL) and refluxed an additional 18 hours. The solvents were removed by evaporation, and the residue was partitioned between ethyl acetate and water. The organic phase was separated and dried over magnesium sulfate and evaporated to dryness. The crude product was then purified by flash chromatography (silica gel, 3:2 (hexane:ethyl acetate)). The butenolide was isolated by evaporation of the appropriate fractions to give 1.05 g (27%) as an oil. The butenolide was identified by $^1$H NMR, IR, MS, [M+H]$^+$=489 Da., and microanalysis.

EXAMPLE 292

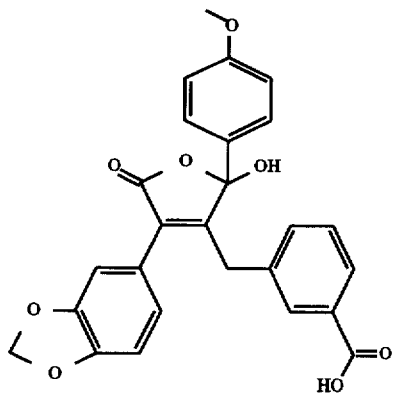

3-[4-Benzo[1,3]dioxol-5-yl-2-hydroxy-2-(4-methoxyphenyl)-5-oxo-2,5-dihydro-furan-3-ylmethyl]-benzoic acid A solution of 286, (3.0 g, 6.3 mmol) in methanol (30 mL) was treated with 1N NaOH (12.6 mL). The mixture was stirred at reflux for 47 hours. The mixture was evaporated to an aqueous mass which was diluted with water and washed with ethyl acetate. The organic washings were discarded, and the aqueous phase made acidic with concentrated HCl. This was extracted with ethyl acetate. The ethyl acetate washed with brine and dried over magnesium sulfate. The solvent was evaporated in vacuo to give the butenolide 2.59 g (89%) of an off-white foam. The butenolide was identified by $^1$H NMR, IR, MS, [M+H]$^+$=460 Da., and microanalysis.

EXAMPLE 293

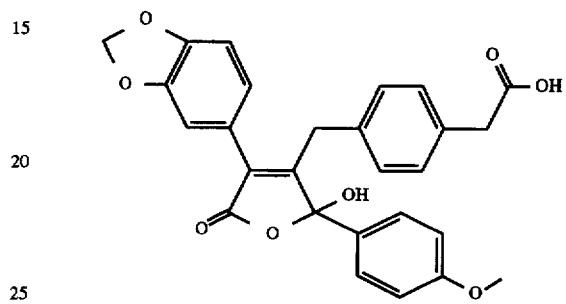

{4-[4-Benzo[1,3]dioxol-5-yl-2-hydroxyl-2-(4-methoxyphenyl)-5-oxo-2,5-dihydro-furan-3-ylmethyl]-phenyl}-acetic acid The butenolide was prepared as in 292 from 291, (0.87 g, 1.8 mmol). This gave 0.80 g (94%) of the butenolide as a white foam which was identified by $^1$H NMR, IR, MS, [M+H]$^+$=474 Da., and microanalysis.

EXAMPLE 294

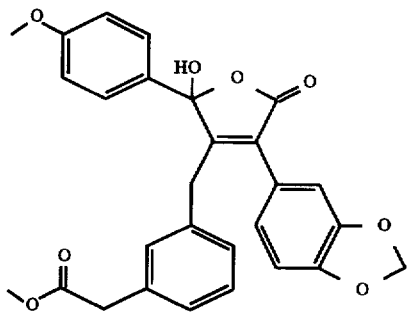

{3-[4-Benzo[1,3]dioxol-5-yl-2-hydroxy-2-(4-methoxyphenyl)-5-oxo-2,5-dihydro-furan-3-ylmethyl]-phenyl}-acetic acid methyl ester To methanol (30 mL) was added sodium metal (190 mg, 8.2 mmol) and stirred to dissolve. To this was added the ester, 19, (2.67 g, 7.8 mmol) then methyl-(3-formylphenyl) acetate (1.8 g, 10.1 mmol). The mixture was heated to reflux for 2 hours. The solution was then treated with acetic acid (30 mL) and refluxed an additional 18 hours. The solvents were removed by evaporation, and the residue was partitioned between ethyl acetate and water. The organic phase was separated and dried over magnesium sulfate and evaporated to dryness. The crude product was then purified by flash chromatography (silica gel, 7:3 (hexane:ethyl acetate)). The butenolide was isolated by evaporation of the appropriate fractions to give 0.52 g (14%) as a thick oil. The butenolide was identified by $^1$H NMR, IR, MS, [M+H]$^+$= 489 Da., and microanalysis.

EXAMPLE 295

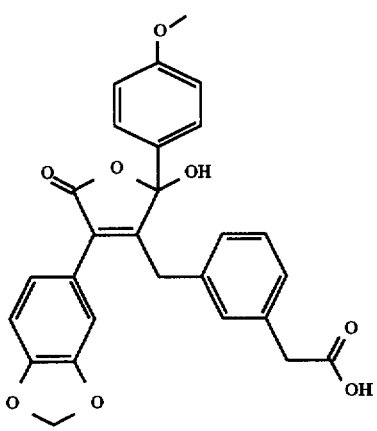

{3-[4-Benzo[1,3]dioxol-5-yl-2-hydroxy-2-(4-methoxyphenyl)-5-oxo-2,5-dihydro-furan-3-ylmethyl]-phenyl}-acetic acid The butenolide was prepared as in 292 from 294, (0.29 g, 0.59 mmol). This gave 0.27 g (96%) of the butenolide as a white foam which was identified by $^1H$ NMR, IR, MS, $[M+H]^+$=475 Da., and microanalysis.

EXAMPLE 296

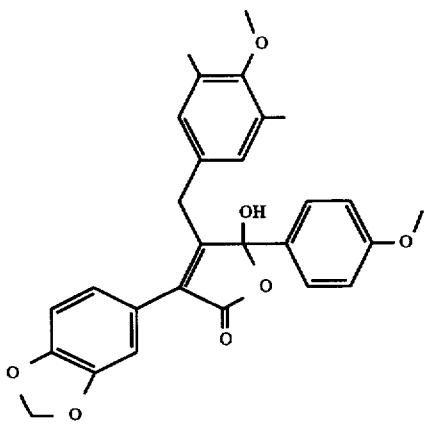

3-Benzo[1,3]dioxol-5-yl-5-hydroxy-4-(4-methoxy-3,5-dimethyl-benzyl)-5-(4-methoxy-phenyl)-5-H-furan-2-one To methanol (12 mL) was added sodium metal (99 mg, 4.3 mmol) and stirred to dissolve. To this was added the ester, 19, (1.37 g, 4.0 mmol) then 3,5-dimethyl-4-methoxybenzaldehyde (722 mg, 4.4 mmol). The mixture was heated to reflux for 18 hours. The solution was then treated with acetic acid (2 mL) and refluxed an additional 24 hours. The solvents were removed by evaporation, and the residue was partitioned between ethyl acetate (75 mL) and water (100 mL). The organic phase was separated and dried over magnesium sulfate and evaporated to dryness. The crude product was then purified by flash chromatography (150 g silica gel, 10% ethyl acetate:methylene chloride). The butenolide was isolated by evaporation of the appropriate fractions to give 1.03 g (55%) as a light yellow foam. The butenolide was identified by $^1H$ NMR, IR, MS, $[M+H]^+$= 475 Da., and microanalysis.

EXAMPLE 297

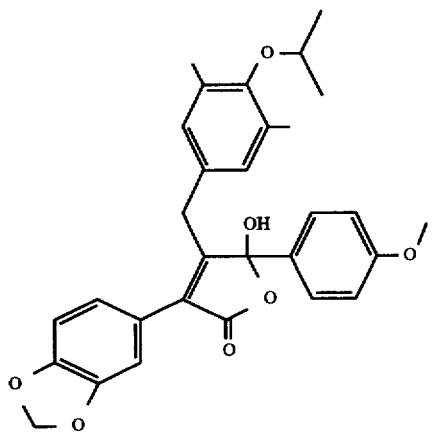

3-Benzo[1,3]dioxol-5-yl-4-(3,5-dimethyl-4-isopropoxybenzyl)-5-hydroxy-5-(4-methoxy-phenyl)-5H-furan-2-one To methanol (8 mL) was added sodium metal (55 mg, 2.4 mmol) and stirred to dissolve. To this was added the ester, 19, (0.79 g, 4.0 mmol) then 3,5-dimethyl-4-ipropoxybenzaldehyde (480 mg, 2.5 mmol). The mixture was heated to reflux for 18 hours. The solution was then treated with acetic acid (1.5 mL) and refluxed an additional 24 hours. The solvents were removed by evaporation, and the residue was partitioned between ethyl acetate (75 mL) and 10% citric acid (75 mL). The organic phase washed with brine, separated, dried over magnesium sulfate, and evaporated to dryness. The crude product was then purified by flash chromatography (150 g silica gel, 10% ethyl acetate: methylene chloride). The butenolide was isolated by evaporation of the appropriate fractions to give 313 mg (27%) as a white foam. The butenolide was identified by $^1H$ NMR, IR, MS, $[M+H]^+$=503 Da., and microanalysis.

EXAMPLE 298

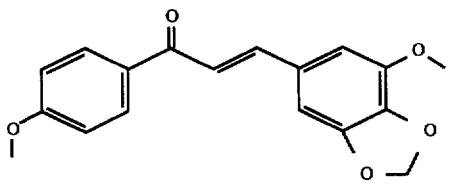

To 4-methoxyacetophenone (15.0 g, 0.1 mmol) in absolute ethanol (100 mL) in an erlenmeyer was added 3-methoxy-4,5-methylenedioxybenzaldehyde (18.0 g, 0.1 mmol). The solution swirled while 10% sodium hydroxide (8 mL) added. The mixture swirled for 10 minutes and allowed to stand to precipitate. The solid was collected by filtration and washed with 80% ethanol (2×200 mL). The solid was dried in vacuo giving 27.2 g (87%) of a solid which was identified by $^1H$ NMR, IR, MS, and microanalysis.

EXAMPLE 299

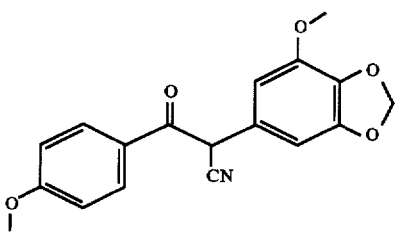

To the chalcone, 298, (25.05 g, 80 mmol) in ethoxy ethanol (100 mL) at 55° C. was added acetic acid (5.8 g) followed by slow addition of potassium cyanide (7.81 g, 120 mmol) in water (30 mL). The solution was stirred at 105° C. for 16 hours. The solution was cooled and treated with water (50 mL). The mixture was then filtered to collect the solid. The solid was washed repeatedly with 10% H$_2$O:ethoxy ethanol (150 mL), air dried, and then dried in vacuo to give the nitrile 19.9 g (73%) as a solid. The nitrile was identified by $^1$H NMR, IR, MS, and microanalysis.

EXAMPLE 300

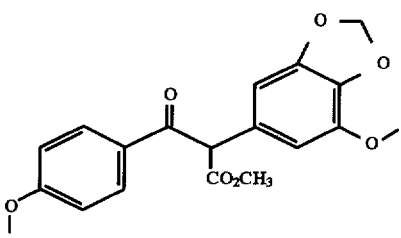

To the nitrile, 299, (18.4 g, 54.2 mmol) was added methanol (100 mL). The mixture was treated with p-toluenesulfonic acid (10.31 g, 54.2 mmol) and dioxane (50 mL) and warmed to reflux for 48 hours. The mixture was evaporated to a small volume and partitioned between ethyl acetate (150 mL) and water (100 mL). The organic phase was dried over MgSO$_4$, treated with charcoal, filtered, and evaporated in vacuo to give the ester as a wet foam 14.1 g (70%) which was identified by $^1$H NMR, IR, MS, and microanalysis.

EXAMPLE 301

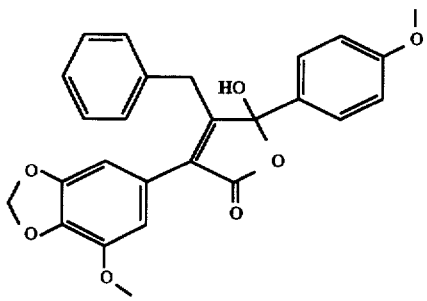

4-Benzyl-5-hydroxy-3-(7-methoxy-benzo[1,3]dioxol-5-yl)-5(4-methoxy-phenyl)-5H-furan-2-one To methanol (12 mL) was added sodium metal (97 mg, 4.3 mmol) and stirred to dissolve. To this was added the ester, 300, (1.48 g, 4.0 mmol) then benzaldehyde (467 mg, 4.4 mmol). The mixture was heated to reflux for 18 hours. The solution was then treated with acetic acid (2 mL) and refluxed an additional 24 hours. The solvents were removed by evaporation, and the residue was partitioned between ethyl acetate (50 mL) and water (50 mL). The organic phase was separated and dried over magnesium sulfate and evaporated to dryness. The crude product was then purified by flash chromatography (150 g silica gel, 7% ethyl acetate: methylene chloride). The butenolide was isolated by evaporation of the appropriate fractions to give 518 mg (29%) as a light orange foam. The butenolide was identified by $^1$H NMR, IR, MS, [M+H]$^+$=447 Da., and microanalysis.

EXAMPLE 302

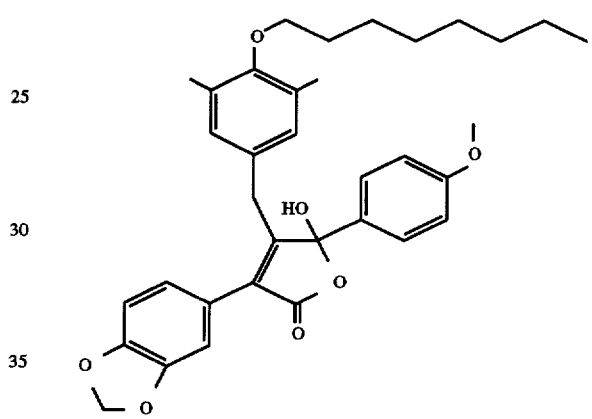

3-Benzo[1,3]dioxol-5-yl-4-(3,5-dimethyl-4-octyloxybenzyl)-5-hydroxy-5-(4-methoxy-phenyl)-5H-furan-2-one To methanol (12 mL) was added sodium metal (97 g, 4.3 mmol) and stirred to dissolve. To this was added the ester, 19, (1.37 g, 4.0 mmol) then 3,5-dimethyl-4-n-octyloxybenzaldehyde (1.15 g, 4.4 mmol). The mixture was heated to reflux for 18 hours. The solution was then treated with acetic acid (2 mL) and refluxed an additional 24 hours. The solvents were removed by evaporation, and the residue was partitioned between ethyl acetate (50 mL) and water (50 mL). The organic phase was separated and dried over magnesium sulfate and evaporated to dryness. The crude product was then purified by flash chromatography (150 g silica gel, 10% ethyl acetate:methylene chloride). The butenolide was isolated by evaporation of the appropriate fractions to give 0.985 g (43%) as an oily wax. The butenolide was identified by $^1$H NMR, IR, MS, [M+H]$^+$= 573 Da., and microanalysis.

EXAMPLE 303

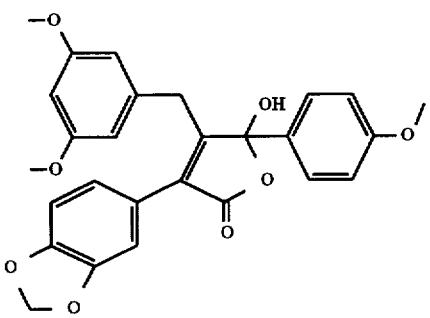

3-Benzo[1,3]dioxol-5-yl-4-(3,5-dimethoxy-benzyl)-5-hydroxy-5-(4-methoxy-phenyl)-5H-furan-2-one To methanol (8 mL) was added sodium metal (97 mg, 4.3 mmol) and stirred to dissolve. To this was added the ester, 19, (1.37 g, 4.0 mmol) then 3,5-dimethoxybenzaldehyde (681 mg, 4.1 mmol). The mixture was heated to reflux for 18 hours. The solution was then treated with acetic acid (2 mL) and refluxed an additional 24 hours. The solvents were removed by evaporation, and the residue was partitioned between ethyl acetate (75 mL) and water (50 mL). The organic phase was separated and dried over magnesium sulfate and evaporated to dryness. The crude product was then purified by flash chromatography (150 g silica gel, 7% ethyl acetate:methylene chloride). The butenolide was isolated by evaporation of the appropriate fractions to give 714 mg (37%) as a white foam. The butenolide was identified by $^1$H NMR, IR, MS, [M+H]$^+$=477 Da., and microanalysis.

EXAMPLE 304

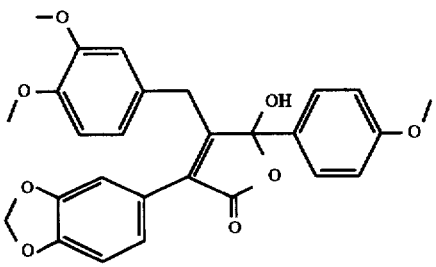

3-Benzo[1,3]dioxol-5-yl-4-(3,4-dimethoxy-benzyl)-5-hydroxy-5-(4-methoxy-phenyl)-5H-furan-2-one To methanol (8 mL) was added sodium metal (97 mg, 4.2 mmol) and stirred to dissolve. To this was added the ester, 19, (1.37 g, 4.0 mmol) then 3,4-dimethoxybenzaldehyde (681 mg, 4.1 mmol). The mixture was heated to reflux for 18 hours. The solution was then treated with acetic acid (7 mL) and refluxed an additional 24 hours. The solvents were removed by evaporation, and the residue was partitioned between ethyl acetate (30 mL) and water (30 mL). The organic phase was separated and dried over magnesium sulfate and evaporated to dryness. The crude product was then purified by flash chromatography (150 g silica gel, 15% ethyl acetate:methylene chloride). The butenolide was isolated by evaporation of the appropriate fractions to give 655 mg (34%) as a beige foam. The butenolide was identified by $^1$H NMR, IR, MS, [M+H]$^+$=477 Da., and microanalysis.

EXAMPLE 305

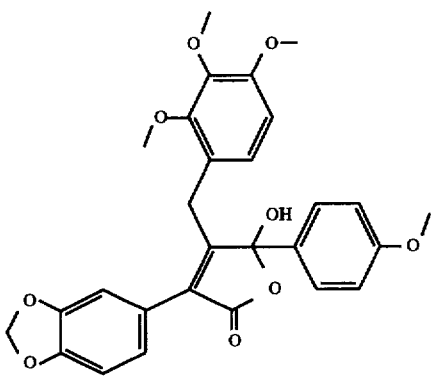

3-Benzo[1,3]dioxol-5-yl-5-hydroxy-5-(4-methoxy-phenyl)-4-(2,3,4-trimethoxy-benzyl)-5H-furan-2-one To methanol (8 mL) was added sodium metal (97 mg, 4.2 mmol) and stirred to dissolve. To this was added the ester, 19, (1.37 g, 4.0 mmol) then 2,3,4-trimethoxybenzaldehyde (804 mg, 4.1 mmol). The mixture was heated to reflux for 18 hours. The solution was then treated with acetic acid (2 mL) and refluxed an additional 24 hours. The solvents were removed by evaporation, and the residue was partitioned between ethyl acetate (50 mL) and water (50 mL). The organic phase was separated and dried over magnesium sulfate and evaporated to dryness. The crude product was then purified by flash chromatography (175 g silica gel, 10% ethyl acetate:methylene chloride). The butenolide was isolated by evaporation of the appropriate fractions to give 819 mg (40%) as a foam. The butenolide was identified by $^1$H NMR, IR, MS, [M+H]$^+$=506 Da., and microanalysis.

EXAMPLE 306

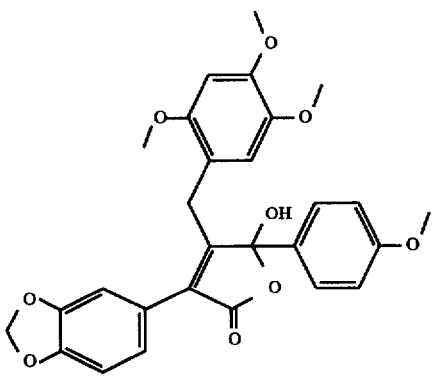

3-Benzo[1,3]dioxol-5-yl-5-hydroxy-5-(4-methoxy-phenyl)-4-(2,4,5-trimethoxy-benzyl)-5H-furan-2-one To methanol (8 mL) was added sodium metal (97 mg, 4.2 mmol) and stirred to dissolve. To this was added the ester, 19, (1.37 g, 4.0 mmol) then 2,4,5-trimethoxybenzaldehyde (804 mg, 4.1 mmol). The mixture was heated to reflux for 18 hours. The solution was then treated with acetic acid (2 mL) and refluxed an additional 24 hours. The solvents were removed by evaporation, and the residue was partitioned between ethyl acetate (50 mL) and water (50 mL). The organic phase was separated and dried over magnesium sulfate and evaporated to dryness. The crude product was then purified by flash chromatography (150 g silica gel, 2-20% ethyl acetate:methylene chloride). The butenolide was isolated by evaporation of the appropriate fractions to

EXAMPLE 307

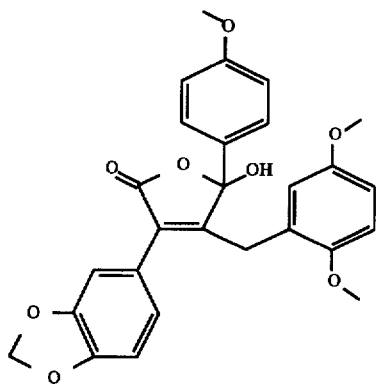

3-Benzo[1,3]dioxol-5-yl-4-(2,5-dimethoxy-benzyl)-5-hydroxy-5-(4-methoxy-phenyl)-5H-furan-2-one To methanol (8 mL) was added sodium metal (97 mg, 4.2 mmol) and stirred to dissolve. To this was added the ester, 19, (1.37 g, 4.0 mmol) then 2,5-dimethoxybenzaldehyde (681 mg, 4.1 mmol). The mixture was heated to reflux for 18 hours. The solution was then treated with acetic acid (2 mL) and refluxed an additional 24 hours. The solvents were removed by evaporation, and the residue was partitioned between ethyl acetate (100 mL) and water (100 mL). The organic phase was separated and dried over magnesium sulfate and evaporated to dryness. The crude product was then purified by flash chromatography (150 g silica gel, 10% ethyl acetate:methylene chloride). The butenolide was isolated by evaporation of the appropriate fractions to give 1.15 g (60%) as a light yellow solid. The butenolide was identified by $^1$H NMR, IR, MS, [M+H]$^+$=477 Da., and microanalysis.

EXAMPLE 308

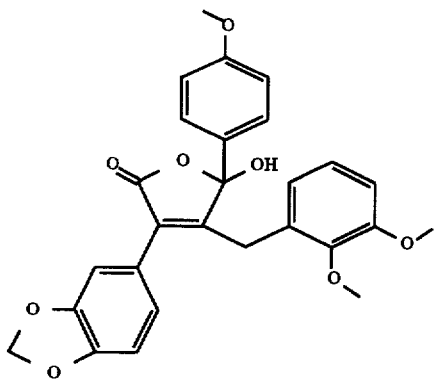

3-Benzo[1,3]dioxol-5-yl-4-(2,3-dimethoxy-benzyl)-5-hydroxy-5-(4-methoxy-phenyl)-5H-furan-2-one To methanol (8 mL) was added sodium metal (97 mg, 4.2 mmol) and stirred to dissolve. To this was added the ester, 19, (1.37 g, 4.0 mmol) then 2,3-dimethoxybenzaldehyde (681 mg, 4.1 mmol). The mixture was heated to reflux for 18 hours. The solution was then treated with acetic acid (2 mL) and refluxed an additional 72 hours. The solvents were removed by evaporation, and the residue was partitioned between ethyl acetate (75 mL) and water (100 mL). The organic phase was separated and dried over magnesium sulfate and evaporated to dryness. The crude product was then purified by flash chromatography (150 g silica gel, 10% ethyl acetate:methylene chloride). The butenolide was isolated by evaporation of the appropriate fractions to give 0.825 g (43%) as a thick oil. The butenolide was identified by $^1$H NMR, IR, MS, [M+H]$^+$=477 Da., and microanalysis.

EXAMPLE 309

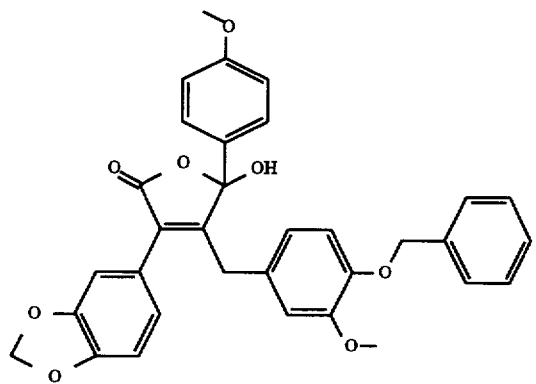

3-Benzo[1,3]dioxol-5-yl-4-(4-benzyloxy-3-methoxybenzyl)-5-hydroxy-5-(4-methoxy-phenyl)-5H-furan-2-one To methanol (8 mL) was added sodium metal (97 mg, 4.2 mmol) and stirred to dissolve. To this was added the ester, 19, (1.37 g, 4.0 mmol) then 3-methoxy-4-benzyloxybenzaldehyde (993 mg, 4.1 mmol). The mixture was heated to reflux for 18 hours. The solution was then treated with acetic acid (2 mL) and refluxed an additional 72 hours. The solvents were removed by evaporation, and the residue was partitioned between ethyl acetate (70 mL) and water (50 mL). The organic phase was separated and dried over magnesium sulfate and evaporated to dryness. The crude product was then purified by flash chromatography (150 g silica gel, 10% ethyl acetate:methylene chloride). The butenolide was isolated by evaporation of the appropriate fractions to give 710 mg (32%) as a white foam. The butenolide was identified by $^1$H NMR, IR, MS, [M+H]$^+$= 553 Da., and microanalysis.

EXAMPLE 310

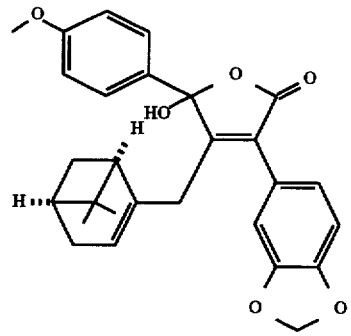

3-Benzo[1,3]dioxol-5-yl-4-(6,6-dimethyl-bicyclo[3.1.1]-hept-2-en-2-ylmethyl)-5-hydroxy-5-(4-methoxy-phenyl)-5H-furan-2-one To methanol (30 mL) was added sodium metal (0.074 g, 3.21 mmol) and stirred to dissolve. To this was added the ester, 19, (1.0 g, 2.92 mmol) then (1R)-(−)-myrtenol (0.57 g, 3.76 mmol). The mixture was heated to reflux for 6 hours.

The solution was then treated with acetic acid (3 mL) and refluxed an additional 25 hours. The solvents were removed by evaporation, and the residue was partitioned between ethyl acetate (50 mL) and water (25 mL). The organic phase was separated and dried over magnesium sulfate and evaporated to dryness. The crude product was then twice purified by flash chromatography (50 g silica gel, eluted with EtOAc:hexane (10:90)). The butenolide was isolated by evaporation of the appropriate fractions to give 38 mg (2.8%) as a yellow solid. The butenolide was identified by $^1$H NMR, MS, [M+H]$^+$=461 Da., and microanalysis.

EXAMPLE 311

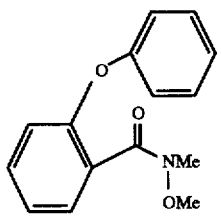

2-Phenoxy-n-methyl, n-methoxybenzamide

To o-phenoxybenzoic acid (50 g, 0.23 mol) in 500 mL CH$_2$Cl$_2$ was added carbonyldiimidazole (39 g, 0.24 mol). The solution was stirred 1.5 hours at 25° C. A solution of 29 mL n-methylpiperidine (0.816 mol) and O,N-dimethylhydroxylamine hydrochloride (22.77 g, 0.233 mol) in 300 mL CH$_2$Cl$_2$ was added. After stirring 24 hours at 25° C., the mixture was evaporated to an oil and resuspended in ethyl acetate. The solution was washed with 1N citric acid, saturated NaHCO$_3$ and brine, followed by drying over MgSO$_4$. The solution was evaporated to an oil in vacuo, 53.44 g, 93% yield. The amide was identified by $^1$H NMR, MS, [M+H]$^+$=258 Da., and microanalysis.

EXAMPLE 312

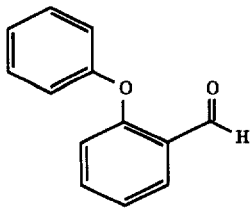

2-Phenoxybenzaldehyde

To 311, (53.25 g, 0.206 mol) in 600 mL tetrahydrofuran at −10° C. was added lithium aluminum hydride (10.16 g, 0.268 mol) over 5 minutes. The mixture was stirred at −5° C. for 1 hour followed by the addition of a solution of sodium hydrogen sulfate, 75 g in 700 mL water. The pH was adjusted to 3 by the addition of 12% HCl solution, and the mixture was filtered. The filtrate was extracted with ethyl acetate, washed with NaHCO$_3$ and brine, followed by drying over MgSO$_4$. The solution was evaporated to an oil in vacuo, 38 g. The crude oil was purified by flash chromatography (700 g silica gel, eluted with EtOAc:hexane (10:90)). Evaporation of the appropriate fractions gave an oil, 32 g, 78% yield. The aldehyde was identified by $^1$H NMR, MS, [M+H]$^+$=197.2 Da., and microanalysis.

EXAMPLE 313

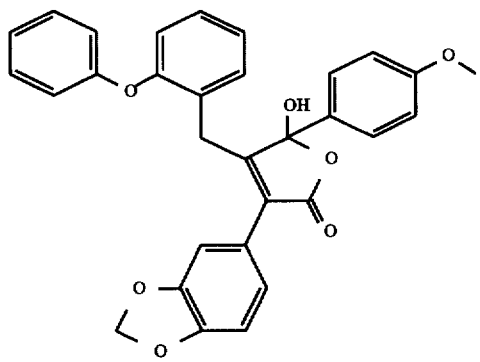

3-Benzo[1,3]dioxol-5-yl-5-hydroxy-5-(4-methoxy-phenyl)-4-(2-phenoxy-benzyl)-5H-furan-2-one To methanol (30 mL) was added sodium metal (0.125 g, 5.46 mmol) and stirred to dissolve. To this was added the ester, 19, (1.70 g, 4.96 mmol) then 2-phenoxybenzaldehyde (1.28 g, 6.4 mmol). The mixture was heated to reflux for 6 hours. The solution was then treated with acetic acid (3 mL) and refluxed an additional 24 hours. The solvents were removed by evaporation, and the residue was partitioned between ethyl acetate (75 mL) and water (50 mL). The organic phase was separated and dried over magnesium sulfate and evaporated to dryness. The crude product was then purified by flash chromatography (50 g silica gel, eluted with EtOAc:hexane (25:75). The butenolide was isolated by evaporation of the appropriate fractions to give 1.78 g (70%) as a pale green solid. The butenolide was identified by $^1$H NMR, IR, MS, [M+H]$^+$=509 Da., and microanalysis.

EXAMPLE 314

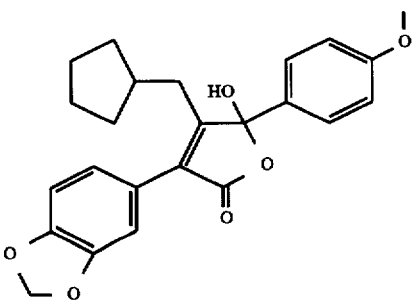

3-Benzo[1,3]dioxol-5-yl-4-cyclopentylmethyl-5-hydroxy-5-(4-methoxy-phenyl)-5H-furan-2-one To methanol (40 mL) was added sodium metal (0.124 g, 5.42 mmol) and stirred to dissolve. To this was added the ester, 19, (1.69 g, 4.93 mmol) then cyclopentanal (0.60 g, 6.1 mmol). The mixture was heated to reflux for 48 hours. The solution was then treated with acetic acid (3 mL) and refluxed an additional 24 hours. The solvents were removed by evaporation, and the residue was partitioned between EtOAc (40 mL) and 1N sodium hydroxide (15 mL). The aqueous phase was separated and acidified with 6N HCl. This acidic solution was extracted with 50 mL ethyl acetate. The organic phase was separated, washed with brine, dried over magnesium sulfate, and evaporated in vacuo. The crude butenolide was purified by flash chromatography (50 g silica gel, eluted with EtOAc:hexane (10:90)). Evaporation of the appropriate fractions gave an oil which was crystallized from Et$_2$O:hexane. This gave the butenolide 100 mg (5%) as a white solid. The butenolide was identified by $^1$H NMR, IR, MS, [M+H]$^+$=409 Da., and microanalysis.

EXAMPLE 315

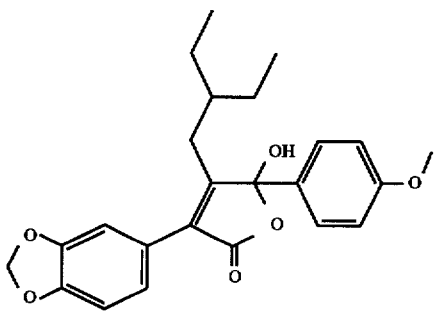

3-Benzo[1,3]dioxol-5-yl-4-(2-ethyl-butyl)-5-hydroxy-5-(4-methoxy-phenyl)-5H-furan-2-one To methanol (40 mL) was added sodium metal (0.124 g, 5.42 mmol) and stirred to dissolve. To this was added the ester, 19, (1.69 g, 4.93 mmol) then 2-ethylbotyraldehyde (0.74 g, 7.39 mmol). The mixture was heated to reflux for 24 hours. The solution was then treated with acetic acid (5 mL) and refluxed an additional 24 hours. The solvents were removed by evaporation, and the residue was partitioned between EtOAc (40 mL) and 1N sodium hydroxide (15 mL). The aqueous phase was separated and acidified with 6N HCl. This acidic solution was extracted with 50 mL ethyl acetate. The organic phase was separated, washed with brine, dried over magnesium sulfate, and evaporated in vacuo. The crude butenolide was purified by flash chromatography (50 g silica gel, eluted with EtOAc:hexane (10:90) ). Evaporation of the appropriate fractions gave an oil which was crystallized from Et$_2$O:pentane. This gave the butenolide 25 mg (1.23%) as a white solid. The butenolide was identified by $^1$H NMR and microanalysis.

EXAMPLE 316

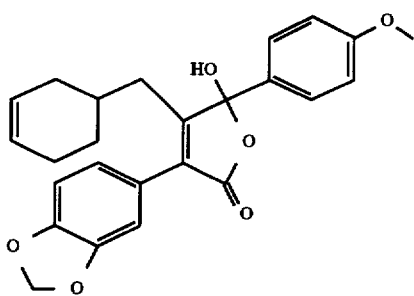

3-Benzo[1,3]dioxol-5-yl-4-cyclohex-3-enylmethyl-5-hydroxy-5-(4-methoxy-phenyl)-5H-furan-2-one To methanol (35 mL) was added sodium metal (0.124 g, 5.42 mmol) and stirred to dissolve. To this was added the ester, 19, (1.68 g, 4.93 mmol) then 1,2,5,6-tetrahydrobenzaldehyde (0.81 g, 7.39 mmol). The mixture was heated to reflux for 48 hours. The solution was then treated with acetic acid (5 mL) and refluxed an additional 18 hours. The solvents were removed by evaporation, and the residue was partitioned between ether (50 mL) and 1N sodium hydroxide (15 mL). The aqueous phase was separated and acidified with 6N HCl. This acidic solution was extracted with 50 mL ethyl acetate. The organic phase was separated, washed with brine, dried over magnesium sulfate, and evaporated in vacuo. The crude butenolide was purified by flash chromatography (50 g silica gel, eluted with EtOAc:hexane (10:90)). Evaporation of the appropriate fractions gave an oil which was crystallized from Et$_2$O:pentane. This gave the butenolide 0.45 g (24%) as a solid. The butenolide was identified by $^1$H NMR, IR, MS, [M+H]$^+$=421 Da., and microanalysis.

EXAMPLE 317

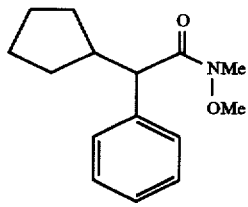

2-Cyclopentyl-2-phenyl-n-methyl, n-methoxyacetamide

To 2-Cyclopentyl-2-phenylacetic acid (17 g, 0.083 mol) was added thionyl chloride (150 mL). The solution was stirred 24 hours at 25° C. The solution was evaporated to an oil, 18.4 g. This was dissolved in 200 mL CH$_2$Cl$_2$ and cooled to −20° C. A solution of n-methylpiperidine (17.39 g, 0.174 mol) and O,N-dimethylhydroxylamine hydrochloride (8.5 g, 0.087 mol) in 200 mL CH$_2$Cl$_2$ was added. After stirring for 24 hours at 25° C., the mixture was evaporated to a paste and resuspended in ethyl ether. The solution was washed with 1N HCl, saturated NaHCO$_3$ and brine, followed by drying over MgSO$_4$. The solution was evaporated to an oil in vacuo. The mixture was crystallized from cold hexane, 18.5 g recovered, 90% yield. The amide was identified by $^1$H NMR, MS, [M+H]$^+$=248 Da., and microanalysis.

EXAMPLE 318

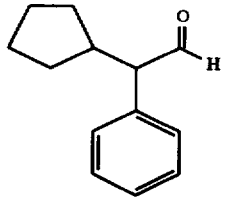

2-Cyclopentyl-2-phenylacetaldehyde

To 317, (18.32 g, 0.074 mol) in 400 mL Et$_2$O at −40° C. was added lithium aluminum hydride (2.92 g, 0.077 mol) over 5 minutes. The mixture was stirred at 25° C. for 6 hours followed by the addition of 125 mL 12% HCl. The organic phase was washed with NaHCO$_3$ and brine, followed by drying over MgSO$_4$. The solution was evaporated to an oil in vacuo. The crude oil was purified by flash chromatography (120 g silica gel, eluted with hexane). Evaporation of the appropriate fractions gave an oil, 11.2 g, 80% yield. The aldehyde was identified by $^1$H NMR, MS, [M+H]$^+$=189 Da., and microanalysis.

EXAMPLE 319

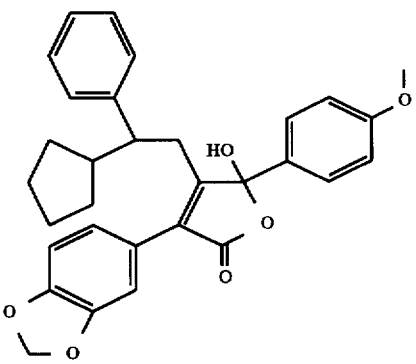

3-Benzo[1,3]dioxol-5-yl-4-(2-cyclopentyl-2-phenylethyl)-5-hydroxy-5-(4methoxy-phenyl)-5H-furan-2-one To methanol (35 mL) was added sodium metal (0.074 g, 3.21 mmol) and stirred to dissolve. To this was added the ester, 19, (1.0 g, 2.92 mmol) then 2-cyclopentyl-2-phenylacetaldehyde (0.69 g, 3.65 mmol). The mixture was heated to reflux for 48 hours. The solution was then treated with acetic acid (5 mL) and refluxed an additional 24 hours. The solvents were removed by evaporation, and the residue was partitioned between ether (50 mL) and 1N sodium hydroxide (15 mL). The aqueous phase was separated and acidified with 6N HCl. This acidic solution was extracted with 50 mL ethyl acetate. The organic phase was separated, washed with brine, dried over magnesium sulfate, and evaporated in vacuo. The crude butenolide was purified by flash chromatography (50 g silica gel, eluted with EtOAc:hexane (5:95)). Evaporation of the appropriate fractions from Et$_2$O gave a solid foam. This gave the butenolide 50 mg (3.4%) as a solid foam. The butenolide was identified by $^1$H NMR, MS, [M+H]$^+$=499 Da., and microanalysis.

EXAMPLE 320

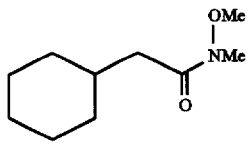

N-methyl, n-methoxy cyclohexylacetic acid

To cyclohexylacetic acid (20 g, 0.14 mol) was added thionyl chloride (150 mL). The solution was stirred 48 hours at 25° C. The solution was evaporated to an oil, 19.16 g. This was dissolved in 200 mL CH$_2$Cl$_2$ and cooled to 0° C. A solution of n-methyl-piperidine 25.45 g (0.255 mol) and O,N-dimethylhydroxylamine hydrochloride (12.27 g, 0.125 mol) in 200 mL CH$_2$Cl$_2$ was added. After stirring 2 hours at 25° C., the mixture was evaporated to a paste and resuspended in ethyl ether. The solution was washed with 1N HCl, saturated NaHCO$_3$ and brine, followed by drying over MgSO$_4$. The solution was evaporated to an oil in vacuo, 24.57 g. The mixture was distilled at 0.75 mm Hg, bp 83°–92° C., 18.73 g recovered, 85% yield. The amide was identified by $^1$H NMR, MS, [M+H]$^+$=186 Da., and microanalysis.

EXAMPLE 321

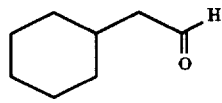

Cyclohexylacetaldehyde

To 320, (18.46 g, 0.099 mol) in 400 mL Et$_2$O at −50° C. was added lithium aluminum hydride (4.0 g, 0.104 mol) over 5 minutes. The mixture was stirred at −10° C. for 3 hours followed by the addition of 125 mL 12% HCl. The organic phase was washed with NaHCO$_3$ and brine, followed by drying over MgSO$_4$. The solution was evaporated to an oil in vacuo, 10.5 g. The crude oil (2.2 g) was purified by flash chromatography (50 g silica gel, eluted with hexane). Evaporation of the appropriate fractions gave an oil, 0.75 g, 28% yield (prorated). The aldehyde was used in the following reaction without further identification.

EXAMPLE 322

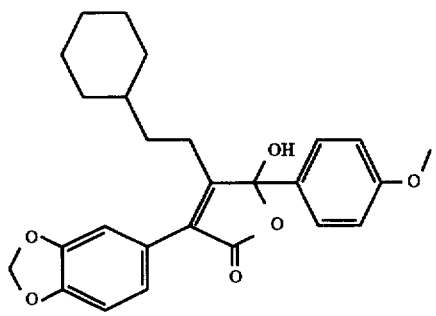

3-Benzo-[1,3]dioxol-5-yl-4-(2-cyclohexyl-ethyl)-5-hydroxy-5-(4-methoxy-phenyl)-5H-furan-2-one To methanol (35 mL) was added sodium metal (0.124 g, 5.42 mmol) and stirred to dissolve. To this was added the ester, 19, (1.68 g, 4.93 mmol) then cyclohexylacetaldehyde 0.93 g (7.39 mmol). The mixture was heated to reflux for 48 hours. The solution was then treated with acetic acid (3 mL) and refluxed an additional 24 hours. The solvents were removed by evaporation, and the residue was partitioned between ether (40 mL) and 1N sodium hydroxide (15 mL). The aqueous phase was separated and acidified with 6N HCl. This acidic solution was extracted with 50 mL ethyl acetate. The organic phase was separated, washed with brine, dried over magnesium sulfate, and evaporated in vacuo. The crude butenolide was purified by flash chromatography (50 g silica gel, eluted with EtOAc:hexane (5:95)). Evaporation of the appropriate fractions gave an oil which was crystallized from Et$_2$O:hexane. This gave the butenolide 0.149 g (6.9%) as a white solid. The butenolide was identified by $^1$H NMR, MS, [M+H]$^+$=437 Da., and microanalysis.

EXAMPLE 323

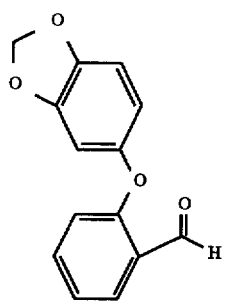

2-((3',4'-Methylenedioxy)phenoxy)benzaldehyde

To a solution of 60% NaH suspension (4 g, 0.1 mol) in 20 mL DMSO was added a solution of sesamol (13.8 g, 0.1 mol) in 20 mL DMSO. The mixture was stirred at 25° C. for 30 minutes, followed by the addition of 2-fluorobenzaldehyde (12.4 g, 0.1 mol). The mixture was heated at 90° C. for 3 hours. The mixture was cooled and poured into ice water and was extracted with ethyl ether. The organic phase was washed with brine, followed by charcoal filtration and drying over Na$_2$SO$_4$. The solution was evaporated to an oil in vacuo, which was purified by flash chromatography (600 g silica gel, eluted with EtOAc:hexane (20:80)). Evaporation of the appropriate fractions gave an oil, 3.35 g. The aldehyde was identified by $^1$H NMR, MS, and microanalysis.

EXAMPLE 324

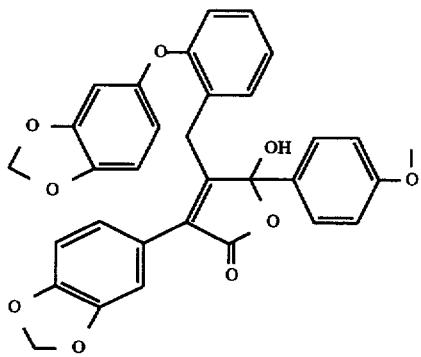

3-Benzo[1,3]dioxol-5-yl-4-[2-(benzo[1,3]dioxol-5-yloxy)-benzyl]-5-hydroxy-5-(4-methoxy-phenyl)-5H-furan-2-one To methanol (35 mL) was added sodium metal (0.074 g, 3.21 mmol) and stirred to dissolve. To this was added the ester, 19, (1.0 g, 2.92 mmol) then 2-((3',4'-methylenedioxy)phenoxy)benzaldehyde (0.88 g, 3.65 mmol). The mixture was heated to reflux for 24 hours. The solution was then treated with acetic acid (5 mL) and refluxed an additional 3 hours. The solvents were removed by evaporation, and the residue was partitioned between ether (50 mL) and 1N sodium hydroxide (20 mL). The aqueous phase was separated and acidified with 6N HCl. This acidic solution was extracted with 50 mL ethyl acetate. The organic phase was separated, washed with brine, dried over magnesium sulfate, and evaporated in vacuo. The crude butenolide was purified by flash chromatography (50 g silica gel, eluted with EtOAc:hexane (5:95)). Evaporation of the appropriate fractions gave an oil which was crystallized from Et$_2$O:hexane at −60° C. This gave the butenolide 0.145 g (9%) as a yellow solid. The butenolide was identified by $^1$H NMR, MS, [M+H]$^+$=553 Da., and microanalysis.

EXAMPLE 325

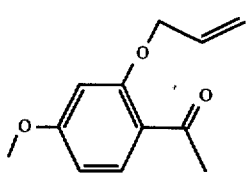

2-Allyloxy, 4-methoxy acetophenone

To 2-hydroxy-4-methoxy acetophenone (20 g, 120 mmol) in acetone (400 mL) was added allyl bromide (37 g, 300 mmol) followed by potassium carbonate (19 g, 132 mmol). The mixture was heated to reflux for 30 hours, evaporated to an oil, and redissolved in ethyl ether. The solution was washed with 1N NaOH, brine, and dried over MgSO$_4$. The solution was evaporated to a solid and recrystallized from Et$_2$O:hexane giving the acetophenone 16.02 g, 65% yield as a white solid. The acetophenone was identified by $^1$H NMR, MS [M+H]$^+$=207 Da., and microanalysis.

EXAMPLE 326

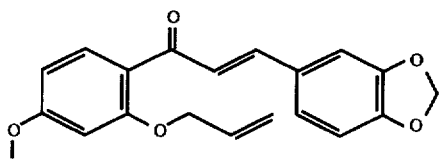

To 325, (16 g, 77.6 mmol) in absolute ethanol (50 mL) in an erlenmeyer was added piperonal (12.81 g, 85 mmol). The solution swirled while 10% sodium hydroxide (5 mL) added. The mixture swirled for 3 hours and allowed to stand to precipitate. The solid was collected by filtration and washed with 80% ethanol (150 mL). The solid was dried in vacuo giving 23.4 g (89%) of a yellow solid which was identified by $^1$H NMR, MS, and microanalysis.

EXAMPLE 327

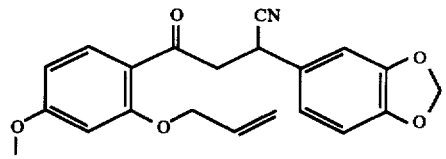

To the chalcone, 326, (23 g, 68 mmol) in absolute ethanol (400 mL) at 55° C. was added acetic acid (8.8 mL) followed by slow addition of potassium cyanide (11 g, 167 mmol) in water (50 mL). The solution was stirred at reflux for 24 hours. The solution was cooled and treated with water (150 mL). The mixture was then filtered to collect the solid. The solid was filtered, redissolved in 750 mL ethyl acetate, filtered through charcoal, and evaporated to 0.5 volume. Addition of hexane gave the nitrile 17.1 g (69%) as a yellow solid. The nitrile was identified by $^1$H NMR, MS, and microanalysis.

EXAMPLE 328

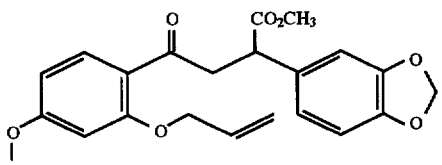

To the nitrile, 327, (17 g, 46.9 mmol) was added methanol (40 mL) and dioxane (20 mL), followed by p-toluenesulfonic acid (8.98 g, 46 mmol). The mixture was heated at reflux for 24 hours, cooled, and evaporated to a solid. The solid was suspended in ethyl acetate, filtered, washed with saturated NaHCO$_3$, brine, and dried over MgSO$_4$. The solution was evaporated to a solid which was filtered and recrystallized from ethyl acetate:hexane. This gave the ester 13.2 g (71%) as a yellow solid which was identified by $^1$H NMR, MS, and microanalysis.

EXAMPLE 329

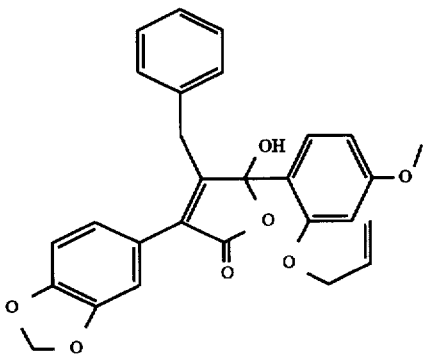

3-Benzo[1,3]dioxol-5-yl-5-hydroxy-5-(2-allyloxy-4-methoxy-phenyl)-4-benzyl-5H-furan-2one To methanol (60 mL) was added sodium metal (0.5 g, 26 mmol) and stirred to dissolve. To this was added the ester, 328, (6.84 g, 17.1 mmol) then benzaldehyde (2.76 g, 26 mmol). The mixture was heated to reflux for 10 hours. The solution was then treated with acetic acid (9 mL) and refluxed an additional 24 hours. The solvents were removed by evaporation, and the residue was partitioned between ether (150 mL) and 1N sodium hydroxide (40 mL). The aqueous phase was separated and acidified with 6N HCl. This acidic solution was extracted with 100 mL ethyl acetate. The organic phase was separated, washed with brine, dried over magnesium sulfate, and evaporated in vacuo. The crude butenolide was purified by flash chromatography (350 g silica gel, eluted with EtOAc:hexane (20:80)). Evaporation of the appropriate fractions from Et$_2$O gave a solid. This gave the butenolide 3.35 g (41%) as a white solid. The butenolide was identified by $^1$H NMR, MS, [M+H]$^+$=473 Da., and microanalysis.

EXAMPLE 330

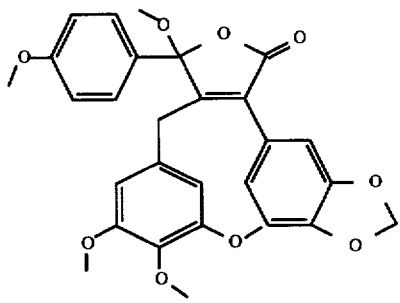

3-Benzo[1,3]dioxol-5-yl-4-(3,4,5-dimethoxybenzyl)-5-methoxy-5-(4-methoxyphenyl)-5H-furan-2-one To 281, (2.5 g, 4.93 mmol) in MeOH (100 mL) was added anhydrous HCl gas until the mixture had reached reflux. The mixture was heated at 70° C. for 24 hours, and the solution was evaporated to a foam. The procedure was repeated, and the resulting foam was purified by flash chromatography (150 g silica gel, eluted with EtOAc:hexane (10:90) with a gradient to (20:80)). Evaporation of the appropriate fractions from Et$_2$O gave the butenolide, 1.85 g, 72% yield as a white solid. The butenolide was identified by $^1$H NMR, IR, MS, [M+H]$^+$=521 Da., and microanalysis.

EXAMPLE 331

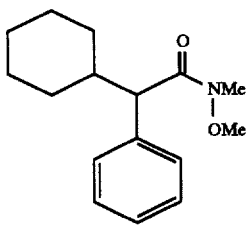

2-Cyclohexyl-2-Phenyl-n-methyl, n-methoxyacetamide

To 2-cyclohexyl-2-phenylacetic acid (14 g, 0.0645 mol) was added thionyl chloride (40 mL). The solution was stirred 24 hours at 25° C. The solution was evaporated to an oil which was dissolved in 100 mL CH$_2$Cl$_2$ and cooled to −10° C. A solution of n-methyl-piperidine 14.75 g (0.134 mol) and O,N-dimethyl-hydroxylamine hydrochloride 6.48 g (0.0664 mol) in 300 mL CH$_2$Cl$_2$ was added. After stirring 5 hours at 25° C., the mixture was evaporated to a paste and resuspended in ethyl acetate. The solution was washed with 1N HCl, saturated NaHCO$_3$ and brine, followed by drying over MgSO$_4$. The solution was evaporated to an oil in vacuo, 17.14 g recovered. The amide was used without further purification in the following step.

EXAMPLE 332

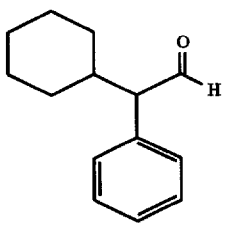

2-Cyclohexyl-2-phenylacetaldehyde

To 332, (16.8 g, 0.0644 mol) in 350 mL Et₂O at 0° C. was added lithium aluminum hydride (2.6 g, 0.0685 mol) over 5 minutes. The mixture was stirred at 25° C. for 2 hours followed by the addition of 120 mL 12% HCl. The organic phase was washed with NaHCO₃ and brine, followed by drying over MgSO₄. The solution was evaporated to an oil in vacuo. The crude oil was purified by flash chromatography (250 g silica gel, eluted with hexane). Evaporation of the appropriate fractions gave an oil, 8.28 g, 63% yield. The aldehyde was identified by ¹H NMR, MS, [M+H]⁺=203 Da., and microanalysis.

EXAMPLE 333

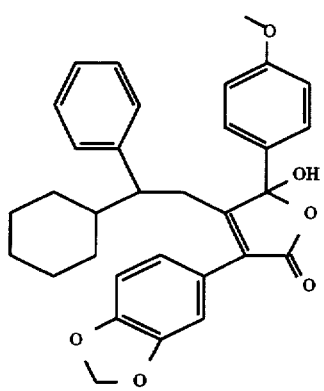

3-Benzo[1,3]dioxol-5-yl-4-(2-cyclohexyl-2-phenyl-ethyl)-5-hydroxy-5-(4-methoxy-phenyl)-5H-furan-2-one To methanol (40 mL) was added sodium metal (0.154 g, 6.42 mmol) and stirred to dissolve. To this was added the ester, 19, (2.0 g, 5.84 mmol) then 2-cyclohexyl-2-phenylacetaldehyde (1.48 g, 7.30 mmol). The mixture was heated to reflux for 48 hours. The solution was then treated with acetic acid (6 mL) and refluxed an additional 24 hours. The solvents were removed by evaporation, and the residue was partitioned between ether (70 mL) and 1N sodium hydroxide (20 mL). The aqueous phase was separated and acidified with 6N HCl. This acidic solution was extracted with 50 mL ethyl acetate. The organic phase was separated, washed with brine, dried over magnesium sulfate, and evaporated in vacuo. The solution was evaporated to a solid which was purified by flash chromatography (50 g silica gel, eluted with EtOAc:hexane (5:95)). Evaporation of the appropriate fractions from Et₂O gave the butenolide 0.22 g (7.4%) as a white solid. The butenolide was identified by ¹H NMR, MS, [M+H]⁺=513 Da., and microanalysis.

EXAMPLE 334

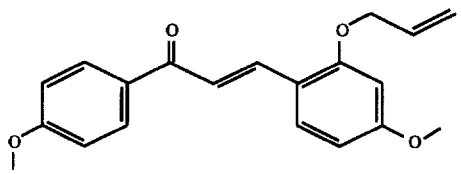

To 4-methoxyacetophenone (8.05 g, 53.6 mmol) in denatured ethanol (35 mL) in an erlenmeyer was added 2-allyloxy-4-methoxybenzaldehyde (11.3 g, 58.8 mmol). The solution swirled while 10% sodium hydroxide (4 mL) added. The mixture swirled for 4 hours and evaporated to a syrup. The mixture was redissolved in Et₂O, washed with 1N citric acid, saturated NaHCO₃, brine, and dried over MgSO₄. Concentration of the solution in vacuo gave a crystalline solid which was filtered. The solid was dried in vacuo giving 16.32 g (94%) of a yellow solid which was identified by ¹H NMR, MS, and microanalysis.

EXAMPLE 335

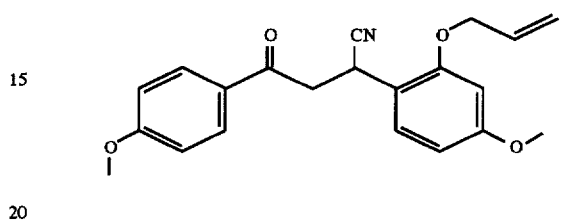

To the chalcone, 334, (14 g, 43 mmol) in absolute EtOH (250 mL) at 55° C. was added acetic acid (6.17 mL) followed by slow addition of potassium cyanide (7.68 g, 118 mmol) in water (30 mL). The solution was stirred at reflux for 24 hours. The solution was cooled and treated with water (150 mL). The mixture was evaporated and the residue was dissolved in ethyl acetate. The solution was filtered and washed with 1N citric acid, saturated NaHCO₃, brine, and dried over MgSO₄. The solution was evaporated to an oil which was suspended in Et₂O, filtered through celite, and triturated with hexane giving a solid. The solid was dried in vacuo to give the nitrile 10.72 g (71%) as a solid. The nitrile was identified by ¹H NMR, MS, and microanalysis.

EXAMPLE 336

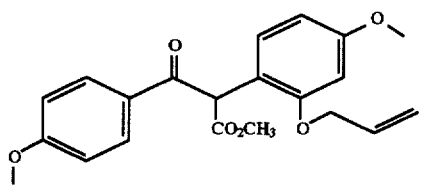

To the nitrile, 335, (10.5 g, 27 mmol) was added methanol (25 mL) and dioxane (30 mL), followed by p-toluenesulfonic acid (5.7 g, 30 mmol). The mixture was heated at reflux for 18 hours, cooled, and evaporated to a solid. The solid was suspended in ethyl acetate, filtered, washed with saturated 1N citric acid, NaHCO₃, brine, and dried over MgSO₄. The solution was evaporated to an oil which was purified by flash chromatography (400 g silica gel, eluted with EtOAc:hexane (5:95)). Evaporation of the appropriate fractions from Et₂O gave the ester as an oil, 6.68 g, 58% yield, which was identified by ¹H NMR, MS, and microanalysis.

EXAMPLE 337

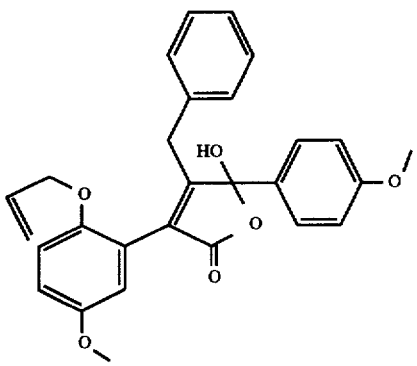

3-(2-Allyloxy-5-methoxy-phenyl)-4-benzyl-5-hydroxy-5-(4-methoxy-phenyl)-5H-furan-2-one To methanol (55 mL) was added sodium metal (0.37 g, 160 mmol) and stirred to dissolve. To this was added the ester, 326, (4.8 g, 125 mmol) then benzaldehyde (2.01 g, 189 mmol). The mixture was heated to reflux for 32 hours. The solution was then treated with acetic acid (10 mL) and refluxed an additional 24 hours. The solvents were removed by evaporation, and the residue was partitioned between ether (75 mL) and 1N sodium hydroxide (30 mL). The aqueous phase was separated and acidified with 6N HCl. This acidic solution was extracted with 75 mL ethyl acetate. The organic phase was separated, washed with brine, dried over magnesium sulfate, and evaporated in vacuo. The oil was crystallized from Et$_2$O and filtered. This gave the butenolide 3.6 g (63%) as a pale yellow solid. The butenolide was identified by $^1$H NMR, IR, MS, [M+H]$^+$=458 Da., and microanalysis.

EXAMPLE 338

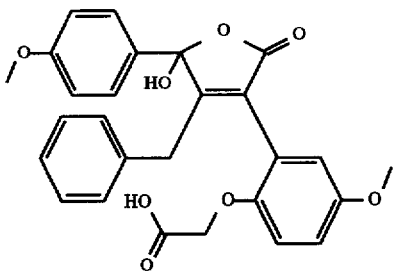

{2-[4-Benzyl-5-hydroxy-5-(4-methoxy-phenyl)-2-oxo-2,5-dihydro-furan-3-yl]-4-methoxy-phenoxy}-acetic acid To the butenolide, 337, (3.3 g, 7.2 mmol) in dioxane (90 mL) was added a solution of 2.5% OsO$_4$ in 2-methyl-2-propanol (2.58 mL). To this mixture was added a solution of NaIO$_4$(6.5 g, 30 mmol) in 40 mL water. After stirring at 25° C. for 6 hours, the mixture was evaporated, resuspended in ethyl acetate, filtered, washed with brine, and dried over MgSO$_4$. The solution was evaporated to a foam (2.84 g) and purified by flash chromatography (150 g silica gel, eluted with EtOAc:hexane (5:95)). Evaporation of the appropriate fractions gave a solid which was crystallized from Et$_2$O, 0.997 g, 36% yield. The butenolide-aldehyde intermediate was identified by $^1$H NMR, MS, [M+H]$^+$=461 Da., and microanalysis.

To the butenolide-aldehyde intermediate (1.25 g, 2.71 mmol) in acetone (60 mL) was added 8N Jones reagent (1.0 mL), followed by stirring for 45 minutes. Isopropyl alcohol (2 mL) was added, and the mixture was evaporated to a solid. The solid was purified by flash chromatography (50 g silica gel, eluted with a gradient of CHCl$_3$ to CHCl$_3$:MeOH (5:95)). Evaporation of the appropriate fractions gave a solid, which was recrystallized from Et$_2$O, 0.355 g, 27% yield as a solid. The butenolide was identified by $^1$H NMR, MS, [M+H]$^+$=476 Da., and microanalysis.

EXAMPLE 339

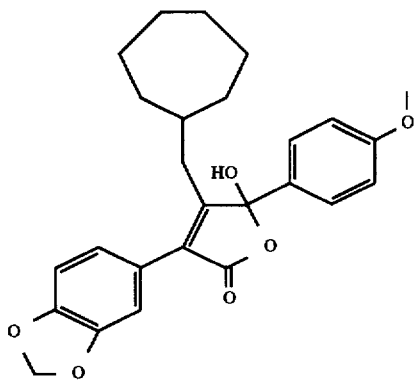

3-Benzo[1,3]dioxol-5-yl-4-cycloheptylmethyl-5-hydroxy-5-(4-methoxy-phenyl)-5H-furan-2-one To methanol (40 mL) was added sodium metal (0.147 g, 6.42 mmol) and stirred to dissolve. To this was added the ester, 19, (2.0 g, 5.84 mmol) then cycloheptylaldehyde (110 mg, 8.76 mmol). The mixture was heated to reflux for 48 hours. The solution was then treated with acetic acid (5 mL) and refluxed an additional 24 hours. The solvents were removed by evaporation, and the residue was partitioned between ether (50 mL) and 1N sodium hydroxide (15 mL). The aqueous phase was separated and acidified with 6N HCl. This acidic solution was extracted with 50 mL ethyl acetate. The organic phase was separated, washed with brine, dried over magnesium sulfate, and evaporated in vacuo. The crude butenolide was purified by flash chromatography (50 g silica gel, eluted with EtOAc:hexane (5:95)). Evaporation of the appropriate fractions from Et$_2$O gave an oil which solidified. This gave the butenolide 121 mg (4.7%) as a solid. The butenolide was identified by $^1$H NMR, MS, [M+H]$^+$=437 Da., and microanalysis.

EXAMPLE 340

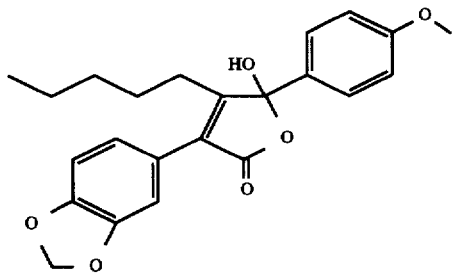

3-Benzo[1,3]dioxol-5-yl-5-hydroxy-5-(4-methoxy-phenyl)-4-pentyl-5H-furan-2-one

To methanol (40 mL) was added sodium metal (0.147 g, 6.42 mmol) and stirred to dissolve. To this was added the ester, 19, (2.0 g, 5.84 mmol) then valeraldehyde (0.93 g, 8.76 mmol). The mixture was heated to reflux for 48 hours. The solution was then treated with acetic acid (5 mL) and refluxed an additional 24 hours. The solvents were removed

EXAMPLE 341 by evaporation, and the residue was partitioned between ether (40 mL) and 1N sodium hydroxide (15 mL). The aqueous phase was separated and acidified with 6N HCl. This acidic solution was extracted with 50 mL ethyl acetate. The organic phase was separated, washed with brine, dried over magnesium sulfate, and evaporated in vacuo. The crude butenolide was purified by flash chromatography (50 g silica gel, eluted with EtOAc:hexane (5:95)). Evaporation of the appropriate fractions from Et$_2$O gave an oil. This gave the butenolide 264 mg (1.14%) as an oil. The butenolide was identified by $^1$H NMR, MS, [M+H]$^+$=397.2 Da., and microanalysis.

EXAMPLE 341

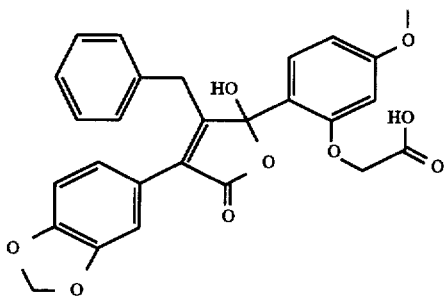

[2-(4-Benzo[1,3]dioxol-5-yl-3-benzyl-2-hydroxy-5-oxo-2,5-dihydro-furan-2-yl)-5-methoxy-phenoxy]-acetic acid To the butenolide 329, (2.74 g, 6.19 mmol) in dioxane (50 mL) was added a solution of 2.5% OsO$_4$ in 2-methyl-2-propanol (1.65 mL). To this mixture was added a solution of NaIO$_4$(4.14 g, 19.3 mmol) in 15 mL water. As the mixture thickened, dioxane (20 mL) was added. After stirring at 25° C. for 5 hours, the mixture was evaporated, resuspended in ethyl acetate, filtered, and washed with 1N HCl, brine, and dried over MgSO$_4$. The solution was evaporated to a foam (2.75 g) and purified by flash chromatography (250 g silica gel, eluted with EtOAc:hexane (10:90)). Evaporation of the appropriate fractions gave a solid which was crystallized from Et$_2$O, 1.03 g, 34% yield. The butenolide-aldehyde intermediate was identified by $^1$H NMR, MS, [M+H]$^+$=475 Da., and microanalysis.

To the butenolide-aldehyde intermediate (1.12 g, 2.36 mmol) in acetone (50 mL) was added 8N Jones reagent (0.87 mL), followed by stirring for 45 minutes. Isopropyl alcohol (3 mL) was added, and the mixture was evaporated to an oil. The mixture was dissolved in CHCl$_3$, washed with brine, and dried over MgSO$_4$. The solution was evaporated to 5 mL in volume and purified by flash chromatography (50 g silica gel, eluted with a gradient of CHCl$_3$ to CHCl$_3$:MeOH (5:95)). Evaporation of the appropriate fractions gave an oil, which was recrystallized from Et$_2$O, 0.493 g, 42% yield as a solid. The butenolide was identified by $^1$H NMR, MS, [M+H]$^+$=491 Da., and microanalysis.

EXAMPLE 342

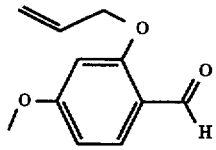

2-Allyloxy, 4-methoxybenzaldehyde

To 2-hydroxy-4-methoxybenzaldehyde (25 g, 164 mmol) in acetone (500 mL) was added allyl bromide (49.6 g, 410 mmol) followed by potassium carbonate (34 g, 246 mmol). The mixture was heated to reflux for 24 hours, filtered, evaporated to an oil, and redissolved in ethyl ether. The solution was washed with 1N NaOH, 1N HCl, brine, and dried over MgSO$_4$. The solution was evaporated to a solid and recrystallized from Et$_2$O:hexane giving the aldehyde 14.54 g, 46% yield as a white solid. The acetophenone was identified by $^1$H NMR, MS, [M+H]$^+$=193 Da., and microanalysis.

EXAMPLE 343

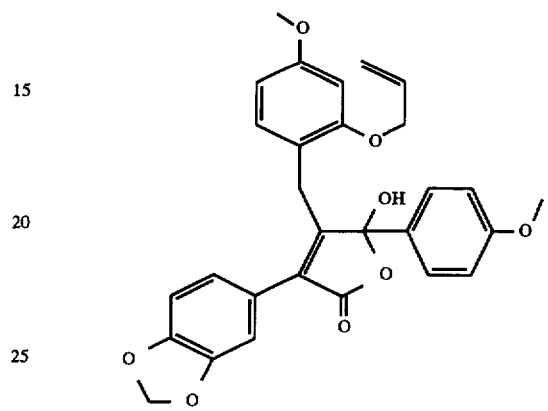

4-(2-Allyloxy-4-methoxy-benzyl)-3-benzo[1,3]dioxol-5-yl-5-hydroxy-5-(4-methoxy-phenyl)-5H-furan-2-one To methanol (40 mL) was added sodium metal (0.295 g, 128 mmol) and stirred to dissolve. To this was added the ester, 19, (4.0 g, 117 mmol) then 342 (2.92 g, 150 mmol). The mixture was heated to reflux for 8 hours. The solution was then treated with acetic acid (9 mL) and refluxed an additional 5 hours. The solvents were removed by evaporation, and the residue was partitioned between ether (100 mL) and 1N sodium hydroxide (30 mL). The aqueous phase was separated and acidified with 6N HCl. This acidic solution was extracted with 75 mL ethyl acetate. The organic phase was separated, washed with brine, dried over magnesium sulfate, and evaporated in vacuo. The crude oil was purified by flash chromatography (350 g silica gel, eluted with EtOAc:hexane (20:80)). Evaporation of the appropriate fractions gave the butenolide 0.72 g (12.5%) as a solid. The butenolide was identified by $^1$H NMR, MS, [M+H]$^+$=503 Da., and microanalysis.

EXAMPLE 344

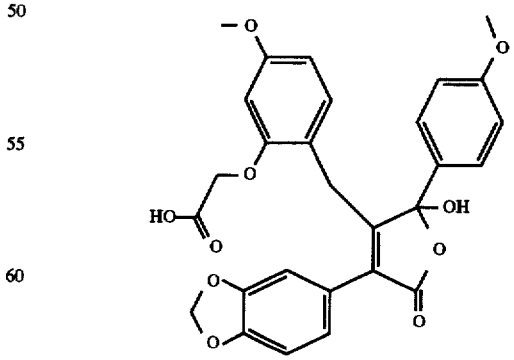

{2-[4-Benzo[1,3]dioxol-5-yl-2-hydroxy-2-(4-methoxy-phenyl)-5-oxo-2,5-dihydro-furan-3-ylmethyl]-5-methoxy-phenoxy}-acetic acid To the butenolide, 343, (2.86 g, 5.69 mmol) in dioxane (70 mL) was added a solution of 2.5% OsO₄ in 2-methyl-2-propanol (2.15 mL). To this mixture was added a solution of NaIO₄ (5 g, 23.3 mmol) in 28 mL water. After stirring at 25° C. for 5.5 hours, the mixture was evaporated, resuspended in ethyl acetate, filtered, and washed with 1N HCl, saturated NaHCO₃, brine, and dried over MgSO₄. The solution was evaporated to a foam (2.83 g) and purified by flash chromatography (150 g silica gel, eluted with EtOAc:hexane (10:90)). Evaporation of the appropriate fractions gave a solid which was evaporated to a foam from Et₂O, 1.72 g, 60% yield. The butenolide-aldehyde intermediate was identified by $^1$H NMR, MS, [M+H]$^+$=505.2 Da., and microanalysis. To the butenolide-aldehyde intermediate (1.60 g, 3.27 mmol) in acetone (70 mL) was added 8N Jones reagent (1.2 mL), followed by stirring for 45 minutes. Isopropyl alcohol (2 mL) was added, and the mixture was evaporated to a solid. The mixture was evaporated, resuspended in ethyl acetate, filtered, washed with brine, and dried over MgSO₄. The solution was evaporated to a foam (1.6 g). The solid was purified by flash chromatography (75 g silica gel, eluted with a gradient of CHCl₃ to CHCl₃:MeOH (5:95)). Evaporation of the appropriate fractions gave a solid, which was recrystallized from Et₂O, 0.374 g, 23% yield. The butenolide was identified by $^1$H NMR, MS, [M+H]$^+$=521 Da., and microanalysis.

EXAMPLE 345

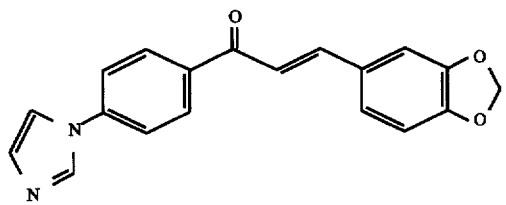

To 4-(1-Imadazol)acetophenone (13.0 g, 70 mmol) in absolute ethanol (400 mL) in an erlenmeyer was added piperonal (12.01 g, 80 mmol). The solution swirled while 10% sodium hydroxide (3 mL) added. The mixture swirled for 10 minutes and allowed to stand to precipitate. The solid was collected by filtration and washed with 80% ethanol. The solid was dried in vacuo giving 18.3 g (82%) of a solid, which was identified by $^1$H NMR, IR, MS, and microanalysis.

EXAMPLE 346

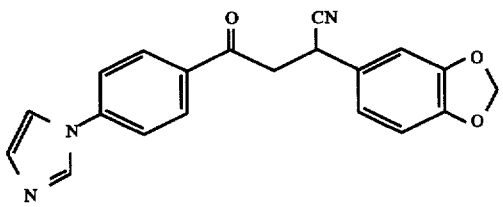

To the chalcone, 345, (17.7 g, 55.6 mmol) in ethanol (400 mL) at 55° C. was added acetic acid (7.5 g) followed by slow addition of potassium cyanide (9.1 g, 140 mmol) in water.

The solution was stirred at reflux for 18 hours. The solution was cooled and treated with water (200 mL). The mixture was then filtered to collect the solid. The solid was washed repeatedly with 70% ethanol, air dried, and then dried in vacuo to give the nitrile 13.3 g (69%) as a solid. The nitrile was identified by $^1$H NMR, IR, MS, and microanalysis.

EXAMPLE 347

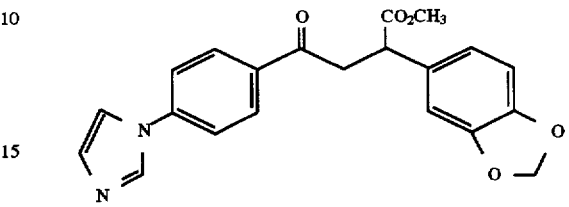

To the nitrile, 346, (10.8 g, 31.3 mmol) was added methanol (80 mL). The mixture was saturated with HCl (g) and heated to 45° C. until no nitrile remained, by thin layer chromatography. The solution was cooled and treated with water (70 mL). The resultant solid was filtered to collect, washed with 10% methanol (50 mL), and dried in vacuo. This gave the ester 4.0 g (34%) as a dark solid, which was identified by $^1$H NMR, IR, MS, and microanalysis.

EXAMPLE 348

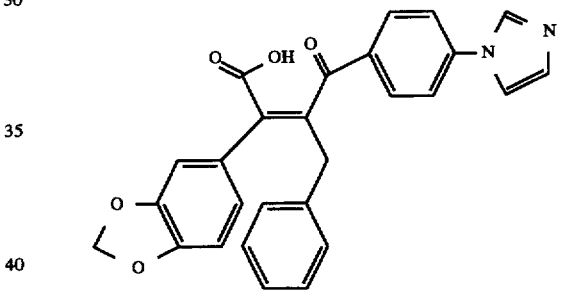

2-Butenoic acid, 2-(1,3-benzodioxol-5-yl)-4-[4-(1H-imidazol-1-yl)phenyl]4-oxo-3-(phenylmethyl)-

To methanol (12 mL) was added sodium metal (101 mg, 4.4 mmol) and stirred to dissolve. To this was added the ester, 347, (1.52 g, 4.0 mmol) then benzaldehyde (467 mg, 4.4 mmol). The mixture was heated to reflux for 120 hours. The solution was then treated with acetic acid (1 mL) and refluxed an additional 24 hours. The solvents were removed by evaporation, and the residue was partitioned between ethyl acetate (75 mL) and water (50 mL). The organic phase was separated and dried over magnesium sulfate and evaporated to dryness. The crude product was then purified by flash chromatography (140 g silica gel, 5% methanol:methylene chloride). The crude butenolide was combined with a second run of above and further purified by silica gel chromatography (200 g silica gel, 3% methanol:methylene chloride). The butenolide was isolated by evaporation of the appropriate fractions to give 221 mg (6%) as a yellow foam. The butenolide was identified by $^1$H NMR, IR, MS, [M+H]$^+$=452 Da., and microanalysis.

EXAMPLE 349

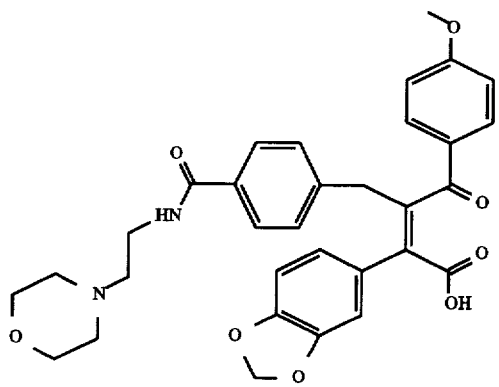

2-benzo[1,3]dioxol-5-yl-4-(4-methoxy-phenyl)-3-[4-(2-morpholin-4-yl-ethylcarbamoyl)-benzyl]-4-oxo-but-2-enoic acid In DMF (12 mL) was dissolved, 279, (1.52 g, 3.3 mmol), and HOBt (459 mg, 3.4 mmol). To this was added N-(2-aminoethyl)morpholine (456 mg, 3.5 mmol) and DCC (702 mg, 3.4 mmol). The mixture stirred at room temperature overnight. The mixture filtered free of precipitate, and the filtrate evaporated free of DMF. The residue was dissolved in ethyl acetate (75 mL) and washed successively with water, saturated sodium bicarbonate, and brine (100 mL each). The organic phase was evaporated in vacuo to give a foam. The butenolide was purified by chromatography (250 g silica gel, 5% methanol:methylene chloride). Evaporation of the appropriate fractions gave 695 mg (37%) of the butenolide which was identified by $^1$H NMR, MS, [M+H]$^+$=571, IR, and microanalysis.

EXAMPLE 350

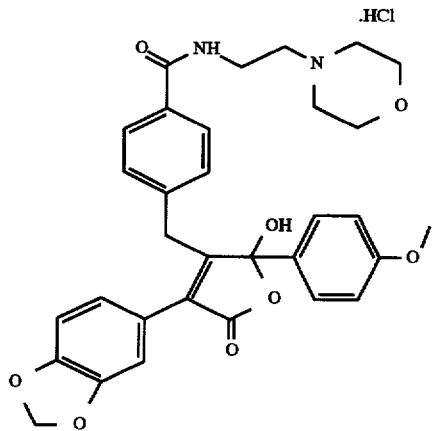

Benzamide, 4-[4-(1,3-benzodioxol-5-yl)-2,5-dihydro-2-hydroxy-2-(4-methoxyphenyl)-5-oxo-3-furanyl]methyl]-N-[2-(4-morpholinyl)ethyl]-, monohydrochloride, (±)-

In dioxane (5 mL) was dissolved 349, (519 mg, 0.90 mmol), and the solution treated with a 4N HCl solution in dioxane (225 µL, 0.9 mmol). The mixture stirred for 5 minutes and evaporated in vacuo to give the butenolide as a white solid 535 mg (97%). The butenolide was identified by $^1$H NMR, IR, MS, [M+H]$^+$=610 Da., and microanalysis.

EXAMPLE 351

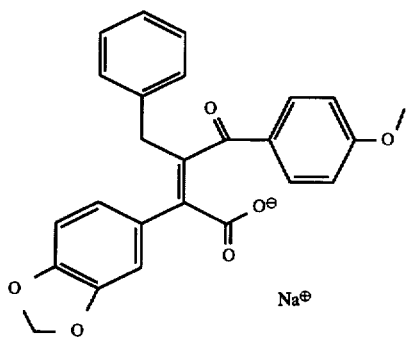

Sodium 2-benzo[1,3]dioxol-5-yl-3-benzyl-4-(4-methoxyphenyl)-4-oxobut-2-enoate

The butenolide, 20, (6.6 g, 15.8 mmol) was dissolved in methanol (150 mL) and treated with 0.4930N sodium hydroxide (aqueous), 31.8 mL (15.7 mmol). The solution stirred for 0.25 hours and evaporated free of methanol. The residue was partitioned between ether (200 mL) and distilled water (200 mL). The ether discarded and the aqueous evaporated free of residual organic solvents, frozen, and lyophilized to give the butenolide salt as a white solid, 6.41 g (93%). This was identified by $^1$H NMR, IR, MS, [M+H]$^+$=417 Da., and microanalysis.

EXAMPLE 352

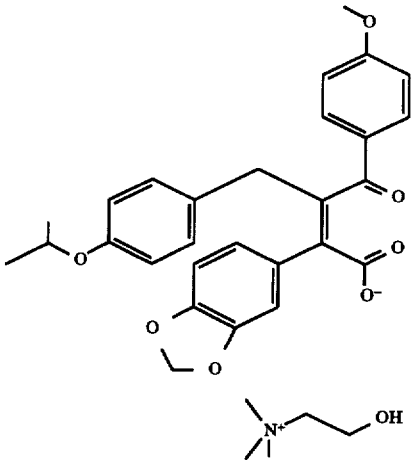

1,3-Benzodioxol-5-acetic acid, α-[2-(4-methoxyphenyl)-1-[[4-(1-methylethoxy)phenyl]methyl]-2-oxoethylene]-, (Z)-, choline salt The butenolide, 84, (2.4 g, 5.06 mmol) was dissolved in methanol (75 mL) and treated with a solution of choline hydroxide in methanol (1.36 g of 45%, 5.06 mmol). The mixture evaporated free of methanol an dissolved in distilled water (100 mL). The aqueous solution was evaporated free of residual methanol, frozen, and lyophilized. This gave the butenolide, 2.55 g (87%), as a hygroscopic white solid which was identified by $^1$H NMR, IR, MS, [M+H]$^+$=475 Da., and microanalysis.

EXAMPLE 353

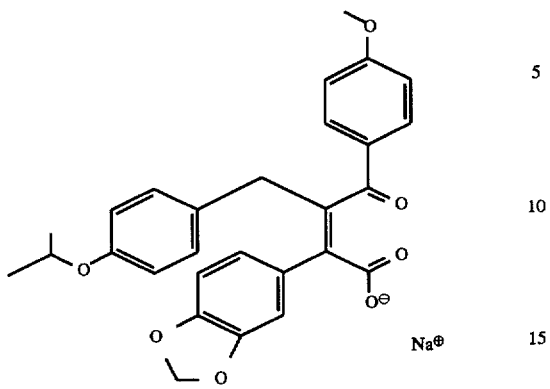

Sodium 2-Benzo[1,3]dioxol-5-yl-3-(4-isopropoxy-benzyl)-4-(4-methoxy-phenyl)-4-oxo-but-2-enoate The butenolide, 84, (4.0 g, 8.42 mmol) was dissolved in methanol (70 mL) and treated with 0.493N sodium hydroxide (aqueous), 16.2 mL (8.0 mmol). The solution stirred for 5 minutes and evaporated in vacuo free of methanol. The residue was partitioned between ether (50 mL) and distilled water (100 mL). The aqueous layer was separated, evaporated free of residual solvents, frozen, and lyophilized. This gave the butenolide salt, 2.53 g (64%), which was identified by $^1$H NMR, MS, [M+H]$^+$=475 Da., and microanalysis.

EXAMPLE 354

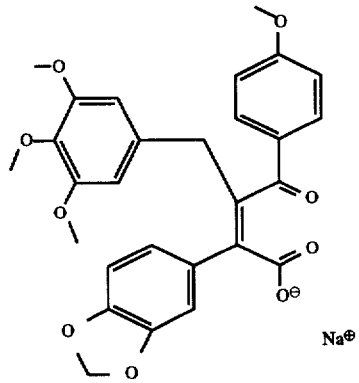

Sodium 2-Benzo[1,3]dioxol-5-yl-4-(4-methoxy-phenyl)-4-oxo-3-(3,4,5-trimethoxy-benzyl)-but-2-enoate The butenolide, 281, (4.04 g, 7.97 mmol) was dissolved in methanol (100 mL) and treated with 0.493N sodium hydroxide (aqueous), 15.8 mL (7.8 mmol). The solution stirred for 5 minutes and evaporated in vacuo to give a paste. The paste was partitioned between ether (100 mL) and distilled water (100 mL). The aqueous phase was separated, evaporated free of residual organic solvents, frozen, and lyophilized. This gave 3.65 g (88%) of the salt which was identified by $^1$H NMR, IR, MS, [M+H]$^+$=505 Da., and microanalysis.

EXAMPLE 355

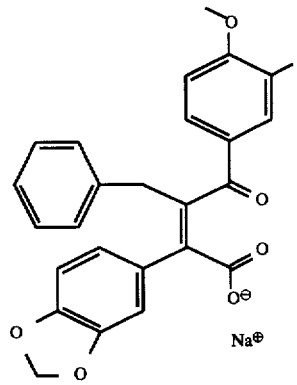

Sodium 2-Benzo[1,3]dioxol-5-yl-3-benzyl-4-(4-methoxy-3-methyl-phenyl)-4-oxo-but-2-enoate The butenolide, 212, (5.2 g, 12.0 mmol) was dissolved in methanol (350 mL) and treated with 1.010N sodium hydroxide (aqueous), 10.9 mL (11.0 mmol). The solution evaporated the residue partitioned between ether (250 mL) and distilled water (400 mL). The aqueous phase was separated, evaporated free of residual organic solvents, frozen, and lyophilized. The butenolide salt, 4.45 g (89%), was identified by $^1$H NMR, IR, MS, [M+H]$^+$=431 Da., and microanalysis.

EXAMPLE 356

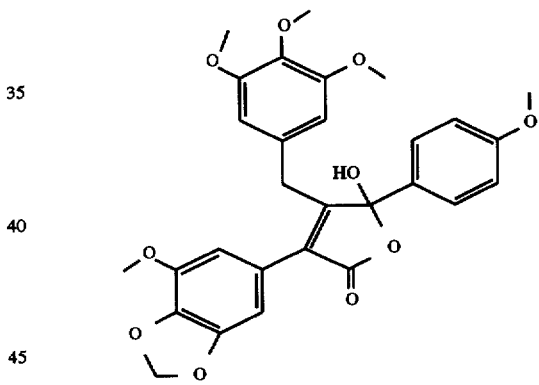

5-Hydroxy-3-(7-methoxy-benzo[1,3]dioxol-5-yl)-5-(4-methoxy-phenyl)-4-(3,4,5-trimethoxy-benzyl)-5 H-furan-2-one To methanol (10 mL) was added sodium metal (97 g, 4.2 mmol) and stirred to dissolve. To this was added the ester, 300, (1.48 g, 4.0 mmol) then 3,4,5-trimethoxybenzaldehyde (800 mg, 4.1 mmol). The mixture was heated to reflux for 18 hours. The solution was then treated with acetic acid (4 mL) and refluxed an additional 72 hours. The solvents were removed by evaporation, and the residue was partitioned between ethyl acetate (75 mL) and water (75 mL). The organic phase was separated and dried over magnesium sulfate and evaporated to dryness. The crude product was then purified by flash chromatography (150 g silica gel, 20% ethyl acetate:methylene chloride). The crude butenolide was isolated by evaporation of the appropriate fractions to give a foam. The foam was partitioned between ether (120 mL) and 1N sodium hydroxide (40 mL). The aqueous phase separated and acidified. The acid solution was extracted with ethyl acetate (2×50 mL). The organic phases combined, washed with brine, dried over magnesium sulfate, and evaporated in vacuo to give 610 mg (28%) as a yellow foam. The butenolide was identified by ¹H NMR, IR, MS, [M+H]⁺=537 Da., and microanalysis.

EXAMPLE 357

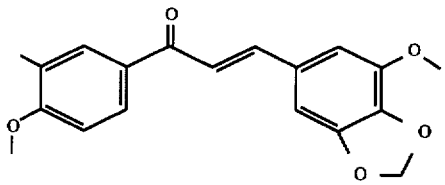

To 3-methyl-4-methoxyacetophenone (34.4 g, 210 mmol) in absolute ethanol (120 mL) in an erlenmeyer was added 3-methoxypiperonal (38.6 g, 214 mmol). The solution swirled while 10% sodium hydroxide (12 mL) added. The mixture swirled for 10 minutes and allowed to stand to precipitate. The solid was collected by filtration and washed with 80% ethanol (3×300 mL). The solid was dried in vacuo giving 45 g (65%) of an off-white solid which was identified by ¹H NMR, IR, MS, and microanalysis.

EXAMPLE 358

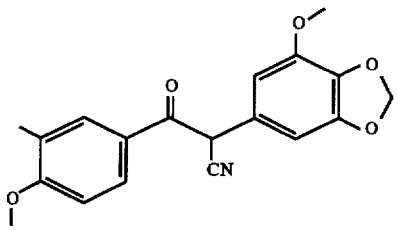

To the chalcone, 357, (32.6 g, 100 mmol) in 2-ethoxyethanol (150 mL) at 55° C. was added acetic acid (7.21 g) followed by slow addition of potassium cyanide (9.8 g, 150 mmol) in water (30 mL). The solution was stirred at 105° C. for 18 hours. The solution was cooled then filtered to collect the solid. The solid was washed repeatedly with 10% water:ethoxyethanol (2×150 mL), air dried, and then dried in vacuo to give the nitrile 29.5 g (84%) as a solid. The nitrile was identified by ¹H NMR, IR, MS, and microanalysis.

EXAMPLE 359

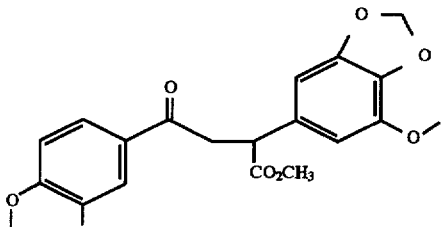

To the nitrile, 358, (23.6 g, 66.8 mmol) was added methanol (150 mL) and dioxane (75 mL), p-toluene-sulfonic acid hydrate (12.7 g, 66.8 mmol). The mixture warmed to reflux and stirred 24 hours. The mixture cooled to room temperature and evaporated to dryness. The residue dissolved in ether (250 mL) and washed successively with water (200 mL), saturated sodium bicarbonate (150 mL), and brine (150 mL). The ethereal solution treated with charcoal, dried, and evaporated to give 20.9 g (81%) of the ester which was identified by ¹H NMR, MS, [M+H]⁺=387 Da.

EXAMPLE 360

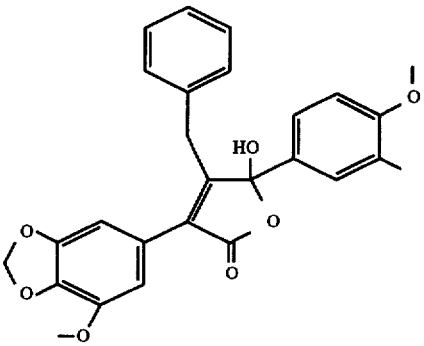

4-Benzyl-5-hydroxy-3-(7-methoxy-benzo[1,3]dioxol-5-yl)-5-(4-methoxy-3-methyl-phenyl)-5H-furan-2-one To methanol (10 mL) was added sodium metal (97 mg, 4.2 mmol) and stirred to dissolve. To this was added the ester, 359, (1.55 g, 4.0 mmol) then benzaldehyde (414 mg, 4.0 mmol). The mixture was heated to reflux for 48 hours. The solution was then treated with acetic acid (2 mL) and refluxed an additional 24 hours. The solvents were removed by evaporation, and the residue was partitioned between ethyl acetate (75 mL) and water (75 mL). The organic phase was separated and dried over magnesium sulfate and evaporated to dryness. The crude product was then purified by flash chromatography (150 g silica gel, 10% ethyl acetate::methylene chloride). The butenolide was isolated by evaporation of the appropriate fractions to give an oil. The oil was partitioned between ether (100 mL) and 1N sodium hydroxide (25 mL). The aqueous phase acidified with 6N HCl and extracted with ethyl acetate (2×25 mL). The combined ethyl acetate layers dried over magnesium sulfate and evaporated in vacuo to give 520 mg (28%) as a foam. The butenolide was identified by ¹H NMR, IR, MS, [M+H]⁺=461 Da., and microanalysis.

EXAMPLE 361

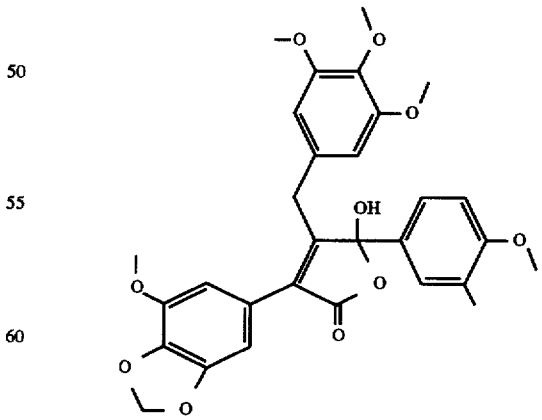

5-Hydroxy-3-(7-methoxy-benzo[1,3]dioxol-5-yl)-5-(4-methoxy-3-methyl-phenyl)-4-(3,4,5-trimethoxy-benzyl)-5 H-furan-2-one To methanol (10 mL) was added sodium metal (97 mg, 4.2 mmol) and stirred to dissolve. To this was added the ester, 359, (1.55 g, 4.0 mmol) then 3,4,5-trimethoxybenzaldehyde (800 mg, 4.1 mmol). The mixture was heated to reflux for 18 hours. The solution was then treated with acetic acid (4 mL) and refluxed an additional 24 hours. The solvents were removed by evaporation, and the residue was partitioned between ethyl acetate (100 mL) and water (100 mL). The organic phase was separated and dried over magnesium sulfate and evaporated to dryness. The solvents were evaporated and the residue dissolved in ether (150 mL). This was extracted into 1N sodium hydroxide (70 mL). The aqueous phase separated, acidified, and extracted with ethyl acetate (2×75 mL). The solvents were evaporated in vacuo to give an oil. The crude product was then purified by flash chromatography (150 g silica gel, 20% ethyl acetate:methylene chloride). The butenolide was isolated by evaporation of the appropriate fractions to give 279 mg (13%) as a white foam. The butenolide was identified by $^1$H NMR, IR, MS, [M+H]$^+$=551 Da., and microanalysis.

EXAMPLE 362

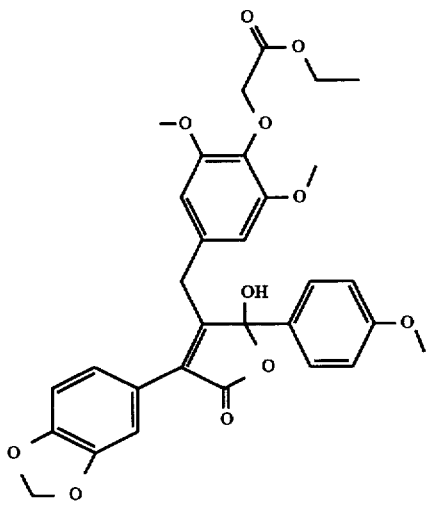

{4-[4-Benzo[1,3]dioxol-5-yl-2-hydroxy-2-(4-methoxyphenyl)-5-oxo-2,5-dihydro-furan-3-ylmethyl]-2,6-dimethoxy-phenoxy}-acetic acid ethyl ester To ethanol (10 mL) was added sodium metal (97 mg, 4.2 mmol) and stirred to dissolve. To this was added the ester, 19, (1.37 g, 4.0 mmol) then 4-(ethylacetoxy)-3,5-dimethoxybenzaldehyde (1.10 g, 4.1 mmol). The mixture was heated to reflux for 18 hours. The solution was then treated with acetic acid (4 mL) and refluxed an additional 24 hours. The solvents were removed by evaporation, and the residue was partitioned between ethyl acetate (100 mL) and water (100 mL). The organic phase was separated and dried over magnesium sulfate and evaporated to dryness. The crude product was then purified by flash chromatography (200 g silica gel, 20% ethyl acetate:methylene chloride). The butenolide was isolated by evaporation of the appropriate fractions to give 356 mg (15%) as a thick oil. The butenolide was identified by $^1$H NMR, IR, MS, [M+H]$^+$=579 Da., and microanalysis.

EXAMPLE 363

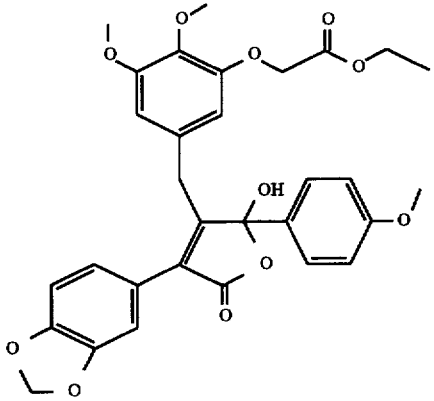

{5-[4-Benzo[1,3]dioxol-5-yl-2-hydroxy-2-(4-methoxyphenyl)-5-oxo-2,5-dihydro-furan-3-ylmethyl]-2,3-dimethoxy-phenoxy}-acetic acid ethyl ester To ethanol (10 mL) was added sodium metal (97 mg, 4.2 mmol) and stirred to dissolve. To this was added the ester, 19, (1.37 g, 4.0 mmol) then 3-(ethylacetoxy)-4,5-dimethoxybenzaldehyde (1.10 g, 4.1 mmol). The mixture was heated to reflux for 18 hours. The solution was then treated with acetic acid (3 mL) and refluxed an additional 24 hours. The solvents were removed by evaporation, and the residue was partitioned between ethyl acetate (75 mL) and water (75 mL). The organic phase was separated and dried over magnesium sulfate and evaporated to dryness. The crude product was then purified by flash chromatography (150 g silica gel, 20% ethyl acetate:methylene chloride). The butenolide was isolated by evaporation of the appropriate fractions to give 410 mg (18%) as an oil. The butenolide was identified by $^1$H NMR, IR, MS, [M+H]$^+$=579 Da., and microanalysis.

EXAMPLE 364

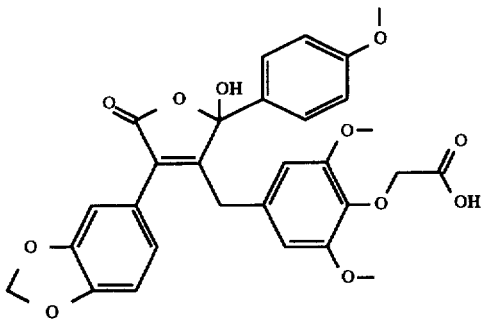

{4-Benzo[1,3]dioxol-5-yl-2-hydroxy-2-(4-methoxyphenyl)-5-oxo-2,5-dihydro-furan-3-ylmethyl]-2,6-dimethoxy-phenoxy}-acetic acid In methanol (5 mL) was dissolved the butenolide, 362, and the solution treated with 1.010N sodium hydroxide (aqueous) 467 µL (0.471 mmol). The mixture stirred 24 hours at room temperature and 24 hours at reflux. The mixture cooled to room temperature and evaporated to a paste. The paste partitioned between ethyl acetate (50 mL) and water (20 mL). The aqueous phase acidified and extracted with fresh ethyl acetate. This ethyl acetate layer washed with brine and dried over magnesium sulfate. The solvents were evaporated in vacuo to give the butenolide 97 mg (37%) as a foam. The compound was identified by $^1$H NMR, IR, MS, [M+H]$^+$=551 Da., and microanalysis.

EXAMPLE 365

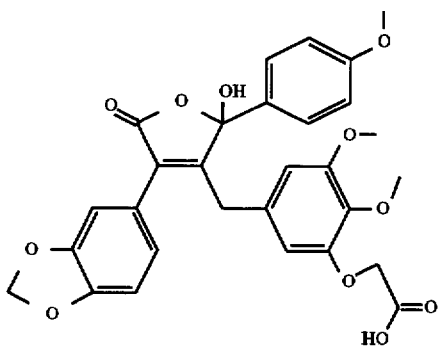

{5-[4-Benzo[1,3]dioxol-5-yl-2-hydroxy-2-(4-methoxyphenyl)-5-oxo-2,5-dihydro-furan-3-ylmethyl]-2,3-dimethoxy-phenoxy}-acetic acid In methanol (15 mL) was dissolved the butenolide, 363, and the solution treated with 1.010N sodium hydroxide 1.13 mL (1.14 mmol), and the solution warmed to reflux for 24 hours. The mixture cooled to room temperature and evaporated free of methanol. The residue partitioned between water (50 mL) and ether (50 mL). The aqueous phase separated and washed with ether (50 mL) and ethyl acetate (50 mL). The aqueous phase was made acidic and extracted with fresh ethyl acetate (2×30 mL). The combined final extraction phases evaporated in vacuo to give an oil, 295 mg (94%). The butenolide was identified by $^1$H NMR, IR, MS, [M+H]$^+$=551 Da., and microanalysis.

EXAMPLE 366

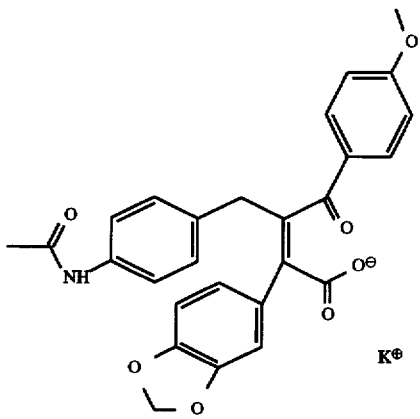

Potassium 3-(4-Acetylamino-benzyl)-2-benzo[1,3]dioxol-5-yl-4-(4-methoxy-phenyl)-4-oxo-but-2-enoate The butenolide, 80, (917 mg, 1.94 mmol) was dissolved in methanol (25 mL) and treated with 1.018N potassium hydroxide (in methanol), (1.86 mL, 1.9 mmol). The solution was stirred for 5 minutes and evaporated free of methanol. The residue was partitioned between ether (100 mL) and distilled water (100 mL). The aqueous solution was separated, evaporated free of residual organic solvents, frozen, and lyophilized. This gave the butenolide salt 0.86 g (88%), which was identified by $^1$H NMR, IR, MS, [M+H]$^+$=472 Da., and microanalysis.

EXAMPLE 367

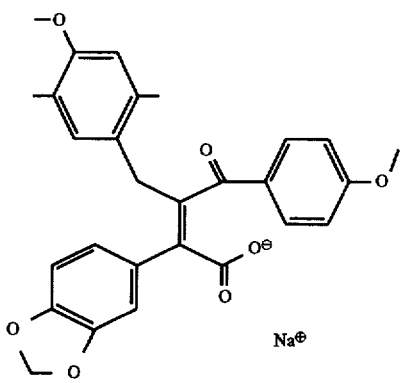

Sodium 2-Benzo[1,3]dioxol-5-yl-3-(4-methoxy-benzoyl)-4-(4-methoxy-2,5-dimethyl-phenyl)-but-2-enoate The butenolide, 251, (2.66 g, 5.60 mmol) was dissolved in methanol (100 mL) and treated with 1.010N sodium hydroxide (aqueous), 5.26 mL (5.32 mmol). The solution was stirred for 5 minutes and evaporated free of methanol. The residue was partitioned between ether (200 mL) and distilled water (200 mL). The aqueous solution was separated, evaporated free of residual organic solvents, frozen, and lyophilized. This gave the butenolide salt 2.19 g (83%), which was identified by $^1$H NMR, IR, MS, [M+H]$^+$=473 Da., and microanalysis.

EXAMPLE 368

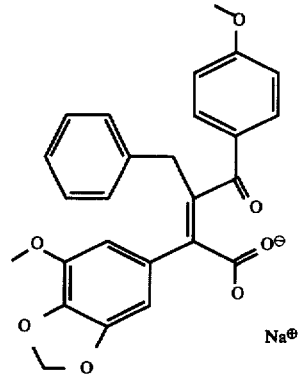

Sodium 3-Benzyl-2-(7-methoxy-benzo[1,3]dioxol-5-yl)-4-(4-methoxy-phenyl)-4-oxo-but-2-enoate The butenolide, 301, (1.066 g, 2.39 mmol) was dissolved in methanol (25 mL) and treated with 1.010N sodium hydroxide (aqueous), 2.20 mL (2.27 mmol). The solution was stirred for 10 minutes and evaporated free of methanol. The residue was partitioned between ether (100 mL) and distilled water (100 mL). The aqueous solution was separated, evaporated free of residual organic solvents, frozen, and lyophilized. This gave the butenolide salt 1.08 g (100%), which was identified by $^1$H NMR, IR, MS, [M+H]$^+$=445 Da., and microanalysis.

EXAMPLE 369

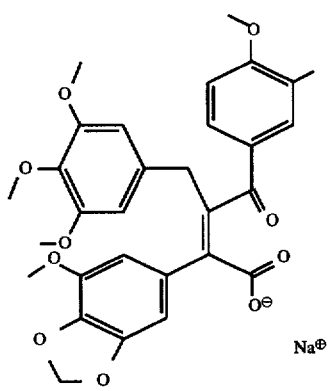

Sodium 2-(7-Methoxy-benzo[1,3]dioxol-5-yl)-3-(4-methoxy-3-methyl-benzoyl)-4-(3,4,5-trimethoxyphenyl)-but-2-enoate The butenolide, 361, (3.0 g, 5.44 mmol) was dissolved in methanol (60 mL) and treated with 1.010N sodium hydroxide (aqueous), 5.12 mL (5.17 mmol). The solution was stirred for 5 minutes and evaporated free of methanol. The residue was partitioned between ether (200 mL) and distilled water (120 mL). The aqueous solution was separated, evaporated free of residual organic solvents, frozen, and lyophilized. This gave the butenolide salt 2.91 g (98%), which was identified by $^1$H NMR, IR, MS, [M+H]$^+$=549 Da., and microanalysis.

EXAMPLE 370

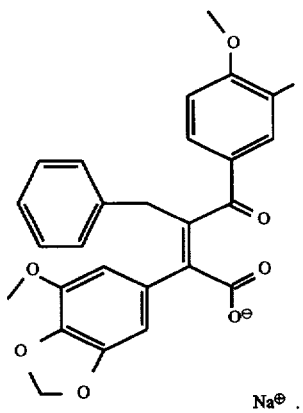

Sodium 3-Benzyl-2-(7-methoxy-benzo[1,3]dioxol-5-yl)-4-(4-methoxy-3-methyl-phenyl)-4-oxo-but-2-enoate The butenolide, 360, (3.2 g, 6.95 mmol) was dissolved in methanol (60 mL) and treated with 1.010N sodium hydroxide (aqueous), 6.5 mL (6.6 mmol). The solution was stirred for 2 minutes and evaporated free of methanol. The residue was partitioned between ether (150 mL) and distilled water (150 mL). The aqueous solution was separated, evaporated free of residual organic solvents, frozen, and lyophilized. This gave the butenolide salt 1.23 g (38%), which was identified by $^1$H NMR, IR, MS, [M+H]$^+$=459 Da., and microanalysis.

EXAMPLE 371

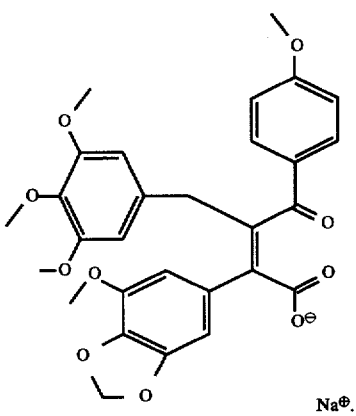

Sodium 2-(7-Methoxy-benzo[1,3]dioxol-5-yl-4-(4-methoxyphenyl)-4-oxo-3-(3,4,5-trimethoxy-benzyl)-but-2-enoate The butenolide, 356, (3.35 g, 6.2 mmol) was dissolved in methanol (60 mL) and treated with 1.010N sodium hydroxide (aqueous), 5.87 mL (5.93 mmol). The solution was stirred for 3 minutes and evaporated free of methanol. The residue was partitioned between ether (200 mL) and distilled water (150 mL). The aqueous solution was separated, evaporated free of residual organic solvents, frozen, and lyophilized. This gave the butenolide salt 3.1 g (94%) which was identified by $^1$H NMR, IR, MS, [M+H]$^+$=535 Da., and microanalysis.

EXAMPLE 372

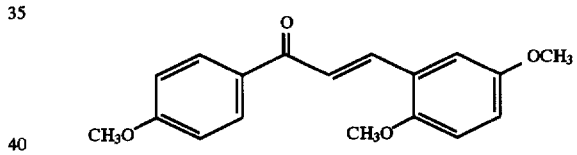

To 4-methoxyacetophenone (4.6 g, 30 mmol) in absolute ethanol (25 mL) in an erlenmeyer was added 2,5-dimethoxybenzaldehyde (6.84 g, 41.60 mmol). The solution swirled while 10% sodium hydroxide (2 mL) added. The mixture stirred 1 hour (no precipitate). EtOH evaporated, residue dissolved in EtOAc (200 mL), and washed with H$_2$O (2×100 mL) and brine (100 mL), then dried (MgSO$_4$) and stripped to 11.1 g crude yellow oil. Chromatographed (100% CH$_2$Cl$_2$). Evaporation of appropriate fractions gave 6.5 g (73%) of a tan glass which was identified by $^1$H NMR, MS, and microanalysis.

EXAMPLE 373

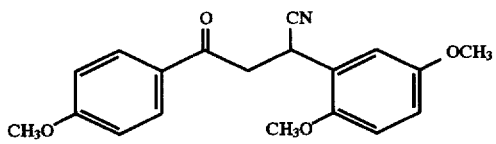

To the chalcone, 372, (6.5 g, 21.79 mmol) in absolute ethanol (120 mL) at 55° C. was added acetic acid (2.8 mL) followed by slow addition of potassium cyanide (3.55 g, 54.48 mmol) in water (25 mL). The solution was stirred at reflux ≈80° C. for 24 hours. The solution was cooled and treated with water (150 mL). The mixture was then decanted and the oily solid dissolved in 150 mL EtOAc and washed with brine (100 mL); then dried (MgSO₄) and evaporated to 6.02 g dark oily solid. Recrystallization from EtOAc:hexane to give the nitrile 2.78 g (39%) as a light green solid. The nitrile was identified by ¹H NMR and MS.

EXAMPLE 374

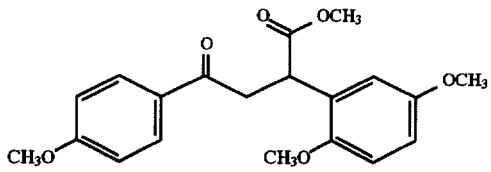

To the nitrile, 373, (2.78 g, 8.55 mmol) was added methanol (50 mL). The mixture was saturated with HCl (g) and heated to reflux until no nitrile remained, by thin layer chromatography. The solution was cooled and treated with water (50 mL). Solution decanted away from the oily dark precipitate. Precipitate dissolved in 200 mL EtOAc and washed with H₂O (2×100 mL) and brine (100 mL), then dried and evaporated to the ester 2.75 g (90%) as a green oil which was identified by ¹H NMR and MS.

EXAMPLE 375

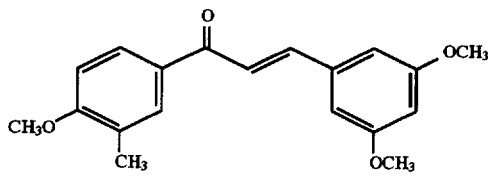

To 3-methyl-4-methoxyacetophenone (25.0 g, 152.24 mmol) in absolute ethanol (110 mL) in an erlenmeyer was added 3,5-dimethoxybenzaldehyde (35.42 g, 208.88 mmol). The solution swirled while 10% sodium hydroxide (11 mL) added. The mixture stirred 1 hour and allowed to stand to precipitate. The solid was collected by filtration and washed with ethanol (3×200 mL). The solid was dried in vacuo giving 37.12 g (78%) of an off-white solid which was identified by ¹H NMR, MS, and microanalysis.

EXAMPLE 376

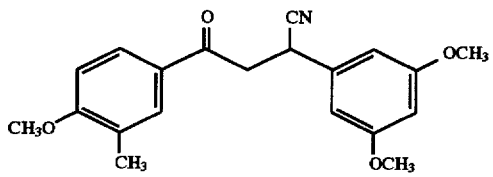

To the chalcone, 375, (37.1 g, 119 mmol) in absolute ethanol (575 mL) at 55° C. was added acetic acid (15.5 mL) followed by slow addition of potassium cyanide (19.34 g, 297 mmol) in water (80 mL). The solution was stirred at reflux ≈80° C. for 24 hours. The solution was cooled and treated with water (225 mL). The mixture was then decanted and the oily solid taken up in EtOAc (600 mL). EtOAc washed with brine and dried (MgSO₄) and evaporated to give the nitrile 31.53 g (78%) as an oily solid. The nitrile was identified by ¹H NMR, MS, and microanalysis.

EXAMPLE 377

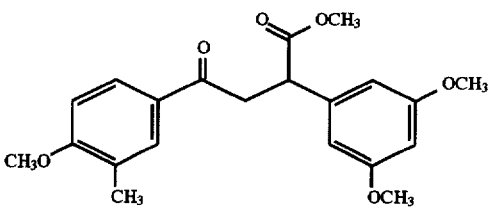

To the nitrile, 376, (31.53 g, 92.91 mmol) was added methanol (275 mL). The mixture was saturated with HCl (g) and heated to reflux until no nitrile remained, by thin layer chromatography. The solution was cooled and treated with water (200 mL). The resultant oily solid was decanted away and dissolved in 400 mL EtOAc, then washed with H₂O (2×150 mL) and brine (2×100 mL). EtOAc layer dried (MgSO₄) and evaporated to the ester. This gave the ester 29.15 g (84%) as a dark oily solid which was identified by ¹H NMR, MS, and microanalysis.

EXAMPLE 378

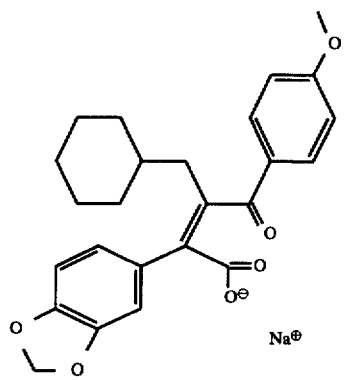

Sodium 2-Benzo[1,3]dioxol-5-yl-3-cyclohexylmethyl-4-(4-methoxy-phenyl)-4-oxo-but-2-enoate To methanol (50 mL) was added the pure butenolide, 221, (1.58 g, 3.74 mmol). Added to this 3.55 mL of a 1.010N NaOH solution (3.59 mmol). Stirred solution 10 minutes, then filtered away small amount of insolubles through glass wool. Evaporated MeOH and residue taken up in distilled water (250 mL). Washed aqueous solution with ethyl ether (100 mL). The aqueous solution was concentrated to remove any ether present, then frozen in a −80° C. bath. The frozen material was lyophilized to 1.33 g (80%) of a fluffy white solid. The butenolide salt was identified by ¹H NMR, MS, [M+H]⁺=422 Da., and microanalysis; including water and Na analysis.

191
EXAMPLE 379

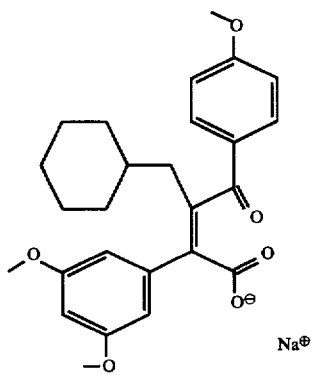

Sodium 3-cyclohexylmethyl-2-(3,5-dimethoxy-phenyl)-4-(4-methoxy-phenyl)-4-oxo-but-2-enoate To methanol (50 mL) was added the pure butenolide, 275, (1.67 g, 3.81 mmol), becoming a slurry. Added to this 3.62 mL of a 1.010N NaOH solution (3.66 mmol), and all dissolved. Stirred solution 10 minutes, then filtered away small amount of insolubles through glass wool. Evaporated MeOH and residue taken up in distilled water (250 mL). Washed aqueous solution with ethyl ether (125 mL). The aqueous solution was concentrated to remove any ether present, then frozen in a −80° C. bath. The frozen material was lyophilized to 1.25 g (71.4%) of a tan fluffy solid. The butenolide salt was identified by $^1$H NMR, MS, [M+H]$^+$= 438 Da., and microanalysis; including water and Na analysis.

EXAMPLE 380

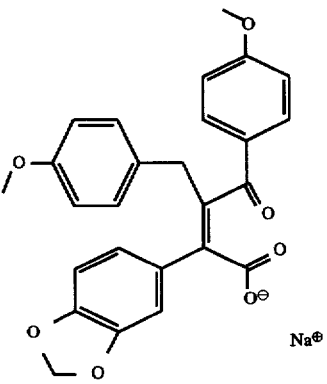

Sodium2-Benzo[1,3]dioxol-5-yl-3-(4-methoxy-benzyl)-4-(4-methoxy-phenyl)-4-oxo-but-2-enoate To methanol (215 mL) was added the pure butenolide, 77, (7.54 g, 16.89 mmol), becoming a slurry. Added to this 15.89 mL of a 1.010N NaOH solution (16.045 mequiv of OH⁻), and all dissolved. Stirred solution 10 minutes, then filtered away small amount of insolubles through glass wool. Evaporated MeOH and residue taken up in distilled water (350 mL). Washed aqueous solution with ethyl ether (150 mL). The aqueous solution was concentrated to remove any ether present, then frozen in a −80° C. bath. The frozen material was lyophilized to 7.05 g (89%) of a white fluffy solid. The butenolide salt was identified by $^1$H NMR, MS, [M+H]$^+$=446 Da., and microanalysis; including water and Na analysis.

192
EXAMPLE 381

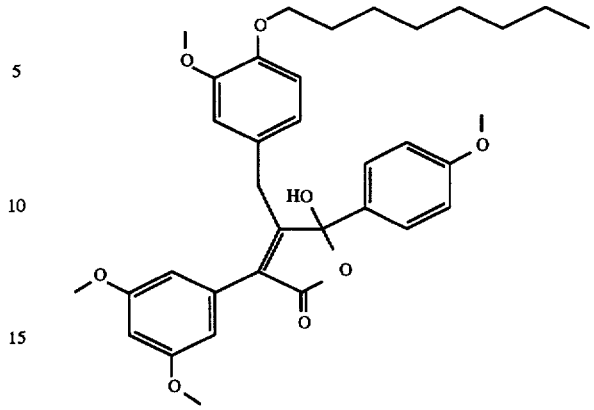

3-(3,5-Dimethoxy-phenyl)-5-hydroxy-4-(3-methoxy-4-octyloxy-benzyl)-5-(4-methoxy-phenyl)-5H-furan-2-one To methanol (20 mL) was added sodium metal (88 mg, 3.81 mmol) and stirred to dissolve. To this was added the ester, 124, (1.30 g, 3.63 mmol) then 3-methoxy-4-O-octylbenzaldehyde (1.06 g, 3.99 mmol). The mixture was heated to reflux for 24 hours. The solution was then treated with acetic acid (4 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by flash chromatography (silica gel, 10% EtOAc:CH$_2$Cl$_2$). The butenolide was isolated by evaporation of the appropriate fractions to give 323 mg (15.1%) as an orange oil. The butenolide was identified by $^1$H NMR, MS, [M+H]$^+$=591 Da., and microanalysis.

EXAMPLE 382

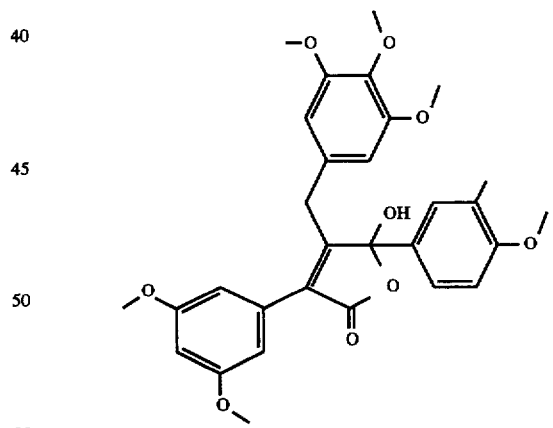

3-(3,5-Dimethoxy-phenyl)-5-hydroxy-5-(4-methoxy-3-methyl-phenyl)-4-(3,4,5-trimethoxy-benzyl)-5H-furan-2-one To methanol (20 mL) was added sodium metal (97 mg, 4.2 mmol) and stirred to dissolve. To this was added the ester, 977, (1.49 g, 4.0 mmol) then 3,4,5-trimethoxybenzaldehyde (881 mg, 4.4 mmol). The mixture was heated to reflux for 24 hours. The solution was then treated with acetic acid (4 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by flash chromatography (silica gel, 15% EtOAc:CH$_2$Cl$_2$). The butenolide was isolated by evaporation of the appropriate fractions to give 720 mg (33.5%) as a tan solid. The butenolide was identified by $^1$H NMR, MS, [M+H]$^+$=537 Da., and microanalysis.

EXAMPLE 383

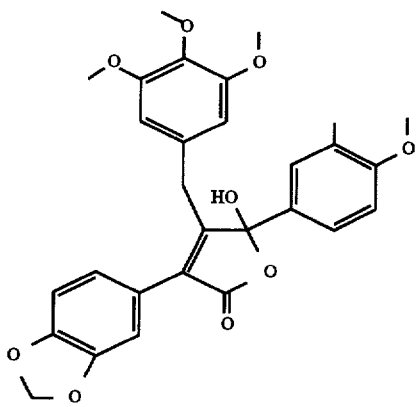

3-Benzo[1,3]dioxol-5-yl-5-hydroxy-5-(4-methoxy-3-methyl-phenyl)-4-(3,4,5-trimethoxy-benzyl)-5 H-furan-2-one To methanol (14 mL) was added sodium metal (97 mg, 4.2 mmol) and stirred to dissolve. To this was added the ester, 289, (1.43 g, 4.0 mmol) then 3,4,5-trimethoxybenzaldehyde (881 mg, 4.4 mmol). The mixture was heated to reflux for 24 hours. The solution was then treated with acetic acid (4 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then slurried in 100 mL 10% EtOAc:CH$_2$Cl$_2$ and filtered to give 1.31 g (63%) as an off-white solid. The butenolide was identified by $^1$H NMR, MS, [M+H]$^+$=521 Da., and microanalysis.

EXAMPLE 384

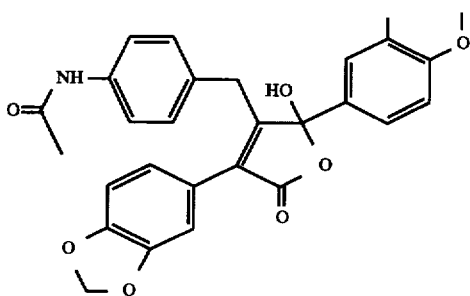

N-{4-[4-Benzo[1,3]dioxol-5-yl-2-hydroxy-2-(4-methoxy-3-methyl-phenyl)-5-oxo-2,5-dihydro-furan-3-ylmethyl]-phenyl}-acetamide To methanol (22 mL) was added sodium metal (148 mg, 6.42 mmol) and stirred to dissolve. To this was added the ester, 289, (2.18 g, 6.12 mmol) then 4-acetamidobenzaldehyde (1.15 g, 7.04 mmol). The mixture was heated to reflux for 24 hours. The solution was then treated with acetic acid (5 mL) and refluxed an additional 24 hours. The solvents were removed by evaporation, and the residue was partitioned between ethyl acetate (150 mL) and 1N sodium hydroxide (40 mL). The aqueous phase was separated and acidified with 6N HCl. This acidic solution was extracted with 100 mL EtOAc. The organic phase was separated, washed with brine, dried over magnesium sulfate, and evaporated in vacuo. Chromatographed crude; 10% EtOAc/CH$_2$Cl$_2$. Combined and evaporated appropriate fractions. This gave the butenolide 2.05 g (70%) as a yellow solid. The butenolide was identified by $^1$H NMR, MS, [M+H]$^+$=488 Da., and microanalysis.

EXAMPLE 385

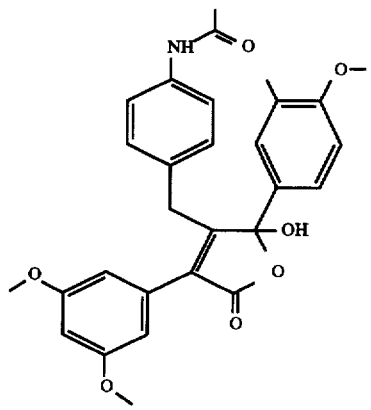

N-{4-[4-(3,5-Dimethoxy-phenyl)-2-hydroxy-2-(4-methoxy-3-methyl-phenyl)-5-oxo-2,5-dihydro-furan-3-ylmethyl]-phenyl}-acetamide To methanol (21 mL) was added sodium metal (97 mg, 4.2 mmol) and stirred to dissolve. To this was added the ester, 777, (1.49 g, 4.0 mmol) then 4-acetamidobenzaldehyde (719 mg, 4.4 mmol). The mixture was heated to reflux for 24 hours. The solution was then treated with acetic acid (4 mL) and refluxed an additional 24 hours. The solvents were removed by evaporation, and the residue was partitioned between EtOAc (200 mL) and 1N sodium hydroxide (100 mL). The aqueous phase was separated and acidified with 6N HCl. This acidic solution was extracted with 3×100 mL ethyl acetate. The organic phase was separated, washed with brine, dried over magnesium sulfate, and evaporated in vacuo. Chromatographed crude; 30% EtOAc/CH$_2$Cl$_2$. Combined and stripped appropriate fractions. This gave the butenolide 561 mg (27.9%) as a tan foam. The butenolide was identified by $^1$H NMR, MS, [M+H]$^+$=504 Da., and microanalysis.

EXAMPLE 386

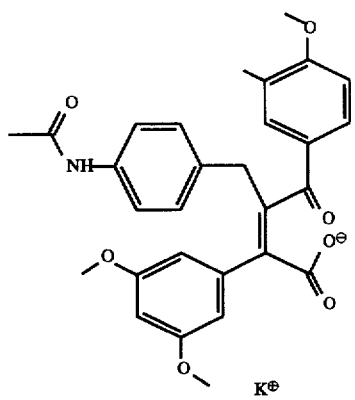

Potassium 3-(4-Acetylamino-benzyl)-2-(3,5-dimethoxyphenyl)-4-(4-methoxy-3-methyl-phenyl)-4-oxo-but-2-enoate To methanol (80 mL) was added the pure butenolide, 385, (3.26 g, 6.474 mmol), becoming a slurry. Added to this 5.76 mL of a 1.018N KOH solution (5.66 mmol), and all dissolved. Stirred solution 10 minutes, then filtered away small amount of insolubles through glass wool. Evaporated MeOH and residue taken up in distilled water (100 mL). Washed aqueous solution with ethyl ether (100 mL). The aqueous solution was concentrated to remove any ether present, then frozen in a −80° C. bath. The frozen material was lyophilized to 2.93 g (93.9%) of a white fluffy powder. The butenolide salt was identified by $^1$H NMR, MS, [M+H]$^+$= 503 Da., and microanalysis; including water and K analysis.

EXAMPLE 387

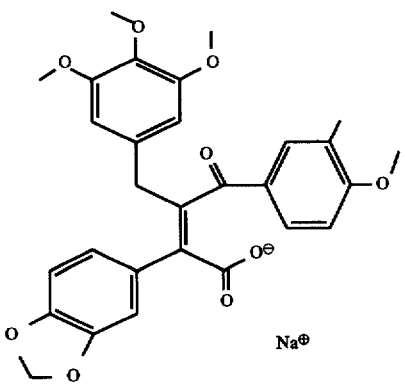

Sodium 2-Benzo[1,3]dioxol-5-yl-4-(4-methoxy-3-methylphenyl)-4-oxo-3-(3,4,5-trimethoxy-benzyl)-but-2-enoate To methanol (110 mL) was added the pure butenolide, 383, (3.45 g, 6.63 mmol), becoming a slurry. Added to this 6.23 mL of a 1.010N NaOH solution (6.30 mmol), and all dissolved. Stirred solution 10 minutes, then filtered away small amount of insolubles through glass wool. Evaporated MeOH and residue taken up in distilled water (120 mL). Washed aqueous solution with ethyl ether (120 mL). The aqueous solution was concentrated to remove any ether present, then frozen in a −80° C. bath. The frozen material was lyophilized to 3.09 g (85.8%) of a white fluffy solid. The butenolide salt was identified by $^1$H NMR, MS, [M+H]$^+$= 520 Da., and microanalysis; including water and Na analysis.

EXAMPLE 388

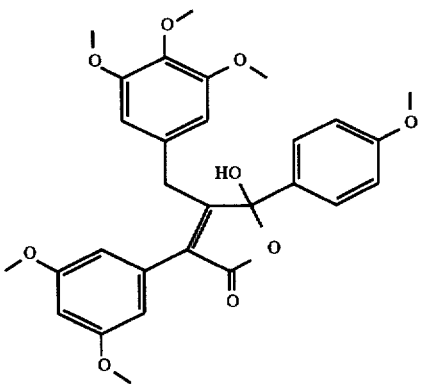

3-(3,5-Dimethoxy-phenyl)-5-hydroxy-5-(4-methoxyphenyl)-4-(3,4,5-trimethoxy-benzyl)-5H-furan-2-one To methanol (17 mL) was added sodium metal (97 mg, 4.2 mmol) and stirred to dissolve. To this was added the ester, 124, (1.43 g, 4.0 mmol) then 3,4,5-trimethoxybenzaldehyde (881 mg, 4.4 mmol). The mixture was heated to reflux for 24 hours. The solution was then treated with acetic acid (4 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by flash chromatography (silica gel, 15% EtOAc:CH$_2$Cl$_2$). The butenolide was isolated by evaporation of the appropriate fractions to give 687 mg (32.7%) as a tan solid. The butenolide was identified by $^1$H NMR, MS, [M+H]$^+$=523 Da., and microanalysis.

EXAMPLE 389

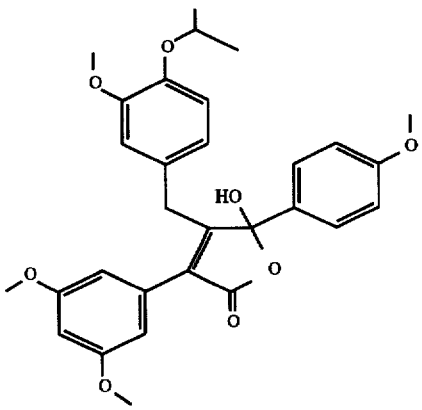

3-(3,5-Dimethoxy-phenyl)-5-hydroxy-4-(4-isopropoxy-3-methoxy-benzyl)-5-(4-methoxy-phenyl)-5H-furan-2-one To methanol (17 mL) was added sodium metal (97 mg, 4.2 mmol) and stirred to dissolve. To this was added the ester, 124, (1.43 g, 4.0 mmol) then 3-methoxy-4-O-iPr-benzaldehyde (855 mg, 4.4 mmol). The mixture was heated to reflux for 24 hours. The solution was then treated with acetic acid (4 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by flash chromatography (silica gel, 20% EtOAc:CH₂Cl₂). The butenolide was isolated by evaporation of the appropriate fractions to give 527 mg (25.1%) as a tan foam. The butenolide was identified by ¹H NMR, MS, [M+H]⁺=521 Da., and microanalysis.

EXAMPLE 390

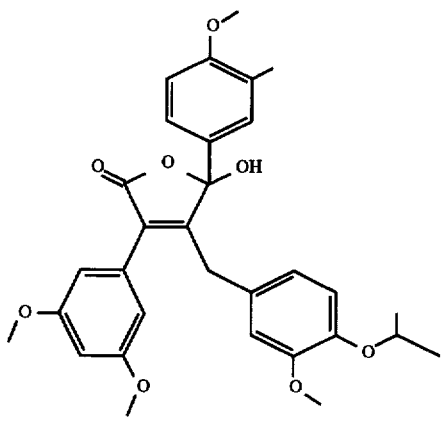

3-(3,5-Dimethoxy-phenyl)-5-hydroxy-4-(4-isopropoxy-3-methoxy-benzyl)-5-(4-methoxy-3-methyl-phenyl)-5H-furan-2-one To methanol (17 mL) was added sodium metal (97 mg, 4.2 mmol) and stirred to dissolve. To this was added the ester, 377, (1.49 g, 4.0 mmol) then 3-methoxy-4-O-isopropylbenzaldehyde (855 mg, 4.4 mmol). The mixture was heated to reflux for 48 hours. The solution was then treated with acetic acid (4 mL) and refluxed an additional 72 hours. The solvents were removed by evaporation, and the residue was partitioned between ethyl acetate (150 mL) and water (100 mL). The organic phase was separated and dried over magnesium sulfate and evaporated to dryness. The crude product was then purified by flash chromatography (silica gel, 10% EtOAc:CH₂Cl₂). The butenolide was isolated by evaporation of the appropriate fractions to give 540 mg (25.2%) as a tan foam. The butenolide was identified by ¹H NMR, MS, [M+H]⁺=535 Da., and microanalysis.

EXAMPLE 391

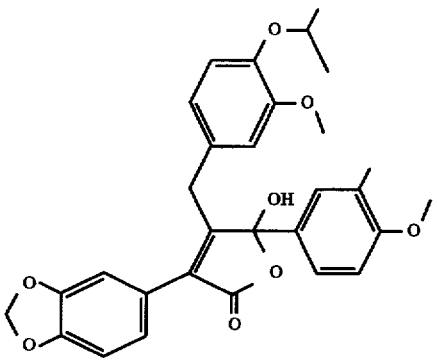

3-Benzo[1,3]dioxol-5-yl-5-hydroxy-4-(4-isopropoxy-3-methoxy-benzyl)-5-(4-methoxy-3-methyl-phenyl)-5 H-furan-2-one To methanol (23 mL) was added sodium metal (97 mg, 4.2 mmol) and stirred to dissolve. To this was added the ester, 289, (1.43 g, 4.0 mmol) then 3-methoxy-4-O-isopropylbenzaldehyde (855 mg, 4.4 mmol). The mixture was heated to reflux for 48 hours. The solution was then treated with acetic acid (4 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 10% EtOAc:CH₂Cl₂). The butenolide was isolated by evaporation of the appropriate fractions to give 849 mg (41%) as an off-white foam. The butenolide was identified by ¹H NMR, MS, [M+H]⁺=519 Da., and microanalysis.

EXAMPLE 392

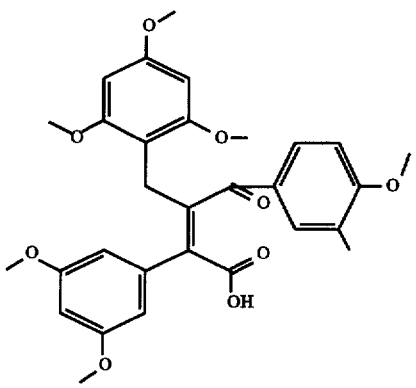

2-(3,5-Dimethoxy-phenyl)-3-(4-methoxy-3-methyl-benzoyl-carbonyl)-4-(2,4,6-trimethoxy-phenyl)-but-2-enoic acid To methanol (20 mL) was added sodium metal (97 mg, 4.0 mmol) and stirred to dissolve. To this was the added ester, 377, (1.49 g, 4.0 mmol) then 2,4,6-trimethoxybenzaldehyde (881 mg, 4.4 mmol). The mixture was heated to reflux for 72 hours. The solution was then treated with acetic acid (4 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by flash chromatography (silica gel, 50% EtOAc:CH₂Cl₂). The butenolide was isolated by evaporation of the appropriate fractions to give 240 mg tan solid. TLC showed slight impurity still present. Triturated solid in 50 mL Et₂O and filtered to give 103 mg (4.8%) as a tan solid. The butenolide was identified by ¹H NMR, MS, [M+H]⁺=537 Da., and microanalysis.

EXAMPLE 393

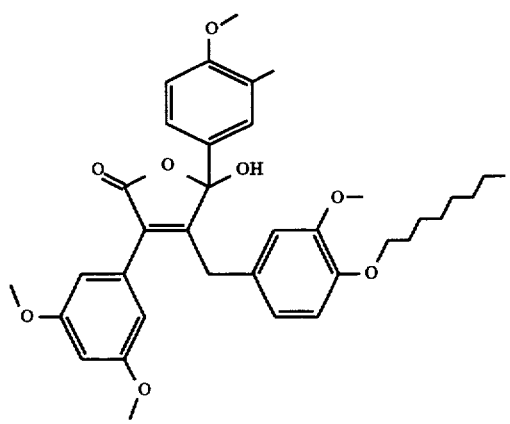

3-(3,5-Dimethoxy-phenyl)-5-hydroxy-5-(4-methoxy-3-methyl-phenyl)-4-(3-methoxy-4-octyloxy-benzyl)-5H-furan-2-one To methanol (20 mL) was added sodium metal (97 mg, 4.2 mmol) and stirred to dissolve. To this was added the ester, 377, (1.49 g, 4.0 mmol) then 3-methoxy-4-O-octylbenzaldehyde (1.16 g, 4.4 mmol). The mixture was heated to reflux for 48 hours. The solution was then treated with acetic acid (4 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 10% EtOAc:CH$_2$Cl$_2$). The butenolide was isolated by evaporation of the appropriate fractions to give 458 mg (18.9%) as an orange oil. The butenolide was identified by $^1$H NMR, MS, [M+H]$^+$=605 Da., and microanalysis.

EXAMPLE 394

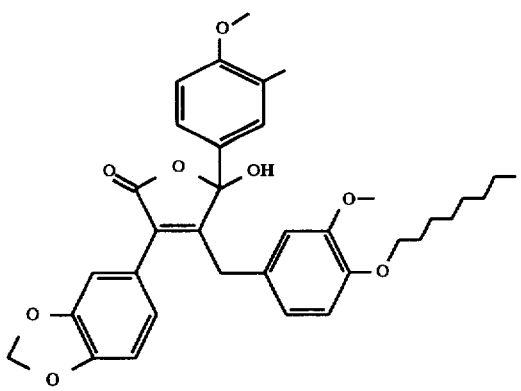

3-Benzo[1,3]dioxol-5-yl-5-hydroxy-5-(4-methoxy-3-methyl-phenyl)-4-(3-methoxy-4-octyloxy-benzyl)-5H-furan-2-one To methanol (20 mL) was added sodium metal (97 mg, 4.2 mmol) and stirred to dissolve. To this was added the ester, 289, (1.43 g, 4.0 mmol) then 3-methoxy-4-O-octylbenzaldehyde (1.16 g, 4.4 mmol). The mixture was heated to reflux for 24 hours. The solution was then treated with acetic acid (4.5 mL) and refluxed an additional 48 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 10% EtOAc:CH$_2$Cl$_2$). The butenolide was isolated by evaporation of the appropriate fractions to give 830 mg (35%) as a tan gloss. The butenolide was identified by $^1$H NMR, MS, [M+H]$^+$=589 Da., and microanalysis.

EXAMPLE 395

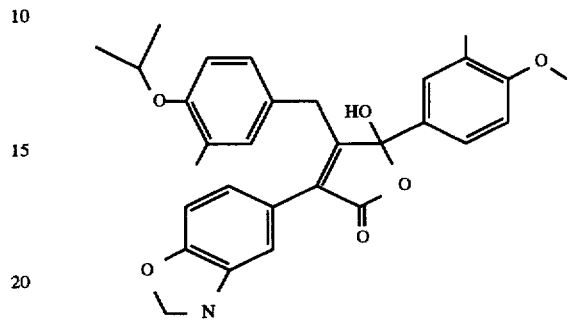

3-Benzo[1,3]dioxol-5-yl-5-hydroxy-4-(4-isopropoxy-3-methyl-benzyl)-5-(4-methoxy-3-methyl-phenyl)-5H-furan-2-one To methanol (20 mL) was added sodium metal (97 mg, 4.2 mmol) and stirred to dissolve. To this was added the ester, 289, (1.43 g, 4.0 mmol) then 3-methyl-4-O-isopropylbenzaldehyde (7.85 mg, 4.4 mmol). The mixture was heated to reflux for 48 hours. The solution was then treated with acetic acid (4 mL) and refluxed an additional 72 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 5% EtOAc:CH$_2$Cl$_2$). The butenolide was isolated by evaporation of the appropriate fractions to give 786 mg (38%) as a pale yellow glass. The butenolide was identified by $^1$H NMR, MS, [M+H]$^+$=503 Da., and microanalysis.

EXAMPLE 396

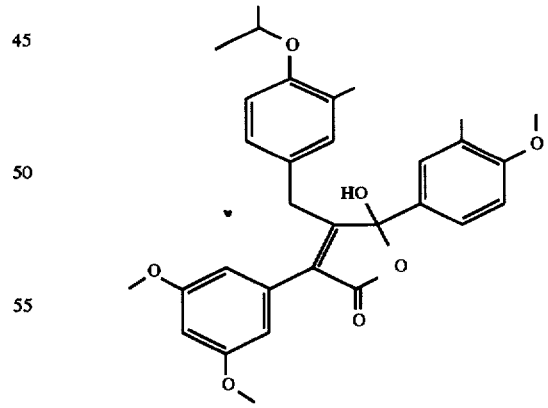

3-(3,5-Dimethoxy-phenyl)-5-hydroxy-4-(4-isopropoxy-3-methyl-benzyl)-5-(4-methoxy-3-methyl-phenyl)-5H-furan-2-one To methanol (20 mL) was added sodium metal (97 mg, 4.2 mmol) and stirred to dissolve. To this was added the ester, 377, (1.49 g, 4.0 mmol) then 3-methyl-4-O-isopropylbenzaldehyde (785 mg, 4.4 mmol). The mixture was heated to reflux for 24 hours. The solution was then treated with acetic acid (4.5 mL) and refluxed an additional 48 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 7% EtOAc:CH$_2$Cl$_2$). The butenolide was isolated by evaporation of the appropriate fractions to give 454 mg (22%) as a tan foam. The butenolide was identified by $^1$H NMR, MS, [M+H]$^+$=519 Da., and microanalysis.

EXAMPLE 397

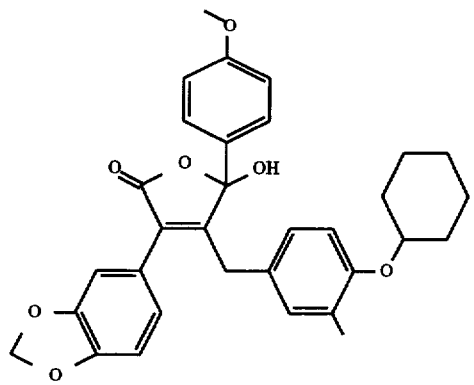

3-Benzo[1,3]dioxol-5-yl-4-(4-cyclohexyloxy-3-methylbenzyl)-5-hydroxy-5-(4-methoxy-phenyl)-5H-furan-2-one To methanol (20 mL) was added sodium metal (39.3 mg, 1.71 mmol) and stirred to dissolve. To this was added the ester, 19, (559 mg, 1.63 mmol) then 3-methyl-4-O-cyclohexylbenzaldehyde (392 mg, 1.80 mmol). The mixture was heated to reflux for 48 hours. The solution was then treated with acetic acid (4.5 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 5% EtOAc:CH$_2$Cl$_2$). The butenolide was isolated by evaporation of the appropriate fractions to give 117.8 mg (13.6%) as a pale yellow oil. The butenolide was identified by $^1$H NMR, MS, [M+H]$^+$=529 Da., and microanalysis.

EXAMPLE 398

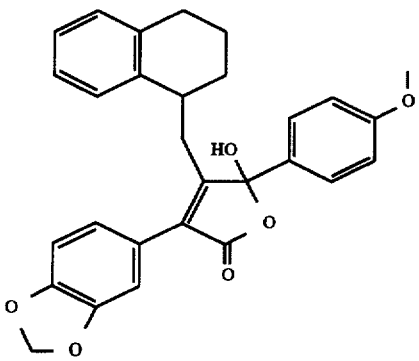

3-Benzo[1,3]dioxol-5-yl-5-hydroxy-5-(4-methoxy-phenyl)-4-(1,2,3,4-tetrahydro-naphthalen-1-ylmethyl)-5H-furan-2-one To methanol (12 mL) was added sodium metal (97 mg, 4.2 mmol) and stirred to dissolve. To this was added the ester, 19, (1.37 g, 4.0 mmol) then α-tetralinylaldehyde (715 mg, 4.4 mmol). The mixture was heated to reflux for 36 hours. The solution was then treated with acetic acid (4.5 mL) and refluxed an additional 48 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 5% EtOAc:CH$_2$Cl$_2$). The butenolide was isolated by evaporation of the appropriate fractions to give 470 mg (25%) as a white foam. The butenolide was identified by $^1$H NMR, MS, [M+H]$^+$=471 Da., and microanalysis.

EXAMPLE 399

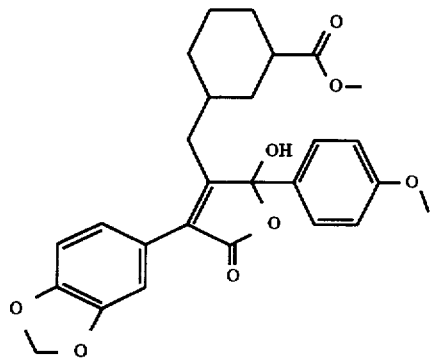

3-[4-Benzo[1,3]dioxol-5-yl-2-hydroxy-2-(4-methoxyphenyl)-5-oxo-2,5-dihydro-furan-3-ylmethyl]-cyclohexanecarboxylic acid methyl ester To methanol (20 mL) was added sodium metal (97 mg, 4.2 mmol) and stirred to dissolve. To this was added the ester, 19, (1.37 g, 4.0 mmol) then ethyl-3-formyl-cyclohexanecarboxylate (810.7 mg, 4.4 mmol). The mixture was heated to reflux for 36 hours. The solution was then treated with acetic acid (4.5 mL) and refluxed an additional 48 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 7% EtOAc:CH$_2$Cl$_2$). The butenolide was isolated by evaporation of the appropriate fractions to give 340 mg (17.2%) as a pale yellow foam. The butenolide was identified by $^1$H NMR, MS, [M+H]$^+$=481 Da., and microanalysis.

EXAMPLE 400

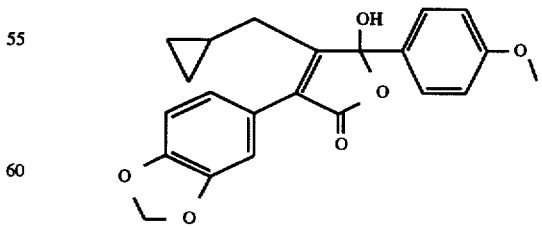

3-Benzo[1,3]dioxol-5-yl-4-cyclopropylmethyl-5-hydroxy-5-(4-methoxy-phenyl)-5H-furan-2-one To methanol (15 mL) was added sodium metal (97 mg, 4.2 mmol) and stirred to dissolve. To this was added the ester, 19, (1.37 g, 4.0 mmol) then cyclopropylcarboxaldehyde (315 mg, 4.4 mmol). The mixture was heated to reflux for 48 hours. The solution was then treated with acetic acid (4.5 mL) and refluxed an additional 48 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 7% EtOAc:CH$_2$Cl$_2$). The butenolide was isolated by evaporation of the appropriate fractions to give 163 mg (10.7%) as a white foam. The butenolide was identified by $^1$H NMR, MS, [M+H]$^+$=381 Da., and microanalysis.

EXAMPLE 401

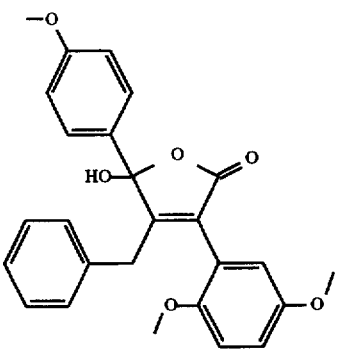

4-Benzyl-3-(2,5-dimethoxy-phenyl)-5-hydroxy-5-(4-methoxy-phenyl)-5H-furan-2-one

To methanol (24 mL) was added sodium metal (76.5 mg, 3.33 mmol) and stirred to dissolve. To this was added the ester, 374, (1.37 g, 3.17 mmol) then benzaldehyde (377.4 mg, 3.49 mmol). The mixture was heated to reflux for 72 hours. The solution was then treated with acetic acid (4.5 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 10% EtOAc:CH$_2$Cl$_2$). The butenolide was isolated by evaporation of the appropriate fractions to give 630 mg (43.8%) as a white foam. The butenolide was identified by $^1$H NMR, MS, [M+H]$^+$=433 Da., and microanalysis.

EXAMPLE 402

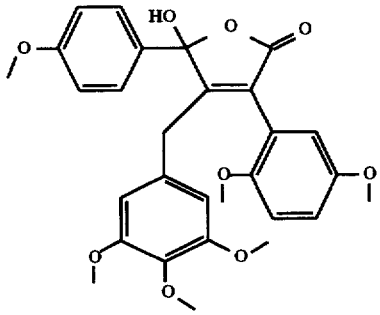

3-(2,5-Dimethoxy-phenyl)-5-hydroxy-5-(4-methoxyphenyl)-4-(3,4,5-trimethoxy-benzyl)-5H-furan-2-one To methanol (20 mL) was added sodium metal (84.2 mg, 3.66 mmol) and stirred to dissolve. To this was added the ester, 374, (1.25 g, 3.49 mmol) then 3,4,5-trimethoxybenzaldehyde (769 mg, 3.84 mmol). The mixture was heated to reflux for 72 hours. The solution was then treated with acetic acid (5 mL) and refluxed an additional 48 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 15% EtOAc:CH$_2$Cl$_2$). The butenolide was isolated by evaporation of the appropriate fractions to give 1.13 mg (62%) as a white foam. The butenolide was identified by $^1$H NMR, MS, [M+H]$^+$=523 Da., and microanalysis.

EXAMPLE 403

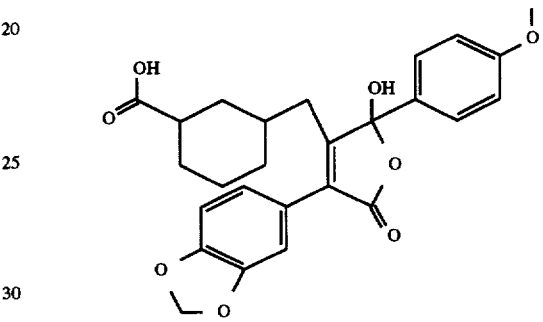

3-[4-Benzo[1,3]dioxol-5-yl-2-hydroxy-2-(4-methoxyphenyl)-5-oxo-2,5-dihydro-furan-3-ylmethyl]-cyclohexanecarboxylic acid To absolute ethanol (23 mL) was added sodium metal (142.5 mg, 6.2 mmol) and stirred to dissolve. To this was added the ester, 19, (2.05 g, 6.0 mmol) then ethyl-3-formylcyclohexanecarboxylate (1179 mg, 6.4 mmol). The mixture was heated to reflux for 48 hours. The solution was then treated with acetic acid (5.5 mL) and refluxed an additional 24 hours. The solvents were removed by evaporation, and the residue was partitioned between ethyl acetate (150 mL) and water (100 mL). The organic phase was separated and dried over magnesium sulfate and evaporated to dryness. The crude product was then purified by MPL chromatography (silica gel, 10% EtOAc:CH$_2$Cl$_2$). The ethyl ester butenolide was isolated by evaporation of the appropriate fractions to give 887 mg (30%) as a white foam. The ethyl ester butenolide was identified by $^1$H NMR, MS, [M+H]$^+$=495 Da., and microanalysis.

Then stirred 495 mg (1.0 mmol) of the ethyl ester butenolide in 8 mL MeOH and treated with 1.98 mL of a 1.010N NaOH solution (2.0 mmol). Refluxed solution, 96 hours, then evaporated MeOH and partitioned residue between 100 mL Et$_2$O and 150 mL H$_2$O. Acidified aqueous layer (12% HCl), then extracted with 150 mL EtOAc and washed with 100 mL H$_2$O and brine. Dried (MgSO$_4$) and stripped to 420 mg characterized [M+H]$^+$=467 Da., $^1$H NMR, and microanalysis.

EXAMPLE 404

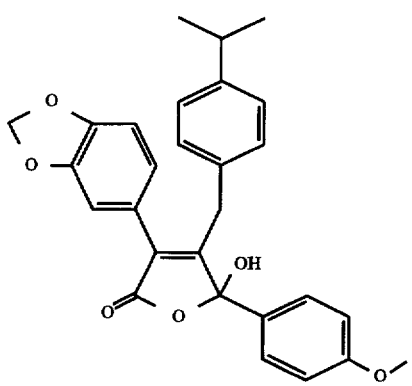

3-Benzo[1,3]dioxol-5-yl-5-hydroxy-4-(4-isopropylbenzyl)-5-(4-methoxy-phenyl)-5H-furan-2-one To methanol (50 mL) was added sodium metal (190 mg, 8.2 mmol) and stirred to dissolve. To this was added the ester, 19, (2.67 g, 7.8 mmol) then 4-isopropylbenzaldehyde (1.53 mL, 10.1 mmol). The mixture was heated to reflux for 4 hours. The solution was then treated with acetic acid (30 mL) and refluxed an additional 18 hours. The solvents were removed by evaporation, and the residue was partitioned between ethyl acetate and water. The organic phase was separated and dried over magnesium sulfate and evaporated to dryness. The crude product was then purified by flash chromatography (silica gel, 7:3 (hexane:ethyl acetate). The butenolide was isolated by evaporation of the appropriate fractions to give 0.50 g (14%) as a foam. The butenolide was identified by $^1$H NMR, IR, MS, [M+H]$^+$=459 Da., and microanalysis.

EXAMPLE 405

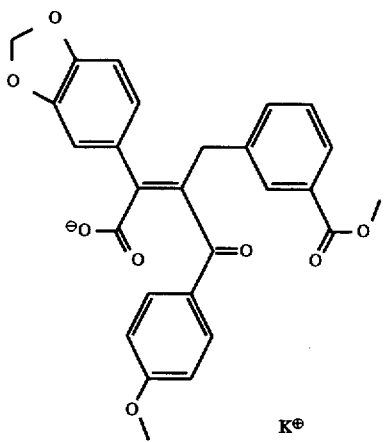

1,3-Benzodioxol-5-acetic acid, α-[1-[[3-(methoxycarbonyl)phenyl]methyl]-2-(4-methoxyphenyl)-2-oxoethylene]-, monopotassium salt The butenolide, 286, (500 mg, 1.05 mmol) was stirred into 0.498N potassium hydroxide (in methanol), 2.11 mL (1.05 mmol) for 1 minute. The methanol evaporated in vacuo and the residue partitioned between water and ether. The aqueous phase frozen and lyophilized to give the salt 510 mg (95%), which was identified by $^1$H NMR, IR, MS, [M+H]$^+$=473 Da., and microanalysis.

EXAMPLE 406

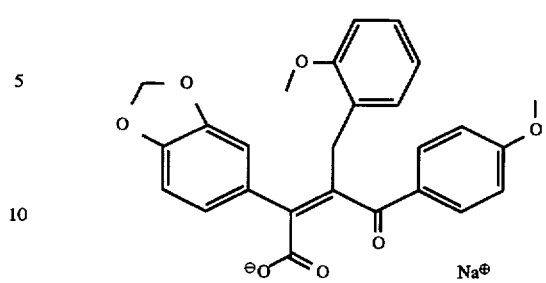

1,3-Benzodioxole-5-acetic acid, α-[1-(4-methoxybenzoyl)-2-(2-methoxyphenyl)ethylidene]-, monosodium salt, (Z)-

To 284, (1.46 g, 3.27 mmol), in methanol (30 mL) was added 1.010N sodium hydroxide (aq.) (3.05 mL, 3.07 mmol). The solution stirred for 5 minutes and evaporated free of methanol. The residue was partitioned between ether (150 mL) and distilled water (100 mL). The aqueous phase separated, evaporated free of residual organic solvents, frozen and lyophilized. This gave 1.21 g (85%) of the butenolide salt as a white solid, which was identified by $^1$H NMR, MS, [M+H]$^{(\pm)}$–447, IR, and microanalysis.

EXAMPLE 407

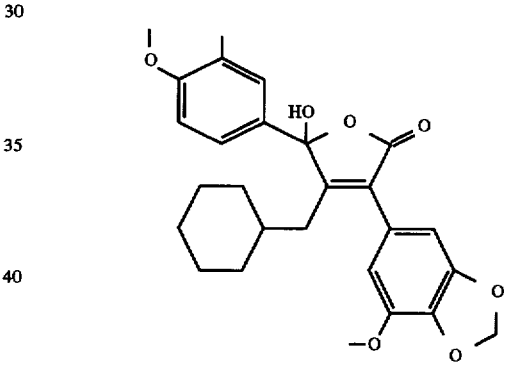

4-Cyclohexylmethyl-5-hydroxy-3-(7-methoxybenzo[1,3]dioxol-5-yl)-5-(4-methoxy-3-methyl-phenyl)-5H-furan-2-one To methanol 15 mL was added sodium metal 95 mg (4.1 mmol) and stirred to dissolve. To this was added the ester, 359, 1.54 g (4.0 mmol) then cyclohexane carboxaldehyde 471 mg (4.2 mmol). The mixture was heated to reflux for 18 hours. The solution was then treated with acetic acid 4 mL and refluxed an additional 24 hours. The solvents were removed by evaporation and the residue was partitioned between ether 100 mL and 1N sodium hydroxide 2×75 mL. The aqueous phase was separated and acidified with 6N HCl. This acidic solution was extracted with 2×75 mL ethyl acetate. The organic phase was separated, washed with brine, dried over magnesium sulfate and evaporated in vacuo. This gave the crude butenolide which was purified by flash chromatography (silica gel ethyl acetate/CH$_2$Cl$_2$) giving 398 mg (21%) as a white solid. The butenolide was identified by $^1$H NMR, IR, MS, [M+H]$^+$=466 Da. and microanalysis.

EXAMPLE 408

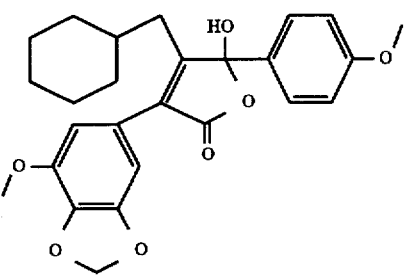

4-Cyclohexylmethyl-5-hydroxy-3-(7-methoxy-benzo[1,3]-dioxol-5-yl)-5-(4-methoxy-phenyl)-5H-furan-2-one To methanol 10 ml was added sodium metal 97 mg (4.2 mmol) and stirred to dissolve. To this was added the ester, 300, 1.49 g (4.0 mmol) then cyclohexane carboxaldehyde 460 mg (4.1 mmol). The mixture was heated to reflux for 18 hours. The solution was then treated with acetic acid 5 mL and refluxed an additional 24 hours. The solvents were removed by evaporation and the residue was partitioned between ethyl acetate 50 mL and water 50 mL. The organic phase was separated, washed with brine, dried over magnesium sulfate, and evaporated in vacuo. The crude oil was chromatographed (silica gel, ethylacetate/$CH_2Cl_2$). This gave the butenolide 450 mg (25%) as a white foam. The butenolide was identified by $^1$H NMR, IR, MS, $[M+H]^+$= 452 Da. and microanalysis.

EXAMPLE 409

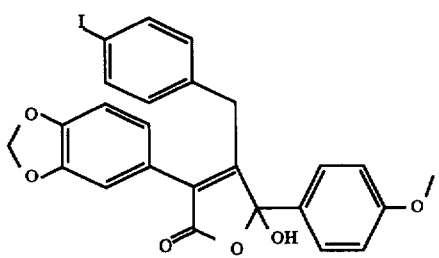

3-Benzo[1,3]dioxol-5-yl-5-hydroxy-4-(4-iodo-benzyl)-5-(4-methoxy-phenyl)-5H-furan-2-one To methanol 15 mL was added sodium metal 97 mg (4.2 mmol) and stirred to dissolve. To this was added the ester, 19, 1.37 g (4.0 mmol) then 4-iodobenzaldehyde 951 mg (4.1 mmol). The mixture was heated to reflux for 18 hours. The solution was then treated with acetic acid 4 mL and refluxed an additional 6 hours. The solvents were removed by evaporation and the residue was partitioned between ether 50 mL and 1N sodium hydroxide 2×50 mL. The aqueous phase was separated and acidified with 6N HCl. This acidic solution was extracted with 2×50 mL ethyl acetate. The organic phase was separated, washed with brine, dried over magnesium sulfate, and evaporated in vacuo. The residue was purified by chromatography (silica gel, 5% ethylacetate/$CH_2Cl$ giving the butenolide 1.295 g (60%) as a white foam. The butenolide was identified by $^1$H NMR, IR, MS, $[M+H]^+$=542 Da. and microanalysis.

EXAMPLE 410

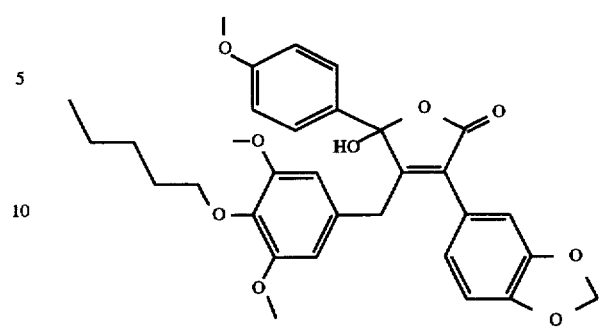

3-Benzo[1,3]dioxol-5-yl-4-(3,5-dimethoxy-4-pentyloxybenzyl)-5-hydroxy-5-(4-methoxy-phenyl)-5H-furan-2-one To methanol 7 mL was added sodium metal 42 mg (1.8 mmol) and stirred to dissolve. To this was added the ester, 19, 580 mg (1.7 mmol) then 3,5-dimethoxy-4-n-pentyloxy benzaldehyde 460 mg (1.8 mmol). The mixture was heated to reflux for 18 hours. The solution was then treated with acetic acid 7 mL and refluxed an additional 24 hours. The solvents were removed by evaporation and the residue was partitioned between ethyl acetate 70 mL and water (100 mL). The organic phase was separated, washed with brine, dried over magnesium sulfate, and evaporated in vacuo. The residue was purified by chromatography (silica gel, 10% ethylacetate/$CH_2Cl_2$) giving the butenolide 415 mg (42%) as a foam. The butenolide was identified by $^1$H NMR< IR, MS, $[M+H]^+$=562 Da. and microanalysis.

EXAMPLE 411

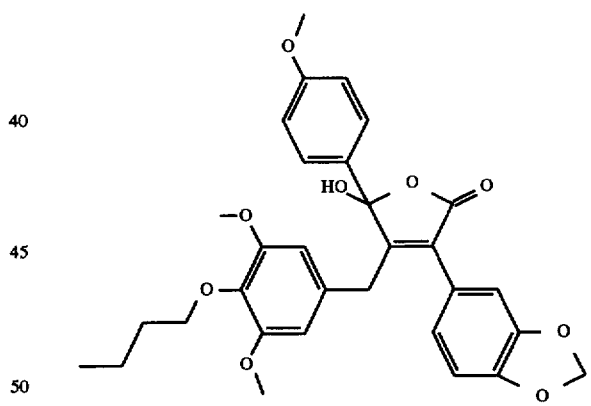

3-Benzo[1,3]dioxol-5-yl-4-(4-butoxy-3,5-dimethoxybenzyl)-5-hydroxy-5-(4-methoxy-phenyl)-5H-furan-2-one To methanol 12 mL was added sodium metal 97 mg (4.2 mmol) and stirred to dissolve. To this was added the ester, 19, 1.37 g (4.0 mmol) then 3,5-dimethoxy-4-n-butoxybenzaldehyde 977 mg (4.1 mmol). The mixture was heated to reflux for 18 hours. The solution was then treated with acetic acid 5 mL and refluxed an additional 24 hours. The solvents were removed by evaporation and the residue was partitioned between ethyl acetate 100 mL and water 100 mL. The organic phase was separated, dried over magnesium sulfate, and evaporated to dryness. The crude product was then purified by flash chromatography (150 g silica gel, 10% ethyl acetate/$CH_2Cl_2$). The butenolide was isolated by

EXAMPLE 412

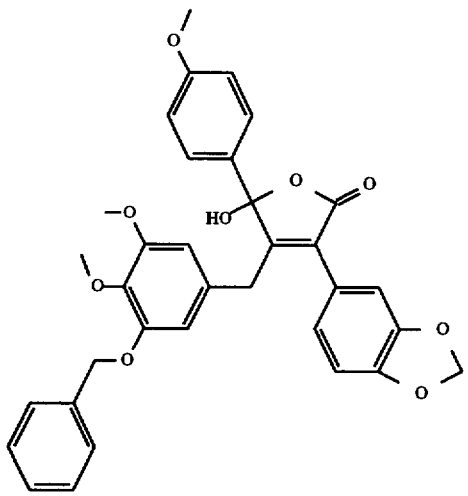

3-Benzo[1,3]dioxol-5-yl-4-(3-benzyloxy-4,5-dimethoxybenzyl)-5-hydroxy-5-(4-methoxy-phenyl)-5H-furan-2-one To methanol 18 mL was added sodium metal 48.6 mg (2.11 mmol) and stirred to dissolve. To this was added the ester, 19, 722 mg (2.11 mmol) then 3,4-dimethoxy-5-benzyloxybenzaldehyde 575 mg (2.11 mmol). The mixture was heated to reflux for 48 hours. The solution was then treated with acetic acid 4.5 mL and refluxed an additional 48 hours. The solvents were removed by evaporation and the residue was partitioned between ethyl acetate 150 mL and water 150 mL. The organic phase was separated, dried over magnesium sulfate, and evaporated to dryness. The crude product was then purified by flash chromatography (150 g silica gel, 10% ethyl acetate/dichloromethane). The butenolide was isolated by evaporation of the appropriate fractions to give 684 mg (56%) as a white foam. The butenolide was identified by $^1$H, NMR, MS, [M+H]$^+$=583 Da. and microanalysis.

EXAMPLE 413

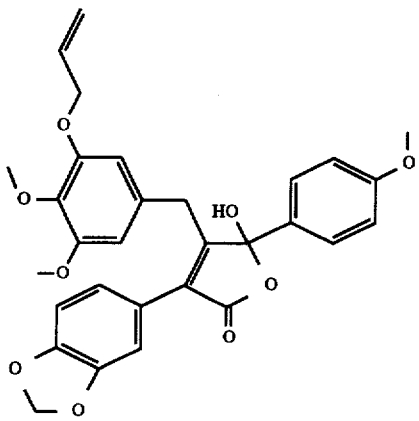

evaporation of the appropriate fractions to give 1.39 g (64%) as a white foam. The butenolide was identified by $^1$H NMR, IR, MS, [M+H]$^+$=548 Da. and microanalysis.

4-(3-Alkyloxy-4,5-dimethoxy-benzyl)-3-benzo[1,3]dioxol-5-yl-5-hydroxy-5-(4-methoxy-phenyl)-5H-furan-2-one To methanol 16 mL was added sodium metal 61 mg (2.65 mmol) and stirred to dissolve. To this was added the ester, 19, 864 mg (2.52 mmol) then 3,4-dimethoxy-5-alkyloxybenzaldehyde 590 mg (2.65 mmol). The mixture was heated to reflux for 24 hours. The solution was then treated with acetic acid 4.5 mL and refluxed an additional 24 hours. The solvents were removed by evaporation and the residue was partitioned between ethyl acetate 150 mL and water 150 mL. The organic phase was separated, dried over magnesium sulfate, and evaporated to dryness. The crude product was then purified by flash chromatography (150 g silica gel, 10% ethyl acetate/dichloromethane). The butenolide was isolated by evaporation of the appropriate fractions to give 737 mg (55%) as a white foam. The butenolide was identified by $^1$H, NMR, MS, [M+H]$^+$=533 Da. and microanalysis.

EXAMPLE 414

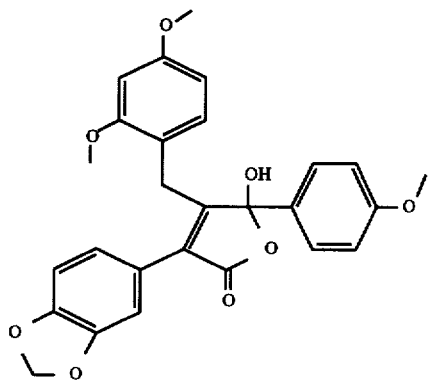

3-Benzo[1,3]dioxol-5-yl-4-(2,4-dimethoxy-benzyl)-5-hydroxy-5-(4-methoxy-phenyl)-5H-furan-2-one To methanol 20 mL was added sodium metal 115 mg (5.0 mmol) and stirred to dissolve. To this was added ester, 19, 1.66 mg (4.85 mmol) then 2,4-dimethoxybenzaldehyde 848 mg (5.0 mmol). The mixture was heated to reflux for 48 hours. The solution was then treated with acetic acid 4.5 mL and refluxed an additional 24 hours. The solvents were removed by evaporation and the residue was partitioned between ethyl acetate 150 mL and water 150 mL. The organic phase was separated, dried over magnesium sulfate, and evaporated to dryness. The crude product was then purified by flash chromatography (150 g silica gel, 7% ethylacetate/dichloromethane). The butenolide was isolated by evaporation of the appropriate fractions to give 687 mg (30%) as a white foam. The butenolide was identified by $^1$H, NMR, MS, [M+H]$^+$=477 Da. and microanalysis.

EXAMPLE 415

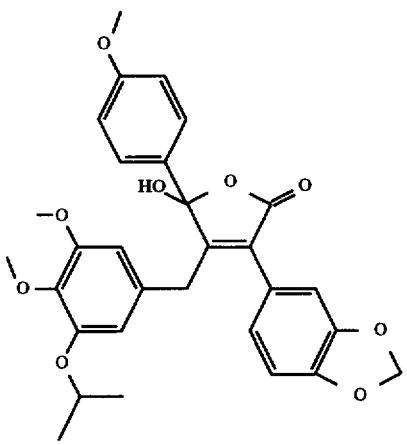

3-Benzo[1,3]dioxol-5-yl-5-hydroxy-4-(3-isopropoxy-4,5-dimethoxy-benzyl)-5-(4-methoxy-phenyl)-5H-furan-2-one To methanol 20 mL was added sodium metal 79 mg (3.43 mmol) and stirred to dissolve. To this was added the ester, 19, 1.12 g (3.27 mmol) then 3,4-dimethoxy-5-isopropyloxybenzaldehyde 770 mg (3.43 mmol). The mixture was heated to reflux for 24 hours. The solution was then treated with acetic acid 4.0 mL and refluxed an additional 24 hours. The solvents were removed by evaporation and the residue was partitioned between ethyl acetate 150 mL and water 150 mL. The organic phase was separated, dried over magnesium sulfate, and evaporated to dryness. The crude product was then purified by flash chromatograph (150 g silica gel, 10% ethylacetate/dichloromethane). The butenolide was isolated by evaporation of the appropriate fractions to give 1.12 g (64%) as a white foam. The butenolide was identified by $^1$H NMR, IR, MS, [M+H]$^+$=535 Da. and microanalysis.

EXAMPLE 416

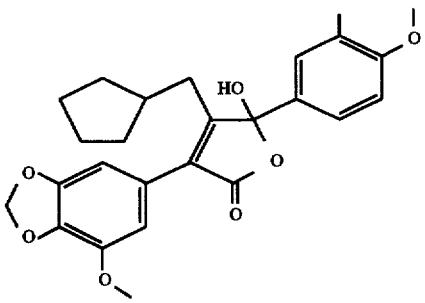

4-Cyclopentylmethyl-5-hydroxy-3-(7-methoxy-benzo[1,3]-dioxol-5-yl)-5-(4-methoxy-3-methyl-phenyl)-5H-furan-2-one To methanol 20 mL was added sodium metal 0.113 g (4.92 mmol) and stirred to dissolve. To this was added the ester, 359, 1.80 g (4.66 mmol) then cyclopentane carboxaldehyde 0.503 g (5.13 mmol). The mixture was heated to reflux for 18 hours. The solution was then treated with acetic acid 5 mL and refluxed an additional 18 hours. The solvents were removed by evaporation and the residue was partitioned between ether 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (150 g silica gel, eluted with EtOAc: hexane (25:75)). Evaporation of the appropriate fractions from ethyl ether/petroleum ether gave the butenolide 0.271 g (12.9%) as a crystalline solid, mp 144°–145° C. The butenolide was identified by $^1$H NMR, MS, [M+H]$^+$=453 Da. and microanalysis.

EXAMPLE 417

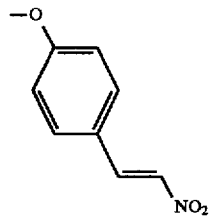

To anisaldehyde 30 g (220 mmol) in benzene (200 mL) was added n-butylamine 135 mL (1360 mmol) and the mixture was evaporated to an oil at 90° C. Nitromethane 39.4 g (220 mmol) was added, followed by glacial acetic acid (250 mL). After stirring 18 hours at 23° C., the mixture was evaporated in vacuo, suspended in ether, washed with 2N HCl and brine, and dried over MgSO$_4$. Evaporation of the solution and addition of petroleum ether gave a crystalline solid which was filtered and dried in vacuo. The resulting yellow solid weighed 11.69 g (29.6%) and was identified by $^1$H NMR, MS, [M+H]$^+$=180 Da. and microanalysis.

EXAMPLE 418

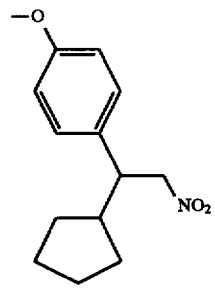

Magnesium metal turnings 3.73 g (61.4 mmol) were added to ether (100 mL) followed by bromo cyclopentane 22.87 g (153 mmol) giving vigorous reaction. The decantate from the suspended solids was placed in a separate flask and cooled to –30° C. To the decantate was added a solution of 417, 11 g (61.4 mmol) in THF (100 mL) and ether (100 mL). After stirring 1 hour at 0° C., the mixture was added to 0.5N HCl (250 mL), and the organic phase was separated, washed with brine, dried over MgSO$_4$, and evaporated to an oil. The crude oil was purified by flash chromatography (800 g silica gel, eluted with EtOAc:hexane (10:90)). Evaporation of the appropriate fractions gave the product as an oil 6.0 g (39.2%), which was identified by $^1$H NMR, MS, [M+H]$^+$= 249 Da. and microanalysis.

EXAMPLE 419

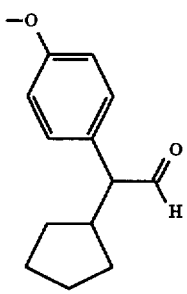

A 60% emulsion of NaH in oil 1.79 g (45 mmol) was washed with petroleum ether and added to t-butanol (25 mL). After stirring for 25 minutes, a solution of 418, 5.6 g (22.5 mmol) in t-butanol (40 mL) was added. After stirring for 15 minutes, petroleum ether (500 mL) was added and the mixture was cooled to −20° C. Ice (50 g) was added, followed by a solution of $KMnO_4$ 3.55 g (22.5 mmol), and $H_3BO_3$ 2.78 g (45 mmol) in cold water (150 mL). After stirring 15 minutes a solution of $Na_2S_2O_5$ 8.55 g (45 mmol) in water (45 mL) was added, followed by a solution of concentrated $H_2SO_4$ (2.5 mL) in water (30 mL). The mixture was filtered and the organic phase was washed with 1N HCl, brine, saturated sodium bicarbonate solution, and brine. The organic phase was separated and dried over magnesium sulfate and evaporated in vacuo to an oil. The crude oil was purified by flash chromatography (150 g silica gel, eluted with EtOAc:hexane (50:50)). Evaporation of the appropriate fractions gave the product as an oil 2.87 g (58%), which was identified by $^1$H NMR, MS, [M+H]$^+$=219 Da.

EXAMPLE 420

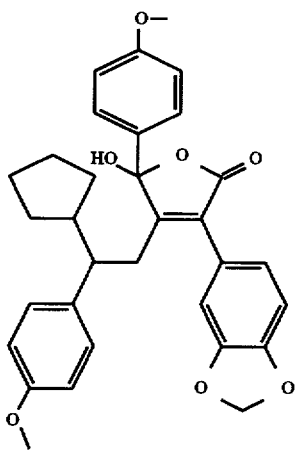

3-Benzo[1,3]dioxol-5-yl-4-[2-cyclopentyl-2-(4-methoxyphenyl)-ethyl]-5-hydroxy-5-(4-methoxy-phenyl)-5H-furan-2-one To methanol 18 mL was added sodium metal 0.149 g (6.48 mmol) and stirred to dissolve. To this was added the ester, 19, 1.59 g (7.30 mmol). The mixture was heated to reflux for 18 hours. The solution was then treated with acetic acid 5 mL and refluxed an additional 5 hours. The solvents were removed by evaporation and the residue was partitioned between ether 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (150 g silica gel, eluted with EtOAc:hexane (20:80)). Evaporation of the appropriate fractions from ether gave the butenolide 0.220 g (7.1%) as a brittle white foam. The butenolide was identified by $^1$H NMR, MS, [M+H]$^+$= 529 Da. and microanalysis.

EXAMPLE 421

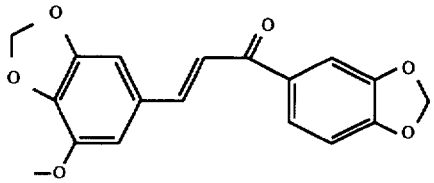

To 3-methoxy-4,5-methylenedioxybenzaldehyde 15.32 g (85 mmol) in absolute ethanol (100 mL) in an erlenmeyer was added 3',4'-(methylenedioxy)acetophenone 12.70 g (77.6 mmol). The solution was warmed while 12.5% sodium hydroxide (5 mL) added. The mixture was warmed for 20 minutes and allowed to stand to precipitate. The solid was collected by filtration and washed with 80% ethanol. The solid was dried in vacuo giving 22.36 g (88.3%) of a yellow solid which was identified by $^1$H NMR, MS, and microanalysis.

EXAMPLE 422

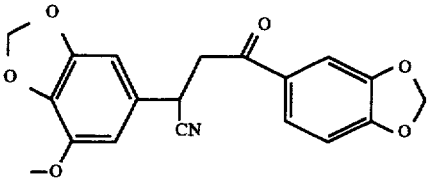

To the chalcone, 421, 24.1 g (73.8 mmol) in 2-ethoxyethanol (60 mL) at 80° C. was added acetic acid (5.3 g) followed by slow addition of potassium cyanide 7.2 g (110 mmol) in water 12.5 mL. The solution was stirred at 120° C. for 0.5 hours. The solution was cooled over 1 hour and evaporated to an oil. The oil was suspended in ethyl acetate, washed with water, brine, 1N HCl, saturated sodium bicarbonate solution, and brine. The organic phase was separated and dried over magnesium sulfate and evaporated in vacuo. The oil was crystallized from ethyl acetate/ether, filtered, and the solid dried in vacuo to give the nitrile 19.15 g (74%) The nitrile was identified by $^1$H NMR, MS, and microanalysis.

EXAMPLE 423

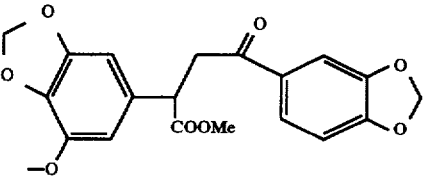

To the nitrile, 422, 18.59 g (52.6 mmol) was added methanol (50 mL) and dioxane (25 mL). To the mixture was

215 added p-toluenesulfonic acid 10 g (52.6 mmol). The mixture was heated to reflux for 18 hours and evaporated to a solid. The solid was suspended in ethyl acetate, washed with saturated sodium bicarbonate solution, brine, 2N HCl, and brine. The organic phase was separated and dried over magnesium sulfate and evaporated in vacuo. The residue was crystallized from ethyl acetate/ether, filtered and dried in vacuo. This gave the ester 9 g (44%) as a crystalline solid which was identified by $^1$H NMR, MS, and microanalysis.

EXAMPLE 424

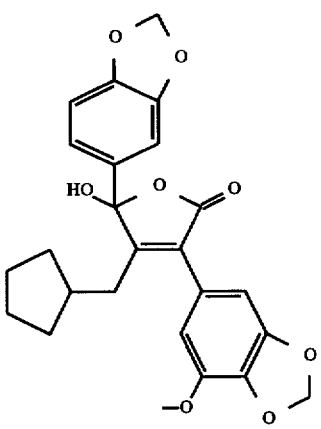

5-Benzo[1,3]dioxol-5-yl-4-cyclopentylmethyl-5-hydroxy-3-(7-methoxy-benzo[1,3]dioxyl-5-yl)-5H-furan-2-one To methanol 20 mL was added sodium metal 0.149 g (6.48 mmol) and stirred to dissolve. To this was added the ester, 423, 2.25 g (5.84 mmol) then cyclopentylcarboxaldehyde 0.72 g (7.30 mmol). The mixture was heated to reflux for 18 hours. The solution was then treated with acetic acid 5 mL and refluxed an additional 18 hours. The solvents were removed by evaporation and the residue was partitioned between ethyl acetate 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (50 g silica gel, eluted with EtOAc:hexane (10:90)). Evaporation of the appropriate fractions from ether gave the butenolide 0.463 g (17.6%) as a brittle white foam. The butenolide was identified by $^1$H NMR, MS, [M+H]$^+$=453 Da. and microanalysis.

216

EXAMPLE 425

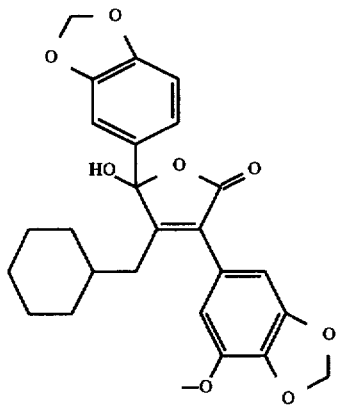

5-Benzo[1,3]dioxol-5-yl-4-cyclohexylmethyl-5-hydroxy-3-(7-methoxy-benzo[1,3]dioxol-5-yl)-5H-furan-2-one To methanol 25 mL was added sodium metal 0.149 g (6.48 mmol) and stirred to dissolve. To this was added the ester, 423, 2.25 g (5.84 mmol) then cyclohexylcarboxaldehyde 0.82 g (7.30 mmol). The mixture was heated to reflux for 18 hours. The solution was then treated with acetic acid 5 mL and refluxed an additional 18 hours. The solvents were removed by evaporation and the residue was partitioned between ether 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (150 g silica gel, eluted with EtOAc:hexane (15:85)). Evaporation of the appropriate fractions from ether/hexane gave the butenolide 1.49 g (54.8%) as a crystalline white solid, mp 116°–169° C. The butenolide was identified by $^1$H NMR, MS, [M+H]$^+$=467 Da. and microanalysis.

EXAMPLE 426

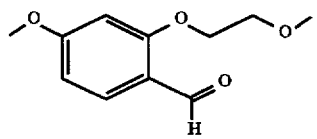

2-Hydroxy-4-methoxybenzaldehyde 11 g (72.2 mmol), $K_2CO_3$ 15 g (108 mmol), and 2-methoxy-1-bromoethane 25.12 g (180 mmol) were dissolved in acetone (250 mL), followed by heating to reflux for 18 hours. An additional 4 g 2-methoxy-1-bromoethane was then added, followed by heating to reflux for 18 hours. The mixture was filtered, evaporated to an oil, and dissolved in ether. The solution was washed with 1N NaOH, brine, 1N HCl, and brine, followed by drying over $MgSO_4$. The product was obtained as a solid by evaporation of the solvent followed by trituration with petroleum ether. The solid was dried in vacuo at 25° C.

EXAMPLE 427

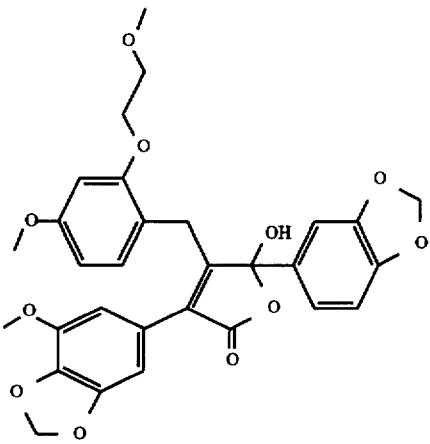

5-Benzo[1,3]dioxol-5-yl-5-hydroxy-3-(7-methoxybenzo[1,3]dioxol-5-yl)-4-[4-methoxy-2-(2-methoxyethoxy)-benzyl]-5H-furan-2-one To methanol 40 mL was added sodium metal 0.23 g (10.1 mmol) and stirred to dissolve. To this was added the ester, 423, 3.7 g (9.58 mmol) then 426, 2.2 g (10.5 mmol). The mixture was heated to reflux for 18 hours. The solution was then treated with acetic acid 5 mL and refluxed an additional 18 hours. The solvents were removed by evaporation and the residue was partitioned between ether 60 mL and 1N sodium hydroxide 55 mL. The aqueous phase was separated and acidified with concentrated HCl. This acidic solution was extracted with 140 mL ether. The organic phase was separated, washed with brine, dried over magnesium sulfate, and evaporated in vacuo. The crude butenolide was purified by flash chromatography (150 g silica gel, eluted with EtOAc:hexane (20:80)). Evaporation of the appropriate fractions from ether gave the butenolide 1.7 g (31%) as a brittle solid. The butenolide was identified by $^1$H NMR, MS, [M+H]$^+$=564 Da. and microanalysis.

EXAMPLE 428

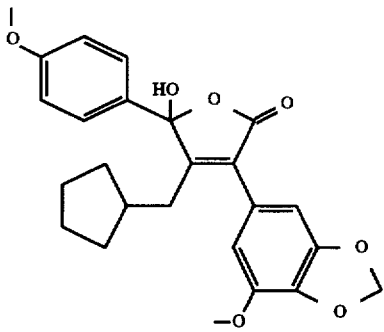

4-Cyclopentylmethyl-5-hydroxy-3-(7-methoxy-benzo[1,3]-dioxol-5-yl)-5-(4-methoxy-phenyl)-5H-furan-2-one To methanol 25 mL was added sodium metal 0.15 g (6.48 mmol) and stirred to dissolve. To this was added the ester, 300, 2.17 g (5.84 mmol) then cyclopentylcarboxaldehyde 0.9 g (9.17 mmol). The mixture was heated to reflux for 18 hours. The solution was then treated with acetic acid 3 mL and refluxed an additional 7 hours. The solvents were removed by evaporation and the residue was partitioned between ethyl acetate 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (50 g silica gel, eluted with EtOAc:hexane (15:85)). Evaporation of the appropriate fractions from ether gave the butenolide as a crystalline solid, 0.176 g (6.5%) mp 139°–140° C. The butenolide was identified by $^1$H NMR, MS, [M+H]$^+$=438 Da. and microanalysis.

EXAMPLE 429

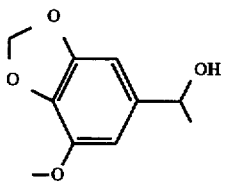

3-Methoxy-4,5-methylenedioxybenzaldehyde 15.32 g (85 mmol) was dissolved in THF (400 mL) and cooled to −20° C. A solution of 1.4M MeLi in ether (65 mL, 91 mmol) was added and the mixture was stirred for 1.5 hours at 20° C. After cooling to −20° C., 1N HCl (100 mL) was added. The organic phase was washed with brine, dried over MgSO$_4$, and evaporated to an oil. The crude oil was purified by flash chromatography (750 g silica gel, eluted with EtOAc:hexane (20:80)). Evaporation of the appropriate fractions gave the product as an oil 16.78 g (100%), which was identified by $^1$H NMR, MS, [M+H]$^+$=197 Da. and microanalysis.

EXAMPLE 430

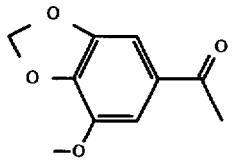

429, 10.78 g (55 mmol) was dissolved in acetone (350 mL) and cooled to −15° C. 8N Jones reagent (19 mL) was added and the mixture was stirred for 20 minutes at 15° C. Isopropanol (20 mL) was added and the mixture was filtered and evaporated to and oil. The oil was dissolved in EtOAc and was washed with brine, saturated sodium bicarbonate solution, 1N HCl, and brine. The organic phase was dried over MgSO$_4$ and diluted with petroleum ether which gave a crystalline solid. The solid was dried in vacuo and weighed 6.78 g (63.5%), and was identified by $^1$H NMR, MS, [M+H]$^+$=195 Da. and microanalysis.

giving 9.24 g (60.8%) and was identified by $^1$H NMR, MS, [M+H]$^+$=211 Da.

EXAMPLE 431

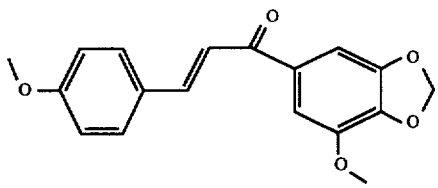

To 4-methoxybenzaldehyde 4.85 g (35.6 mmol) in absolute ethanol (30 mL) in an erlenmeyer was added 430, 6.78 g (35 mmol). The solution was warmed while 12.5% sodium hydroxide (4 mL) added. The mixture was warmed for 20 minutes and allowed to stand to precipitate. The solid was collected by filtration and washed with 80% ethanol. The solid was dried in vacuo giving 10.46 g (95.6%) of a yellow solid which was identified by $^1$H NMR, MS [M+H]$^+$=313 Da. and microanalysis.

EXAMPLE 432

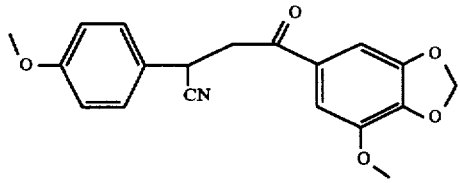

To the chalcone, 431, 10.46 g (33.5 mmol) in 2-ethoxyethanol (30 mL) at 40° C. was added acetic acid (2.4 g) followed by slow addition of potassium cyanide 3.25 g (50 mmol) in water 8 mL. The solution was stirred at reflux for 0.5 hours. The solution was cooled over 1 hour and evaporated to an paste. Filter, wash with ethyl acetate, water, and ether. The filtrate also precipitated a solid which was combined with the solid above and dried in vacuo which gave the nitrile as a grey solid, mp 145°–146° C., 9.68 g (85.2%). The nitrile was identified by $^1$H NMR, MS, [M+H]$^+$=340 Da. and microanalysis.

EXAMPLE 433

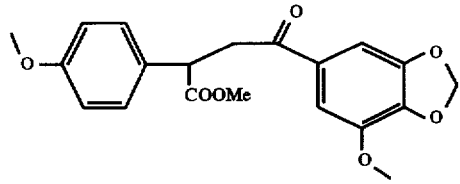

To the nitrile, 432, 9.55 g (28 mmol) was added methanol (25 mL) and dioxane (12 mL). To the mixture was added p-toluenesulfonic acid 6.67 g (35 mmol). The mixture was heated to reflux for 48 hours and filtered. The solid was washed with methanol and dried in vacuo. The solid was then resuspended in a mixture of ethyl acetate and saturated sodium bicarbonate solution and warmed to give solution. The organic phase was washed with brine, and dried over magnesium sulfate and crystallized from ethyl acetate/ether, filtered, and dried in vacuo. This gave the ester 8.93 g (85.6%) as a crystalline solid which was identified by $^1$H NMR, MS, [M+H]$^+$=373 Da. and microanalysis.

EXAMPLE 434

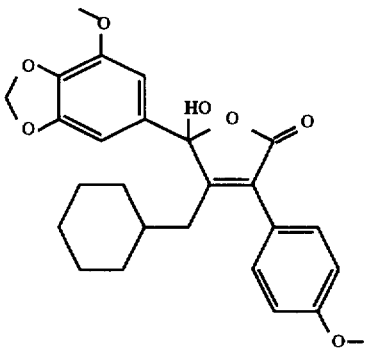

4-Cyclohexylmethyl-5-hydroxy-5-(7-methoxy-benzo[1,3]-dioxol-5-yl)-3-(4-methoxy-phenyl)-5H-furan-2-one To methanol 30 mL was added sodium metal 0.11 g (4.84 mmol) and stirred to dissolve. To this was added the ester, 432, 1.67 g (4.48 mmol) then cyclohexylcarboxaldehyde 0.55 g (4.90 mmol). The mixture was heated to reflux for 18 hours. The solution was then treated with acetic acid 4 mL and refluxed an additional 8 hours. The solvents were removed by evaporation and the residue was partitioned between ether 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (70 g silica gel, eluted with EtOAc:hexane (20:80)). Evaporation of the appropriate fractions from ether gave the butenolide 0.564 g (28%) as a brittle white foam. The butenolide was identified by $^1$H NMR, MS, [M+H]$^+$=453 Da. and microanalysis.

EXAMPLE 435

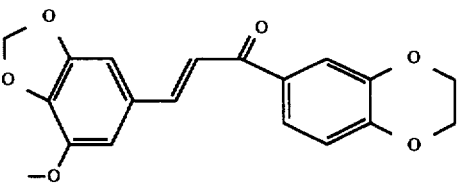

To 3-methoxy-4,5-methylenedioxybenzaldehyde 15.32 g (85 mmol) in absolute ethanol (100 mL) in an erlenmeyer was added 1,4-benzodioxan-6-yl methyl ketone 13.83 g (77.6 mmol). The solution was warmed while 12.5% sodium hydroxide (7 mL) added. The mixture was warmed for 30 minutes and allowed to stand to precipitate. The solid was collected by filtration and washed with 80% ethanol. The solid was dried in vacuo giving 17.78 g (61%) of a yellow solid which was identified by $^1$H NMR, MS and microanalysis.

EXAMPLE 436

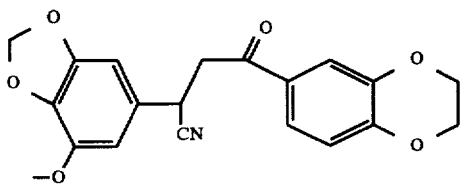

To the chalcone, 435, 17.25 g (50.7 mmol) in 2-ethoxyethanol (50 mL) at 50° C. was added acetic acid (3.7 g) followed by slow addition of potassium cyanide 4.92 g (75.5 mmol) in water 9 mL. The solution was stirred at reflux for 0.75 hours. The solution was cooled over 3 hours and evaporated to a paste which was filtered and washed with ethanol. The solid was suspended in ethyl acetate, washed with brine and dried over magnesium sulfate. The solution was evaporated in vacuo and the residue was crystallized from ethyl acetate/ether, filtered, and the solid dried in vacuo to give the nitrile 13.24 g (71%). The nitrile was identified by $^1$H NMR, MS, and microanalysis.

EXAMPLE 437

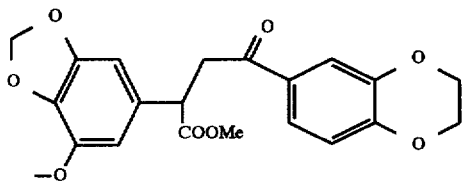

To the nitrile, 436, 12.93 g (35.2 mmol) was added methanol (30 mL) and dioxane (20 mL). To the mixture was added p-toluenesulfonic acid 8.03 g (42.2 mmol). The mixture was heated to reflux for 18 hours and evaporated to a paste. The paste was suspended in ethyl acetate, washed with saturated sodium bicarbonate solution, brine, 1N HCl, and brine. The organic phase was separated and dried over magnesium sulfate and evaporated in vacuo. The residue was crystallized from ethyl acetate/ether, filtered and dried in vacuo. This gave the ester 11.12 g (78.9%) as a crystalline solid which was identified by $^1$H NMR, MS, and microanalysis.

EXAMPLE 438

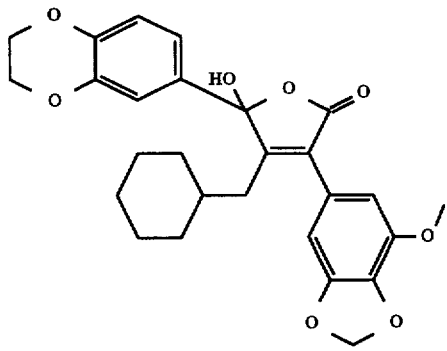

4-Cyclohexylmethyl-5-(2,3-dihydro-benzo[1,4]dioxin-6-yl)-5-hydroxy-3-(7-methoxy-benzo[1,3]dioxol-5-yl)-5H-furan-2-one To methanol 20 mL was added sodium metal 0.149 g (6.48 mmol) and stirred to dissolve. To this was added the ester, 437, 2.34 g (5.84 mmol) then cyclohexylcarboxaldehyde 0.82 g (7.30 mmol). The mixture was heated to reflux for 18 hours. The solution was then treated with acetic acid 3 mL and refluxed an additional 8 hours. The solvents were removed by evaporation and the residue was partitioned between ether 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (150 g silica gel, eluted with EtOAc:hexane (30:70)). Evaporation of the appropriate fractions from ether/hexane gave the butenolide 1.60 g (57%) as a brittle white foam. The butenolide was identified by $^1$H NMR, MS, [M+H]$^+$=481 Da. and microanalysis.

EXAMPLE 439

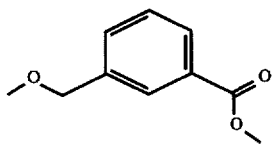

Sodium metal 3.55 g (154 mmol) was dissolved in methanol (350 mL) and 3-(bromomethyl)methyl benzoate 32 g (139.6 mmol) was added. After stirring 18 hours, the mixture was heated to 50° C. for 1 hour and cooled. The mixture was acidified by the addition of 6N HCl, and was evaporated in vacuo to remove methanol. The aqueous-oily residue was extracted with ether and the organic phase was washed with brine, saturated sodium bicarbonate solution, brine, 1N HCl, and brine. The organic phase was dried over MgSO$_4$, evaporated to an oil, 25.64 g (100%), and was identified by 1H NMR.

EXAMPLE 440

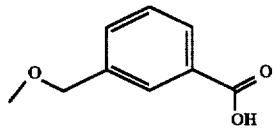

439, 25.4 g (139.6 mmol) was dissolved in methanol (100 mL) and 1N NaOH (155 ml) was added. After stirring 4 hours, the mixture was evaporated in vacuo to remove methanol. The aqueous-oily residue was extracted with ether and the organic phase was washed with 1N HCl and brine. The organic phase was dried over MgSO$_4$. Evaporation of the solution and addition of hexane gave a crystalline solid which was filtered and dried in vacuo. The resulting solid weighed 16.75 g (72.2%) and was identified by $^1$H NMR, MS, [M+H]$^+$=167 Da. and microanalysis.

EXAMPLE 441

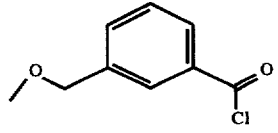

To a solution of SOCl$_2$ (85 mL) in dichloromethane (250 mL) was added a solution of 440, 16.5 g (99.3 mmol) in dichloromethane (150 mL). After stirring 18 hours, the mixture was evaporated in vacuo to an oil 18.91 g (100%). The material was used without further identification in the following step.

EXAMPLE 442

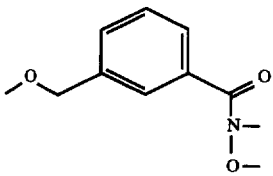

To a solution of 441, 16.5 g (99.3 mmol) in dichloromethane (350 mL) was added a solution of O,N dimethylhydroxylamine hydrochloride 10.05 g (103 mmol) and triethyl amine 28.7 mL (206 mmol) in dichloromethane (250 mL). After stirring 18 hours, the mixture was washed with 1N HCl, brine, 1N NaOH, and brine. The solution was dried over MgSO$_4$, evaporated in vacuo to an oil 15.0 g (72.1%) and was identified by $^1$H NMR, MS, [M+H]$^+$=210 Da. and microanalysis.

EXAMPLE 443

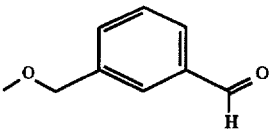

To a solution of 443, 14.8 g (70.7 mmol) in ether (300 mL) at −8° C. was added LiAlH4 2.82 g (74.3 mmol). After stirring 2 hours at 20° C., the mixture was cooled to 0° C., and 6N HCl (200 mL) was added. The organic phase was washed with brine, dried over MgSO$_4$ and evaporated in vacuo to an oil. The crude oil was purified by flash chromtography (200 g silica gel, eluted with EtOAc:hexane (15:85)). Evaporation of the appropriate fractions gave the product as an oil 6.75 g (63.5%) and was identified by $^1$H NMR, MS, [M+H]$^+$=151 Da. and microanalysis.

EXAMPLE 444

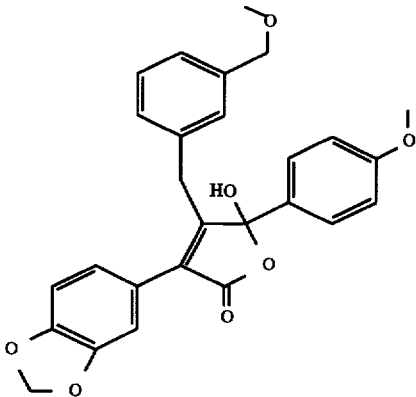

3-Benzo[1,3]dioxol-5-yl-5-hydroxy-4-(3-methoxymethylbenzyl)-5-(4-methoxy-phenyl)-5H-furan-2-one To methanol 35 mL was added sodium metal 0.149 g (6.48 mmol) and stirred to dissolve. To this was added the ester, 19, 2.0 g (5.84 mmol) then 443, 1.1 g (7.30 mmol). The mixture was heated to reflux for 18 hours. The solution was then treated with acetic acid 2 mL and refluxed an additional 18 hours. The solvents were removed by evaporation and the residue was partitioned between ether 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (100 g silica gel, eluted with EtOAc:hexane (30:70)). Evaporation of the appropriate fractions from ether gave the butenolide 2.46 g (91.8%) as a gummy solid. The butenolide was identified by $^1$H NMR, MS, [M+H]$^+$=461 Da. and microanalysis.

EXAMPLE 445

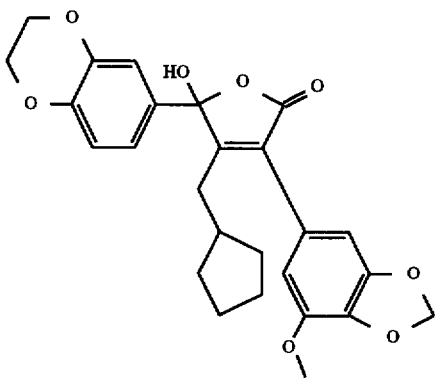

4-Cyclopentylmethyl-5-(2,3-dihydro-benzo[1,4]dioxin-6-yl)-5-hydroxy-3-(7-methoxy-benzo[1,3]dioxol-5-yl)-5H-furan-2-one To methanol 20 mL was added sodium metal 0.149 g (6.48 mmol) and stirred to dissolve. To this was added the ester, 437, 2.34 g (5.84 mmol) then cyclopentylaldehyde 0.8 g (7.30 mmol). The mixture was heated to reflux for 18 hours. The solution was then treated with acetic acid 5 mL and refluxed an additional 18 hours. The mixture was filtered, solvents were removed by evaporation, and the residue was partitioned between ether 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (100 g silica gel, eluted with EtOAc:hexane (25:75)). Evaporation of the appropriate fractions from ether gave the butenolide 0.52 g (19%) as a brittle yellow foam. The butenolide was identified by $^1$H NMR, MS, [M+H]$^+$=466 Da. and microanalysis.

EXAMPLE 446

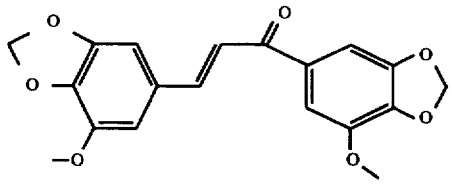

To 3-methoxy-4,5-methylenedioxybenzaldehyde 8.63 g (44 mmol) in,solute ethanol (300 mL) in an erlenmeyer was added 3-methoxy-4,5-methylenedioxyphenylacetophenone 8.0 g (44 mmol). The solution was warmed while 12.5% sodium hydroxide (4 mL) added. The mixture was warmed for 45 minutes and allowed to stand to precipitate. After 18 hours, the solid was collected by filtration and washed with 80% ethanol. The solid was dried in vacuo giving 12.71 g (80.3%) of a yellow solid which was identified by ¹N NMR, MS and microanalysis.

EXAMPLE 447

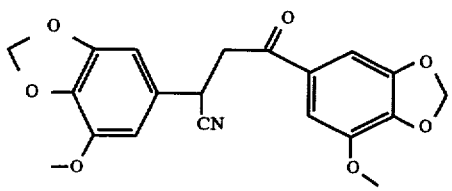

To the chalcone, 446, 12.36 g (34.7 mmol) in 2-ethoxyethanol (30 mL) at 50° C. was added acetic acid (2.5 g) followed by slow addition of potassium cyanide 3.5 g (52.1 mmol) in water 12 mL. The solution was stirred at reflux for 1.6 hours. The solution was cooled giving a paste which was filtered and washed with 50% ethanol. The solid was washed with ether and dried in vacuo to give the nitrile 10.8 g (81%). The nitrile was identified by ¹H NMR, MS, and microanalysis.

EXAMPLE 448

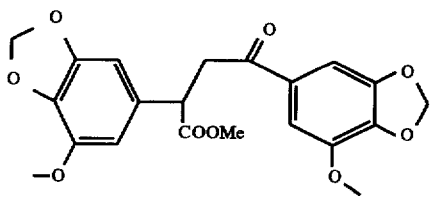

To the nitrile, 447, 10.56 g (27.5 mmol) was added methanol (45 mL) and dioxane (20 mL). To the mixture was added p-toluenesulfonic acid 6.28 g (33 mmol). The mixture was heated to reflux for 42 hours and evaporated to a paste. The paste was suspended in ethyl acetate, washed with saturated sodium bicarbonate solution, brine, 1N HCl, and brine. The organic phase was separated, dried over magnesium sulfate, and evaporated in vacuo. The residue was crystallized from ether, filtered and dried in vacuo. This gave the ester 9.61 g (83.9%) as a crystalline solid which was identified by ¹H NMR, MS, and microanalysis.

EXAMPLE 449

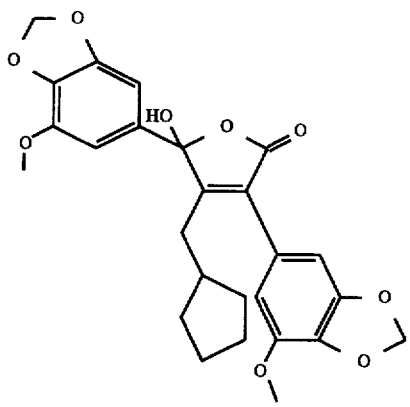

4-Cyclopentylmethyl-5-hydroxy-3,5-bis -(7-methoxy-benzo-[1.3]dioxol-5-yl)-5H-furan-2-one To methanol 20 mL was added sodium metal 0.149 g (6.48 mmol) and stirred to dissolve. To this was added the ester, 448, 2.43 g (5.84 mmol) then cyclopentylaldehyde 0.8 g (7.30 mmol). The mixture was heated to reflux for 18 hours. The solution was then treated with acetic acid 5 mL and refluxed an additional 18 hours. The mixture was filtered, solvents were removed by evaporation, and the residue was partitioned between ether 50 mL and 1N sodium hydroxide 50 mL. The aqueous phase was separated and acidified with concentrated HCl. This acidic solution was extracted with 120 mL ether. The organic phase was separated, washed with brine, dried over magnesium sulfate, and evaporated in vacuo. The crude butenolide was purified by flash chromatography (100 g silica gel, eluted with EtOAc:hexane (25:75)). Evaporation of the appropriate fractions from ether gave the butenolide 0.608 g (21.5%) as a brittle yellow foam. The butenolide was identified by ¹H NMR, MS, [M+H]⁺=483 Da. and microanalysis.

We claim:
1. A compound of formula

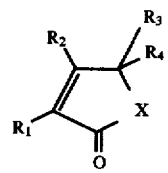

or a tautomeric open chain keto-acid form thereof or a pharmaceutically acceptable salt thereof wherein $R_1$ is cycloalkyl substituted or unsubstituted of from 3 to 12 carbon atoms, phenyl substituted with from 1 to 5 substituents, naphthyl unsubstituted or substituted with from 1 to 5 substituents, or heteroaryl unsubstituted or substituted with from 1 to 5 substituents;

$R_2$ is alkyl substituted or unsubstituted straight, or branched of from 1 to 12 carbon atoms, cycloalkyl substituted or unsubstituted of from 3 to 12 carbon atoms, aryl which is unsubstituted or substituted with from 1 to 5 substituents, heteroaryl which is unsubstituted or substituted with from 1 to 3 substituents;

$R_3$ is alkyl substituted or unsubstituted straight, or branched, of from 1 to 12 carbon atoms,
cycloalkyl substituted or unsubstituted of from 3 to 12 carbon atoms,
aryl which is unsubstituted or substituted with from 1 to 5 substituents,
heteroaryl which is unsubstituted or substituted with from 1 to 3 substituents;

$R_4$ is hydroxy or $OR_5$,
$SR_5$, wherein $R_5$ is alkyl or substituted alkyl of from 1 to 7 carbon atoms, or
$(CH_2)_nOR_5$ wherein n is an integer of from 1 to 3;

X is O or S;

with the proviso that when $R_1$ is monosubstituted phenyl and the substituent is p-methoxy, $R_3$ is not unsubstituted phenyl, monosubstituted phenyl, or mesityl and with the further proviso when $R_2$ is alkyl substituted, the substituent is not oxygen at the α-position to the furanone ring; and with the proviso that any of $R_1$ through $R_4$ are heterocyclic containing.

2. A compound according to claim 1 wherein
$R_1$ is phenyl substituted with from 1 to 5 substituents,
naphthyl unsubstituted or substituted with from 1 to 5 substituents, or
heteroaryl unsubstituted or substituted with from 1 to 5 substituents;

$R_2$ is alkyl substituted or unsubstituted straight, or branched, of from 1 to 7 carbon atoms, $R_3$ is aryl substituted or unsubstituted,
heteroaryl substituted or unsubstituted;

$R_4$ is hydroxy,
$OR_5$, or
$SR_5$;

X is O or S;
with the proviso that when $R_1$ is monosubstituted phenyl and the substituent is p-methoxy, $R_3$ is not unsubstituted phenyl, monosubstituted phenyl, or mesityl and with the further proviso that when $R_2$ is alkyl substituted the substituent is not oxygen at the α-position to the furanone.

3. A compound according to claim 1 wherein
$R_1$ is 4-piperonyl,
3,4-dichlorophenyl,
3-methoxyphenyl,
3,5-dimethoxyphenyl,

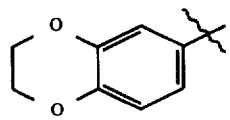

or
3-methoxy-4,5-methylenedioxyphenyl;

$R_2$ is benzyl,
4-piperonylmethyl,
4-isopropylbenzyl,
1-naphthylmethyl,
2-naphthylmethyl,
3-thiophenylmethyl,
2-thiophenylmethyl,
3,4-dichlorobenzyl,
3 (N—Me) indolylmethyl,
3,4-dimethoxybenzyl,
4-Me₂aminobenzyl,
4-isopropylbenzyl,
4-chlorobenzyl,
4-methoxybenzyl,
4-methylbenzyl,
3-methylbenzyl,
4-isopropoxybenzyl,
4-acetamidobenzyl,
4-methylsulfonylbenzyl,
3-methyl-4-methoxybenzyl,
3-allyloxy-4-methoxybenzyl,
3,4,5-trimethoxybenzyl,
3,4,5-triethoxybenzyl,
3-n-propoxybenzyl,
4-thiomethylbenzyl,
3-carbethoxybenzyl,
4-carbethoxybenzyl,
3-methoxybenzyl,
2-methoxybenzyl, or
3-chlorobenzyl;

$R_3$ is phenyl,
4-methylphenyl,
4-methoxyphenyl,
2-methylphenyl,
3-methylphenyl,
3-methoxyphenyl,

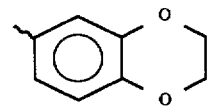

3-methyl-4-methoxyphenyl,
3,4-dimethoxyphenyl, or
2,4-dimethoxyphenyl;

$R_4$ is hydroxy,
$OCH_3$,
$OCH_2CHO$,
$OCH_2COOH$,
$OCH_2CH(OH)CH_2OH$, or
$OCH_2$(m-OH-phenyl), and X is oxygen.

4. A compound according to claim 1 wherein
is 4-piperonyl,
3,5-dimethoxyphenyl, or
3-methoxy-4,5-methylenedioxyphenyl;

$R_2$ is 4-piperonylmethyl,
4-isopropylbenzyl,
2-naphthylmethyl,
1-naphthylmethyl,
benzyl,
2-thiophenylmethyl,
3-thiophenylmethyl,
3-(N—Me) indolylmethyl,
4-chlorophenyl,
4-methoxyphenyl,
4-methylphenyl,
4-isopropoxybenzyl,
4-acetamidobenzyl,
4-methylsulfonylbenzyl,
3-methyl-4-methoxybenzyl,
3-allyloxy-4-methoxybenzyl,
3,4,5-trimethoxybenzyl,
3-n-propoxybenzyl,
4-thiomethylbenzl,
3-carbethoxybenzyl,
4-carbethoxybenzyl,
2-methoxybenzyl,
3-methoxybenzyl, or 3-chlorobenzyl;

$R_3$ is 4-methoxyphenyl,
3,4-dimethoxyphenyl,
3-methyl-4-methoxyphenyl, or
2,4-dimethoxyphenyl;

$R_4$ is OH; and

X is oxygen.

5. A compound selected from 2-benzo-[1,3]dioxol-5-yl-4-(4-methoxyphenyl)-4-oxo-3-(3,4,5-trimethoxybenzyl)-but-2-enoic acid and the pharmacologically acceptable salts thereof.

6. A pharmaceutical composition comprising a therapeutically effective amount of a compound according to claim 1 in admixture with a pharmaceutically acceptable excipient, diluent, and/or carrier.

7. A method of treating subarachnoid hemorrhage comprising administering to a host suffering therefrom a therapeutically effective amount of a compound according to claim 1 in unit dosage form.

8. A method of treating subarachnoid hemorrhage comprising administering to a host suffering therefrom a therapeutically effective amount of a compound according to claim 5 in unit dosage form.

9. A compound selected from the group:

(±)-3-(1,3-benzodioxol-5-yl)-5-(4-chlorophenyl)-4 (phenylmethyl)-5-(2-propenyloxy)-2 (5H)-furanone, acetaldehyde, [[4-(1,3-benzodioxol-5-yl)-2-(4-chlorophenyl)-2,5-dihydro-5-oxo-3-(phenylmethyl)-2-furanyl]oxo]-, (±)-, 2(5H)-furanone, 3-(1,3-benzodioxol-5-yl)-5-(4-chlorophenyl)-5-(2,3-dihydroxypropoxy)-4-(phenylmethyl)-, (±)-, acetic acid, [[4-(1,3-benzodioxol-5-yl)-2-(4-chlorophenyl)-2,5-dihydro-3-(phenylmethyl)-5-oxo-2-furanyl]oxy]-, (±)-, 2(5H)-furanone, 3-(1,3-benzodioxol-5-yl)-5-(4-chlorophenyl)-5-[(3-hydroxyphenyl)methoxy]-4-(phenylmethyl)-, (±)-, 2(5H)-furanone, 3-(1,3-benzodioxol-5-yl)-5-hydroxy-5-(4-methylphenyl)-4-(phenylmethyl)-, 2(5H)-furanone, 3-(1,3-benzodioxol-5-yl)-5-hydroxy-5-phenyl-4-(phenylmethyl)-, 2(5H)-furanone, 3-(1,3-benzodioxol-5-yl)-5-hydroxy-5-phenyl-4-(2-thienylmethyl)-, 2(5H)-furanone, 3-(1,3-benzodioxol-5-yl)-5-hydroxy-5-phenyl-4-(3-thienylmethyl)-, 2(5H)-furanone, 5-(4-chlorophenyl)-3-(2,3-dihydro-1,4-benzodioxin-6-yl)-5-hydroxy-4-(phenylmethyl)-, 2(5H)-furanone, 3-(1,3-benzodioxol-5-yl)-5-(4-chlorophenyl)-5-hydroxy-4-(2-thienylmethyl)-, 2(5H)-furanone, 3-(1,3-benzodioxol-5-yl)-5-(4-chlorophenyl)-5-hydroxy-4-(1-naphthalenylmethyl)-, (±)-, 2(5H)-furanone, 4-(1,3-benzodioxol-5-ylmethyl)-5-(4-chlorophenyl)-5-hydroxy-3-[4-(1-methylethyl)phenyl]-, (±)-, 2(5H)-furanone, 3-(1,3-benzodioxol-5-yl)-5-(4-chlorophenyl)-5-hydroxy-4-(2-naphthalenylmethyl)-, (±)-, 2(5H)-furanone, 3-(1,3-benzodioxol-5-yl)-5-(4-chlorophenyl)-5-hydroxy-4-[[4-(1-methylethyl)phenyl]methyl]-, (±)-, 2(5H)-furanone, 3-(1,3-benzodioxol-5-yl)-4-(1,3-benzodioxol-5-ylmethyl)-5-(4-chlorophenyl)-5-hydroxy-, (±)-, 2(5H)-Furanone, 3-(1,3-benzodioxol-5-yl)-5-(4-chlorophenyl)-5-hydroxy-4-(3-thienylmethyl)-, 2(5H)-Furanone, 4-(1,3-benzodioxol-5-ylmethyl)-5-(4-chlorophenyl)-3-[4-(dimethyl-amino)phenyl]-5-hydroxy-, (±)-, 2(5H)-Furanone, 4-(1,3-benzodioxol-5-ylmethyl)-5-(4-chlorophenyl)-3-(3,4-dimethoxy-phenyl)-5-hydroxy, (±)-, 2(5H)-Furanone, 4-(1,3-benzodioxol-5-ylmethyl)-5-(4-chlorophenyl)-3-(3,4-dichloro-phenyl)-5-hydroxy-, (±)-, 2(5H)-Furanone, 3-(1,3-benzodioxol-5-yl)-5-(4-chlorophenyl)-4-(phenylmethyl)-5-propoxy-, (±)-, 2(5H)-Furanone, 3-(1,3-benzodioxol-5-yl)-5-(4-chlorophenyl)-4-[(3-chlorophenyl)methyl]-5-hydroxy, 3-Benzo[1,3]dioxol-5-yl-4-(4-chlorobenzyl)-5-hydroxy-5-(4-methoxyphenyl)-5H-furan-2-one, 3-Benzo[1,3]dioxol-5-yl-4-(4-bromobenzyl)-5-hydroxy-5-(4-methoxy-phenyl)-5H-furan-2-one, 3-Benzo[1,3]dioxol-5-yl-4-(4-benzyloxy-benzyl)-5-hydroxy-5-(4-methoxyphenyl)-5H-furan-2-one, 3-Benzo[1,3]dioxol-5-yl-5-hydroxy-5-(4-methoxyphenyl)-4-(4-trifluoromethylbenzyl)-5H-furan-2-one, 3-Benzo[1,3]dioxol-5-yl-4-ethyl-5-hydroxy-5-(4-methoxyphenyl)-5H-furan-2-one, 3-Benzo[1,3]dioxol-5-yl-4-benzyl-5-(2,6-difluorophenyl)-5-hydroxy-5H-furan-2-one, 3-Benzo[1,3]dioxol-5-yl-5-hydroxy-5-(4-methoxyphenyl)-4-pyridin-3-ylmethyl-5H-furan-2-one, 3-Benzo[1,3]dioxol-5-yl-5-hydroxy-4-isoquinolin-4-ylmethyl-5-(4-methoxyphenyl)-5H-furan-2-one, 3-Benzo[1,3]dioxol-5-yl-4-biphenyl-4-ylmethyl-5-hydroxy-5-(4-methoxyphenyl)-5H-furan-2-one, 2(5H)-Furanone, 3-(1,3-benzodioxol-5-yl)-5-hydroxy-4-(4-isoquinolinyl)-5-(4-methoxy-phenyl)-, (±)-, monohydrochloride, 2(5H)-Furanone, 3-(1,3-benzodioxol-5-yl)-5-hydroxy-5-(4-methoxyphenyl)-4-(3-pyridinyl-methyl)-, (±)-, monohydrochloride, 2-Butenoic acid, 2-(1,3-benzodioxol-5-yl)-3-[(4-methoxy-4-methylphenyl)methyl]-4-(4-methoxyphenyl)-4-oxo-, (Z)-, ion(1-) compd. with 2-hydroxy-N,N,N-trimethylethanaminium (1:1), 2-Butenoic acid, 2-(1,3-benzodioxol-5-yl)-4-(4-methoxyphenyl)-4-oxo-3-[[4-trifluoromethyl)phenyl]methyl]-, (Z)-, ion(1-) compd. with 2-hydroxy-N,N,N-trimethylethanaminium (1:1), 4'-Benzyl-5'-hydroxy-5'-(4-methoxyphenyl)-5'H-[2,3'] bifuranyl-2-one, 4-Benzyl-5-hydroxy-5(4-methoxyphenyl)-3-thiophen-2-yl-5H-furan-2-one, 4-Benzyl-5-hydroxy-5-(4-methoxyphenyl)-5H-[3,3'] bifuranyl-2-one, 3-Benzo[1,3]dioxol-5-yl-4-benzyl-5-(3,4-dimethoxyphenyl)-5-hydroxy-5H-furan-2-one, 3-Benzo[1,3]dioxol-5-yl-4-benzyl-5-(3,4-dichlorophenyl)-5-hydroxy-5H-furan-2-one, 4-(4-Benzo[1,3]dioxol-5-yl-3-benzyl-2-hydroxy-5-oxo-2,5-dihydrofuran-2-yl) benzoic acid methyl ester, 4-[4Benzo[1,3]dioxol-5-yl-3-benzyl-2-hydroxy-5-oxo-2,5-dihydrofuran-2-yl) benzoic acid, 3-Benzo[1,3]dioxol-5-yl-4-benzyl-5-hydroxy-5-(4-isopropoxyphenyl)-5H-furan-2-one, 3-Benzo[1,3]dioxol-5-yl-4-benzyl-5-(4-benzyloxyphenyl)-5-hydroxy-5H-furan-2-one, 3-Benzo[1,3]dioxol-5-yl-4-benzyl-5-(3,4-dimethylphenyl)-5-hydroxy-5H-furan-2-one, 3-Benzo[1,3]dioxol-5-yl-4-benzyl-5-hydroxy-5-o-tolyl-5H-furan-2-one, 3-Benzo[1,3]dioxol-5-yl-4-benzyl-5-hydroxy-5-(3-methoxyphenyl)-5H-furan-2-one, 3-Benzo[1,3]dioxol-5-yl-4-benzyl-5-methoxy-5-(4-methoxyphenyl)-5H-furan-2-one, 3-Benzo[1,3]dioxol-5-yl-4-benzyl-5-hydroxy-5-m-tolyl-5H-furan-2-one, 3-Benzo[1,3]dioxol-5-yl-4-benzyl-5-(3-chlorophenyl)-5-hydroxy-5H-furan-2-one, 3,5-Bis-benzo[1,3]dioxol-5-yl-4-benzyl-5-hydroxy-5H-furan-2-one, 3-Benzo[1,3]dioxol-5-yl-4-benzyl-5-hydroxy-5-(2-methoxyphenyl)-5H-furan-2-one, 3-Benzo[1,3]dioxol-5-yl-5-hydroxy-5-(4-methoxyphenyl)-4-naphthalen-1-ylmethyl-5H-furan-2-one, 3-Benzo[1,3]dioxol-5-yl-5-hydroxy-5-(4-methoxyphenyl)-4-(2-phenoxybenzyl-5H-furan-2-one, 3-Benzo[1,3]dioxol-5-yl-4-benzyl-5-(4-ethylphenyl)-5-hydroxy-5H-furan-2-one, 3-Benzo[1,3]dioxol-5-yl-4-benzyl-5-hydroxy-5-(4-methylsulfanylphenyl)-5H-furan-2-one, 4-[4-benzo[1,3]dioxol-5-yl-2-hydroxy-2-(4-methoxyphenyl)-5-oxo-2,5-dihydrofuran-3-ylmethyl] benzoic acid, 1,3-Benzodioxol-5-acetic acid, α-[2-[(4-carboxyphenyl)methyl]-2-(4-methoxybenzoyl)ethylidene]-, disodium salt, 3-Benzo[1,3]dioxol-5-yl-5-hydroxy-5-(4-methoxyphenyl)-4-(3,4,5-trimethoxy-benzyl)-5H-furan-2-one, 3-Benzo[1,3]dioxol-5-yl-4-(2-chlorobenzyl-5-hydroxy-5-(4-methoxyphenyl)-5H-furan-2-one, 3-Benzo[1,3]dioxol-5-yl-5-hydroxy-5-(4-methoxyphenyl)-4-(2-methylbenzyl)-5H-furan-2-one, 3-Benzo[1,3]dioxol-5-yl-5-hydroxy-4-(2-methoxybenzyl)-5-(4-methoxyphenyl)-5H-furan-2-one, 3-Benzo[1,3]dioxol-5-yl-5-hydroxy-4,5-bis-(4-methoxyphenyl)-5H-furan-2-one, 3-[4-Benzo[1,3]dioxol-5-yl-2-hydroxy-2-(4-methoxyphenyl)-5-oxo-2,5-dihydro-furan-3-ylmethyl]-benzoic acid, {4-[4Benzo[1,3]dioxol-5-yl-2-hydroxy-2-(4-methoxyphenyl)-5-oxo-2,5-dihydro-furan-3-ylmethyl]-phenyl}-acetic acid, {3-[4Benzo[1,3]dioxol-5-yl-2-hydroxy-2-(4-methoxyphenyl)-5-oxo-2,5-dihydro-furan-3-ylmethyl]-phenyl}-acetic acid, 3-Benzo[1,3]dioxol-5-yl-5-hydroxy-4-(4-methoxy-3,5-dimethyl-benzyl)-5-(4-methoxy-phenyl)-5H-furan-2-one, 3-Benzo[1,3]dioxol-5-yl-4-(3,5-dimethyl-4-isoproxy-benzyl)-5-hydroxy-5-(4-methoxy-phenyl)-5H-furan-2-one, 3-Benzo[1,3]dioxol-5-yl-4-(6,6-dimethylbicyclo[3.1.1]hept-2-en-2-ylmethyl)-5-hydroxy-5-(4-methoxyphenyl)-5H-furan-2-one, 3-Benzo[1,3]dioxol-5-yl-5-hydroxy-5-(4-methoxyphenyl)-4-(2-phenoxy-benzyl)-5H-furan-2-one, 3-Benzo[1,3]dioxol-5-yl-4-(2-cyclohexylethyl)-5-hydroxy-5-(4-methoxy-phenyl)-5H-furan-2-one, 3-Benzo[1,3]dioxol-5-yl-5-hydroxy-5-(2-allyloxy-4-methoxyphenyl)-4-benzyl-5H-furan-2-one, 3-Benzo[1,3]dioxol-5-yl-4-(2-cyclohexyl-2-phenyl-ethyl)-5-hydroxy-5-(4-methoxy-phenyl)-5H-furan-2-one, 3-Benzo[1,3]dioxol-5-yl-4-cycloheptylmethyl-5-hydroxy-5-(4-methoxy-phenyl)-5H-furan-2-one, 3-Benzo[1,3]dioxol-5-yl-5-hydroxy-5-(4-methoxyphenyl)-4-pentyl-5H-furan-2-one,

[2-(4-Benzo[1,3]dioxol-5-yl-3-benzyl-2-hydroxy-5-oxo-2,5-dihydro-furan-2-yl)-5-methoxy-phenoxy]-acetic acid, {2-[4-Benzo[1,3]dioxol-5-yl-2-hydroxy-2-(4-methoxyphenyl)-5-oxo-2,5-dihydro-furan-3-ylmethyl]-5-methoxy-phenoxy}-acetic acid, 2-Butenoic acid, 2-(1,3-benzodioxol-5-yl)-4-[4-(1H-imidazol-1-yl)phenyl]4-oxo-3-(phenyl-methyl)-, 2-Benzo[1,3]dioxol-5-yl-4-(4-methoxy-phenyl)-3-[4-(2-morpholin-4-yl-ethylcarbamoyl)-benzyl]-4-oxo-but-2-enoic acid, Benzamide, 4-[[4-(1,3-benzodioxol-5-yl)-2,5-dihydro-2-hydroxy-2-(4-methoxyphenyl)-5-oxo-3-furanyl]methyl]-N-[2-(4-morpholinyl)ethyl]-, monohydrochloride, (±)-, {4-[4Benzo[1,3]dioxol-5-yl-2-hydroxy-2-(4-methoxyphenyl)-5-oxo-2,5-dihydro-furan-3-ylmethyl]-2,6-dimethoxy-phenoxy}-acetic acid, 3-Benzo[1,3]dioxol-5-yl-5-hydroxy-5-(4-methoxy-3-methyl-phenyl)-4-(3-methoxy-4-octyloxy-benzyl)-5H-furan-2-one, 3-Benzo[1,3]dioxol-5-yl-4-(cyclohexyloxy-3-methyl-benzyl)-5-hydroxy-5-(4-methoxy-phenyl)-5H-furan-2-one, 3-Benzo[1,3]dioxol-5-yl-5-hydroxy-5-(4-methoxyphenyl)-4-(1,2,3,4-tetrahydro-naphthalen-1-ylmethyl)-5H-furan-2-one, 3-[4Benzo[1,3]dioxol-5-yl-2-hydroxy-2-(4-methoxyphenyl)-5-oxo-2,5-dihydro-furan-3-ylmethyl]-cyclohexanecarboxylic acid, 3-Benzo[1,3]dioxol-5-yl-5-hydroxy-4-(4-isopropyl-benzyl)-5-(4-methoxy-phenyl)-5H-furan-2-one, 2(5H)-Furanone, 3-(1,3-benzodioxol-5-yl)-5-(4-chlorophenyl)-4-[(4-chlorophenyl)methyl]-5-hydroxy-, 2(5H)-Furanone, 3-(1,3-benzodioxol-5-yl)-5-(4-chlorophenyl)-5-hydroxy-4-[(4-methoxyphenyl)methyl]-, 2(5H)-Furanone, 3-(1,3-benzodioxol-5-yl)-5-(4-chlorophenyl)-5-hydroxy-4-[(4-methylphenyl)methyl]-, 2(5H)-Furanone, 3-(1,3-benzodioxol-5-yl)-5-(4-chlorophenyl)-5-hydroxy-4-[(3-methylphenyl)methyl]-, 2(5H)-Furanone, 3-(1,3-benzodioxol-5-yl)-5-(4-chlorophenyl)-5-hydroxy-4-[(3-methoxyphenyl)methyl]-, 2(5H)-Furanone, 3-(1,3-benzodioxol-5-yl)-5-(4-chlorophenyl)-5-hydroxy-4-[(1-methyl-1H-indol-3-yl)methyl], (±)-, 3-Benzo[1,3]dioxol-5-yl-4-(3,5-dimethyl-4-octyloxybenzyl)-5-hydroxy-5-(4-methoxy-phenyl)-5H-furan-2-one, 3-Benzo[1,3]dioxol-5-yl-4-(3,5-dimethoxybenzyl)-5-methoxy-5-(4-methoxyphenyl)-5H-furan-2-one.

10. A compound named:

2(5H)-Furanone, 3-(1,3-benzodioxol-5-yl)-5-hydroxy-5-(4-methoxyphenyl)-4-(phenylmethyl)-, 3-Benzo[1,3]dioxol-5-yl-4-(3-chlorobenzyl)-5-hydroxy-5-(4-methoxyphenyl)-5H-furan-2-one, 3-Benzo[1,3]dioxol-5-yl-5-hydroxy-5-(4-methoxyphenyl)-4-(4-methylbenzyl)-5H-furan-2-one, 3-Benzo[1,3]dioxol-5-yl-5-hydroxy-4-(4-methoxybenzyl)-5-(4-methoxyphenyl)-5H-furan-2-one, 3-Benzo[1,3]dioxol-5-yl-4-(4-tert-butylbenzyl)-5-hydroxy-5-(4-methoxyphenyl)-5H-furan-2-one, 3-Benzo[1,3]dioxol-5-yl-5-hydroxy-5-(4-methoxyphenyl)-4-(3-trifluoromethylbenzyl)-5H-furan-2-one, 3-Benzo[1,3]dioxol-5-yl-5-hydroxy-4-(isopropoxybenzyl)-5-(4-methoxyphenyl)-5H-furan-2-one, 3-Benzo[1,3]dioxol-5-yl-4-(4-dimethylaminobenzyl)-5-hydroxy-5-(4-methoxylphenyl)-5H-furan-2-one, 3-Benzo[1,3]dioxol-5-yl-4-benzo[1,3]dioxol-5-ylmethyl-5-hydroxy-5-(4-methoxyphenyl)-5H-furan-2-one, 3-Benzo[1,3]dioxol-5-yl-5-hydroxy-4-(4-methoxy-3-methylbenzyl)-5-(4-methoxyphenyl)-5H-furan-2-one, 3-Benzo[1,3]dioxol-5-yl-5-hydroxy-5-(4-methoxyphenyl)-4-(3-methylbenzyl)-5H-furan-2-one, 3-Benzo[1,3]dioxol-5-yl-4-(3-chloro-4-methoxybenzyl)-5-hydroxy-5-(4-methoxyphenyl)-5H-furan-2-one, 3-Benzo[1,3]dioxol-5-yl-4-(4-butoxybenzyl)-5-hydroxy-5-(4-methoxyphenyl)-5H-furan-2-one, 3-(3,5-Dimethoxyphenyl)-5-hydroxy-5-(4-methoxyphenyl)-4-pyridin-3-ylmethyl-5H-furan-2-one, 3-Benzo[1,3]dioxol-5-yl-5-hydroxy-5-(4-methoxyphenyl)-4-(3-propoxybenzyl)-5H-furan-2-one, 4-(3-Allyloxy-4-methoxy-enzyl)-3-benzo[1,3]dioxol-5-yl-5-hydroxy-5-(4-methoxyphenyl)-5H-furan-2-one, 2(5H)-Furanone, 3-(3,5-dimethoxyphenyl)-5-hydroxy-5-(4-methoxyphenyl)-4-(3-pyridinyl-methyl)-, (±)-, monohydrochloride, 2-Butenoic acid, 2-(1,3-benzodioxol-5-yl)-4-(4-methoxyphenyl)-4-oxo-3-(phenylmethyl)-, (Z)-, ion (1-) compound with 2-hydroxy-N,N,N-triethanaminium (1:1), 3-Benzo[1,3]dioxol-5-yl-4-cyclohexylmethyl-5-hydroxy-5-(4-methoxyphenyl)-5H-furan-2-one, 3-Benzo[1,3]dioxol-5-yl-5-hydroxy-4-(4-methanesulfonylbenzyl)-5-(4-methoxyphenyl)-5H-furan-2-one, 3-Benzo[1,3]dioxol-5-yl-4-benzyl-5-(2,4-dimethoxyphenyl)-5-hydroxy-5H-furan-2-one, 3-Benzo[1,3]dioxol-5-yl-5-hydroxy-4-(4-methoxy-2,5-dimethylbenzyl)-5-(4-methoxy-phenyl)-5H-furan-2-one, 2-Butenoic acid, 2-(1,3-benzodioxol-5-yl)-4-(4-methoxyphenyl)-4-oxo-3-[(3-propoxyphenyl)-methyl]-, (Z)-, ion(1-) compound with 2-hydroxy-N,N,N-trimethylethanaminium (1:1), 3-Benzo[1,3]dioxol-5-yl-5-hydroxy-4-(4-methoxy-2,3-dimethylbenzyl)-5-(4-methoxy-phenyl)-5H-furan-2-one, 4-(3-Allyloxy-4-methoxybenzyl)-3-benzo[1,3]dioxol-5-yl-5-(2,4-dimethoxyphenyl)-5-hydroxy-5H-furan-2-one, Benzoic acid, 3-[[4-(1,3-benzodioxol-5-yl)-2,5-dihydro-2-hydroxy-2-(4-methoxyphenyl)-5-oxo-3-furanyl]methyl]-, methyl ester, 2(5H)-Furanone, 3-(1,3-benzodioxol-5-yl)-5-hydroxy-5-(4-methoxy-3-methylphenyl)-4-(phenylmethyl)-, (±)-, {4-[4-Benzo[1,3]dioxol-5-yl-2-hydroxy-2-(4-methoxyphenyl)-5-oxo-2,5-dihydro-furan-3-ylmethyl]-phenyl}-acetic acid methyl ester, {3-[4-Benzo[1,3]dioxol-5-yl-2-hydroxy-2-(4-methoxyphenyl)-5-oxo-2,5-dihydro-furan-3-ylmethyl]-phenyl}-acetic acid methyl ester, 4-Benzyl-5-hydroxy-3-(7-methoxy-benzo[1,3]-dioxol-5-yl)-5-(4-methoxy-phenyl)-5H-furan-2-one, 3-Benzo[1,3]dioxol-5-yl-4-(3,5-dimethoxybenzyl)-5-hydroxy-5-(4-methoxy-phenyl)-5H-furan-2-one, 3-Benzo[1,3]dioxol-5-yl-4-(3,4-dimethoxy-benzyl)-5-hydroxy-5-(4-methoxy-phenyl)-5H-furan-2-one, 3-Benzo[1,3]dioxol-5-yl-5-hydroxy-5-(4-methoxyphenyl)-4-(2,3,4-trimethoxy-benzyl)-5H-furan-2-one, 3-Benzo[1,3]dioxol-5-yl-5-hydroxy-5-(4-methoxyphenyl)-4-(2,4,5-trimethoxy-benzyl)-5H-furan-2-one, 3-Benzo[1,3]dioxol-5-yl-4-(2,5-dimethoxybenzyl)-5-hydroxy-5-(4-methoxy-phenyl)-5H-furan-2-one, 3-Benzo[1,3]dioxol-5-yl-4-(2,3-dimethoxybenzyl)-5-hydroxy-5-(4-methoxy-phenyl)-5H-furan-2-one, 3-Benzo[1,3]dioxol-5-yl-4-(4-benzyloxy-3-methoxybenzyl)-5-hydroxy-5-(4-methoxy-phenyl)-5H-furan-2-one, 3-Benzo[1,3]dioxol-5-yl-4-cyclopentylmethyl-5-hydroxy-5-(4-methoxy-phenyl)-5H-furan-2-one, 3-Benzo[1,3]dioxol-5-yl-4-cyclohex-3-enyl-methyl-5-hydroxy-5-(4-methoxy-phenyl)-5H-furan-2-one, 3-Benzo[1,3]dioxol-5-yl-4-(2-cyclopentyl-2-phenylethyl)-5-hydroxy-5-(4-methoxy-phenyl)-5H-furan-2-one, 3-Benzo[1,3]dioxol-5-yl-4-[2-(benzo[1,3]-dioxol-5-yloxy)-benzyl]-5-hydroxy-5-(4-methoxyphenyl)-5H-furan-2-one, 4-(2-Allyloxy-4-methoxy-benzyl)-3-benzo[1,3]-dioxol-5-yl-5-hydroxy-5-(4-methoxy-phenyl)-5H-furan-2-one, Sodium 2-benzo[1,3]dioxol-5-yl-3-benzyl-4-(4-methoxyphenyl)-4-oxobut-2-enoate, 1,3-Benzodioxol-5-acetic acid, α-[2-(4-methoxyphenyl)-1-[[4-(1-methylethoxy)phenyl]methyl]-2-oxoethylene]-, (Z)-, choline salt, Sodium 2-benzo[1,3]dioxol-5-yl-3-benzyl-4-(4-methoxyphenyl)-4-oxobut-2-enoate, Sodium 2-benzo[1,3]dioxol-5-yl-3-(4-isopropoxybenzyl)-4-(4-methoxy-phenyl)-4-oxobut-2-enoate, 5-Hydroxy-3-(7-methoxy-benzo[1,3]dioxol-5-yl)-5-(4-methoxy-phenyl)-4-(3,4,5-trimethoxybenzyl)-5H-furan-2-one, 4-Benzyl-5-hydroxy-3-(7-methoxy-benzo[1,3]-dioxol-5-yl)-5-(4-methoxy-3-methyl-phenyl)-5H-furan-2-one, 5-Hydroxy-3-(7-methoxy-benzo[1,3]dioxol-5-yl)-5-(4-methoxy-3-methyl-phenyl)-4-(3,4,5-trimethoxy-benzyl)-5H-furan-2-one, {4-[4-Benzo[1,3]dioxol-5-yl-2-hydroxy-2-(4-methoxy-phenyl)-5-oxo-2,5-dihydro-furan-3-ylmethyl]-2,6-dimethoxy-phenoxy}-acetic acid ethyl ester, {5-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-acetic acid ethyl ester, {4-[4-Benzo[1,3]dioxol-5-yl-2-hydroxy-2-(4-methoxy-phenyl)-5-oxo-2,5-dihydro-furan-3-ylmethyl]-2,3-dimethoxy-phenoxy}-acetic acid, Sodium 2-benzo[1,3]dioxol-5-yl-3-(4-methoxybenzoyl)-4-(4-methoxy-2,5-dimethylphenyl)-but-2-enoate, Sodium 3-benzyl-2-(7-methoxybenzo[1,3]dioxol-5-yl)-4-(4-methoxyphenyl)-4-oxobut-2-enoate, Sodium 2-(7-methoxybenzo-[1,3]dioxol-5-yl)-3-(4-methoxy-3-methylbenzoyl-4-(3,4,5-trimethoxy-phenyl)-but-2-enoate, Sodium 2-(7-methoxybenzo-[1,3]dioxol-5-yl)-4-(4-methoxyphenyl)-4-oxo-3-(3,4,5-trimethoxy-benzyl)-but-2-enoate, Sodium 2-Benzo[1,3]dioxol-5-yl-3-cyclohexylmethyl-4-(4-methoxy-phenyl)-4-oxo-but-2-enoate, Sodium 2-Benzo[1,3]dioxol-5-yl-3-(4-methoxybenzyl)-4-(4-methoxy-phenyl)-4-oxo-but-2-enoate, 3-Benzo[1,3]dioxol-5-yl-5-hydroxy-5-(4-methoxy-3-methyl-phenyl)-4-(3,4,5-trimethoxy-benzyl)-5H-furan-2-one, N -{4-[4-Benzo[1,3]dioxol-5-yl-2-hydroxy-2-(4-methoxy-3-methyl-phenyl)-5-oxo-2,5-dihydro-furan-3-ylmethyl]-phenyl}-acetamide, 3-Benzo[1,3]dioxol-5-yl-5-hydroxy-4-(4-isopropoxy-3-methoxy-benzyl)-5-(4-methoxy-3-methyl-phenyl)-5H-furan-2-one, 3-Benzo[1,3]dioxol-5-yl-5-hydroxy-4-(4-isopropoxy-3-methyl-benzyl)-5-(4-methoxy-3-methyl-phenyl)-5H-furan-2-one, 3-[4-Benzo[1,3]dioxol-5-yl-2-hydroxy-2-(4-methoxyphenyl)-5-oxo-2,5-dihydro-furan-3-ylmethyl]-cyclohexanecarboxylic acid methyl ester, 3-Benzo[1,3]dioxol-5-yl-4-cyclopropylmethyl-5-hydroxy-5-(4-methoxy-phenyl)-5H-furan-2-one, 1,3-Benzodioxol-5-acetic acid, α-[1-[[3-(methoxycarbonyl)phenyl]methyl]-2-(4-methoxyphenyl)-2-oxoethylene]-, monopotassium salt, 1,3-Benzodioxole-5-acetic acid, α-[1-(4-methoxybenzoyl)-2-(2-methoxyphenyl)ethylidene]-, monosodium salt, (Z)-, 4-Cyclohexylmethyl-5-hydroxy-3-(7-methoxybenzo[1,3]dioxol-5-yl)-5-(4-methoxy-3-methyl-phenyl)-5H-furan-2-one, 4-Cyclohexylmethyl-5-hydroxy-3-(7-methoxybenzo[1,3]dioxol-5-yl)-5-(4-methoxy-phenyl)-5H-furan-2-one, 3-Benzo[1,3]dioxol-5-yl-5-hydroxy-4-(4-iodobenzyl)-5-(4-methoxy-phenyl)-5H-furan-2-one, 3-Benzo[1,3]dioxol-5-yl-4-(3,5-dimethoxy-4-pentyloxybenzyl)-5-hydroxy-5-(4-methoxy-phenyl)-5H-furan-2-one, 3-Benzo[1,3]dioxol-5-yl-4-(4-butoxy-3,5-dimethoxybenzyl)-5-hydroxy-5-(4-methoxy-phenyl)-5H-furan-2-one, 3-Benzo[1,3]dioxol-5-yl-4-(3-benzyloxy-4,5-dimethoxybenzyl)-5-hydroxy-5-(4-methoxy-phenyl)-5H-furan-2-one, 4-(3-Alkyloxy-4,5-dimethoxy-benzyl)-3-benzo-[1,3]dioxol-5-yl-5-hydroxy-5-(4-methoxy-phenyl)-5H-furan-2-one, 3-Benzo[1,3]dioxol-5-yl-4-(2,4-dimethoxy-benzyl)-5-hydroxy-5-(4-methoxy-phenyl)-5H-furan-2-one, 3-Benzo[1,3]dioxol-5-yl-5-hydroxy-4-(3-isopropoxy-4,5-dimethoxy-benzyl)-5-(4-methoxy-phenyl)-5H-furan-2-one, 4-Cyclopentylmethyl-5-hydroxy-3-(7-methoxybenzo[1,3]dioxol-5-yl)-5-(4-methoxy-3-methyl-phenyl)-5H-furan-2-one, 3-Benzo[1,3]dioxol-5-yl-4-[2-cyclopentyl-2-(4-methoxyphenyl)-ethyl]-5-hydroxy-5-(4-methoxy-phenyl)-5H-furan-2-one, 5-Benzo[1,3]dioxol-5-yl-4-cyclopentylmethyl-5-hydroxy-3-(7-methoxy-benzo[1,3]dioxyl-5-yl)-5H-furan-2-one, 5-Benzo[1,3]dioxol-5-yl-4-cyclohexylmethyl-5-hydroxy-3-(7-methoxy-benzo[1,3]dioxol-5-yl)-5H-furan-2-one, 5-Benzo[1,3]dioxol-5-yl-5-hydroxy-3-(7-methoxybenzo[1,3]dioxol-5-yl)-4-[4-methoxy-2-(2-methoxyethoxy)-benzyl]-5H-furan-2-one, 4-Cyclopentylmethyl-5-hydroxy-3-(7-methoxybenzo[1,3]dioxol-5-yl)-5-(4-methoxy-phenyl)-5H-furan-2-one, 4-Cyclohexylmethyl-5-hydroxy-5-(7-methoxybenzo[1,3]dioxol-5-yl)-3-(4-methoxy-phenyl)-5H-furan-2-one, 4-Cyclohexylmethyl-5-(2,3-dihydro-benzo[1,4]dioxin-6-yl)-5-hydroxy-3-(7-methoxy-benzo[1,3]-dioxol-5-yl)-5H-furan-2-one, 3-Benzo[1,3]dioxol-5-yl-5-hydroxy-4-(3-methoxymethyl-benzyl)-5-(4-methoxy-phenyl)-5H-furan-2-one, 4-Cyclopentylmethyl-5-(2,3-dihydro-benzo[1,4]dioxin-6-yl)-5-hydroxy-3-(7-methoxy-benzo[1,3]-dioxol-5-yl)-5H-furan-2-one, and 4-Cyclopentylmethyl-5-hydroxy-3,5-bis-(7-methoxybenzo[1,3]dioxol-5-yl)-5H-furan-2-one, 3-Benzo[1,3]dioxol-5-yl-4-(3,4-dichlorobenzyl)-5-hydroxy-5-(4-methoxyphenyl)-5H-furan-2-one, N-{4-[4-Benzo[1,3]dioxol-5-yl-2-hydroxy-2-(4-methoxyphenyl)-5-oxo-2,5-dihydro-furan-3-ylmethyl]-phenyl}-acetamide, Sodium 2-Benzo[1,3]dioxol-5-yl-4-(4-methoxyphenyl)-4-oxo-3-(3,4,5-trimethoxy-benzyl)-but-2-enoate, Potassium 3-(4-Acetylamino-benzyl)-2-benzo[1,3]-dioxol-5-yl-4-(4-methoxy-phenyl)-4-oxo-but-2-enoate, Sodium 3-Benzyl-2-(7-methoxy-benzo[1,3]dioxol-5-yl)-4-(4-methoxy-3-methyl-phenyl)-4-oxo-but-2-enoate, Sodium 2-Benzo[1,3]dioxol-5-yl-4-(4-methoxy-3-methyl-phenyl)-4-oxo-3-(3,4,5-trimethoxy-benzyl)-but-2-enoate.

* * * * *

UNITED STATES PATENT AND TRADEMARK OFFICE
CERTIFICATE OF CORRECTION

PATENT NO. : 5,691,373

DATED : November 25, 1997

INVENTOR(S) : Berryman, et al.

It is certified that error appears in the above-identified patent and that said Letters Patent is hereby corrected as shown below:

Column 228, line 42, insert --$R_1$-- before "is".

Signed and Sealed this

Fifteenth Day of May, 2001

Attest:

NICHOLAS P. GODICI

Attesting Officer     Acting Director of the United States Patent and Trademark Office